US010214726B2

(12) United States Patent
Childs et al.

(10) Patent No.: US 10,214,726 B2
(45) **Date of Patent: *Feb. 26, 2019**

(54) COMPOSITIONS AND METHODS FOR PREVENTION OR TREATMENT OF NEOPLASTIC DISEASE IN A MAMMALIAN SUBJECT

(71) Applicant: The United States of America, as represented by the Secretary, Dept. of Health and Human Services, Washington, DC (US)

(72) Inventors: Richard William Wyatt Childs, Rockville, MD (US); Yoshiyuki Takahashi, Showa-ku (JP); Sachiko Kajigaya, Rockville, MD (US); Nanae Harashima, Rockville, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/821,523

(22) Filed: Nov. 22, 2017

(65) Prior Publication Data

US 2018/0112178 A1 Apr. 26, 2018

Related U.S. Application Data

(60) Division of application No. 14/549,296, filed on Nov. 20, 2014, now Pat. No. 9,856,453, which is a continuation of application No. 12/293,180, filed as application No. PCT/US2007/064237 on Mar. 16, 2007, now Pat. No. 8,921,050.

(60) Provisional application No. 60/783,350, filed on Mar. 17, 2006.

(51) Int. Cl.

| | |
|---|---|
| *C12N 5/0783* | (2010.01) |
| *A61K 39/21* | (2006.01) |
| *C07K 14/005* | (2006.01) |
| *A61K 39/12* | (2006.01) |
| *A61K 35/12* | (2015.01) |
| *A61K 35/17* | (2015.01) |
| *A61K 39/00* | (2006.01) |

(52) U.S. Cl.

CPC ............ *C12N 5/0638* (2013.01); *A61K 35/12* (2013.01); *A61K 35/17* (2013.01); *A61K 39/12* (2013.01); *A61K 39/21* (2013.01); *C07K 14/005* (2013.01); *A61K 39/00* (2013.01); *A61K 2039/585* (2013.01); *C12N 2740/10022* (2013.01); *C12N 2740/10034* (2013.01)

(58) Field of Classification Search

None

See application file for complete search history.

(56) References Cited

U.S. PATENT DOCUMENTS

| | | | |
|---|---|---|---|
| 4,522,752 A | 6/1985 | Sisto et al. | |
| 4,897,268 A | 1/1990 | Tice et al. | |
| 5,073,627 A | 12/1991 | Curtis et al. | |
| 5,075,109 A | 12/1991 | Tice et al. | |
| 5,108,910 A | 4/1992 | Curtis et al. | |
| 5,199,942 A | 4/1993 | Gillis | |
| 5,229,496 A | 7/1993 | Deeley et al. | |
| 6,497,876 B1 | 12/2002 | Maraskovsky et al. | |
| 6,812,339 B1 * | 11/2004 | Venter .................. | C12Q 1/6883 435/6.11 |
| 8,921,050 B2 * | 12/2014 | Childs .................... | A61K 39/21 424/185.1 |
| 2006/0057725 A1 | 3/2006 | Leboulch et al. | |

FOREIGN PATENT DOCUMENTS

| | | |
|---|---|---|
| EP | 423980 | 4/1991 |
| EP | 0627487 | 12/1994 |
| JP | 9-252780 | 9/1997 |
| WO | WO 93/04701 | 3/1993 |
| WO | WO 94/16737 | 4/1994 |
| WO | WO 94/28391 | 12/1994 |
| WO | WO 95/00632 | 1/1995 |
| WO | WO 95/22618 | 8/1995 |
| WO | WO 95/27062 | 10/1995 |
| WO | WO 95/26718 | 12/1995 |
| WO | WO 98/11244 | 3/1998 |
| WO | WO 99/61601 | 12/1999 |

OTHER PUBLICATIONS

Dyall et al. (Gene Therapy, 2001, p. 114-121).*
Holtl et al. (The Journal of Urology, 1999, vol. 161, p. 777-782).*
Tsang et al. (Clinical Cancer Research, 2005, p. 1597-1607).*
Altschul et al., "Basic local alignment search tool," *J. Mol. Biol.*, vol. 215, No. 3, pp. 403-410, 1990.
Altschul et al., "Gapped BLAST and PSI-BLAST: a new generation of protein database search programs," *Nucleic Acids Res.*, vol. 25, No. 17, pp. 3389-3402, 1997.
Andersson et al., "ERV3 and related sequences in humans: structure and RNA expression," *J. Virol.*, vol. 79, No. 14, pp. 9270-9284, 2005.

(Continued)

*Primary Examiner* — Agnieszka Boesen

(74) *Attorney, Agent, or Firm* — Klarquist Sparkman, LLP

(57) ABSTRACT

Compositions and methods are provided for preventing or treating neoplastic disease in a mammalian subject. A composition is provided which comprises an enriched immune cell population reactive to a human endogenous retrovirus type E antigen on a tumor cell. A method of treating a neoplastic disease in a mammalian subject is provided which comprises administering to a mammalian subject a composition comprising an enriched immune cell population reactive to a human endogenous retrovirus type E antigen, in an amount effective to reduce or eliminate the neoplastic disease or to prevent its occurrence or recurrence.

11 Claims, 37 Drawing Sheets

Specification includes a Sequence Listing.

(56) References Cited

OTHER PUBLICATIONS

Applied Biosystems. *User Bulletin #2, ABI PRISM 7700 Sequence Detection System*, Dec. 11, 1997, 1-36.
Baggiolini, "Chemokines and leukocyte traffic," *Nature*, vol. 392, No. 6676, pp. 565-568, 1998.
Berardi et al., "Functional isolation and characterization of human hematopoietic stem cells," *Science*, vol. 267, No. 5194, pp. 104-108, 1995.
Berenson et al., "Positive selection of viable cell populations using avidin-biotin immunoadsorption," *J Immunol Methods*, vol. 91, No. 1, pp. 11-19, 1986.
Bishop et al., "High-dose therapy and peripheral blood progenitor cell transplantation: effects of recombinant human granulocyte-macrophage colony-stimulating factor on the autograft," *Blood*, vol. 83, No. 2, pp. 610-616, 1994.
Bock et al., "Endogenous retroviruses and the human germline," *Curr Opin Genet Dev.*, vol. 10, No. 6, pp. 651-655, 2000.
Bregni et al., "The second international meeting on allogeneic transplantation in solid tumors," *Bone Marrow Transplant*, vol. 38, No. 8, pp. 527-537, 2006.
Büscher et al., "Expression of human endogenous retrovirus K in melanomas and melanoma cell lines," *Cancer Res.*, vol. 65, No. 10, pp. 4172-4180, 2005.
Campbell et al., "6-C-kine (SLC), a lymphocyte adhesion-triggering chemokine expressed by high endothelium, is an agonist for the MIP-3beta receptor CCR7" *J. Cell Biol.*, vol. 141, No. 4, pp. 1053-1059, 1998.
Caux et al., "Activation of human dendritic cells through CD40 cross-linking," *J. Exp. Med.*, vol. 180, No. 4, pp. 1263-1272, 1994.
Childs et al., "Engraftment kinetics after nonmyeloablative allogeneic peripheral blood stem cell transplantation: full donor T-cell chimerism precedes alloimmune responses," *Blood*, vol. 94, No. 9, pp. 234-241, 1999.
Childs et al., "Regression of metastatic renal-cell carcinoma after nonmyeloablative allogeneic peripheral-blood stem-cell transplantation," *N. Engl. J. Med.*, vol. 343, No. 11, pp. 750-758, 2000.
Clerici et al., "Immune responses to antigens of human endogenous retroviruses in patients with acute or stable multiple sclerosis," *J. Neuroimmunol.*, vol. 99, No. 2, pp. 173-182, 1999.
Davidson et al., "A model system for in vivo gene transfer into the central nervous system using an adenoviral vector," *Nat. Genet.*, vol. 3, No. 3, pp. 219-223, 1993.
Depil et al., "Expression of a human endogenous retrovirus, HERV-K, in the blood cells of leukemia patients," *Leukemia*, vol. 16, No. 2, pp. 254-259, 2002.
Dutton et al., "T cell memory," *Annu. Rev. Immunol.*, vol. 16, pp. 201-223, 1998.
Dyall et al., "Lentivirus-transduced human monocyte-derived dendritic cells efficiently stimulate antigen-specific cytotoxic T lymphocytes," *Blood*, vol. 97, No. 1, pp. 114-121, 2001.
Florl et al, "DNA methylation and expression of LINE-1 and HERV-K provirus sequences in urothelial and renal cell carcinomas," *British J. Cancer*, vol. 80, pp. 1312-1321, 1999.
Geller et al., "An HSV-1 vector expressing tyrosine hydroxylase causes production and release of L-dopa from cultured rat striatal cells," *J. Neurochem.*, vol. 64, No. 2, pp. 487-496, 1995.
Geller, "Infection of cultured central nervous system neurons with a defective herpes simplex virus 1 vector results in stable expression of *Escherichia coli* beta-galactosidase," *Proc. Natl. Acad. Sci. USA.*, vol. 87, No. 3, pp. 149-153, 1990.
GenBank Accession No. AB062274.1, Apr. 6, 2007.
GenBank Accession No. AL133408, Jan. 13, 2009.
Germain, "MHC-dependent antigen processing and peptide presentation: providing ligands for T lymphocyte activation," *Cell*, vol. 76, No. 2, pp. 287-299, 1994.
Griffiths, "Endogenous retroviruses in the human genome sequence," *Genome Biology*, 2:reviews1017-reviews1017.5, 2001.
Hanada et al., "Immune recognition of a human renal cancer antigen through posttranslational protein splicing," *Nature*, vol. 427, No. 6971, pp. 252-256, 2004.
Höltl et al., Cellular and Humoral Immune Responses in Patients with Metastatic Renal Cell Carcinoma After Vaccination with Antigen Pulsed Dendritic Cells, *The Journal of Urology*, vol. 161, pp. 777-782, 1999.
Idzerda et al. "Human interleukin 4 receptor confers biological responsiveness and defines a novel receptor superfamily," *J. Exp. Med.*, vol. 171, No. 3, pp. 861-873, 1990.
Igarashi et al., "Enhanced cytotoxicity of allogeneic NK cells with killer immunoglobulin-like receptor ligand incompatibility against melanoma and renal cell carcinoma cells," *Blood*, vol. 4, pp. 170-177, 2004.
Iscove et al., "Complete replacement of serum by albumin, transferrin, and soybean lipid in cultures of lipopolysaccharide-reactive B lymphocytes," *J. Exp. Med.* vol. 147, No. 3, pp. 923-933, 1978.
James et al., "Benzodiazepine peptidomimetics: potent inhibitors of Ras farnesylation in animal cells," *Science*, vol. 260, No. 5116, pp. 1937-1942, 1993.
Johnston et al., "Monocyte activation and differentiation augment human endogenous 51 retrovirus expression: implications for inflammatory brain disease," *Annals of Neurology*, vol. 50, pp. 434-442, 2001.
Kanehisa, "Use of statistical criteria for screening potential homologies in nucleic acid sequences," *Nucleic Acids Res.*, vol. 12, pp. 203-213, 1984.
Kaplitt et al., "Long-term gene expression and phenotypic correction using adeno-associated virus vectors in the mammalian brain," *Nat. Genet.*, vol. 8, No. 2, pp. 148-154, 1994.
Le Gal La Salle G, et al., "An adenovirus vector for gene transfer into neurons and glia in the brain," *Science*, vol. 259, No. 5097, pp. 988-990, 1993.
Li et al., "Evolutionary analyses of the human genome," *Nature*, vol. 409, No. 6822, pp. 847-849, 2001.
Löwer et al., "The viruses in all of us: characteristics and biological significance of human endogenous retrovirus sequences," *Proc. Natl. Acad. Sci. USA.*, vol. 93, No. 11, pp. 5177-5184, 1996.
McDonald et al., "Are magnetic resonance findings predictive of clinical outcome in therapeutic trials in multiple sclerosis? The dilemma of interferon-beta," *Ann. Neural.*, vol. 36, No. 1, pp. 14-18, 1994.
Miura et al., "Association of Foxp3 regulatory gene expression with graft-versus-host disease," *Blood*, vol. 104, No. 7, pp. 2187-2193, 2004.
Mosley et al., "The murine interleukin-4 receptor: molecular cloning and characterization of secreted and membrane bound forms," *Cell*, vol. 59, No. 2, pp. 335-348, 1989.
Mullen et al., "Hlx is induced by and genetically interacts with T-bet to promote heritable T(H)1 gene induction," *Nat. Immunol.*, vol. 3, No. 7, pp. 652-658, 2002.
Muster et al., "An endogenous retrovirus derived from human melanoma cells," *Cancer Res.*, vol. 63, No. 24, pp. 8735-8741, 2003.
Myers et al., "Optimal alignments in linear space," *Comput. Appl. Biosci.*, vol. 4, No. 1, pp. 11-17, 1988.
Paty et al., "Interferon beta-1b is effective in relapsing-remitting multiple sclerosis. II. MRI analysis results of a multicenter, randomized, double-blind, placebo-controlled trial. UBC MS/MRI Study Group and the IFNB Multiple Sclerosis Study Group," *Neurology*, vol. 43, No. 4, pp. 662-667, 1993.
Paul, Fundamental Immunology, 3rd ed., pp. 243-247 (Raven Press), 1993.
Piotrowski et al., "Expression of human endogenous retrovirus 65 clone 4-1 may correlate with blood plasma concentration of anti-U1 RNP and anti-Sm nuclear antibodies," *Clin. Rheumatol.*, vol. 24, No. 6, pp. 620-624, 2005.
Rakoff-Nahoum et al., "Detection of T lymphocytes specific for human endogenous retrovirus K (HERV-K) in patients with seminoma," *AIDS Res. Hum. Retroviruses.*, vol. 22, No. 1, pp. 52-56, 2006.
Romani et al., "Proliferating dendritic cell progenitors in human blood," *J. Exp. Med.*, vol. 180, No. 1, pp. 52-56, 2006.

(56) References Cited

OTHER PUBLICATIONS

Schiavetti et al., "A human endogenous retroviral sequence encoding an antigen recognized on melanoma by cytolytic T lymphocytes," *Cancer Res*., vol. 62, No. 19, pp. 5510-5516, 2002.
Schrader, "Peptide regulatory factors and optimization of vaccines," *Mol. Immunol.*, vol. 28, No. 3, pp. 295-299, 1991.
Seifarth et al., "Comprehensive analysis of human endogenous retrovirus transcriptional activity in human tissues with a retrovirus-specific microarray," *J. Viral.*, vol. 79, No. 1, pp. 341-352, 2005.
Sette et al., "Nine major HLA class I supertypes account for the vast preponderance of HLA-A and -B polymorphism," *Immunogenetics*, vol. 50, Nos. 3-4, pp. 201-212, 1999.
Sidney et al., "Practical, biochemical and evolutionary implications of the discovery of HLA class I supermotifs," *Immunol. Today*, vol. 17, No. 6, pp. 261-266, 1996.
Smit, "Interspersed repeats and other mementos of transposable elements in mammalian genomes," *Curr. Opin. Genet. Dev.*, vol. 9, No. 6, pp. 657-663, 1999.
Smith et al., "A receptor for tumor necrosis factor defines an unusual family of cellular and viral proteins," *Science*, vol. 248, No. 4958, pp. 1019-1023, 1990.
Stamenkovic et al., "A B-lymphocyte activation molecule related to the nerve growth factor receptor and induced by cytokines in carcinomas," *EMBO J.*, vol. 8, No. 5, pp. 1403-1410, 1989.
Steinman, "The dendritic cell system and its role in immunogenicity," *Annu. Rev. Immunol.*, vol. 9, pp. 271-296, 1991.
Takahashi et al., "In vitro and in vivo evidence of PNH cell sensitivity to immune attack after nonmyeloablative allogeneic hematopoietic cell transplantation," *Blood*, vol. 103, No. 4, pp. 1383-1390, 2004.
Takahashi et al., "Regression of human kidney cancer following allogeneic stem cell transplantation is associated with recognition of an HERV-E antigen by T cells," *The Journal of Clinical Investigation*, vol. 118, No. 3, pp. 1099-1110, 2008.
Tangemann et al., "A high endothelial cell-derived chemokine induces rapid, efficient, and subset-selective arrest of rolling T lymphocytes on a reconstituted endothelial substrate," *J. Immunol.*, vol. 161, No. 11, pp. 6330-6337, 1998.
Thomas et al., "Site-directed mutagenesis by gene targeting in mouse embryo-derived stem cells," *Cell*, vol. 51, No. 3, pp. 503-512, 1987.
Turbeville et al., "Characterization of a Putative Retroviral Env-Related Human Protein," *Pathobiology*, vol. 65, pp. 123-128, 1997.
Tykodi et al., "Allogeneic hematopoietic cell transplantation for metastatic renal cell carcinoma after nonmyeloablative conditioning: toxicity, clinical response, and immunological response to minor histocompatibility antigens," *Clin. Cancer Res.*, vol. 10, No. 23, pp. 7799-7811, 2004.
Wang-Johanning et al., "Detecting the Expression of Human Endogenous Retrovirus E Envelope Transcripts in Human Prostate Adenocarcinoma," *Cancer*, vol. 98, pp. 187-197, 2003.
Yang et al., "Cellular and humoral immune responses to viral antigens create barriers to lung-directed gene therapy with recombinant adenoviruses," *J. Viral*, vol. 69, No. 4, pp. 2004-2015, 1995.

* cited by examiner

Patient HLA type: HLA A 11, 11, HLA B 51, 55

Structures and Sequences of CT-RCC 8 and CT-RCC 9 cDNAs

Figure 11A cDNA Structure

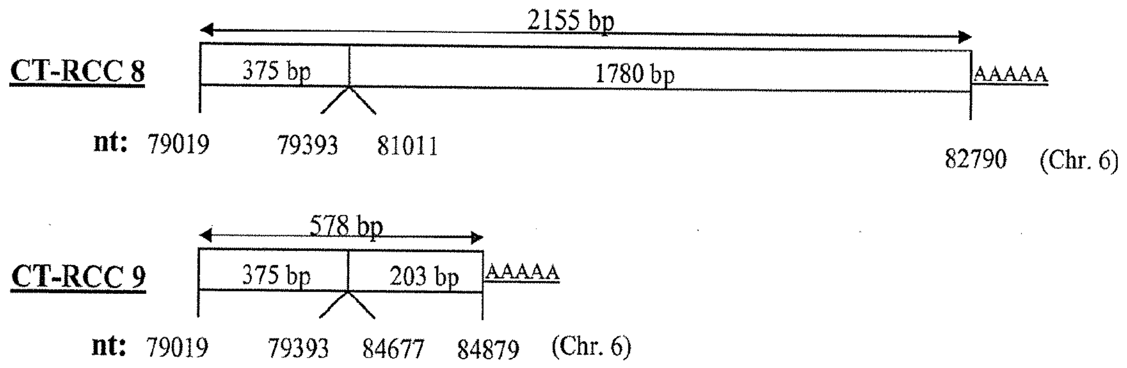

Figure 11B

Common Sequence Region of CT-RCC 8 and CT-RCC 9 (375 bp)

```
GGAGCTCAGA TCATGAGATG CGAGTCTACC AATGCTCCCA GCTGATTAAA GCCTCTTCCT  60
TCATAAAACC AGTGTCCGAG AGGTTTTGTC TGCAACCATT CCTGCTACAT TTCTTGGTTC  120
CCTGACCTGG AAGCGAGGTG ATTAGTGGAC AGTTGAGGCA GCCTCTTAGG CGGCTTAGGC  180
CTGCCCTGTG GAGCATCCCT GGGGAGGACT CCGGCGAGCT TAAGCAAAGC AGATCCTGGG  240
AGCACTCTCG CGTAGGCAAT TGCCCTGGTC AAATGCCTTG CCACAGCAGT GTGCGGCAGA  300
CCCCCGTGGA GAATTAACAC AGCGGTTGAA CACCGGGAAG GAATCGGCGA TTGGAGTCTG  360
GACATCTGGA ACATG                                                   375
```

Localization of CT-RCC 8, CT-RCC 9 and HERV on Chromosome 6

Localization of CT-RCC8 and CT-RCC9 sequences on Chromosome 6

Plasmid Constructs Encoding Short peptides for Identification of the Tumor-Specific Antigen Peptide Recognized by CTL (SEQ ID NO)

1

ATT-101P-142D (+)
cacc gcaaccattcctgctacatttcttggttccctgacctggaagcgaggtgattag (24)
gtgg cgttggtaaggacgatgtaaagaaccaagggactggaccttcgctccactaatc (50)
A T I P A T F L G S L T W K R G D * (2)

ATG-101P-142D (+)
cacc gcaaccatgcctgctacatttcttggttccctgacctggaagcgaggtgattag (25)
gtgg cgttggtacggacgatgtaaagaaccaagggactggaccttcgctccactaatc (51)
A T M P A T F L G S L T W K R G D * (3)

GCA-101P-142D (+)
cacc gcaaccgctcctgctacatttcttggttccctgacctggaagcgaggtgattag (26)
gtgg cgttggcgaggacgatgtaaagaaccaagggactggaccttcgctccactaatc (52)
A T A P A T F L G S L T W K R G D * (4)

ATTdel-101P-142D (+)
cacc gcaacc---cctgctacatttcttggttccctgacctggaagcgaggtgattag (27)
gtgg cgttgg---ggacgatgtaaagaaccaagggactggaccttcgctccactaatc (53)
A T P A T F L G S L T W K R G D * (5)

ATG-104N-138R (-)
cacc atgaatcactcctgctacatttcttggttccctgacctggaagcgaggtga (28)
gtgg tacttagtgaggacgatgtaaagaaccaagggactggaccttcgctccact (54)
M N H S C Y I S W F P D L E A R * (6)

2

101P-133K (+)
cacc atgcctgctacatttcttggttccctgacctggaagtag (29)
gtgg tacggacgatgtaaagaaccaagggactggaccttcatc (55)
M P A T F L G S L T W K * (7)

101P-130W (-)
cacc atgcctgctacatttcttggttccctgacctggtag (60)
gtgg tacggacgatgtaaagaaccaagggactggaccatc (61)
M P A T F L G S L T W * (62)

101P-127T (-)
cacc atgcctgctacatttcttggttccctgacctag (63)
gtgg tacggacgatgtaaagaaccaagggactggatc (64)
M P A T F L G S L T * (65)

101P-124L (-)
cacc atgcctgctacatttcttggttccctgtag (66)
Gtgg tacggacgatgtaaagaaccaagggacatc (67)
M P A T F L G S L * (68)

104A-136R (+)
cacc atggctacatttcttggttccctgacctggaagcgatag (69)
gtgg taccgatgtaaagaaccaagggactggaccttcgctatc (70)
M A T F L G S L T W K R * (71)

104A-133K (+)
cacc atggctacatttcttggttccctgacctggaagtag (72)
gtgg taccgatgtaaagaaccaagggactggaccttcatc (73)
M A T F L G S L T W K * (74)

104A-130W (-)
cacc atggctacatttcttggttccctgacctggtag (30)
gtgg taccgatgtaaagaaccaagggactggaccatc (56)
M A T F L G S L T W * (8)

104A-127T (-)
cacc atggctacatttcttggttccctgacctag (75)
gtgg taccgatgtaaagaaccaagggactggatc (76)
M A T F L G S L T * (77)

107T-136R (+)
cacc atgacatttcttggttccctgacctggaagcgatag (31)
gtgg tactgtaaagaaccaagggactggaccttcgctatc (57)
M T F L G S L T W K R * (9)

107T-133K (+)
cacc atgacatttcttggttccctgacctggaagtag (32)
gtgg tactgtaaagaaccaagggactggaccttcatc (58)
M T F L G S L T W K * (10)

107T-130W (-)
cacc atgacatttcttggttccctgacctggtag (78)
gtgg tactgtaaagaaccaagggactggaccatc (79)
M T F L G S L T W * (80)

Figure 16

ELISA Analysis for Identification of the Tumor-Specific Antigenic Epitope recognized by CTL

4 candidate peptides synthesized:

| | | |
|---|---|---|
| Pep-P101-W130: | PATFLGSLTW | (10mer) |
| Pep-A104-K133: | ATFLGSLTWK | (10mer) |
| Pep-T107-R136: | TFLGSLTWKR | (10mer) |
| Pep-T107-K133: | TFLGSLTWK | (9mer) |

CTL recognition of HLA A11+ Cos cells pulsed with peptides

| | | |
|---|---|---|
| Pep-P101-W130: | PATFLGSLTWK | (10 mer) |
| Pep-A104-K133: | ATFLGSLTWK | (10 mer) |
| Pep-T107-R136: | TFLGSLTWKR | (10 mer) |
| Pep-T107-K133: | TFLGSLTWK | (9 mer) |

Location of the Tumor-Specific Antigenic 10 mer Peptide in the Common Region of CT-RCC 8 and CT-RCC 9

```
ggagctcagatcatgagatgcgagtctaccaatgctcccagctgattaaagcctcttcct 60
G  A  Q  I  M  R  C  E  S  T  N  A  P  S  -  L  K  P  L  P
 E  L  R  S  -  D  A  S  L  P  M  L  P  A  D  -  S  L  F  L
  S  S  D  H  E  M  R  V  Y  Q  C  S  Q  L  I  K  A  S  S  F
tcataaaaccagtgtccgagaggttttgtctgcaaccattcctgctacatttcttggttc 120
S  -  N  Q  C  P  R  G  F  V  C  N  H  S  C  Y  I  S  W  F
 H  K  T  S  V  R  E  V  L  S  A  T  I  P  A  T  F  L  G  S
  I  K  P  V  S  E  R  F  C  L  Q  P  F  L  L  H  F  L  V  P
cctgacctggaagcgaggtgattagtggacagttgaggcagcctcttaggcggcttaggc 180
P  D  L  E  A  R  -  L  V  D  S  -  G  S  L  L  G  G  L  G
 L  T  W  K  R  G  D  -  W  T  V  E  A  A  S  -  A  A  -  A
  -  P  G  S  E  V  I  S  G  Q  L  R  Q  P  L  R  R  L  R  P
ctgccctgtggagcatccctggggaggactccggcgagcttaagcaaagcagatcctggg 240
L  P  C  G  A  S  L  G  R  T  P  A  S  L  S  K  A  D  P  G
 C  P  V  E  H  P  W  G  G  L  R  R  A  -  A  K  Q  I  L  G
  A  L  W  S  I  P  G  E  D  S  G  E  L  K  Q  S  R  S  W  E
agcactctcgcgtaggcaattgccctggtcaaatgccttgccacagcagtgtgcggcaga 300
S  T  L  A  -  A  I  A  L  V  K  C  L  A  T  A  V  C  G  R
 A  L  S  R  R  Q  L  P  W  S  N  A  L  P  Q  Q  C  A  A  D
  H  S  R  V  G  N  C  P  G  Q  M  P  C  H  S  S  V  R  Q  T
cccccgtggagaattaacacagcggttgaacaccgggaaggaatcggcgattggagtctg 360
P  P  W  R  I  N  T  A  V  E  H  R  E  G  I  G  D  W  S  L
 P  R  G  E  L  T  Q  R  L  N  T  G  K  E  S  A  I  G  V  W
  P  V  E  N  -  H  S  G  -  T  P  G  R  N  R  R  L  E  S  G
gacatctggaacatg                                              375
D  I  W  N  M
 T  S  G  T
  H  L  E  H
```

Figure 18

Expression Analysis of CT-RCC 8 and CT-RCC 9 in Renal Cell Carcinoma by Semi-Quantitative RT-PCR (30-Cycle PCR) (A) and Quantitative real time PCR (B)

2: Expression Analysis of CT-RCC 8 and CT-RCC 9 in Cancer Cell Lines by Semi-Quantitative RT-PCR (30-Cycle PCR) (1) and Quantitative real-time PCR (2)

Expression Analysis of CT-RCC8 & CT-RCC9 in Tissue samples from RCC patients by Quantitative Real-time PCR

Detection of CT-RCC Peptide (ATFLGSLTWK)
Reactive CTL In Bulk CTL Line
Generation of an HLA A-11 tetramer containing the CT-RCC 10 mer (ATFLGSLTWK)
CTL Day 1213 PBL stimulated w/ RCC
(CD3+CD8+:95%, CD3+CD4+:3%)
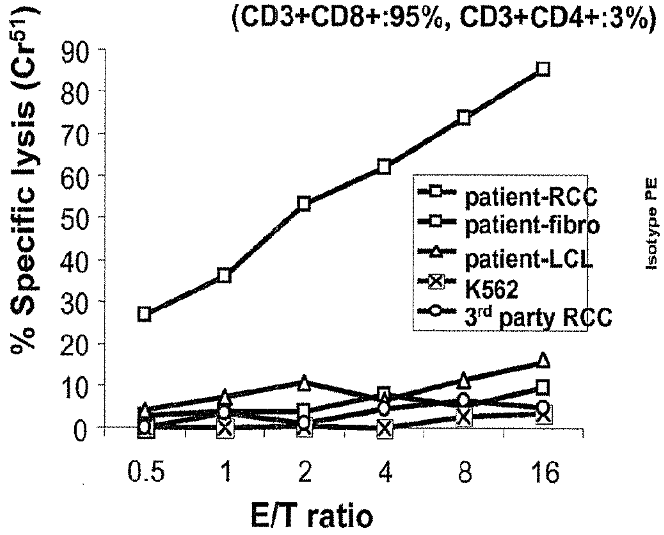
*HLA-A11/CT-RCC (ATFLGSLTWK)*
*Tetramer-specific CD8+ Cells*
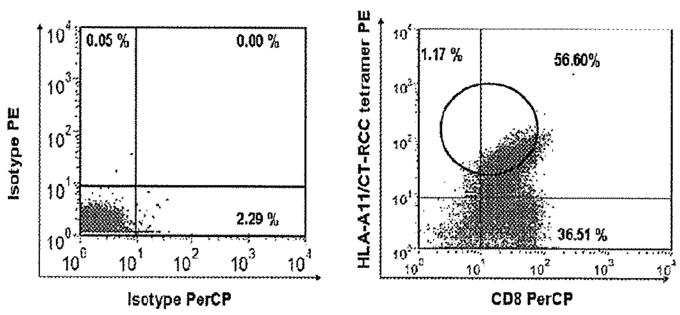
Figure 27

*HLA-A11+ RCC Patients with HCT: #2 (JACSC)*

*Kinetics of HLA-A11/CT-RCC-1-specific CD8+ cells in unstimulated-PBMCs in a RCC patient before and after HCT* cultured PBMCs from RCC patient (Gate: lymphocytes and $CD3^+$ population)

HLA-A11+ RCC Patients with HCT: #3 (HERT)
Kinetics of HLA-A11/CT-RCC-1-specific CD8+ cells in unstimulated-PBMCs in a RCC patient before and after HCT
Uncultured PBMCs from RCC patient (Gate: lymphocytes and CD3+ population)
Pre-HCT
0.65 %
Post-HCT +Day180
3.94 %
PE TETRAMER
PerCP CD8
CD8
HLA-A11 / CT-RCC-1 Tetramer Figure 31
Localization of CT-RCC 8, CT-RCC 9 and HERV on Chromosome 6
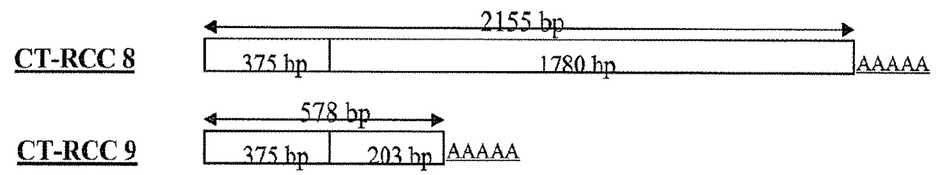
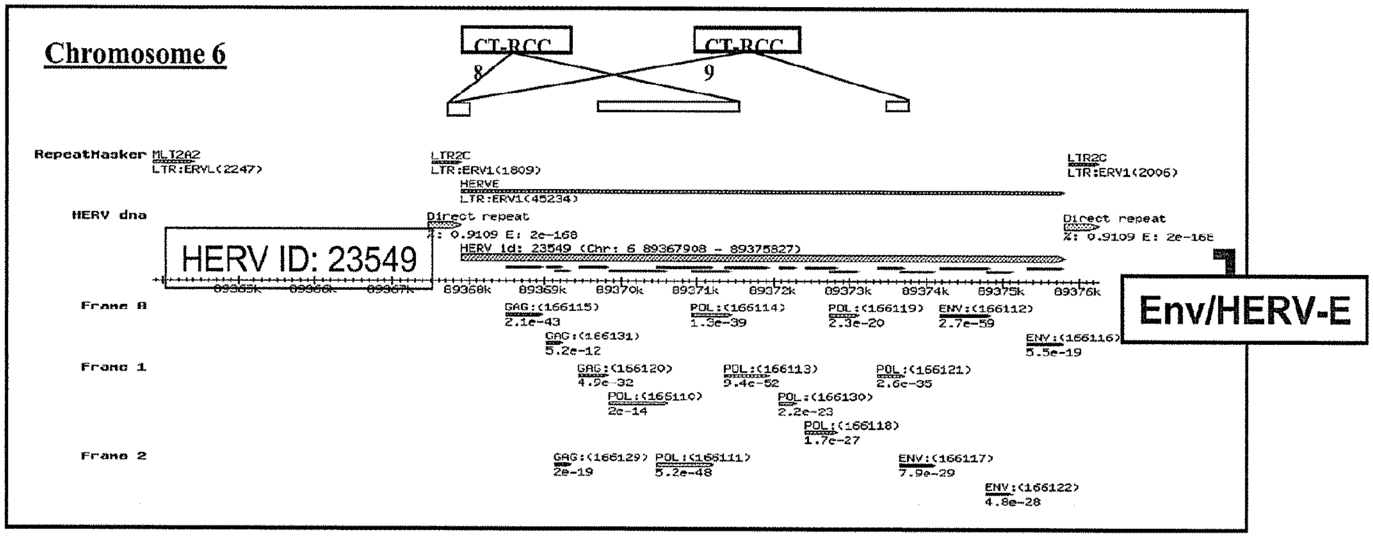

Characteristic Features of Env/HERV-E

Figure 32 mRNA

- Length: 2331 bp (nt 89435013 – 89437343)
- 5'UTR: 309 bp
- 3'UTR: 1386 bp followed by polyA
polyadenylation signal → ATTAAA instead of standard AATAAA
- a single exon

Coding Sequence of Env/HERV-E SEQ ID NO: 47

1 [illegible] 100
101 [illegible] 200
201 [illegible] 300
301 [illegible] 400
401 [illegible] 500
501 [illegible] 600
601 [illegible] 636

Protein (predicted protein)

- 211 aa
- 23.6 kDa
- isoelectric point (pI) 5.5
- cellular localization: cytoplasm
- no protein domains or characteristic motifs
- does not belong to any recognized protein family MAENKYICHELGLYGIIECSYWSYVINATWKKDEKDPVCLQKGKSNSSCTSGNCNPLELIIITNPQDPHWKTGENVNLGIDGTGLDPRVNLLIQGE
IHKRSPKPVFQTFYDELNVPIPELPGKTKDLFLQLAENIAHSLNITSCYVCRGTTMGDQWPXEARELVPMDPVPDIIPVQKAHTGNFWVLKTSII
GQ YCLAREGK DFTIPVGSSIA SEQ ID NO: 48

"retrosearch.dk"

Expression Analysis of Env/HERV-E in Cancer Cell Lines by Semi-Quantitative RT-PCR

SEQUENCE LISTING

```
<160> NUMBER OF SEQ ID NOS: 118

<210> SEQ ID NO 1
<211> LENGTH: 10
```

<212> TYPE: PRT
<213> ORGANISM: Artificial Sequence
<220> FEATURE:
<223> OTHER INFORMATION: Synthetic

<400> SEQUENCE: 1

Ala Thr Phe Leu Gly Ser Leu Thr Trp Lys
1 5 10

<210> SEQ ID NO 2
<211> LENGTH: 17
<212> TYPE: PRT
<213> ORGANISM: Artificial Sequence
<220> FEATURE:
<223> OTHER INFORMATION: Synthetic

<400> SEQUENCE: 2

Ala Thr Ile Pro Ala Thr Phe Leu Gly Ser Leu Thr Trp Lys Arg Gly
1 5 10 15

Asp

<210> SEQ ID NO 3
<211> LENGTH: 17
<212> TYPE: PRT
<213> ORGANISM: Artificial Sequence
<220> FEATURE:
<223> OTHER INFORMATION: Synthetic

<400> SEQUENCE: 3

Ala Thr Met Pro Ala Thr Phe Leu Gly Ser Leu Thr Trp Lys Arg Gly
1 5 10 15

Asp

<210> SEQ ID NO 4
<211> LENGTH: 17
<212> TYPE: PRT
<213> ORGANISM: Artificial Sequence
<220> FEATURE:
<223> OTHER INFORMATION: Synthetic

<400> SEQUENCE: 4

Ala Thr Ala Pro Ala Thr Phe Leu Gly Ser Leu Thr Trp Lys Arg Gly
1 5 10 15

Asp

<210> SEQ ID NO 5
<211> LENGTH: 16
<212> TYPE: PRT
<213> ORGANISM: Artificial Sequence
<220> FEATURE:
<223> OTHER INFORMATION: Synthetic

<400> SEQUENCE: 5

Ala Thr Pro Ala Thr Phe Leu Gly Ser Leu Thr Trp Lys Arg Gly Asp
1 5 10 15

<210> SEQ ID NO 6
<211> LENGTH: 16
<212> TYPE: PRT
<213> ORGANISM: Artificial Sequence
<220> FEATURE:
<223> OTHER INFORMATION: Synthetic

<400> SEQUENCE: 6

Met Asn His Ser Cys Tyr Ile Ser Trp Phe Pro Asp Leu Glu Ala Arg

```
1               5                   10                  15


<210> SEQ ID NO 7
<211> LENGTH: 12
<212> TYPE: PRT
<213> ORGANISM: Artificial Sequence
<220> FEATURE:
<223> OTHER INFORMATION: Synthetic

<400> SEQUENCE: 7

Met Pro Ala Thr Phe Leu Gly Ser Leu Thr Trp Lys
1               5                   10


<210> SEQ ID NO 8
<211> LENGTH: 12
<212> TYPE: PRT
<213> ORGANISM: Artificial Sequence
<220> FEATURE:
<223> OTHER INFORMATION: Synthetic

<400> SEQUENCE: 8

Met Ala Thr Phe Leu Gly Ser Leu Thr Trp Lys Arg
1               5                   10


<210> SEQ ID NO 9
<211> LENGTH: 11
<212> TYPE: PRT
<213> ORGANISM: Artificial Sequence
<220> FEATURE:
<223> OTHER INFORMATION: Synthetic

<400> SEQUENCE: 9

Met Thr Phe Leu Gly Ser Leu Thr Trp Lys Arg
1               5                   10


<210> SEQ ID NO 10
<211> LENGTH: 10
<212> TYPE: PRT
<213> ORGANISM: Artificial Sequence
<220> FEATURE:
<223> OTHER INFORMATION: Synthetic

<400> SEQUENCE: 10

Met Thr Phe Leu Gly Ser Leu Thr Trp Lys
1               5                   10


<210> SEQ ID NO 11
<211> LENGTH: 578
<212> TYPE: DNA
<213> ORGANISM: Artificial Sequence
<220> FEATURE:
<223> OTHER INFORMATION: Synthetic

<400> SEQUENCE: 11

ggagctcaga tcatgagatg cgagtctacc aatgctccca gctgattaaa gcctcttcct      60

tcataaaacc agtgtccgag aggttttgtc tgcaaccatt cctgctacat ttcttggttc     120

cctgacctgg aagcgaggtg attagtggac agttgaggca gcctcttagg cggcttaggc     180

ctgccctgtg gagcatccct ggggaggact ccggcgagct taagcaaagc agatcctggg     240

agcactctcg cgtaggcaat tgccctggtc aaatgccttg ccacagcagt gtgcggcaga     300

cccccgtgga gaattaacac agcggttgaa caccgggaag gaatcggcga ttggagtctg     360

gacatctgga acatggtgat cgagtgtgga tcaaagactg gaacatagcc cctttgtggc     420

cacggtggaa aggatgccag accatcatcc tgaccactcc caccaccatg aaggtagaag     480
```

-continued gaattccggc ctggatccac cacagccacg tgaaacccac agcacctgag acctgggagg 540
tgagaccaag cccggacaat ccctacaaag tgactctg 578

<210> SEQ ID NO 12
<211> LENGTH: 375
<212> TYPE: DNA
<213> ORGANISM: Artificial Sequence
<220> FEATURE:
<223> OTHER INFORMATION: Synthetic

<400> SEQUENCE: 12
ggagctcaga tcatgagatg cgagtctacc aatgctccca gctgattaaa gcctcttcct 60
tcataaaacc agtgtccgag aggttttgtc tgcaaccatt cctgctacat ttcttggttc 120
cctgacctgg aagcgaggtg attagtggac agttgaggca gcctcttagg cggcttaggc 180
ctgccctgtg gagcatccct ggggaggact ccggcgagct taagcaaagc agatcctggg 240
agcactctcg cgtaggcaat tgccctggtc aaatgccttg ccacagcagt gtgcggcaga 300
cccccgtgga gaattaacac agcggttgaa caccgggaag gaatcggcga ttggagtctg 360
gacatctgga acatg 375

<210> SEQ ID NO 13

<400> SEQUENCE: 13

000

<210> SEQ ID NO 14

<400> SEQUENCE: 14

000

<210> SEQ ID NO 15

<400> SEQUENCE: 15

000

<210> SEQ ID NO 16

<400> SEQUENCE: 16

000

<210> SEQ ID NO 17

<400> SEQUENCE: 17

000

<210> SEQ ID NO 18

<400> SEQUENCE: 18

000

<210> SEQ ID NO 19

<400> SEQUENCE: 19

000

<210> SEQ ID NO 20

<400> SEQUENCE: 20

000

<210> SEQ ID NO 21

<400> SEQUENCE: 21

000

<210> SEQ ID NO 22

<400> SEQUENCE: 22

000

<210> SEQ ID NO 23
<211> LENGTH: 30
<212> TYPE: DNA
<213> ORGANISM: Artificial Sequence
<220> FEATURE:
<223> OTHER INFORMATION: Synthetic

<400> SEQUENCE: 23
atgcctgcta catttcttgg ttccctgacc 30

<210> SEQ ID NO 24
<211> LENGTH: 58
<212> TYPE: DNA
<213> ORGANISM: Artificial Sequence
<220> FEATURE:
<223> OTHER INFORMATION: Synthetic

<400> SEQUENCE: 24
caccgcaacc attcctgcta catttcttgg ttccctgacc tggaagcgag gtgattag 58

<210> SEQ ID NO 25
<211> LENGTH: 58
<212> TYPE: DNA
<213> ORGANISM: Artificial Sequence
<220> FEATURE:
<223> OTHER INFORMATION: Synthetic

<400> SEQUENCE: 25
caccgcaacc atgcctgcta catttcttgg ttccctgacc tggaagcgag gtgattag 58

<210> SEQ ID NO 26
<211> LENGTH: 58
<212> TYPE: DNA
<213> ORGANISM: Artificial Sequence
<220> FEATURE:
<223> OTHER INFORMATION: Synthetic

<400> SEQUENCE: 26
caccgcaacc gctcctgcta catttcttgg ttccctgacc tggaagcgag gtgattag 58

<210> SEQ ID NO 27
<211> LENGTH: 55
<212> TYPE: DNA
<213> ORGANISM: Artificial Sequence
<220> FEATURE:
<223> OTHER INFORMATION: Synthetic

<400> SEQUENCE: 27
caccgcaacc cctgctacat ttcttggttc cctgacctgg aagcgaggtg attag 55

<210> SEQ ID NO 28
<211> LENGTH: 55
<212> TYPE: DNA
<213> ORGANISM: Artificial Sequence
<220> FEATURE:
<223> OTHER INFORMATION: Synthetic

<400> SEQUENCE: 28
caccatgaat cactcctgct acatttcttg gttccctgac ctggaagcga ggtga 55

<210> SEQ ID NO 29
<211> LENGTH: 43
<212> TYPE: DNA
<213> ORGANISM: Artificial Sequence
<220> FEATURE:
<223> OTHER INFORMATION: Synthetic

<400> SEQUENCE: 29
caccatgcct gctacatttc ttggttccct gacctggaag tag 43

<210> SEQ ID NO 30
<211> LENGTH: 43
<212> TYPE: DNA
<213> ORGANISM: Artificial Sequence
<220> FEATURE:
<223> OTHER INFORMATION: Synthetic

<400> SEQUENCE: 30
caccatggct acatttcttg gttccctgac ctggaagcga tag 43

<210> SEQ ID NO 31
<211> LENGTH: 40
<212> TYPE: DNA
<213> ORGANISM: Artificial Sequence
<220> FEATURE:
<223> OTHER INFORMATION: Synthetic

<400> SEQUENCE: 31
caccatgaca tttcttggtt ccctgacctg gaagcgatag 40

<210> SEQ ID NO 32
<211> LENGTH: 37
<212> TYPE: DNA
<213> ORGANISM: Artificial Sequence
<220> FEATURE:
<223> OTHER INFORMATION: Synthetic

<400> SEQUENCE: 32
caccatgaca tttcttggtt ccctgacctg gaagtag 37

<210> SEQ ID NO 33

<400> SEQUENCE: 33

000

<210> SEQ ID NO 34

<400> SEQUENCE: 34

000

<210> SEQ ID NO 35
<211> LENGTH: 272
<212> TYPE: DNA

<213> ORGANISM: Artificial Sequence
<220> FEATURE:
<223> OTHER INFORMATION: Synthetic

<400> SEQUENCE: 35
ggagctcaga tcatgagatg cgagtctacc aatgctccca gctgattaaa gcctcttcct 60
tcataaaacc agtgtccgag aggttttgtc tgcaaccatt cctgctacat ttcttggttc 120
cctgacctgg aagcgaggtg attagtggac agttgaggca gcctcttagg cggcttaggc 180
ctgccctgtg gagcatccct ggggaggact ccggcgagct taagcaaagc agatcctggg 240
agcactctcg cgtaggcaat tgccctggtc aa 272

<210> SEQ ID NO 36
<211> LENGTH: 242
<212> TYPE: DNA
<213> ORGANISM: Artificial Sequence
<220> FEATURE:
<223> OTHER INFORMATION: Synthetic

<400> SEQUENCE: 36
ggagctcaga tcatgagatg cgagtctacc aatgctccca gctgattaaa gcctcttcct 60
tcataaaacc agtgtccgag aggttttgtc tgcaaccatt cctgctacat ttcttggttc 120
cctgacctgg aagcgaggtg attagtggac agttgaggca gcctcttagg cggcttaggc 180
ctgccctgtg gagcatccct ggggaggact ccggcgagct taagcaaagc agatcctggg 240
ag 242

<210> SEQ ID NO 37
<211> LENGTH: 212
<212> TYPE: DNA
<213> ORGANISM: Artificial Sequence
<220> FEATURE:
<223> OTHER INFORMATION: Synthetic

<400> SEQUENCE: 37
ggagctcaga tcatgagatg cgagtctacc aatgctccca gctgattaaa gcctcttcct 60
tcataaaacc agtgtccgag aggttttgtc tgcaaccatt cctgctacat ttcttggttc 120
cctgacctgg aagcgaggtg attagtggac agttgaggca gcctcttagg cggcttaggc 180
ctgccctgtg gagcatccct ggggaggact cc 212

<210> SEQ ID NO 38
<211> LENGTH: 182
<212> TYPE: DNA
<213> ORGANISM: Artificial Sequence
<220> FEATURE:
<223> OTHER INFORMATION: Synthetic

<400> SEQUENCE: 38
ggagctcaga tcatgagatg cgagtctacc aatgctccca gctgattaaa gcctcttcct 60
tcataaaacc agtgtccgag aggttttgtc tgcaaccatt cctgctacat ttcttggttc 120
cctgacctgg aagcgaggtg attagtggac agttgaggca gcctcttagg cggcttaggc 180
ct 182

<210> SEQ ID NO 39
<211> LENGTH: 152
<212> TYPE: DNA
<213> ORGANISM: Artificial Sequence
<220> FEATURE:
<223> OTHER INFORMATION: Synthetic

<400> SEQUENCE: 39
ggagctcaga tcatgagatg cgagtctacc aatgctccca gctgattaaa gcctcttcct 60
tcataaaacc agtgtccgag aggttttgtc tgcaaccatt cctgctacat ttcttggttc 120
cctgacctgg aagcgaggtg attagtggac ag 152

<210> SEQ ID NO 40
<211> LENGTH: 241
<212> TYPE: DNA
<213> ORGANISM: Artificial Sequence
<220> FEATURE:
<223> OTHER INFORMATION: Synthetic

<400> SEQUENCE: 40
atgctcccag ctgattaaag cctcttcctt cataaaacca gtgtccgaga ggttttgtct 60
gcaaccattc ctgctacatt tcttggttcc ctgacctgga agcgaggtga ttagtggaca 120
gttgaggcag cctcttaggc ggcttaggcc tgccctgtgg agcatccctg ggaggactc 180 cggcgagctt aagcaaagca gatcctggga gcactctcgc gtaggcaatt gccctggtca 240
a 241

<210> SEQ ID NO 41
<211> LENGTH: 211
<212> TYPE: DNA
<213> ORGANISM: Artificial Sequence
<220> FEATURE:
<223> OTHER INFORMATION: Synthetic

<400> SEQUENCE: 41
cataaaacca gtgtccgaga ggttttgtct gcaaccattc ctgctacatt tcttggttcc 60
ctgacctgga agcgaggtga ttagtggaca gttgaggcag cctcttaggc ggcttaggcc 120
tgccctgtgg agcatccctg ggaggactc cggcgagctt aagcaaagca gatcctggga 180
gcactctcgc gtaggcaatt gccctggtca a 211

<210> SEQ ID NO 42
<211> LENGTH: 181
<212> TYPE: DNA
<213> ORGANISM: Artificial Sequence
<220> FEATURE:
<223> OTHER INFORMATION: Synthetic

<400> SEQUENCE: 42
gcaaccattc ctgctacatt tcttggttcc ctgacctgga agcgaggtga ttagtggaca 60
gttgaggcag cctcttaggc ggcttaggcc tgccctgtgg agcatccctg ggaggactc 120 cggcgagctt aagcaaagca gatcctggga gcactctcgc gtaggcaatt gccctggtca 180
a 181

<210> SEQ ID NO 43
<211> LENGTH: 223
<212> TYPE: DNA
<213> ORGANISM: Artificial Sequence
<220> FEATURE:
<223> OTHER INFORMATION: Synthetic

<400> SEQUENCE: 43
agcctcttcc ttcataaaac cagtgtccga gaggttttgt ctgcaaccat tcctgctaca 60
tttcttggtt ccctgacctg gaagcgaggt gattagtgga cagttgaggc agcctcttag 120

-continued

```
gcggcttagg cctgccctgt ggagcatccc tggggaggac tccggcgagc ttaagcaaag    180

cagatcctgg gagcactctc gcgtaggcaa ttgccctggt caa                      223


<210> SEQ ID NO 44
<211> LENGTH: 206
<212> TYPE: DNA
<213> ORGANISM: Artificial Sequence
<220> FEATURE:
<223> OTHER INFORMATION: Synthetic

<400> SEQUENCE: 44

aaccagtgtc cgagaggttt tgtctgcaac cattcctgct acatttcttg gttccctgac     60

ctggaagcga ggtgattagt ggacagttga ggcagcctct taggcggctt aggcctgccc    120

tgtggagcat ccctggggag gactccggcg agcttaagca aagcagatcc tgggagcact    180

ctcgcgtagg caattgccct ggtcaa                                         206


<210> SEQ ID NO 45
<211> LENGTH: 2155
<212> TYPE: DNA
<213> ORGANISM: Artificial Sequence
<220> FEATURE:
<223> OTHER INFORMATION: Synthetic

<400> SEQUENCE: 45

ggagctcaga tcatgagatg cgagtctacc aatgctccca gctgattaaa gcctcttcct     60

tcataaaacc agtgtccgag aggttttgtc tgcaaccatt cctgctacat ttcttggttc    120

cctgacctgg aagcgaggtg attagtggac agttgaggca gcctcttagg cggcttaggc    180

ctgccctgtg gagcatccct ggggaggact ccggcgagct taagcaaagc agatcctggg    240

agcactctcg cgtaggcaat tgccctggtc aaatgccttg ccacagcagt gtgcggcaga    300

cccccgtgga gaattaacac agcggttgaa caccgggaag gaatcggcga ttggagtctg    360

gacatctgga acatggatgc agcaagccgc agagagagcc gcaaagaagg tgaatgccaa    420

cccggtgaaa tgctgaccta ctagctgcag ctattagagg ggtcccccctg aaaggacaag    480

ggaatggggg ctccaggaaa aatacccagt ctgaccgtcc acgcttgcaa cgtaaccagt    540

gcgcctattg taaagagaca ggacattgga aagataagtg ccctcagctg aaagaaaagc    600

aaggtggttc agagcaaaag accccagaca aggacgaagg agccttgttc aatctggctg    660

aggggttatt ggaccgaagg ggaccaggct cacgtgcccc caaggagccc atggtcagaa    720

tgacagttgg gggcaaggac attaagtttc tggtcaatac tggtgctgaa cattcagtag    780

tgaccacccc ggtcgccccc ttgtctaaaa aggctattga tataattgga gcaacaggag    840

ttttgacaaa gcaggctttc tgtttgcccc ggacctgctc ggtgggggga catgaagtga    900

ttcaccagtt cctgtacatc cctgactgcc ccttgccttt gttaggaagg gacctgctta    960

gcaagctgag agctatcttc ctttaccaag caaggctctt tacaactgaa gttgcctgga   1020

acaggagtta tcatggccct gacagttccc cgagaggaag agtagcgact cttcctaacc   1080

aaaccaggca aagagatagg gccagctctg gcccagtggt ggccaaaagt atgcgcagaa   1140

gacaaccctc ctggattggc agtcaatcaa gctcctgtac tcagggaagt taagccagag   1200

gcccagccag tcaggcaaaa ccagtatcca gtccccagag aagccctgga aggtatccag   1260

gttcatctta agcacctgag gacttttgga attatagtgc cttgtcagtc tccatggaac   1320

accccccctcc tacctgttcc caagccaggg accaaggact acaggccagt acaggacttg   1380

cgattggtca atcaagccac agtgactttc catccaacag tacctaaccc gtacacattg   1440
```

ttggggttat tgccagctaa ggacagctgg ttcacctgcc tagacctgaa ggacgccttc 1500
tttagcatca gattagctcc agagagccag aaactgtttg cctttcagtg ggaggatccg 1560
gggtcaggtg tcaccactca ttacacttgg acccggcttc cccaggggtt caagaacttc 1620
ccccaccatc tttggggagg cactggctcg agacctccaa aagtttcctg ccagagacct 1680
aggctgcgtg ttgttccagt acatcgacaa cctcctgctg ggacgcccca tggcagtcgg 1740
gtgcgtcaaa ggaacagacg ccctgcttca gcacctggag gactatgggt ataaggtgtc 1800
caagaagaaa gctcagatct gcagacagca ggtacgctac ctgggattta ctatccgaca 1860
gcgggagtgc agcctaggat cagaaagaaa gcaggtcatt tgcaacctac tggagcctaa 1920
gaccagaagg cagttgagag aattattagg agctgtgggg ttctgcaggt tatggatccc 1980
aaattttgca gtactggcca aacctctggt accaagttac aaagggggt gacatggaac 2040 catttgaatg gggtcccaa cagcaacagg cttttcatga gttaaaagaa aaactcatgt 2100
cagccccagc cctgggtcta cctgacctga caaagccatt tacattgtat gtgtc 2155

<210> SEQ ID NO 46

<400> SEQUENCE: 46

000

<210> SEQ ID NO 47
<211> LENGTH: 636
<212> TYPE: DNA
<213> ORGANISM: Artificial Sequence
<220> FEATURE:
<223> OTHER INFORMATION: Synthetic

<400> SEQUENCE: 47
atggcagaaa ataagtacat ttgtcatgaa ttaggactat atggtattat tgaatgtagt 60
tattggtcct atgtcatttg ggccacctgg aaaaaggatg aaaaagaccc tgtttgccta 120
caaaaaggaa aaagtaattc atcttgcacc tccggtaact gtaacccatt agaattaata 180
attactaacc cccaggatcc ccactggaag acaggagaaa atgtaaacct aggaattgat 240
ggaactgggc ttgacccccg agtcaacctt ttaatccaag gggagatcca caagcgctcc 300
cccaaaccag tgttccagac cttttatgat gaactaaatg tgccaatacc agaactgcca 360
gggaagacaa aagatttgtt cctgcagtta gcagaaaata tagcccattc cctcaacatt 420
acttcctgtt atgtatgcag ggaactact atgggagacc aatggccttg ggaggcccga 480
gaattagtgc ccatggatcc agttcctgat ataattccag tccagaaggc ccacactggt 540
aacttttggg tcttaaaaac ctcaattatt gggcaatact gcttagctag agaaggaaaa 600
gacttcacca tccccgtagg aagctcaatt gcctag 636

<210> SEQ ID NO 48
<211> LENGTH: 211
<212> TYPE: PRT
<213> ORGANISM: Artificial Sequence
<220> FEATURE:
<223> OTHER INFORMATION: Synthetic

<400> SEQUENCE: 48

Met Ala Glu Asn Lys Tyr Ile Cys His Glu Leu Gly Leu Tyr Gly Ile
1 5 10 15

Ile Glu Cys Ser Tyr Trp Ser Tyr Val Ile Trp Ala Thr Trp Lys Lys
20 25 30

```
Asp Glu Lys Asp Pro Val Cys Leu Gln Lys Gly Lys Ser Asn Ser Ser
        35                  40                  45

Cys Thr Ser Gly Asn Cys Asn Pro Leu Glu Leu Ile Ile Thr Asn Pro
    50                  55                  60

Gln Asp Pro His Trp Lys Thr Gly Glu Asn Val Asn Leu Gly Ile Asp
65                  70                  75                  80

Gly Thr Gly Leu Asp Pro Arg Val Asn Leu Leu Ile Gln Gly Glu Ile
                85                  90                  95

His Lys Arg Ser Pro Lys Pro Val Phe Gln Thr Phe Tyr Asp Glu Leu
            100                 105                 110

Asn Val Pro Ile Pro Glu Leu Pro Gly Lys Thr Lys Asp Leu Phe Leu
        115                 120                 125

Gln Leu Ala Glu Asn Ile Ala His Ser Leu Asn Ile Thr Ser Cys Tyr
    130                 135                 140

Val Cys Arg Gly Thr Thr Met Gly Asp Gln Trp Pro Trp Glu Ala Arg
145                 150                 155                 160

Glu Leu Val Pro Met Asp Pro Val Pro Asp Ile Ile Pro Val Gln Lys
                165                 170                 175

Ala His Thr Gly Asn Phe Trp Val Leu Lys Thr Ser Ile Ile Gly Gln
            180                 185                 190

Tyr Cys Leu Ala Arg Glu Gly Lys Asp Phe Thr Ile Pro Val Gly Ser
        195                 200                 205

Ser Ile Ala
    210
```

<210> SEQ ID NO 49
<211> LENGTH: 110
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(50)
<223> OTHER INFORMATION: Xaa, if present, is any amino acid
<220> FEATURE:
<221> NAME/KEY: misc_feature
<222> LOCATION: (61)..(110)
<223> OTHER INFORMATION: Xaa, if present, is any amino acid

<400> SEQUENCE: 49

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Ala Thr Phe Leu Gly Ser Leu Thr Trp Lys Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa
            100                 105                 110
```

<210> SEQ ID NO 50
<211> LENGTH: 58

<212> TYPE: DNA
<213> ORGANISM: Artificial Sequence
<220> FEATURE:
<223> OTHER INFORMATION: Synthetic

<400> SEQUENCE: 50
ctaatcacct cgcttccagg tcagggaacc aagaaatgta gcaggaatgg ttgcggtg 58

<210> SEQ ID NO 51
<211> LENGTH: 58
<212> TYPE: DNA
<213> ORGANISM: Artificial Sequence
<220> FEATURE:
<223> OTHER INFORMATION: Synthetic

<400> SEQUENCE: 51
ctaatcacct cgcttccagg tcagggaacc aagaaatgta gcaggcatgg ttgcggtg 58

<210> SEQ ID NO 52
<211> LENGTH: 58
<212> TYPE: DNA
<213> ORGANISM: Artificial Sequence
<220> FEATURE:
<223> OTHER INFORMATION: Synthetic

<400> SEQUENCE: 52
ctaatcacct cgcttccagg tcagggaacc aagaaatgta gcaggagcgg ttgcggtg 58

<210> SEQ ID NO 53
<211> LENGTH: 55
<212> TYPE: DNA
<213> ORGANISM: Artificial Sequence
<220> FEATURE:
<223> OTHER INFORMATION: Synthetic

<400> SEQUENCE: 53
ctaatcacct cgcttccagg tcagggaacc aagaaatgta gcaggggttg cggtg 55

<210> SEQ ID NO 54
<211> LENGTH: 55
<212> TYPE: DNA
<213> ORGANISM: Artificial Sequence
<220> FEATURE:
<223> OTHER INFORMATION: Synthetic

<400> SEQUENCE: 54
tcacctcgct tccaggtcag ggaaccaaga aatgtagcag gagtgattca tggtg 55

<210> SEQ ID NO 55
<211> LENGTH: 43
<212> TYPE: DNA
<213> ORGANISM: Artificial Sequence
<220> FEATURE:
<223> OTHER INFORMATION: Synthetic

<400> SEQUENCE: 55
ctacttccag gtcagggaac caagaaatgt agcaggcatg gtg 43

<210> SEQ ID NO 56
<211> LENGTH: 43
<212> TYPE: DNA
<213> ORGANISM: Artificial Sequence
<220> FEATURE:
<223> OTHER INFORMATION: Synthetic

<400> SEQUENCE: 56
ctatcgcttc caggtcaggg aaccaagaaa tgtagccatg gtg 43

<210> SEQ ID NO 57
<211> LENGTH: 40
<212> TYPE: DNA
<213> ORGANISM: Artificial Sequence
<220> FEATURE:
<223> OTHER INFORMATION: Synthetic

<400> SEQUENCE: 57
ctatcgcttc caggtcaggg aaccaagaaa tgtcatggtg 40

<210> SEQ ID NO 58
<211> LENGTH: 37
<212> TYPE: DNA
<213> ORGANISM: Artificial Sequence
<220> FEATURE:
<223> OTHER INFORMATION: Synthetic

<400> SEQUENCE: 58
ctacttccag gtcagggaac caagaaatgt catggtg 37

<210> SEQ ID NO 59
<211> LENGTH: 11859
<212> TYPE: DNA
<213> ORGANISM: Homo sapiens

<400> SEQUENCE: 59
gagaaatgca aaatacactg gaaagtttca acaatagact agaacaagta gaagaaagaa 60
tttcagagct tgaagacagg cttttgaatt aacccaatca gacaaagaca aagagaaaaa 120
gaattaaaaa aaaaaaatga acaaagcctc caagaaattt gggattatgt taaaatgacc 180
aaacataaga ataactggtg ttcctgagga agaagagaaa tctagaaatt tagaaaactt 240
atttgaggga atagtcaata aaaacttccc tggtcttgct agagatctag acatccaaat 300
acaggacgct caaagaacac ccgggaagtt catcacaaaa agatgattgc ctaggcacat 360
agtcatcagg ttatctaaag tcaagataaa ggaaataatc ttaacagcta tgagacaaaa 420
gcatcaggta acctataaag gaaaacctat cagattaaca gctcatttct cagcagaaac 480
cttacaaacc agcaggcatt ggggtcctat ctttactctc ctgaaacaaa ataactgtca 540
ggaaaaaagt ttgtatccag caaaattaag cttcataaat gaaggcgaga tagtctgttt 600
tagacaaaca aatgctgaga taatttgcca ctactaagcc agcactacaa gaaatgctaa 660
aaaagttcta aatcttaaaa cctcgaaatg caccaaaata gaacctcctt aaagcataaa 720
tctcacaggg cctataaaac aacacaatga aaacaaaaca aaagcccaag gtattcaggc 780
aacaactagc atgatgaata gaacagtacc tcacatctca gtactaacat tgaatgtaaa 840
tggccaaaat gctccactta aaagatacag aatagcagaa tggataaaaa tccaccaacc 900
aagtatccta tctgttgtct tcaagagact caactaacac ataaggactc aaataaactc 960
caggtaaaga ggtgaaaaaa gatattccat gcaaatgaac accaaaagtg agcaggagtg 1020
gctattctta tattagacaa aacagacttt aaagcaacaa tggtaaaaaa aaagaaagaa 1080
aaggagagac attatacaat gataaaagga ttagtctcca acaggaaaat atcacaatcc 1140
taaatacatg cacctagcac tggagctccc aaatttatac aacaattact actagaccta 1200
agaaacgaga tagatggcaa caccataata gtgggggact tcaatactcc attgacagca 1260
ctggacaggt catcaagaca gaaagtcaac aaagaaacaa tggacttaaa ctataccta 1320 gaacaaatgg acttaacaga tatttacaca acattctacc caacaactgc agaatataca 1380

-continued

```
ttcttttcat cagcacatgt aacattctcc aagacagacc ataagatagg tcacaaaaca   1440
agtctcaata aatttaagat aactgaaatt atatcaagta ctttctcaga ccacagtgga   1500
ataaaattga aaattaactc caaaaggaac cctccaaacc atacaaatac atagaaatta   1560
aattatctac tcctgaatga tctttgggtc aacaatgaaa tcaagatgga aattaaaaag   1620
ttctttgaat tgaatgatga tagtgacaca acctatcaaa acctctggga tacagcaaaa   1680
gcggtactaa gaggaaagtt catagcatta aacgcctaca tcaaaaagtc tgaaagagca   1740
caaacagaca atctaaactc gcaccccaag aaactagaga aacaacaaca aaccaaaccc   1800
aaaccctgca gaaaagaaat aacaaagatc agagcagaac taaacgaaat tgaaacaaac   1860
aaaaagcaat acaaaagata aataaaacga aatgctggtt ccttgaaaag gttaaaaaaa   1920
attgacagac cgttagtgag attaaccaaa aaagaagaaa gagagaagaa tcaaacaagc   1980
tcaagtagaa atgaaatggg agatactaca actgatacca cagaaataca aaaaaatcat   2040
tcaatgctac tatgaataac ttcaggcaca caaactagaa aacctagagg agagggataa   2100
attcctggaa atatacaacc ctcctagatt aaaccaggaa gaaacagaaa ctctgaacag   2160
accaataaca agtagtgaga ttgatatagt aataaaaaaa attgccaaca aaaaaagtcc   2220
aggaccagat ggattcacag ctaaattcta tcacatattc aaagagttgg taccaatcct   2280
actgaaacta ttccaaaaga taaagaggga atcctcccta aatcattccc tgaaaccatt   2340
attgccctaa tattaaaacc agggaaggac ataacaaaaa agaaaactat agaccaatat   2400
ctctgatgaa cacagatgca aaaaatcctc aacaaaatac tgtgtaactg aatccaacag   2460
catatttaaa aggtaataca tcactttcaa gtggctttca taccagagat gcagggttgg   2520
tttaacatat gcaagttaat aaatgtgata caccacataa acagaattaa aaacaaaaac   2580
catatcaatg gatccagaaa aagcatttga caaaatctag cattccttgt gattacaacc   2640
ctaggcaaaa tcggcataga ggaaacacac ctttaaggaa gtagaccacc tctcccattg   2700
tctcctattt catgagaaag caaaaggtta aaagaagaag tgagatcaat agccagatgg   2760
cttggtgcca agaaccgtgc ctggtagtta aacatcaact cctgacctaa ccgcttgtgg   2820
attccagaca ttgtatgagg aagacttctg aaactttctg ttctgttctg ctagccccca   2880
tcactgatgc atgtagctct cagtcacgta gcccccactt gcacaatgta tcatgaccct   2940
gaaatataca accctcctag attaaaccag gaagaaacag aaactctgaa cagaccaata   3000
acaagtagtg agattgatat agtaataaaa aaaattgcca acaaaaaaag tccaggacca   3060
gatggattca cagctaaatt ctatcacata ttcaaagagt tggtaccaat cctactgaaa   3120
ctattccaaa agataaagag ggaatcctcc ctaaatcatt ccctgaaacc attattgccc   3180
taatattaaa accagggaag gacataacaa aaaagaaaac tatagaccaa tatctctgat   3240
gaacacagat gcaaaaaatc ctcaacaaaa tactgtgtaa ctgaatccaa cagcatattt   3300
aaaaggtaat acatcacttt caagtggctt tcataccaga gatgcagggt tggtttaaca   3360
tatgcaagtt aataaatgtg atacaccaca taaacagaat taaaaacaaa aaccatatca   3420
atggatccag aaaaagcatt tgacaaaatc tagcattcct tgtgattaca accctaggca   3480
aaatcggcat agaggaaaca cacctttaag gaagtagacc acctctccca ttgtctccta   3540
tttcatgaga aagcaaaagg ttaaaagaag aagtgagatc aatagccaga tggcttggtg   3600
ccaagaaccg tgcctggtag ttaaacatca actcctgacc taaccgcttg tggattccag   3660
acattgtatg aggaagactt ctgaaacttt ctgttctgtt ctgctagccc ccatcactga   3720
```

-continued

```
tgcatgtagc tctcagtcac gtagccccca cttgcacaat gtatcatgac cctttcacat   3780
ggacccctca gagttgtaag ccccttaaaag ggacaggaat ctttactttg gggagctcag   3840
atcatgagat gcgagtctac caatgctccc agctgattaa agcctcttcc ttcataaaac   3900
cagtgtccga gaggttttgt ctgcaaccat tcctgctaca tttcttggtt ccctgacctg   3960
gaagcgaggt gattagtgga cagttgaggc agcctcttag gcggcttagg cctgccctgt   4020
ggagcatccc tggggaggac tccggcgagc ttaagcaaag cagatcctgg gagcactctc   4080
gcgtaggcaa ttgccctggt caaatgcctt gccacagcag tgtgcggcag acccccgtgg   4140
agaattaaca cagcggttga acaccgggaa ggaatcggcg attggagtct ggacatctgg   4200
aacatggtaa gactggcctt ggaactggcc cactccatct gagtggaagt gtgggctgat   4260
cacccacagc atggctttct tggcactttg gttttggttt tcattttgac tagatttgaa   4320
ctgttttggt ttagatttca ctattgactt ttggatttga actgttctgg ctatgatttc   4380
ggctctgact tggctcaaat tgcttgatga atgagtaatt ccttatccat actttgattt   4440
tagtgtgaat tgcttggtga gtgagtgacc ttttgcccct ttttcccttc cccctttgtg   4500
gtaagagtgt tgttttgtct cctgagagag gaaaatgtgt aaaatacaaa gtaagcctac   4560
cctgttagga actatgttaa agaatttcaa gaaaggattc aatggggact atggaattgc   4620
tatgacacct ggaaagctta aggctttatg tgagatagac tatccagcat tagaggtgag   4680
atggccatca gaaggaagcc tagacaggtc cctagtttca aaggtatggc acaaagtaac   4740
tgataaatca ggacacccag accagttacc atacatagat acttggttgc agctagtttt   4800
agacccctca cagtggctaa gaggacaggc tgcagcagta ctagtagcaa agggacagat   4860
agccaaggaa aagtcttgct ccacccgccg agggaagtca gctcctacgg ttctgtccga   4920
ccccacatca gaggatgcat ggcagaaatg gcaccaatgg tgcccctcct taccaagaag   4980
agaggctccc cacatcgaag cccacagccc ctgagcctct gcaaggtgtg cacaccccaa   5040
ggccacctaa aatagacaaa agaggatatg aagcttggga gaaacccctc ccttggcagc   5100
ttgcttgcaa cctaaaactg ggacacaaat gcccctaaga gagcaacggt atactggggt   5160
aaatgaggag gggcatatgg taggggtgcc tttgtgtacc aacctttttac ctctgccgat   5220
ctcctcaact ggaaaaataa catcccatcc tatacagaaa agctgcaagc tctgattgac   5280
ttgctccaaa ctattatcca aactcataac cccacttggg ctgattgcca ccagttgctc   5340
atgtacctct ttaacacgga tgagggagga gagtgctcga ggtagcaact aagtggctgg   5400
aagagcatgt tccagctgat tatcagaacc cccaagagta tgtgaggatc cagctaccag   5460
gaactgaccc ttaataggat ccaaacgaga cagagggtat gcaaaggcta atgcggtata   5520
gggaagcact cttagaaggg ttgaggagag gagcccaaaa ggccacaaac gtaaacaagg   5580
tctccgaggt tatccaagga aagcaagaaa gtccagtgca attttatgag agactgtgtg   5640
aggcctatcg catgtacact ccctttgacc cagacagccc tgaaaatcag cgcatgatta   5700
acatggcctt agttagtcaa agcgcagagg atattaggag aaagctgaag aaacgggctg   5760
ggtttgcagg tatgaatacg tcgccaatta ctggaaatag ccaaccaagt gtttgtaaat   5820
acagatgcag caagccgcag agagagccgc aaagaaggtg aatgccaacc cggtgaaatg   5880
ctgacctact agctgcagct attagagggg tccccctgaa aggacaaggg aatgggggct   5940
ccaggaaaaa tacccagtct gaccgtccac gcttgcaacg taaccagtgc gcctattgta   6000
aagagacagg acattggaaa gataagtgcc ctcagctgaa agaaaagcaa ggtggttcag   6060
agcaaaagac cccagacaag gacgaaggag ccttgttcaa tctggctgag ggttattgg    6120
```

-continued

```
accgaagggg accaggctca cgtgccccca aggagcccat ggtcagaatg acagttgggg   6180
gcaaggacat taagtttctg gtcaatactg gtgctgaaca ttcagtagtg accaccccgg   6240
tcgccccctt gtctaaaaag gctattgata taattggagc aacaggagtt ttgacaaagc   6300
aggctttctg tttgccccgg acctgctcgg tgggggggaca tgaagtgatt caccagttcc   6360
tgtacatccc tgactgcccc ttgcctttgt taggaaggga cctgcttagc aagctgagag   6420
ctatcttcct ttaccaagca aggctcttta caactgaagt tgcctggaac aggagttatc   6480
atggccctga cagttccccg agaggaagag tagcgactct tcctaaccaa accaggcaaa   6540
gagatagggc cagctctggc ccagtggtgg ccaaaagtat gcgcagaaga caaccctcct   6600
ggattggcag tcaatcaagc tcctgtactc agggaagtta agccagaggc ccagccagtc   6660
aggcaaaacc agtatccagt ccccagagaa gccctggaag gtatccaggt tcatcttaag   6720
cacctgagga cttttggaat tatagtgcct tgtcagtctc catggaacac ccccctccta   6780
cctgttccca agccagggac caaggactac aggccagtac aggacttgcg attggtcaat   6840
caagccacag tgactttcca tccaacagta cctaacccgt acacattgtt ggggttattg   6900
ccagctaagg acagctggtt cacctgccta gacctgaagg acgccttctt tagcatcaga   6960
ttagctccag agagccagaa actgtttgcc tttcagtggg aggatccggg gtcaggtgtc   7020
accactcatt acacttggac ccggcttccc caggggttca agaacttccc ccaccatctt   7080
tggggaggca ctggctcgag acctccaaaa gtttcctgcc agagacctag gctgcgtgtt   7140
gttccagtac atcgacaacc tcctgctggg acgccccatg gcagtcgggt gcgtcaaagg   7200
aacagacgcc ctgcttcagc acctggagga ctatgggtat aaggtgtcca agaagaaagc   7260
tcagatctgc agacagcagg tacgctacct gggatttact atccgacagc gggagtgcag   7320
cctaggatca gaaagaaagc aggtcatttg caacctactg gagcctaaga ccagaaggca   7380
gttgagagaa ttattaggag ctgtggggtt ctgcaggtta tggatcccaa attttgcagt   7440
actggccaaa cctctggtac caagttacaa aggggggtga catggaacca tttgaatggg   7500
ggtcccaaca gcaacaggct tttcatgagt taaaagaaaa actcatgtca gccccagccc   7560
tgggtctacc tgacctgaca aagccattta cattgtatgt gtcagaaaga aaaaaaatag   7620
cagtcggagt tttaacccaa gacgtaaggc cgtggctgag gcctgtggcc tacctctcta   7680
aacagctaga cagagtttct aaaggttggc ccccgtgttt gagggtctta gcaccaactg   7740
ccctgctaac acaagaagtg gataaactaa ctcttaggca aaacttaaac ataaaggccc   7800
ctcatgcagt ggtgacttta atgaatacca aaggacatca ctggctgaca aatgccagac   7860
taaccaagta ccaaagcctg ctctgtgaaa atccccatat aaccactgaa gtttgtaaca   7920
atgaaccccg ccactgcttc tggtatcaga gagcccagtt gaacataact gtgtagaggt   7980
gttggactaa gtttattcta gcagaccgga cctccgggac aaaccttgga tgtctgtaga   8040
ctgggagctg tatgtggacg gaagcagctt cattaaccca cagagagaga tgtccgctgg   8100
atatgcagtg gtaaaccttg gacactgtta ttgaagccaa atcgctgcct cagggaactt   8160
cagcccagaa ggccgaactc attgctttaa ctcaggcctt agagctaagt gaaggtaaga   8220
ctgtaaacat ttatactgac tctcggtatg cctttttaac cctccaagtg catggggcat   8280
tatacaaaga aaaaggccta ttgaactcag gggaaaggga catttagtat cagcaagaaa   8340
ttttacagtt attagaagca gtatggaagc ctcggagggt ggcagtaatg cattgtaaag   8400
gacatcagtg agtcaccact tctgttgcct tagggaattc tggagcagac tcctaagctc   8460
```

-continued

```
gcagagcagc atccactccc ttccgagcat cagtcacggc ccctctgctc tctcaggcac   8520
cgcatctagt gcctacttat tctaaagagg aaagagactt tttcaaggca gaaggggggc   8580
aagtgataaa ggaaggatgg atctggttac cagacagaag agtagccatg ccacagctac   8640
taggggccac agttgtgctg gctgtgcatg agaccaccca tctaggccaa gagtcacttg   8700
aaaagttgtt aggctggcac ttctacattt catgtcttgt cggcccttgc caaaacagta   8760
acagcaatgt gtcacctgcc agcagcaaaa tgctaggcag ggtccaacca tcccgctcag   8820
catacaagct tatggagcag ccccctttga agatctccaa gtagacttca ccgagatgcc   8880
caaatgtgga ggtaacaagt atctgctggt tctagtgtgt acatactctg ggtgggtaga   8940
ggcttatcca acacgaactg agaaagctcg tgaagtaacc cgtgtgcttc ttcgagatct   9000
catccctagg tttggactgc ccttacggat tggctcagac aatgggccgg catttgtggc   9060
tgacttggta cagaagacgg caaaggtatt ggggatcaca tggaaactgc atgccaacta   9120
ccaaccttgg agttccggaa aggtggagtg aatgaatcgg actataaaaa atagcttagg   9180
gaaagtgtgt caagaaacag gattaggctt agggaaagtg tgtcaagaaa tgggtacagg   9240
ctctccccac agtattgttt aaaatcaggt gtactccttc taaaagaaca ggatattccc   9300
cttatgagat attgtatcat agaccccctc ccatattacg aggacttcca ggcactcctc   9360
aggagctagg agaaattgag ctgcaatgac agctacaggc tttagaaaaa gttacacaaa   9420
caatttcagc ttgggtaaat gagagatgcc ccattagctt attctcccca gtttaccctt   9480
tctccccagg tgatcgagtg tggatcaaag actggaacat agcccctttg tggccacggt   9540
ggaaaggatg ccagaccatc atcctgacca ctcccaccac catgaaggta gaaggaattc   9600
cggcctggat ccaccacagc cacgtgaaac ccacagcacc tgagacctgg gaggtgagac   9660
caagcccgga caatccctac aaagtgactc tgaaaaagac aacaagccct gctccagtca   9720
cacctggaag ctgactggtc tatgcacagc caaagcataa ggaaactcat cgtgggactc   9780
atttttctca aaatttggac ttgttcaata agaacttcag ctgattttcc ccacatggag   9840
gactgtaccc agtgtattca tcaggttaca gaggtagggc aacaagttaa aataaccttt   9900
ctgttttata gttattatga atgtctagga attttgaaag ggatctgctt atataatgcc   9960
actcagtata atgtgtgtag cccagggaat gaccaacctc atgtgtctta caacctgtct  10020
gagcctccta tgaccacagt tttgaaata agattaagaa ctgaggactg gtggggactc  10080
atgaaagata caagtaaagt aataccagaa cagaagaaaa aggagctccc aaacaagtca  10140
ccttaagatt tgatgcctgt gcagtcatta atagtaacaa gctagggatg ggatgtggtt  10200
ctctcagtcg ggtgaaaaa aaaagctata tatggcagaa aataagtaca tttgtcatga  10260
attaggacta tatggtatta ttgaatgtag ttattggtcc tatgtcattt gggccacctg  10320
gaaaaaggat gaaaaagacc ctgtttgcct acaaaaagga aaaagtaatt catcttgcac  10380
ctccggtaac tgtaacccat tagaattaat aattactaac ccccaggatc cccactggaa  10440
gacaggagaa aatgtaaacc taggaattga tggaactggg cttgaccccc gagtcaacct  10500
tttaatccaa ggggagatcc acaagcgctc ccccaaacca gtgttccaga ccttttatga  10560
tgaactaaat gtgccaatac cagaactgcc agggaagaca aaagatttgt tcctgcagtt  10620
agcagaaaat atagcccatt ccctcaacat tacttcctgt tatgtatgca ggggaactac  10680
tatgggagac caatggcctt gggaggcccg agaattagtg cccatggatc cagttcctga  10740
tataattcca gtccagaagg cccacactgg taacttttgg gtcttaaaaa cctcaattat  10800
tgggcaatac tgcttagcta gagaaggaaa agacttcacc atccccgtag gaagctcaat  10860
```

```
tgcctagggc aaaagctgta taacggcaca agaagaacag tcacctggtg ggtctaaac  10920

catattgaga agaacccatt tagtaagttt actaagttgc aaactgtttg ggcccatcca  10980

gagtctcacc aggactggac ggctccagct agactatact ggatatgtgg acatagagcc  11040

tatgccaagc tacctgatca atgggcaggc agttgtgtca ttggcaccat taagccatcc  11100

tttttcctgc tgcccataaa aacaggtgat gagctcctag gcttccctgt ctatgcttcc  11160

tgagaaaaca gaagcatagc cataggcaat tggaaagatg atgagtggtc ccgtgaaaga  11220

atcatatagt actatgggcc tgccaactgg gcacaagatg gttcgtgggg ataccaaacc  11280

cccatttaca tgctcaactg gattatatgg ttccaagctg tcttagaaat aatcactaat  11340

gaaactggca gaactttgac tgttagcccg gcaagaaacc cagataagaa atgctattta  11400

tcaaaataga ttggccctag actacttgct agcagtggaa agaggggtct gtggaaaatt  11460

caacctgacc aattgctgtc tgcatataga tgaccaaggc caagtagtcg aaaacatcgt  11520

cagagacatg acaaagctag cacatatgcc tgtgcaggtt tggcatggat ttgatcctgg  11580

gtctgtattt ggaaaatggt tcccagcatt aggatttaaa actcttataa taggagtaat  11640

aacagtatta ggaacctgct tgttgctccc ctgcttgctg cctttgctcc ttcaaataat  11700

gagaagcttt gtcactactt taattcacca aaatagttca gcacaagtgt attacatgaa  11760

tcactatcgg tctgtctcgc aaaaagacct agatagtgag gatgaaagtg aaaattccca  11820

ctaataagtg agattctaaa agggggaat aaggaagga                          11859
```

<210> SEQ ID NO 60
<211> LENGTH: 40
<212> TYPE: DNA
<213> ORGANISM: Artificial Sequence
<220> FEATURE:
<223> OTHER INFORMATION: Synthetic

<400> SEQUENCE: 60

```
caccatgcct gctacatttc ttggttccct gacctggtag                          40
```

<210> SEQ ID NO 61
<211> LENGTH: 40
<212> TYPE: DNA
<213> ORGANISM: Artificial Sequence
<220> FEATURE:
<223> OTHER INFORMATION: Synthetic

<400> SEQUENCE: 61

```
ctaccaggtc agggaaccaa gaaatgtagc aggcatggtg                          40
```

<210> SEQ ID NO 62
<211> LENGTH: 11
<212> TYPE: PRT
<213> ORGANISM: Artificial Sequence
<220> FEATURE:
<223> OTHER INFORMATION: Synthetic

<400> SEQUENCE: 62

```
Met Pro Ala Thr Phe Leu Gly Ser Leu Thr Trp
1               5                   10
```

<210> SEQ ID NO 63
<211> LENGTH: 37
<212> TYPE: DNA
<213> ORGANISM: Artificial Sequence
<220> FEATURE:
<223> OTHER INFORMATION: Synthetic

<400> SEQUENCE: 63
caccatgcct gctacatttc ttggttccct gacctag 37

<210> SEQ ID NO 64
<211> LENGTH: 37
<212> TYPE: DNA
<213> ORGANISM: Artificial Sequence
<220> FEATURE:
<223> OTHER INFORMATION: Synthetic

<400> SEQUENCE: 64
ctaggtcagg gaaccaagaa atgtagcagg catggtg 37

<210> SEQ ID NO 65
<211> LENGTH: 10
<212> TYPE: PRT
<213> ORGANISM: Artificial Sequence
<220> FEATURE:
<223> OTHER INFORMATION: Synthetic

<400> SEQUENCE: 65

Met Pro Ala Thr Phe Leu Gly Ser Leu Thr
1 5 10

<210> SEQ ID NO 66
<211> LENGTH: 34
<212> TYPE: DNA
<213> ORGANISM: Artificial Sequence
<220> FEATURE:
<223> OTHER INFORMATION: Synthetic

<400> SEQUENCE: 66
caccatgcct gctacatttc ttggttccct gtag 34

<210> SEQ ID NO 67
<211> LENGTH: 34
<212> TYPE: DNA
<213> ORGANISM: Artificial Sequence
<220> FEATURE:
<223> OTHER INFORMATION: Synthetic

<400> SEQUENCE: 67
ctacagggaa ccaagaaatg tagcaggcat ggtg 34

<210> SEQ ID NO 68
<211> LENGTH: 9
<212> TYPE: PRT
<213> ORGANISM: Artificial Sequence
<220> FEATURE:
<223> OTHER INFORMATION: Synthetic

<400> SEQUENCE: 68

Met Pro Ala Thr Phe Leu Gly Ser Leu
1 5

<210> SEQ ID NO 69
<211> LENGTH: 43
<212> TYPE: DNA
<213> ORGANISM: Artificial Sequence
<220> FEATURE:
<223> OTHER INFORMATION: Synthetic

<400> SEQUENCE: 69
caccatggct acatttcttg gttccctgac ctggaagcga tag 43

<210> SEQ ID NO 70
<211> LENGTH: 43
<212> TYPE: DNA
<213> ORGANISM: Artificial Sequence
<220> FEATURE:
<223> OTHER INFORMATION: Synthetic

<400> SEQUENCE: 70
ctatcgcttc caggtcaggg aaccaagaaa tgtagccatg gtg 43

<210> SEQ ID NO 71
<211> LENGTH: 12
<212> TYPE: PRT
<213> ORGANISM: Artificial Sequence
<220> FEATURE:
<223> OTHER INFORMATION: Synthetic

<400> SEQUENCE: 71

Met Ala Thr Phe Leu Gly Ser Leu Thr Trp Lys Arg
1 5 10

<210> SEQ ID NO 72
<211> LENGTH: 40
<212> TYPE: DNA
<213> ORGANISM: Artificial Sequence
<220> FEATURE:
<223> OTHER INFORMATION: Synthetic

<400> SEQUENCE: 72
caccatggct acatttcttg gttccctgac ctggaagtag 40

<210> SEQ ID NO 73
<211> LENGTH: 40
<212> TYPE: DNA
<213> ORGANISM: Artificial Sequence
<220> FEATURE:
<223> OTHER INFORMATION: Synthetic

<400> SEQUENCE: 73
ctacttccag gtcagggaac caagaaatgt agccatggtg 40

<210> SEQ ID NO 74
<211> LENGTH: 11
<212> TYPE: PRT
<213> ORGANISM: Artificial Sequence
<220> FEATURE:
<223> OTHER INFORMATION: Synthetic

<400> SEQUENCE: 74

Met Ala Thr Phe Leu Gly Ser Leu Thr Trp Lys
1 5 10

<210> SEQ ID NO 75
<211> LENGTH: 34
<212> TYPE: DNA
<213> ORGANISM: Artificial Sequence
<220> FEATURE:
<223> OTHER INFORMATION: Synthetic

<400> SEQUENCE: 75
caccatggct acatttcttg gttccctgac ctag 34

<210> SEQ ID NO 76
<211> LENGTH: 34
<212> TYPE: DNA
<213> ORGANISM: Artificial Sequence
<220> FEATURE:
<223> OTHER INFORMATION: Synthetic

<400> SEQUENCE: 76
ctaggtcagg gaaccaagaa atgtagccat ggtg 34

<210> SEQ ID NO 77
<211> LENGTH: 9
<212> TYPE: PRT
<213> ORGANISM: Artificial Sequence
<220> FEATURE:
<223> OTHER INFORMATION: Synthetic

<400> SEQUENCE: 77

Met Ala Thr Phe Leu Gly Ser Leu Thr
1 5

<210> SEQ ID NO 78
<211> LENGTH: 34
<212> TYPE: DNA
<213> ORGANISM: Artificial Sequence
<220> FEATURE:
<223> OTHER INFORMATION: Synthetic

<400> SEQUENCE: 78
caccatgaca tttcttggtt ccctgacctg gtag 34

<210> SEQ ID NO 79
<211> LENGTH: 34
<212> TYPE: DNA
<213> ORGANISM: Artificial Sequence
<220> FEATURE:
<223> OTHER INFORMATION: Synthetic

<400> SEQUENCE: 79
ctaccaggtc agggaaccaa gaaatgtcat ggtg 34

<210> SEQ ID NO 80
<211> LENGTH: 9
<212> TYPE: PRT
<213> ORGANISM: Artificial Sequence
<220> FEATURE:
<223> OTHER INFORMATION: Synthetic

<400> SEQUENCE: 80

Met Thr Phe Leu Gly Ser Leu Thr Trp
1 5

<210> SEQ ID NO 81
<211> LENGTH: 120
<212> TYPE: PRT
<213> ORGANISM: Artificial Sequence
<220> FEATURE:
<223> OTHER INFORMATION: Synthetic

<400> SEQUENCE: 81

Gly Ala Gln Ile Met Arg Cys Glu Ser Thr Asn Ala Pro Ser Leu Lys
1 5 10 15

Pro Leu Pro Ser Asn Gln Cys Pro Arg Gly Phe Val Cys Asn His Ser
20 25 30

Cys Tyr Ile Ser Trp Phe Pro Asp Leu Glu Ala Arg Leu Val Asp Ser
35 40 45

Gly Ser Leu Leu Gly Gly Leu Gly Leu Pro Cys Gly Ala Ser Leu Gly
50 55 60

```
Arg Thr Pro Ala Ser Leu Ser Lys Ala Asp Pro Gly Ser Thr Leu Ala
65                  70                  75                  80

Ala Ile Ala Leu Val Lys Cys Leu Ala Thr Ala Val Cys Gly Arg Pro
                85                  90                  95

Pro Trp Arg Ile Asn Thr Ala Val Glu His Arg Glu Gly Ile Gly Asp
            100                 105                 110

Trp Ser Leu Asp Ile Trp Asn Met
        115                 120


<210> SEQ ID NO 82
<211> LENGTH: 118
<212> TYPE: PRT
<213> ORGANISM: Artificial Sequence
<220> FEATURE:
<223> OTHER INFORMATION: Synthetic

<400> SEQUENCE: 82

Glu Leu Arg Ser Asp Ala Ser Leu Pro Met Leu Pro Ala Asp Ser Leu
1               5                   10                  15

Phe Leu His Lys Thr Ser Val Arg Glu Val Leu Ser Ala Thr Ile Pro
            20                  25                  30

Ala Thr Phe Leu Gly Ser Leu Thr Trp Lys Arg Gly Asp Trp Thr Val
        35                  40                  45

Glu Ala Ala Ser Ala Ala Ala Cys Pro Val Glu His Pro Trp Gly Gly
    50                  55                  60

Leu Arg Arg Ala Ala Lys Gln Ile Leu Gly Ala Leu Ser Arg Arg Gln
65                  70                  75                  80

Leu Pro Trp Ser Asn Ala Leu Pro Gln Gln Cys Ala Ala Asp Pro Arg
                85                  90                  95

Gly Glu Leu Thr Gln Arg Leu Asn Thr Gly Lys Glu Ser Ala Ile Gly
            100                 105                 110

Val Trp Thr Ser Gly Thr
115


<210> SEQ ID NO 83
<211> LENGTH: 121
<212> TYPE: PRT
<213> ORGANISM: Artificial Sequence
<220> FEATURE:
<223> OTHER INFORMATION: Synthetic

<400> SEQUENCE: 83

Ser Ser Asp His Glu Met Arg Val Tyr Gln Cys Ser Gln Leu Ile Lys
1               5                   10                  15

Ala Ser Ser Phe Ile Lys Pro Val Ser Glu Arg Phe Cys Leu Gln Pro
            20                  25                  30

Phe Leu Leu His Phe Leu Val Pro Pro Gly Ser Glu Val Ile Ser Gly
        35                  40                  45

Gln Leu Arg Gln Pro Leu Arg Arg Leu Arg Pro Ala Leu Trp Ser Ile
    50                  55                  60

Pro Gly Glu Asp Ser Gly Glu Leu Lys Gln Ser Arg Ser Trp Glu His
65                  70                  75                  80

Ser Arg Val Gly Asn Cys Pro Gly Gln Met Pro Cys His Ser Ser Val
                85                  90                  95

Arg Gln Thr Pro Val Glu Asn His Ser Gly Thr Pro Gly Arg Asn Arg
            100                 105                 110

Arg Leu Glu Ser Gly His Leu Glu His
        115                 120
```

<210> SEQ ID NO 84
<211> LENGTH: 20
<212> TYPE: DNA
<213> ORGANISM: Artificial Sequence
<220> FEATURE:
<223> OTHER INFORMATION: Synthetic

<400> SEQUENCE: 84
gcagatcctg ggagcactct 20

<210> SEQ ID NO 85
<211> LENGTH: 24
<212> TYPE: DNA
<213> ORGANISM: Artificial Sequence
<220> FEATURE:
<223> OTHER INFORMATION: Synthetic

<400> SEQUENCE: 85
tgttcaaccg ctgtgttaat tctc 24

<210> SEQ ID NO 86
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Labeled with FAM and TAMRA at the 5' and 3'ends, respectively

<400> SEQUENCE: 86
tgccctggtc aaatgccttg cc 22

<210> SEQ ID NO 87
<211> LENGTH: 19
<212> TYPE: DNA
<213> ORGANISM: Artificial Sequence
<220> FEATURE:
<223> OTHER INFORMATION: Synthetic

<400> SEQUENCE: 87
gaacaccggg aaggaatcg 19

<210> SEQ ID NO 88
<211> LENGTH: 17
<212> TYPE: DNA
<213> ORGANISM: Artificial Sequence
<220> FEATURE:
<223> OTHER INFORMATION: Synthetic

<400> SEQUENCE: 88
tctgcggctt gctgcat 17

<210> SEQ ID NO 89
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Labeled with FAM and TAMRA at the 5' and 3'ends, respectively

<400> SEQUENCE: 89
catgttccag atgtccagac tccaatcg 28

<210> SEQ ID NO 90
<211> LENGTH: 20
<212> TYPE: DNA
<213> ORGANISM: Artificial Sequence
<220> FEATURE:
<223> OTHER INFORMATION: Synthetic

<400> SEQUENCE: 90
tggaacatag cccctttgtg 20

<210> SEQ ID NO 91
<211> LENGTH: 18
<212> TYPE: DNA
<213> ORGANISM: Artificial Sequence
<220> FEATURE:
<223> OTHER INFORMATION: Synthetic

<400> SEQUENCE: 91
ggatccaggc cggaattc 18

<210> SEQ ID NO 92
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Labeled with FAM and TAMRA at the 5' and 3'ends, respectively

<400> SEQUENCE: 92
tggtctggca tcctttccac cg 22

<210> SEQ ID NO 93
<211> LENGTH: 20
<212> TYPE: DNA
<213> ORGANISM: Artificial Sequence
<220> FEATURE:
<223> OTHER INFORMATION: Synthetic

<400> SEQUENCE: 93
gcgagaagat gacccagatc 20

<210> SEQ ID NO 94
<211> LENGTH: 19
<212> TYPE: DNA
<213> ORGANISM: Artificial Sequence
<220> FEATURE:
<223> OTHER INFORMATION: Synthetic

<400> SEQUENCE: 94
ccagtggtac ggccagagg 19

<210> SEQ ID NO 95
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Labeled with FAM and TAMRA at the 5' and 3'ends, respectively

<400> SEQUENCE: 95
ccagccatgt acgttgctat ccaggc 26

<210> SEQ ID NO 96
<211> LENGTH: 25
<212> TYPE: DNA
<213> ORGANISM: Artificial Sequence
<220> FEATURE:
<223> OTHER INFORMATION: Synthetic

<400> SEQUENCE: 96
gagctcagat catgagatgc gagtc 25

<210> SEQ ID NO 97
<211> LENGTH: 25
<212> TYPE: DNA
<213> ORGANISM: Artificial Sequence
<220> FEATURE:
<223> OTHER INFORMATION: Synthetic

<400> SEQUENCE: 97
gtcaggtcag gtagacccag ggctg 25

<210> SEQ ID NO 98
<211> LENGTH: 24
<212> TYPE: DNA
<213> ORGANISM: Artificial Sequence
<220> FEATURE:
<223> OTHER INFORMATION: Synthetic

<400> SEQUENCE: 98
gtctcacctc ccaggtctca ggtg 24

<210> SEQ ID NO 99
<211> LENGTH: 20
<212> TYPE: DNA
<213> ORGANISM: Artificial Sequence
<220> FEATURE:
<223> OTHER INFORMATION: Synthetic

<400> SEQUENCE: 99
gcagatcctg ggagcactct 20

<210> SEQ ID NO 100
<211> LENGTH: 24
<212> TYPE: DNA
<213> ORGANISM: Artificial Sequence
<220> FEATURE:
<223> OTHER INFORMATION: Synthetic

<400> SEQUENCE: 100
tgttcaaccg ctgtgttaat tctc 24

<210> SEQ ID NO 101
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Labeled with FAM and TAMRA at the 5' and
3'ends, respectively

<400> SEQUENCE: 101
tgccctggtc aaatgccttg cc 22

-continued

<210> SEQ ID NO 102
<211> LENGTH: 19
<212> TYPE: DNA
<213> ORGANISM: Artificial Sequence
<220> FEATURE:
<223> OTHER INFORMATION: Synthetic

<400> SEQUENCE: 102
gaacaccggg aaggaatcg 19

<210> SEQ ID NO 103
<211> LENGTH: 17
<212> TYPE: DNA
<213> ORGANISM: Artificial Sequence
<220> FEATURE:
<223> OTHER INFORMATION: Synthetic

<400> SEQUENCE: 103
tctgcggctt gctgcat 17

<210> SEQ ID NO 104
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Labeled with FAM and TAMRA at the 5' and 3'ends, respectively

<400> SEQUENCE: 104
catgttccag atgtccagac tccaatcg 28

<210> SEQ ID NO 105
<211> LENGTH: 20
<212> TYPE: DNA
<213> ORGANISM: Artificial Sequence
<220> FEATURE:
<223> OTHER INFORMATION: Synthetic

<400> SEQUENCE: 105
tggaacatag cccctttgtg 20

<210> SEQ ID NO 106
<211> LENGTH: 18
<212> TYPE: DNA
<213> ORGANISM: Artificial Sequence
<220> FEATURE:
<223> OTHER INFORMATION: Synthetic

<400> SEQUENCE: 106
ggatccaggc cggaattc 18

<210> SEQ ID NO 107
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Labeled with FAM and TAMRA at the 5' and 3'ends, respectively

<400> SEQUENCE: 107
tggtctggca tcctttccac cg 22

<210> SEQ ID NO 108
<211> LENGTH: 20
<212> TYPE: DNA
<213> ORGANISM: Artificial Sequence
<220> FEATURE:
<223> OTHER INFORMATION: Synthetic

<400> SEQUENCE: 108
gcgagaagat gacccagatc 20

<210> SEQ ID NO 109
<211> LENGTH: 19
<212> TYPE: DNA
<213> ORGANISM: Artificial Sequence
<220> FEATURE:
<223> OTHER INFORMATION: Synthetic

<400> SEQUENCE: 109
ccagtggtac ggccagagg 19

<210> SEQ ID NO 110
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Labeled with FAM and TAMRA at the 5' and 3'ends, respectively

<400> SEQUENCE: 110
ccagccatgt acgttgctat ccaggc 26

<210> SEQ ID NO 111
<211> LENGTH: 10
<212> TYPE: PRT
<213> ORGANISM: Artificial Sequence
<220> FEATURE:
<223> OTHER INFORMATION: Synthetic

<400> SEQUENCE: 111

Arg Val Tyr Gln Cys Ser Gln Leu Ile Lys
1 5 10

<210> SEQ ID NO 112
<211> LENGTH: 9
<212> TYPE: PRT
<213> ORGANISM: Artificial Sequence
<220> FEATURE:
<223> OTHER INFORMATION: Synthetic

<400> SEQUENCE: 112

Val Tyr Gln Cys Ser Gln Leu Ile Lys
1 5

<210> SEQ ID NO 113
<211> LENGTH: 10
<212> TYPE: PRT
<213> ORGANISM: Artificial Sequence
<220> FEATURE:
<223> OTHER INFORMATION: Synthetic

<400> SEQUENCE: 113

Gln Leu Ile Lys Ala Ser Ser Phe Ile Lys
1 5 10

```
<210> SEQ ID NO 114
<211> LENGTH: 9
<212> TYPE: PRT
<213> ORGANISM: Artificial Sequence
<220> FEATURE:
<223> OTHER INFORMATION: Synthetic

<400> SEQUENCE: 114

Leu Ile Lys Ala Ser Ser Phe Ile Lys
1               5


<210> SEQ ID NO 115
<211> LENGTH: 9
<212> TYPE: PRT
<213> ORGANISM: Artificial Sequence
<220> FEATURE:
<223> OTHER INFORMATION: Synthetic

<400> SEQUENCE: 115

Thr Phe Leu Gly Ser Leu Thr Trp Lys
1               5


<210> SEQ ID NO 116
<211> LENGTH: 10
<212> TYPE: PRT
<213> ORGANISM: Artificial Sequence
<220> FEATURE:
<223> OTHER INFORMATION: Synthetic

<400> SEQUENCE: 116

Ala Thr Phe Leu Gly Ser Leu Thr Trp Lys
1               5                   10


<210> SEQ ID NO 117
<211> LENGTH: 10
<212> TYPE: PRT
<213> ORGANISM: Artificial Sequence
<220> FEATURE:
<223> OTHER INFORMATION: Synthetic

<400> SEQUENCE: 117

Thr Phe Leu Gly Ser Leu Thr Trp Lys Arg
1               5                   10


<210> SEQ ID NO 118
<211> LENGTH: 11
<212> TYPE: PRT
<213> ORGANISM: Artificial Sequence
<220> FEATURE:
<223> OTHER INFORMATION: Synthetic

<400> SEQUENCE: 118

Pro Ala Thr Phe Leu Gly Ser Leu Thr Trp Lys
1               5                   10
```

COMPOSITIONS AND METHODS FOR PREVENTION OR TREATMENT OF NEOPLASTIC DISEASE IN A MAMMALIAN SUBJECT

CROSS REFERENCE TO RELATED APPLICATIONS

This application is a divisional of U.S. application Ser. No. 14/549,296, filed Nov. 20, 2014, which is a continuation of U.S. application Ser. No. 12/293,180, filed Mar. 19, 2009, now U.S. Pat. No. 8,921,050, issued Dec. 30, 2014, which is the National Stage of International Application No. PCT/US2007/064237, filed Mar. 16, 2007 which claims the benefit of U.S. Provisional Application No. 60/783,350, filed Mar. 17, 2006, the disclosure of each is incorporated by reference in its entirety.

FIELD

The invention generally relates to compositions and methods for preventing or treating neoplastic disease in a mammalian subject. The invention further relates to a composition which comprises an isolated enriched $CD8^+$ T cell population or a dendritic cell population reactive to a human endogenous retrovirus type E antigen on a metastatic solid tumor cell. The human endogenous retrovirus type E antigen includes an envelope protein, a polymerase protein, or another protein or peptide fragment or variant thereof derived from this human endogenous retrovirus type E. The invention further relates to a composition which comprises a human endogenous retrovirus type E antigen, or a fragment or variant thereof. A method of treating or diagnosing a neoplastic disease or a solid tumor is provided.

BACKGROUND

Donor T-cells mediating graft-versus-leukemia (GVL) effects can cure patients with a variety of different hematological malignancies. Until recently, few studies supported a similar susceptibility of solid tumors to allogeneic immunotherapy. It has recently been reported that metastatic RCC can regress following nonmyeloablative allogeneic HCT as a consequence of a donor immune mediated graft-versus-tumor (GVT) effect. Childs et al., *Blood* 94:3234-41, 1999. Although these GVT effects can be durable and sometimes complete, more than half of patients undergoing HCT fail to achieve a disease response. Bregni et al., *Bone Marrow Transplant* 38:527-37, 2006. A better understanding of the immune cells and their target antigens that mediate the regression of these tumors is needed to develop more effective transplant approaches for RCC.

For hematological malignancies, GVL effects appear to be primarily mediated by allogeneic T-cells targeting polymorphic peptides expressed on malignant T-cells of the recipient (i.e., minor histocompatibility antigens, mHas). Several lines of clinical evidence suggest donor T-cells targeting antigens expressed on the tumor also mediate regression of metastatic renal cancer. The majority of patients who achieve a disease response have tumor growth early after transplantation, when the newly engrafted donor immune system is suppressed by cyclosporine or when mixed T-cell chimerism leading to T-cell "tolerance" of host tissues (including the tumor) occurs. In responding patients, tumor regression is typically delayed by 4-6 months occurring after immunosuppression has been withdrawn following the conversion from mixed to full donor T-cell chimerism. As observed with hematological malignancies, graft-versus-host disease (GVHD) is also associated with disease regression. These clinical observations and recent in vitro findings suggest regression of metastatic RCC may result from alloreactive T-cells targeting mHas broadly expressed on both normal tissues and tumor cells of the recipient. Seifarth et al., *J Virol* 79:341-52, 2005. However, the observation that tumor shrinkage sometimes occurs in the absence or temporally distant from GVHD implies antigens over-expressed or even selectively expressed on the tumor might also be a target for immune cells mediating RCC regression. Although cytotoxic T-lymphocytes (CTLs) have been used to identify antigens expressed on a variety of tumors, to date relatively few RCC-associated antigens recognized by human CTL have been identified. Bock, M. and Stoye, J. P., *Curr Opin Genet Dev* 10:651-5, 2000; Childs et al., *N Engl J Med* 343:750-8, 2000; Li et al., *Nature* 409:847-9, 2001; Lower et al., *Proc Natl Acad Sci USA* 93:5177-84, 1996; Smit, A. F., *Curr Opin Genet Dev* 9:657-63, 1999; Tykodi et al., *Clin Cancer Res* 10:7799-811, 2004.

A need exists in the art for a better understanding of the immune cells and their target antigens that mediate the regression of solid tumors to develop more effective transplant approaches for RCC. The current treatment of renal cell carcinoma cancers can have adverse effects on subjects undergoing such therapies and are usually ineffective. Accordingly, there is a need for improved, safer treatments that have long-lasting protective effects for the prevention and treatment of neoplastic disease, for example, renal cell carcinoma. In particular, there is a need for treatments that are more specific and less toxic than the currently available therapeutic agents.

SUMMARY

The present invention generally relates to a composition and method for preventing or treating neoplastic disease in a mammalian subject. A composition is provided which comprises an isolated enriched immune cell population reactive to a human endogenous retrovirus type E antigen on a tumor cell, for example, a metastatic solid tumor cell. The isolated enriched immune cell population can be a $CD8^+$ T cell population or a dendritic cell population. The immune cell population can be an allogeneic cell population or an autologous cell population. The $CD8^+$ T cell population or dendritic cell population includes, but is not limited to, an HLA-$A11^+$ restricted population. A pharmaceutical composition is provided which comprises a human endogenous retrovirus type E antigen. The human endogenous retrovirus type E antigen includes an envelope protein, a polymerase protein, or another protein or peptide fragment or variant thereof derived from this human endogenous retrovirus type E. The antigen can comprises a polypeptide encoded by HERV ID: 23549 (Chr 6: 89367908-89375827), or a fragment or variant thereof. The antigen can further comprise amino acid sequences of any one of SEQ ID NO: 1 through 22, 46 and 48, or a fragment or variant thereof. The antigen can further comprise amino acid sequences encoded by a nucleotide sequence CT-RCC9 (SEQ ID NO: 11), CT-RCC8 (SEQ ID NO: 45), Env HERV-E (SEQ ID NO: 47), or SEQ ID NO:12 (375 bp). A method of treating a neoplastic disease is provided which comprises administering to a mammalian subject a composition comprising an enriched allogeneic $CD8^+$ T cell population reactive to a human endogenous retrovirus type E antigen, in an amount effective to reduce or eliminate the solid tumor or to prevent its occurrence or recurrence. A method of treating a neoplastic disease is provided which comprises administering to a mammalian subject a pharmaceutical composition comprising a human endogenous retrovirus type E antigen, in an amount effective to reduce or eliminate the solid tumor or to prevent its occurrence or recurrence. In a further embodiment, a method for treating a subject suffering from or susceptible to a tumor expressing a HERV-E antigen is provided which comprises administering the vaccine to a healthy donor who will be used as a stem cell donor for a patients suffering from a HERV tumor undergoing an allogeneic stem cell transplant.

A composition is provided which comprises an isolated enriched immune cell population reactive to a human endogenous retrovirus type E antigen on a neoplastic cell. The immune cell population can be HLA-A11 restricted. The immune cell population includes, but is not limited to, a $CD8^+$ T cell population or a dendritic cell population. The immune cell population can be an allogeneic cell population or an autologous cell population. The neoplastic cell includes, but is not limited to, a solid tumor cell, metastatic tumor cell, renal cell carcinoma, melanoma, lymphoma or leukemia. In an aspect of the composition, the human endogenous retrovirus type E antigen is an envelope protein, a polymerase protein, or a fragment or variant thereof. An antigen is provided which comprises an amino acid sequence encoded by HERV ID: 23549 (Chr 6: 89367908-89375827), or a fragment or variant thereof. The antigen is provided which comprises an amino acid sequence encoded by nucleotide sequence, including, but not limited to, CT-RCC8 (SEQ ID NO: 45), CT-RCC9 (SEQ ID NO: 11), Env HERV-E (SEQ ID NO: 47), SEQ ID NO: 12 (375 bp), or an amino acid sequence encoded by Env HERV-E (SEQ ID NO: 48). The antigen can be $NH_2$-ATFLGSLTWK-COOH (SEQ ID NO: 1) or a function variant or mimetic thereof. The antigen can be $X_1$-ATFLGSLTWK-$X_2$ or a function variant or mimetic thereof, wherein each $X_1$ and $X_2$ independently of one another represents any amino acid sequence of n amino acids, n varying from 0 to 50, and n being identical or different in $X_1$ and $X_2$.

A pharmaceutical composition is provided which comprises a human endogenous retrovirus type E antigen. In an aspect of the composition, the human endogenous retrovirus type E antigen is an envelope protein, a polymerase protein, or a fragment or variant thereof. An antigen is provided which comprises an amino acid sequence encoded by HERV ID: 23549 (Chr 6: 89367908-89375827), or a fragment or variant thereof. The antigen is provided which comprises an amino acid sequence encoded by nucleotide sequence, including, but not limited to, CT-RCC8 (SEQ ID NO: 45), CT-RCC9 (SEQ ID NO: 11), Env HERV-E (SEQ ID NO: 47), SEQ ID NO:12 (375 bp), or an amino acid sequence encoded by Env HERV-E (SEQ ID NO: 48). The antigen can be $NH_2$-ATFLGSLTWK-COOH (SEQ ID NO: 1) or a function variant or mimetic thereof. The antigen can be $X_1$-ATFLGSLTWK-$X_2$ or a function variant or mimetic thereof, wherein each $X_1$ and $X_2$ independently of one another represents any amino acid sequence of n amino acids, n varying from 0 to 50, and n being identical or different in $X_1$ and $X_2$.

A method of treating a neoplastic disease in a mammalian subject is provided which comprises administering a composition comprising an isolated enriched immune cell population reactive to a human endogenous retrovirus type E antigen to the mammalian subject, in an amount effective to reduce or eliminate the neoplastic disease or to prevent its occurrence or recurrence in the mammalian subject. The immune cell population can be HLA-A11 restricted. The immune cell population includes, but is not limited to, a $CD8^+$ T cell population or a dendritic cell population. The immune cell population can be an allogeneic cell population or an autologous cell population. The neoplastic cell includes, but is not limited to, a solid tumor cell, metastatic tumor cell, renal cell carcinoma, melanoma, lymphoma or leukemia.

In an aspect of the method, the human endogenous retrovirus type E antigen is an envelope protein, a polymerase protein, or a fragment or variant thereof. An antigen is provided which comprises an amino acid sequence encoded by HERV ID: 23549 (Chr 6: 89367908-89375827), or a fragment or variant thereof. The antigen is provided which comprises an amino acid sequence encoded by nucleotide sequence, including, but not limited to, CT-RCC8 (SEQ ID NO: 45), CT-RCC9 (SEQ ID NO: 11), Env HERV-E (SEQ ID NO: 47), SEQ ID NO: 12 (375 bp), or an amino acid sequence encoded by Env HERV-E (SEQ ID NO: 48). The antigen can be $NH_2$-ATFLGSLTWK-COOH (SEQ ID NO: 1) or a function variant or mimetic thereof. The antigen can be $X_1$-ATFLGSLTWK-$X_2$ or a function variant or mimetic thereof, wherein each $X_1$ and $X_2$ independently of one another represents any amino acid sequence of n amino acids, n varying from 0 to 50, and n being identical or different in $X_1$ and $X_2$.

A method of treating a neoplastic disease in a mammalian subject is provided which comprises administering a pharmaceutical composition comprising a human endogenous retrovirus type E antigen to the mammalian subject, in an amount effective to reduce or eliminate the neoplastic disease or to prevent its occurrence or recurrence in the mammalian subject.

A method for inducing tumor cell death or inhibiting tumor cell proliferation in a mammalian subject is provided which comprises administering a pharmaceutical composition comprising a human endogenous retrovirus type E antigen to the mammalian subject, in an amount effective to induce the tumor cell death or inhibit the tumor cell proliferation in the mammalian subject.

In an aspect of the method, the human endogenous retrovirus type E antigen is an envelope protein, a polymerase protein, or a fragment or variant thereof. An antigen is provided which comprises an amino acid sequence encoded by HERV ID: 23549 (Chr 6: 89367908-89375827), or a fragment or variant thereof. The antigen is provided which comprises an amino acid sequence encoded by nucleotide sequence, including, but not limited to, CT-RCC8 (SEQ ID NO: 45), CT-RCC9 (SEQ ID NO: 11), Env HERV-E (SEQ ID NO: 47), SEQ ID NO: 12 (375 bp), or an amino acid sequence encoded by Env HERV-E (SEQ ID NO: 48). The antigen can be $NH_2$-ATFLGSLTWK-COOH (SEQ ID NO: 1) or a function variant or mimetic thereof. The antigen can be $X_1$-ATFLGSLTWK-$X_2$ or a function variant or mimetic thereof, wherein each $X_1$ and $X_2$ independently of one another represents any amino acid sequence of n amino acids, n varying from 0 to 50, and n being identical or different in $X_1$ and $X_2$. In a further aspect, the mammalian subject can express HLA-A11 restricted minor histocompatibility antigen. The neoplastic disease includes, but is not limited to, a solid tumor, metastatic tumor, renal cell carcinoma, melanoma, lymphoma or leukemia.

A method for diagnosing neoplastic disease in a mammalian subject is provided which comprises detecting a human endogenous retrovirus type E antigen on a neoplastic tumor cell wherein the presence of the human endogenous retrovirus type E antigen is indicative of neoplastic disease or metastatic neoplastic disease.

In an aspect of the method, the human endogenous retrovirus type E antigen is an envelope protein, a polymerase protein, or a fragment or variant thereof. An antigen is provided which comprises an amino acid sequence encoded by HERV ID: 23549 (Chr 6: 89367908-89375827), or a fragment or variant thereof. The antigen is provided which comprises an amino acid sequence encoded by nucleotide sequence, including, but not limited to, CT-RCC8 (SEQ ID NO: 45), CT-RCC9 (SEQ ID NO: 11), Env HERV-E (SEQ ID NO: 47), SEQ ID NO:12 (375 bp), or an amino acid sequence encoded by Env HERV-E (SEQ ID NO: 48). The antigen can be $NH_2$-ATFLGSLTWK-COOH (SEQ ID NO: 1) or a function variant or mimetic thereof. The antigen can be $X_1$-ATFLGSLTWK-$X_2$ or a function variant or mimetic thereof, wherein each $X_1$ and $X_2$ independently of one another represents any amino acid sequence of n amino acids, n varying from 0 to 50, and n being identical or different in $X_1$ and $X_2$. The neoplastic disease includes, but is not limited to, a solid tumor, metastatic tumor, renal cell carcinoma, melanoma, lymphoma or leukemia. In a further aspect, the mammalian subject can express HLA-A11 restricted minor histocompatibility antigen.

An embodiment of the invention provides the identification and characterization of anti-tumor cytotoxic T lymphocyte (CTL) epitopes. In particular, HERV CTL epitopes in the non-variable number of tandem repeat (VNTR) region extracellular region of HERV are described. The VNTR is not a region of HERV, which is traditionally known to have immunogenic epitopes. The invention also describes the generation of enhancer agonist epitopes which generate stronger immune cell reaction than native peptides. CTL epitope sequences outside traditional human endogenous retrovirus (HERV) immunogenic tumor antigens have been identified. In particular, the invention describes a method for T-cell activation by modifying HLA-anchor residues to provide a stronger immune response to native antigens associated with solid tumors, leukemias, or lymphomas.

T-cells play a key role in the induction of GVHD and the GVL effects in hematological malignancies. Thus, it was hypothesized that donor T-cells capable of killing patient tumor cells could be isolated from patients who had regression of metastatic RCC following HCT. To identify potential antigens targeted by donor T-cells, peripheral blood mononuclear cells (PBMCs) obtained from patients after allogeneic transplantation were stimulated in vitro with patient autologous RCC cell lines established in the laboratory from surgically resected tumors. In 2 patients who had disease regression consistent with a GVT effect, T-cells of donor origin that killed patient RCC cells in vitro were expanded from the blood. In one responder, RCC-reactive CTL with a cytotoxicity profile consistent with recognition of a mHa expressed broadly on both the tumor and patient hematopoietic cells was identified. In the other responding patient who had a GVT effect associated with prolonged survival, CTL with in vitro tumor-specific cytotoxicity were isolated. Using cDNA expression cloning, a new RCC tumor antigen recognized by HLA-A11 restricted donor T-cells was identified. The antigen-encoding gene, named CT-RCC, was found to be a HERV type E that is highly expressed on RCC but not normal tissues. Cloning and expression patterns are provided of the first solid tumor antigen identified using donor T-cells from a patient undergoing an allogeneic HCT.

An embodiment of the invention provides a human endogenous retrovirus with selective expression in renal carcinoma cells (RCC) in a mammalian subject. A peptide derived from the CT-RCC genes called CT-RCC-1 is immunogenic in vitro. Tumor regression has been observed concomitant with expansion of CT-RCC-1 reactive CD8+ CTL in 3 of 3 HLA $A11^+$ RCC patients who underwent an allogeneic HCT.

In an embodiment, the invention provides an isolated nucleic acid molecule which encodes an agonist polypeptide antigen derived from a tumor antigen, such as for example, HERV.

In one aspect of the invention, the generated immune response is a cellular immune response. Cellular immune responses include cytotoxic T cell responses, T helper cell responses, and B cell immune responses.

In another embodiment, the invention provides a nucleic acid molecule comprising a nucleic acid sequence corresponding to (e.g. that can code for) any one of the amino acid sequences as identified by SEQ ID NO: 1 through 22 and 45, fragments or variants thereof. SEQ ID NO: 1 through 22 and 45 are identified by:

| SEQ ID NO (peptide) | Peptide sequence | Identifier | Nucleotide sequence | SEQ ID NO (n.t.) |
|---|---|---|---|---|
| 1 | ATFLGS LTWK | Pep-A104-K133 | atgcctgctacatttcaggaccctgacc | 23 |
| 2 | ATIPAT FLGSLT WKRGD | ATT-101P-142D | caccgcaaccattcctgctacatacaggaccctgacctggaa gcgaggtgattaggtggcgttggtaaggacgatgtaaagaacc aagggactggaccttcgctccactaatc | 24 |
| 3 | ATMPA TFLGSL TWKRG D | ATG-101P-142D | caccgcaaccatgcctgctacatacaggaccctgacctggaa gcgaggtgattaggtggcgttggtacggacgatgtaaagaacc aagggactggaccttcgctccactaatc | 25 |
| 4 | ATAPA TFLGSL TWKRG D | GCA-101P-142D | caccgcaaccgctcctgctacatacaggaccctgacctggaa gcgaggtgattaggtggcgttggcgaggacgatgtaaagaac caagggactggaccttcgctccactaatc | 26 |

-continued

| SEQ ID NO (peptide) | Peptide sequence | Identifier | Nucleotide sequence | SEQ ID NO (n.t.) |
|---|---|---|---|---|
| 5 | ATPATF LGSLT WKRGD | ATTdel-101P-142D | cacc gcaacc—<br>cctgctacatacaggaccctgacctggaagcgaggtgattag<br>gtgg cgttgg---<br>ggacgatgtaaagaaccaagggactggaccttcgctccactaa<br>tc | 27 |
| 6 | MNHSC YISWFP DLEAR | ATG-104N-138R | caccatgaatcactcctgctacatacaggaccctgacctggaa<br>gcgaggtgagtggtacttagtgaggacgatgtaaagaaccaa<br>gggactggaccttcgctccact | 28 |
| 7 | MPATF LGSLT WK | 101P-133K | caccatgcctgctacatacaggaccctgacctggaagtaggt<br>ggtacggacgatgtaaagaaccaagggactggaccttcatc | 29 |
| 8 | MATFL GSLTW KR | 104A-136R | caccatggctacatacaggaccctgacctggaagcgataggt<br>ggtaccgatgtaaagaaccaagggactggaccttcgctatc | 30 |
| 9 | MTFLG SLTWK R | 107T-136R | caccatgacatacaggaccctgacctggaagcgataggtgg<br>tactgtaaagaaccaagggactggaccttcgctatc | 31 |
| 10 | MTFLG SLTWK | 107T-133K | cacc atgacatttcttggttccctgacctggaagtaggtgg<br>tactgtaaagaaccaagggactggaccttcatc | 32 |
| | | 1-578 | ggagctcagatcatgagatgcgagtctaccaatgctcccagct<br>gattaaagcctatccttcataaaaccagtgtccgagaggttttgt<br>ctgcaaccattcctgctacatttcttggttccctgacctggaagcg<br>aggtgattagtggacagttgaggcagcctcttaggcggcttag<br>gcctgccctgtggagcatccctggggaggactccggcgagct<br>taagcaaagcagatcctgggagcactctcgcgtaggcaattgc<br>cctggtcaaatgccttgccacagcagtgtgcggcagacccccg<br>tggagaattaacacagcggttgaacaccgggaaggaatcggc<br>gattggagtctggacatctggaacatggtgatcgagtgtggatc<br>aaagactggaacatagcccctttgtggccacggtggaaaggat<br>gccagaccatcatcctgaccactcccaccaccatgaaggtaga<br>aggaattccggcctggatccaccacagccacgtgaaacccac<br>agcacctgagacctgggaggtgagaccaagcccggacaatc<br>cctacaaagtgactctg | 11 [RCC9] |
| | | 1-375 | ggagctcagatcatgagatgcgagtctaccaatgctcccagct<br>gattaaagcctatccttcataaaaccagtgtccgagaggttttgt<br>ctgcaaccattcctgctacatttcttggttccctgacctggaagcg<br>aggtgattagtggacagttgaggcagcctcttaggcggcttag<br>gcctgccctgtggagcatccctggggaggactccggcgagct<br>taagcaaagcagatcctgggagcactctcgcgtaggcaattgc<br>cctggtcaaatgccttgccacagcagtgtgcggcagacccccg<br>tggagaattaacacagcggttgaacaccgggaaggaatcggc<br>gattggagtctggacatctggaacatg | 12 [375 bp common region] |
| 13 | | 1-272 | ggagctcagatcatgagatgcgagtctaccaatgctcccagct<br>gattaaagcctatccttcataaaaccagtgtccgagaggttttgt<br>ctgcaaccattcctgctacatttcttggttccctgacctggaagcg<br>aggtgattagtggacagttgaggcagcctcttaggcggcttag<br>gcctgccctgtggagcatccctggggaggactccggcgagct<br>taagcaaagcagatcctgggagcactctcgcgtaggcaattgc<br>cctggtcaa | 35 |
| 14 | | 1-242 | ggagctcagatcatgagatgcgagtctaccaatgctcccagct<br>gattaaagcctcaccacataaaaccagtgtccgagaggattgt<br>ctgcaaccattcctgctacatacaggaccctgacctggaagcg<br>aggtgattagtggacagttgaggcagcctcttaggcggcttag<br>gcctgccctgtggagcatccctggggaggactccggcgagct<br>taagcaaagcagatcctgggag | 36 |
| 15 | | 1-212 | ggagctcagatcatgagatgcgagtctaccaatgctcccagct<br>gattaaagcctcaccacataaaaccagtgtccgagaggattgt<br>ctgcaaccattcctgctacatacaggaccctgacctggaagcg<br>aggtgattagtggacagttgaggcagcctcttaggcggcttag<br>gcctgccctgtggagcatccctggggaggactcc | 37 |

-continued

| SEQ ID NO (peptide) | Peptide sequence | Identifier | Nucleotide sequence | SEQ ID NO (n.t.) |
|---|---|---|---|---|
| 16 | | 1-182 | ggagctcagatcatgagatgcgagtctaccaatgctcccagct gattaaagcctcaccacataaaaccagtgtccgagaggattgt ctgcaaccattcctgctacatacaggaccctgacctggaagcg aggtgattagtggacagttgaggcagcctcttaggcggcttag gcct | 38 |
| 17 | | 1-152 | ggagctcagatcatgagatgcgagtctaccaatgctcccagct gattaaagcctcaccacataaaaccagtgtccgagaggattgt ctgcaaccattcctgctacatacaggaccctgacctggaagcg aggtgattagtggacag | 39 |
| 18 | | 32-272 | atgctcccagctgattaaagcctcttccttcataaaaccagtgtcc gagaggttttgtctgcaaccattcctgctacatttcttggttccctg acctggaagcgaggtgattagtggacagttgaggcagcctctt aggcggcttaggcctgccctgtggagcatccctggggaggac tccggcgagcttaagcaaagcagatcctgggagcactctcgcg taggcaattgccctggtcaa | 40 |
| 19 | | 62-272 | cataaaaccagtgtccgagaggattgtctgcaaccattcctgct acatttcaggaccctgacctggaagcgaggtgattagtggaca gttgaggcagcctcttaggcggcttaggcctgccctgtggagc atccctggggaggactccggcgagcttaagcaaagcagatcct gggagcactctcgcgtaggcaattgccctggtcaa | 41 |
| 20 | | 92-272 | gcaaccattcctgctacatttcttggttccctgacctggaagcga ggtgattagtggacagttgaggcagcctcttaggcggcttagg cctgccctgtggagcatccctggggaggactccggcgagctta agcaaagcagatcctgggagcactctcgcgtaggcaattgccc tggtcaa | 42 |
| 21 | | 50-272 | agcctcttccttcataaaaccagtgtccgagaggttttgtctgcaa ccattcctgctacatttcttggttccctgacctggaagcgaggtg attagtggacagttgaggcagcctcttaggcggcttaggcctgc cctgtggagcatccctggggaggactccggcgagcttaagca aagcagatcctgggagcactctcgcgtaggcaattgccctggt caa | 43 |
| 22 | | 67-272 | aaccagtgtccgagaggtatgtctgcaaccattcctgctacattt cttggttccctgacctggaagcgaggtgattagtggacagttga ggcagcctcttaggcggcttaggcctgccctgtggagcatccc tggggaggactccggcgagcttaagcaaagcagatcctggga gcactctcgcgtaggcaattgccctggtcaa | 44 |

1-2155 (RCC 8 sequence)

(SEQ ID NO: 45)

GGAGCTCAGATCATGAGATGCGAGTCTACCAATGCTCCCAGCTGATTAAA

GCCTCTTCCTTCATAAAACCAGTGTCCGAGAGGTTTTGTCTGCAACCATT

CCTGCTACATTTCTTGGTTCCCTGACCTGGAAGCGAGGTGATTAGTGGAC

AGTTGAGGCAGCCTCTTAGGCGGCTTAGGCCTGCCCTGTGGAGCATCCCT

GGGGAGGACTCCGGCGAGCTTAAGCAAAGCAGATCCTGGGAGCACTCTCG

CGTAGGCAATTGCCCTGGTCAAATGCCTTGCCACAGCAGTGTGCGGCAGA

CCCCCGTGGAGAATTAACACAGCGGTTGAACACCGGGAAGGAATCGGCGA

TTGGAGTCTGGACATCTGGAACATGGATGCAGCAAGCCGCAGAGAGAGCC

GCAAAGAAGGTGAATGCCAACCCGGTGAAATGCTGACCTACTAGCTGCAG

CTATTAGAGGGGTCCCCCTGAAAGGACAAGGGAATGGGGGCTCCAGGAAA

AATACCCAGTCTGACCGTCCACGCTTGCAACGTAACCAGTGCGCCTATTG

TAAAGAGACAGGACATTGGAAAGATAAGTGCCCTCAGCTGAAAGAAAAGC

AAGGTGGTTCAGAGCAAAAGACCCCAGACAAGGACGAAGGAGCCTTGTTC

AATCTGGCTGAGGGGTTATTGGACCGAAGGGGACCAGGCTCACGTGCCCC

-continued

CAAGGAGCCCATGGTCAGAATGACAGTTGGGGGCAAGGACATTAAGTTTC

TGGTCAATACTGGTGCTGAACATTCAGTAGTGACCACCCCGGTCGCCCCC

TTGTCTAAAAAGGCTATTGATATAATTGGAGCAACAGGAGTTTTGACAAA

GCAGGCTTTCTGTTTGCCCCGGACCTGCTCGGTGGGGGACATGAAGTGA

TTCACCAGTTCCTGTACATCCCTGACTGCCCCTTGCCTTTGTTAGGAAGG

GACCTGCTTAGCAAGCTGAGAGCTATCTTCCTTTACCAAGCAAGGCTCTT

TACAACTGAAGTTGCCTGGAACAGGAGTTATCATGGCCCTGACAGTTCCC

CGAGAGGAAGAGTAGCGACTCTTCCTAACCAAACCAGGCAAAGAGATAGG

GCCAGCTCTGGCCCAGTGGTGGCCAAAAGTATGCGCAGAAGACAACCCTC

CTGGATTGGCAGTCAATCAAGCTCCTGTACTCAGGGAAGTTAAGCCAGAG

GCCCAGCCAGTCAGGCAAAACCAGTATCCAGTCCCCAGAGAAGCCCTGGA

AGGTATCCAGGTTCATCTTAAGCACCTGAGGACTTTTGGAATTATAGTGC

CTTGTCAGTCTCCATGGAACACCCCCCTCCTACCTGTTCCCAAGCCAGGG

ACCAAGGACTACAGGCCAGTACAGGACTTGCGATTGGTCAATCAAGCCAC

-continued

```
AGTGACTTTCCATCCAACAGTACCTAACCCGTACACATTGTTGGGGTTAT
TGCCAGCTAAGGACAGCTGGTTCACCTGCCTAGACCTGAAGGACGCCTTC
TTTAGCATCAGATTAGCTCCAGAGAGCCAGAAACTGTTTGCCTTTCAGTG
GGAGGATCCGGGGTCAGGTGTCACCACTCATTACACTTGGACCCGGCTTC
CCCAGGGGTTCAAGAACTTCCCCCACCATCTTTGGGGAGGCACTGGCTCG
AGACCTCCAAAAGTTTCCTGCCAGAGACCTAGGCTGCGTGTTGTTCCAGT
ACATCGACAACCTCCTGCTGGGACGCCCCATGGCAGTCGGGTGCGTCAAA
GGAACAGACGCCCTGCTTCAGCACCTGGAGGACTATGGGTATAAGGTGTC
CAAGAAGAAAGCTCAGATCTGCAGACAGCAGGTACGCTACCTGGGATTTA
CTATCCGACAGCGGGAGTGCAGCCTAGGATCAGAAAGAAAGCAGGTCATT
TGCAACCTACTGGAGCCTAAGACCAGAAGGCAGTTGAGAGAATTATTAGG
AGCTGTGGGGTTCTGCAGGTTATGGATCCCAAATTTTGCAGTACTGGCCA
AACCTCTGGTACCAAGTTACAAAGGGGGGTGACATGGAACCATTTGAATG
GGGGTCCCAACAGCAACAGGCTTTTCATGAGTTAAAAGAAAAACTCATGT
CAGCCCCAGCCCTGGGTCTACCTGACCTGACAAAGCCATTTACATTGTAT
GTGTC
```

DNA coding sequence of Env/HERV-E:

(SEQ ID NO: 47)

```
ATGGCAGAAAATAAGTACATTTGTCATGAATTAGGACTATATGGTATTAT
TGAATGTAGTTATTGGTCCTATGTCATTTGGGCCACCTGGAAAAAGGATG
AAAAAGACCCTGTTTGCCTACAAAAAGGAAAAAGTAATTCATCTTGCACC
TCCGGTAACTGTAACCCATTAGAATTAATAATTACTAACCCCCAGGATCC
CCACTGGAAGACAGGAGAAAATGTAAACCTAGGAATTGATGGAACTGGGC
TTGACCCCCGAGTCAACCTTTTAATCCAAGGGGAGATCCACAAGCGCTCC
CCCAAACCAGTGTTCCAGACCTTTTATGATGAACTAAATGTGCCAATACC
AGAACTGCCAGGGAAGACAAAAGATTTGTTCCTGCAGTTAGCAGAAAATA
TAGCCCATTCCCTCAACATTACTTCCTGTTATGTATGCAGGGGAACTACT
ATGGGAGACCAATGGCCTTGGGAGGCCCGAGAATTAGTGCCCATGGATCC
AGTTCCTGATATAATTCCAGTCCAGAAGGCCCACACTGGTAACTTTTGGG
TCTTAAAAACCTCAATTATTGGGCAATACTGCTTAGCTAGAGAAGGAAAA
GACTTCACCATCCCCGTAGGAAGCTCAATTGCCTAG
```

Amino acid coding sequence predicted of Env/HERV-E:

(SEQ ID NO: 48)

```
MAENKYICHELGLYGIIECSYWSYVIWATWKKDEKDPVCLQKGKSNSSCT
SGNCNPLELIITNPQDPHWKTGENVNLGIDGTGLDPRVNLLIQGEIHKRS
PKPVFQTFYDELNVPIPELPGKTKDLFLQLAENIAHSLNITSCYVCRGTT
MGDQWPWEARELVPMDPVPDIIPVQKAHTGNFWVLKTSIIGQYCLAREGK
DFTIPVGSSIA
```

In another embodiment, the invention provides for a vector comprising an isolated nucleic acid molecule expressing any one of amino acids identified by SEQ ID NO: 1 through 22 and 45.

In another embodiment, the vector comprises nucleic acid molecules encoding immune cell co-stimulatory molecules, such as for example, B7-1, ICAM-1 and LFA-331.

In yet another embodiment, the invention provides for the transduction of dendritic cells with a vector comprising any one of the molecules as identified by SEQ ID NO: 1 through 22 and 45, fragments or variants thereof, and optionally, immune cell co-stimulatory molecules, such as for example, B7-1, ICAM-1 and LFA-3.35.

In one aspect of the invention, dendritic cells transduced with the vector comprising any one of the molecules as identified by SEQ ID NO: 1 through 22 and 45, fragments or variants thereof, and optionally, immune cell co-stimulatory molecules, generates an immune response, such as activation of a cytotoxic T cell response.

In another embodiment, the invention provides a nucleic acid vector comprising one or more nucleic acid sequences encoding polypeptides as identified by any one of SEQ ID NO: 1 through 22 and 45, fragments or variants thereof, operably linked to an inducible promoter.

In another embodiment the nucleic acid vector is a viral vector, plasmid and the like. Preferably the nucleic acid vector comprises an inducible promoter which is tissue specific, and optionally, immune cell co-stimulatory molecules.

In another embodiment, the vector comprising a nucleic acid sequence encoding any one of the polypeptides identified by SEQ ID NO: 1 through 22 and 45.

In another embodiment, the vector codes for any one of the polypeptides identified by any one of SEQ ID NO: 1 through 22 and 45 having a sequence identity to any one of SEQ ID NO: 1 through 22 and 45 of at least about 10%, more preferably, 25%, even more preferably a sequence identity of about 40%, 50%, 60%, 70%, 80%, 90%, or 99.9% to any of the SEQ ID NO: 1 through 22 and 45.

In another embodiment, the vector contains a sequence identified by any one of SEQ ID NO: 23 through 44 having a sequence identity to anyone one of SEQ ID NO: 20 through 37 of at least about 10%, more preferably. More preferably, 25%, even more preferably about 40%, 50%, 60%, 70%, 80%, 90%, or 99.9% sequence identity to any one of SEQ ID NO: 23-44.

In another embodiment, the invention provides a host cell expressing the polypeptide products of the vector as identified by any one of SEQ ID NO: 1 through 22 and 45 having a sequence identity to anyone one of SEQ ID NO: 1 through 22 and 45 of at least about 10%, more preferably, 25%, even more preferably about 40%, 50%, 60%, 70%, 80%, 90%, or 99.9%. Preferably the host cell is an antigen presenting cell, such as for example, a monocyte/macrophage, dendritic cell or the like.

In another embodiment, the invention provides a method for treating a subject suffering from or susceptible to a HERV tumor comprising administering to a subject any one of the peptides identified by SEQ ID NO: 1 through 22 and 45, fragments or variants thereof.

In another embodiment, the invention provides a method for treating a subject suffering from or susceptible to a HERV tumor comprising administering to a subject any one of the nucleic acids identified by SEQ ID NO: 23 through 44, fragments or variants thereof.

In another embodiment, the invention provides a method for generating an immune response to a HERV tumor antigen comprising administering an isolated nucleic acid molecule in a therapeutically effective dose sufficient to generate a cellular immune response, wherein the isolated nucleic acid molecule encodes any one of polypeptides identified by SEQ ID NO: 1 through 22 and 45, fragments or variants thereof, and optionally immune cell co-stimulatory molecules. Preferably, the vector can express polypeptides as identified by any one of SEQ ID NO: 1 through 22 and 45 having a sequence identity to anyone one of SEQ ID NO: 1 through 22 and 45 of at least about 10%, more preferably, 25%, even more preferably about 40%, 50%, 60%, 70%, 80%, 90%, or 99.9%.

In another embodiment, the invention provides for a method for treating a subject suffering from or susceptible to a HERV tumor comprising isolating dendritic cells from a subject suffering from cancer; and, treating the dendritic cells with one or more of the polypeptides identified by SEQ ID NO: 1 through 22 and 45; fragments, and variants thereof. Preferably, the treated dendritic cells are administered to the subject.

In another embodiment, the invention provides a method for generating an immune response to a weakly immunogenic antigen comprising administering to an subject a polypeptide with a high avidity for HLA fused to the weak immunogen.

In one aspect of the invention, the polypeptide comprises the HLA binding fragment of SEQ ID NO: 14.

In another aspect of the invention, the weak immunogen is a differentiation antigen, or a tumor antigen.

In another embodiment, the HLA binding fragment of SEQ ID NO: 14 is fused to a carcinoembryonic antigen, tumor antigen, self antigen, viral antigen and the like.

In another embodiment, the invention provides for an isolated polypeptide comprising an amino acid sequence set forth in SEQ ID NO: 1 through 22 and 45, fragments or variants thereof.

In another embodiment, the invention provides for a polypeptide identified by any one of SEQ ID NO: 1 through 22 and 45 having a sequence identity to anyone one of SEQ ID NO: 1 through 22 and 45 of at least about 10%, more preferably, 25%, even more preferably about 40%, 50%, 60%, 70%, 80%, 90%, or 99.9%.

In another aspect of the invention, antigen presentation, by antigen presenting cells of the polypeptides induces an immune response, preferably a cellular immune response. For example, the cellular immune response is a cytotoxic T cell response, a T helper cell response, or a B cell immune response.

In another embodiment, the invention provides for an agonist polypeptide comprising an amino acid sequence which is at least about 60% identical to the amino acid sequence of SEQ ID NO: 1 through 22 and 45, fragments, or variants thereof, more preferably, the agonist polypeptide comprises an amino acid sequence which is at least about 80% identical to the amino acid sequence of SEQ ID NO: 1 through 22 and 45., more preferably, the agonist polypeptide comprises an amino acid sequence which is at least about 90%, 95%, or 99.9% identical to the amino acid sequence of SEQ ID NO: 1 through 22 and 45.

In another embodiment, a method of treating a subject suffering from or susceptible to a HERV tumor is disclosed. The method may include the isolating dendritic cells from a subject suffering from cancer, treating the dendritic cells with one or more of polypeptides identified by SEQ ID NO: 1 through 22 and 45, activating peripheral blood mononuclear cells with the treated dendritic cells, and administering the activated PBMC cells to the subject.

In one aspect, presented herein are isolated nucleic acid molecules which encodes an agonist polypeptide antigen derived from HERV, wherein the agonist polypeptide stimulates an immune response.

In one embodiment, the agonist polypeptide binds to HLA molecules with a high avidity.

In one embodiment, the agonist polypeptide has a higher association constant ($K_a$) for the HLA than a native polypeptide.

In one embodiment, an agonist polypeptide comprises up to about 12 amino acids in length.

In one embodiment, the immune response is a cellular immune response.

In one embodiment, the cellular immune response is one or more of a cytotoxic T cell response or a T helper cell response.

In one embodiment, the cellular immune response is a B cell immune response.

In one embodiment, a nucleic acid sequence corresponds to any one of the amino acid sequences as identified by SEQ ID NO: 1 through 22 and 45, fragments or variants thereof.

In one embodiment, a nucleic acid sequence corresponds to the amino acid sequence as identified by SEQ ID NO: 1, or fragments thereof.

Presented herein, according to one aspect, are isolated polypeptides comprising an amino acid sequence set forth in SEQ ID NO: 1 through 22 and 45, fragments or variants thereof.

Presented herein, according to one aspect, are isolated polypeptides comprising an amino acid sequence set forth in SEQ ID NO: 1, fragments or variants thereof.

In one embodiment, the polypeptide comprises SEQ ID NO: 14, fragments or variants thereof.

In one embodiment, the polypeptide induces an immune response.

In one embodiment, the immune response is a cellular immune response.

In one embodiment, the cellular immune response is one or more of a cytotoxic T cell response, a T helper cell response or a B cell immune response.

Presented herein, according to one aspect, are methods for generating an immune response to a HERV tumor antigen comprising administering an isolated nucleic acid molecule in a therapeutically effective dose sufficient to generate a cellular immune response, wherein the isolated nucleic acid molecule encodes any one or more of polypeptides identified by SEQ ID NO: 1 through 22 and 45 or fragments or variants thereof.

In one embodiment, the isolated nucleic acid molecule comprises a vector encoding any one or more of amino acid sequences identified by SEQ ID NO: 1 through 22 and 45.

In one embodiment, the isolated nucleic acid molecule comprises a vector encoding a polypeptide identified by SEQ ID NO: 14.

In one embodiment, an immune response is generated against a HERV tumor.

In one embodiment, the immune response is a cytotoxic T cell response.

According to one aspect, presented herein are nucleic acid vectors comprising one or more nucleic acid sequences encoding polypeptides identified by any one or more of SEQ ID NO: 1 through 22 and 45, operably linked to an inducible promoter.

In one embodiment, the vector is a viral vector.

In one related embodiment, the vector is a plasmid.

In one embodiment, the inducible promoter is one or more of tissue specific or non-specific.

Presented herein, according to one aspect, are recombinant vectors comprising a nucleic acid sequence encoding any one of the polypeptides identified by SEQ ID NO: 1 through 22 and 45.

In one aspect, presented herein are host cells comprising a vector of any one of claims 29 through 33.

In one aspect, presented herein are methods for treating a subject suffering from or susceptible to a HERV tumor comprising administering to a subject any one or more of the peptides identified by SEQ ID NO: 1 through 22 and 45.

In one aspect, presented herein are methods for treating a subject suffering from or susceptible to a HERV tumor comprising isolating antigen presenting cells from a subject suffering from cancer; treating the antigen presenting cells with one or more of polypeptides identified by SEQ ID NO: 1 through 22 and 45; and administering the treated antigen presenting cells to the subject.

In one embodiment, the antigen presenting cells comprise one or more of monocytes, dendritic cells, T cell, B cell or hematopoietic cells.

In one embodiment, the methods may further comprise transfecting an antigen presenting cell with a nucleic acid encoding a polypeptide encoded by one or more of SEQ ID NO: 1 through 22 and 45.

In one aspect, presented herein are methods for generating an immune response to a weakly immunogenic antigen comprising administering to a subject a polypeptide with a high avidity for HLA fused to a weak immunogen.

In one embodiment, the weak immunogen is a tumor antigen.

In one embodiment, HLA binding fragment of SEQ ID NO: 1 is fused to a carcinoembryonic antigen.

In one aspect, presented herein are methods of screening for a molecule to generate an immune response to a HERV tumor antigen, comprising altering a nucleic acid encoding a portion of HERV; expressing the altered nucleic acid to produce a molecule; contacting a dendritic cell with the molecule; and contacting a T-cell with the dendritic cell, In one embodiment, a modulation of the IFN-γ production of the T-cell indicates that the molecule may generate an immune response.

In one embodiment, the dendritic cell is from a subject diagnosed with cancer.

In one embodiment, the dendritic cell after it is treated with the molecule is contacted with a peripheral blood mononuclear cell.

In one aspect, presented herein are methods for treating a subject suffering from or susceptible to a HERV tumor comprising isolating antigen presenting cells from a subject suffering from cancer; treating the antigen presenting cells with one or more of polypeptides identified by SEQ ID NO: 1 through 22 and 45; activating peripheral blood mononuclear cells with the treated antigen presenting cells; and administering the activated PBMC cells to the subject.

In one embodiment, the PBMC is a T cell.

In one aspect, presented herein are methods for generating an immune response to a HERV tumor antigen comprising administering an isolated nucleic acid molecule in a therapeutically effective dose sufficient to generate a cellular immune response, wherein the isolated nucleic acid molecule encode one or more of SEQ ID NO: 1-14.

In one aspect, presented herein are methods for generating an immune response to a HERV tumor antigen comprising administering one or more of an isolated RNA molecule, an isolated DNA molecule, an isolated polypeptide in a therapeutically effective dose sufficient to generate a cellular immune response, wherein the isolated nucleic acid molecule or its product is identified by SEQ ID NO: 1-14.

In one embodiment, the administration comprises one or more of transfection, transduction or injection.

In one aspect, presented herein are methods for treating a subject suffering from or susceptible to a HERV tumor comprising administering to the subject a therapeutically effective amount of an antibody specific for a polypeptide encoded by one or more of SEQ ID NO: 1-14.

In one aspect, presented herein are antibodies specific for polypeptide encoded by one or more of SEQ ID NO: 1-14.

BRIEF DESCRIPTION OF THE DRAWINGS

FIG. 11A and FIG. 11B depict the structure and sequences of CT-RCC8 and CT-RCC9 cDNAs (SEQ ID NO: 12).

FIG. 16 depicts plasmid constructs encoding short peptides used for the identification of tumor specific antigen peptides recognized by CTL.

FIG. 18 depicts location of a tumor specific antigenic 10 mer peptide in the common region of CT-RCC8 and CT-RCC9. Nucleic acid sequence: SEQ ID NO: 12; amino acid sequences (3 reading frames): SEQ ID NOs: 81-83, respectively.

FIG. 21A Semi-quantitative RT-PCR was performed using cDNAs prepared from RCC cell lines generated from the tumors of 14 different patients. cDNAs isolated from EBV-LCL (donor) and fibroblast cells (SAUJ-Fibro) of the patient were used as controls in a similar manner as described elsewhere. Semi-quantitative RT-PCR showed expression of CT-RCC 8 and CT-RCC 9 in 8/14 RCC tumor lines tested. FIG. 21B Quantitative real-time PCR was carried out in a total 25 μL of reaction volume containing cDNA, the TaqMan Universal PCR Master Mix (Applied Biosystems), an appropriate primer set and a TaqMan probe.

FIG. 27 shows detection of CT-RCC Peptide (ATFLGSLTWK) Reactive CTL In Bulk CTL Line.

FIG. 31 shows the localization of CT-RCC 8, CT-RCC 9 and HERV on Chromosome 6.

FIG. 32 shows characteristic Features of Env/HERV-E, the DNA coding sequence of Env/HERV-E (SEQ ID NO: 47) and the predicted protein sequence (SEQ ID NO: 48).

DETAILED DESCRIPTION

Figure 1:
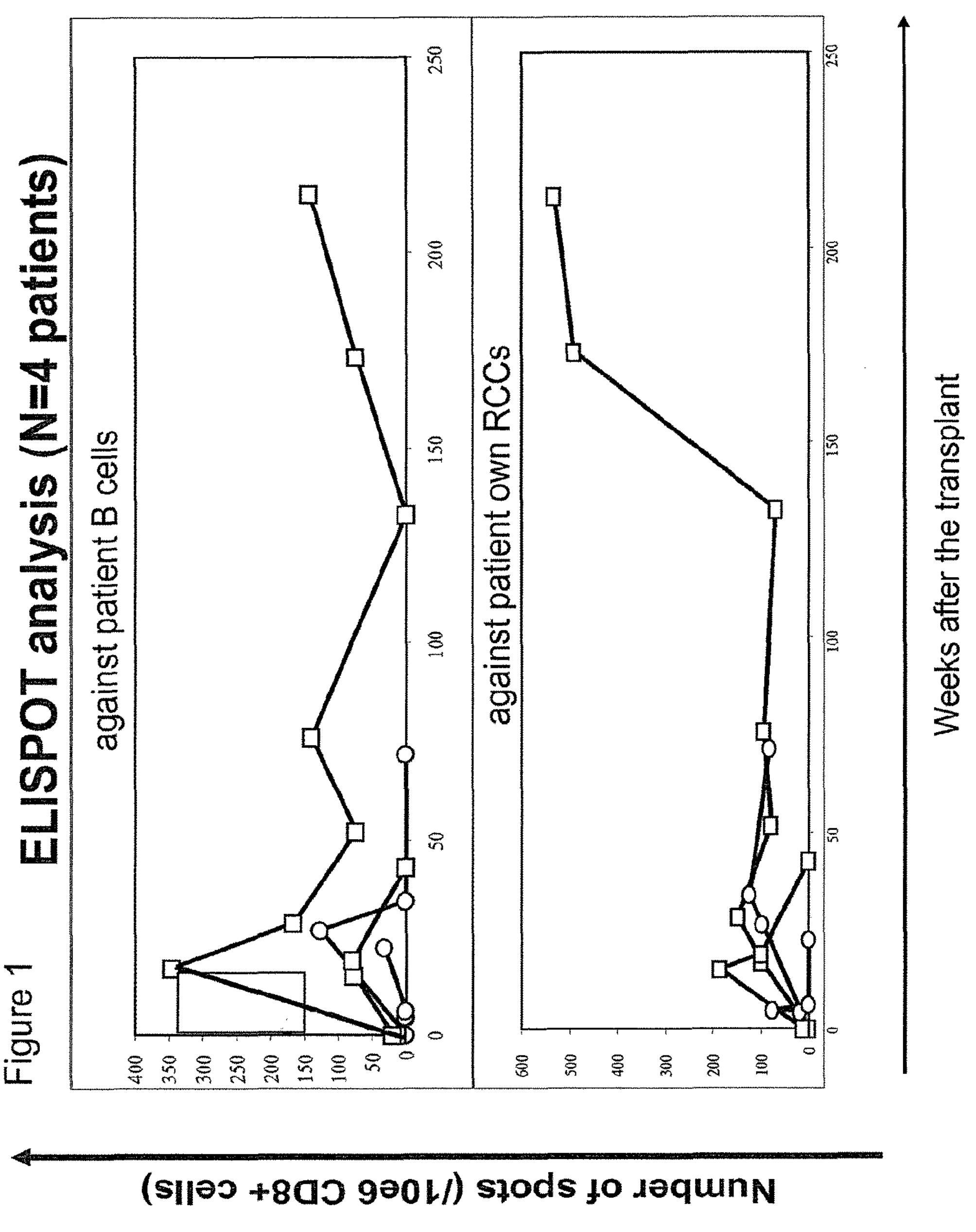
FIG. 1 depicts an ELISPOT for IFN-g secretion showing that following in vivo priming, RCC reactive CD8+ T-cells of donor origin were identified in 3 of 4 patients providing evidence that donor CD8+ T-cells can be primed in vivo to recognize patient RCC cells following allogeneic HCT. ELISPOT analysis showed RCC reactive T-cells were detectable as early as +119 days post transplant and persisted for more than 4 years post transplant.

The present invention generally relates to a composition and method for preventing or treating neoplastic disease in a mammalian subject. A composition is provided which comprises an isolated enriched immune cell population reactive to a human endogenous retrovirus type E antigen on a tumor cell, for example, a metastatic solid tumor cell. The isolated enriched immune cell population can be a $CD8^+$ T cell population or a dendritic cell population. The immune cell population can be an allogeneic cell population or an autologous cell population. The $CD8^+$ T cell population or dendritic cell population includes, but is not limited to, an HLA-$A11^+$ restricted population. A pharmaceutical composition is provided which comprises a human endogenous retrovirus type E antigen. The human endogenous retrovirus type E antigen includes an envelope protein, a polymerase protein, or another protein or peptide fragment or variant thereof derived from this human endogenous retrovirus type E. A method of treating a neoplastic disease is provided which comprises administering to a mammalian subject a composition comprising an enriched allogeneic $CD8^+$ T cell population reactive to a human endogenous retrovirus type E antigen, or comprising a pharmaceutical composition comprising a human endogenous retrovirus type E antigen, in an amount effective to reduce or eliminate the solid tumor or to prevent its occurrence or recurrence.

Vaccine protocols according to one aspect, to boost a cytotoxic T-cell response against this antigen in patients with metastatic RCC. Such strategies could include: (1) Vaccination with the immunogenic 10 amino acid peptide derived from this CT-RCC gene in RCC patients who are HLA A11+; (2) Vaccination with other immunogenic peptides derived from this CT-RCC gene presented in the context of other HLA class I molecules in RCC patients; (3) The adoptive infusion of autologous patient or allogeneic donor (in the transplant setting) CT-RCC specific T-cells expanded in vitro with tumor specific cytotoxicity; and (4) The adoptive infusion of autologous patient or allogeneic donor (in the transplant setting) dendritic cells that have been transfected with the entire common sequence region or other c-DNAs derived from the CT-RCC gene, or RNA derived from this gene.

Clinical evidence suggests that transplanted donor immune cells mediate regression of metastatic renal cell carcinoma (RCC) following allogeneic stem cell transplantation (HCT). RCC-reactive $CD8^+$ T-cells were detected by ELISPOT analysis in the blood of patients with metastatic RCC following HCT that were absent before transplantation. In one responding patient, cytotoxic T-lymphocytes and T-cell clones with RCC-specific tumor cytotoxicity were isolated from the blood after transplantation. Utilizing cDNA expression cloning, an HLA-A11-restricted 10-mer peptide (named CT-RCC-1) was identified as the target antigen of these RCC-specific T-cells. CT-RCC-1-specific T-cells were detected by tetramer analysis in the patient's blood after tumor regression but not before HCT. The genes encoding this antigen were derived from a human endogenous retrovirus (HERV)-E and were found to be expressed in 8/14 RCC cell lines and fresh RCC tissue but not normal tissues. This is the first solid tumor antigen identified using allogeneic T-cells from a patient undergoing HCT. These data suggest this HERV-derived antigen over-expressed in RCC is immunogenic and a potential target for RCC immunotherapy.

We describe herein, inter alia, the identification of novel HLA A-11 epitopes of an endogenous HERV that are important for immune based therapies in the treatment of cancer. We have demonstrated the ability of these epitopes to activate human T cells as measured by IFN-γ production. In particular, one epitope, ATFLGSLTWK (SEQ ID NO: 1), at nucleotide position 104-133, demonstrated the highest level of binding the HLA A-11 and which induced the highest level of IFN-γ secretion by human T cells.

The following definitions of certain terms that are used herewith, are set forth below.

As used herein, "molecule" is used generically to encompass any vector, antibody, protein, drug and the like which are used in therapy and can be detected in a subject by the methods of the invention. For example, multiple different types of nucleic acid delivery vectors encoding different types of genes which may act together to promote a therapeutic effect, or to increase the efficacy or selectivity of gene transfer and/or gene expression in a cell. The nucleic acid delivery vector may be provided as naked nucleic acids or in a delivery vehicle associated with one or more molecules for facilitating entry of a nucleic acid into a cell. Suitable delivery vehicles include, but are not limited to: liposomal formulations, polypeptides; polysaccharides; lipopolysaccharides, viral formulations (e.g., including viruses, viral particles, artificial viral envelopes and the like), cell delivery vehicles, and the like.

As used herein, the term "administering a molecule to a cell" (e.g., an expression vector, nucleic acid, cytokines, a delivery vehicle, agent, and the like) refers to transducing, transfecting, microinjecting, electroporating, or shooting, the cell with the molecule. In some aspects, molecules are introduced into a target cell by contacting the target cell with a delivery cell (e.g., by cell fusion or by lysing the delivery cell when it is in proximity to the target cell).

The term "or" may be inclusive or exclusive.

A "genetic modification" refers to any addition, deletion or disruption to a cell's normal nucleotides. Any method which can achieve the genetic modification of APCs are within the spirit and scope of this invention. Art recognized methods include viral mediated gene transfer, liposome mediated transfer, transformation, transfection and transduction.

The terms "nucleic acid molecule" or "polynucleotide" will be used interchangeably throughout the specification, unless otherwise specified. As used herein, "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogues thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (e.g., the strand having a sequence homologous to the mRNA). A "recombinant DNA molecule" is a DNA molecule that has undergone a molecular biological manipulation.

It must be noted that as used herein and in the appended claims, the singular forms "a," "an," and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

As used herein, the term "fragment or segment," as applied to a nucleic acid sequence, gene or polypeptide, will ordinarily be at least about 5 contiguous nucleic acid bases (for nucleic acid sequence or gene) or amino acids (for polypeptides), typically at least about 10 contiguous nucleic acid bases or amino acids, more typically at least about 20 contiguous nucleic acid bases or amino acids, usually at least about 30 contiguous nucleic acid bases or amino acids, preferably at least about 40 contiguous nucleic acid bases or amino acids, more preferably at least about 50 contiguous nucleic acid bases or amino acids, and even more preferably at least about 60 to 80 or more contiguous nucleic acid bases or amino acids in length. "Overlapping fragments" as used herein, refer to contiguous nucleic acid or peptide fragments which begin at the amino terminal end of a nucleic acid or protein and end at the carboxy terminal end of the nucleic acid or protein. Each nucleic acid or peptide fragment has at least about one contiguous nucleic acid or amino acid position in common with the next nucleic acid or peptide fragment, more preferably at least about three contiguous nucleic acid bases or amino acid positions in common, most preferably at least about ten contiguous nucleic acid bases amino acid positions in common.

A significant "fragment" in a nucleic acid context is a contiguous segment of at least about 17 nucleotides, generally at least 20 nucleotides, more generally at least 23 nucleotides, ordinarily at least 26 nucleotides, more ordinarily at least 29 nucleotides, often at least 32 nucleotides, more often at least 35 nucleotides, typically at least 38 nucleotides, more typically at least 41 nucleotides, usually at least 44 nucleotides, more usually at least 47 nucleotides, preferably at least 50 nucleotides, more preferably at least 53 nucleotides, and in particularly embodiments will be at least 56 or more nucleotides.

A "vector" is a composition which can transduce, transfect, transform or infect a cell, thereby causing the cell to express nucleic acids and/or proteins other than those native to the cell, or in a manner not native to the cell. A cell is "transduced" by a nucleic acid when the nucleic acid is translocated into the cell from the extracellular environment. Any method of transferring a nucleic acid into the cell may be used; the term, unless otherwise indicated, does not imply any particular method of delivering a nucleic acid into a cell. A cell is "transformed" by a nucleic acid when the nucleic acid is transduced into the cell and stably replicated. A vector includes a nucleic acid (ordinarily RNA or DNA) to be expressed by the cell. A vector optionally includes materials to aid in achieving entry of the nucleic acid into the cell, such as a viral particle, liposome, protein coating or the like. A "cell transduction vector" is a vector which encodes a nucleic acid capable of stable replication and expression in a cell once the nucleic acid is transduced into the cell.

"Transcriptional regulatory sequence" is a generic term used throughout the specification to refer to DNA sequences, such as initiation signals, enhancers, promoters, silencing elements, which induce, inhibit or control transcription of protein coding sequences with which they are operably linked.

"HERV tumor" refers to any tumor expressing a human endogenous retrovirus (HERV) antigen. For example, certain renal cell carcinoma tumors described herein express antigens derived from a HERV, e.g., HERV-E.

As used herein, the term "downstream" when used in reference to a direction along a nucleotide sequence means in the direction from the 5' to the 3' end. Similarly, the term "upstream" means in the direction from the 3' to the 5' end.

As used herein, the term “gene” means the gene and all currently known variants thereof and any further variants which may be elucidated.

The term “variant,” when used in the context of a polynucleotide sequence, may encompass a polynucleotide sequence related to a wild type gene. This definition may also include, for example, “allelic,” “splice,” “species,” or “polymorphic” variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. Of particular utility in the invention are variants of wild type target genes. Variants may result from at least one mutation in the nucleic acid sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides. Each of these types of changes may occur alone, or in combination with the others, one or more times in a given sequence.

As used herein, “variant” of polypeptides refers to an amino acid sequence that is altered by one or more amino acid residues. The variant may have “conservative” changes, wherein a substituted amino acid has similar structural or chemical properties (e.g., replacement of leucine with isoleucine). More rarely, a variant may have “nonconservative” changes (e.g., replacement of glycine with tryptophan). Analogous minor variations may also include amino acid deletions or insertions, or both. Guidance in determining which amino acid residues may be substituted, inserted, or deleted without abolishing biological activity may be found using computer programs well known in the art, for example, LASERGENE software (DNASTAR).

The resulting polypeptides generally will have significant amino acid identity relative to each other. A polymorphic variant is a variation in the polynucleotide sequence of a particular gene between subjects of a given species. Polymorphic variants also may encompass “single nucleotide polymorphisms” (SNPs,) or single base mutations in which the polynucleotide sequence varies by one base.

The terms, “complementary” or “complements” are used interchangeably throughout and mean that two sequences are complementary when the sequence of one can bind to the sequence of the other in an anti-parallel sense wherein the 3'-end of each sequence binds to the 5'-end of the other sequence and each A, T(U), G, and C of one sequence is then aligned with a T(U), A, C, and G, respectively, of the other sequence. Normally, the complementary sequence of the oligonucleotide has at least 80% or 90%, preferably 95%, most preferably 100%, complementarity to a defined sequence. Preferably, alleles or variants thereof can be identified. A BLAST program also can be employed to assess such sequence identity.

The term “complementary sequence,” as it refers to a polynucleotide sequence, relates to the base sequence in another nucleic acid molecule by the base-pairing rules. More particularly, the term or like term refers to the hybridization or base pairing between nucleotides or nucleic acids, such as, for instance, between the two strands of a double stranded DNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be substantially complementary when the nucleotides of one strand, optimally aligned and compared and with appropriate nucleotide insertions or deletions, pair with at least about 95% of the nucleotides of the other strand, usually at least about 98%, and more preferably from about 99% to about 100%. Complementary polynucleotide sequences can be identified by a variety of approaches including use of well-known computer algorithms and software, for example the BLAST program.

The term “substantial sequence identity,” when used in connection with peptides/amino acid sequences, refers to peptides/amino acid sequences, which are substantially identical to or similar in sequence, giving rise to a sequence identity in conformation and thus to similar biological activity. The term is not intended to imply a common evolution of the sequences.

Typically, peptides/amino acid sequences having “substantial sequence identity” are sequences that are at least 50%, more preferably at least 80%, identical in sequence, at least over any regions known to be involved in the desired activity. Most preferably, no more than five residues, other than at the termini, are different. Preferably, the divergence in sequence, at least in the aforementioned regions, is in the form of “conservative modifications.”

To determine the percent sequence identity of two peptides/amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). For example, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the first amino acid sequence which has for example 100 amino acid residues, at least 30, preferably at least 40, more preferably at least 50, even more preferably at least 60, and even more preferably at least 70, 80 or 90 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid “identity” is equivalent to amino acid or nucleic acid “sequence identity”). The percent identity between the two sequences is a function of the number of identical positions shared by the sequences, taking into account the number of gaps, and the length of each gap, which need to be introduced for optimal alignment of the two sequences.

The terms “protein” and “polypeptide” are used interchangeably herein. The term “peptide” is used herein to refer to a chain of two or more amino acids or amino acid analogs (including non-naturally occurring amino acids), with adjacent amino acids joined by peptide (—NHCO—) bonds. Thus, the peptides of the invention include oligopeptides, polypeptides, proteins, mimetopes and peptidomimetics. Methods for preparing mimetopes and peptidomimetics are known in the art.

The terms “mimetope” and “peptidomimetic” are used interchangeably herein. A “mimetope” of a compound X refers to a compound in which chemical structures of X necessary for functional activity of X have been replaced with other chemical structures which mimic the conformation of X. Examples of peptidomimetics include peptidic compounds in which the peptide backbone is substituted with one or more benzodiazepine molecules (see e.g., James, G. L. et al. (1993) Science 260:1937-1942) and "retro-inverso" peptides (see U.S. Pat. No. 4,522,752 to Sisto). The terms "mimetope" and "peptidomimetic" also refer to a moiety, other than a naturally occurring amino acid, that conformationally and functionally serves as a substitute for a particular amino acid in a peptide-containing compound without adversely interfering to a significant extent with the function of the peptide. Examples of amino acid mimetics include D-amino acids. Peptides substituted with one or more D-amino acids may be made using well known peptide synthesis procedures. Additional substitutions include amino acid analogs having variant side chains with functional groups, for example, b-cyanoalanine, canavanine, djenkolic acid, norleucine, 3-phosphoserine, homoserine, dihydroxyphenylalanine, 5-hydroxytryptophan, 1-methylhistidine, or 3-methylhistidine.

As used herein an "analog" of a compound X refers to a compound which retains chemical structures of X necessary for functional activity of X, yet which also contains certain chemical structures which differ from X. An example of an analog of a naturally-occurring peptide is a peptide which includes one or more non-naturally-occurring amino acids. The term "analog" is also intended to include modified mimetopes and/or peptidomimetics, modified peptides and polypeptides, and allelic variants of peptides and polypeptides. Analogs of a peptide will therefore produce a peptide analog that is substantially homologous or, in other words, has substantial sequence identity to the original peptide. The term "amino acid" includes its art recognized meaning. Preferred amino acids include the naturally occurring amino acids, as well as synthetic derivatives, and amino acids derived from proteins, e.g., proteins such as casein, e.g., casamino acids, or enzymatic or chemical digests of, e.g., yeast, an animal product, e.g., a meat digest, or a plant product, e.g., soy protein, cottonseed protein, or a corn steep liquor (see, e.g., Traders' Guide to Fermentation Media, Traders Protein, Memphis, Tenn. (1988), Biotechnology: A Textbook of Industrial Microbiology, Sinauer Associates, Sunderland, Mass. (1989), and Product Data Sheet for Corn Steep Liquor, Grain Processing Corp., IO).

Recombinant polypeptides of the present invention may be prepared by processes well known in the art from genetically engineered host cells comprising expression systems. Accordingly, in a further aspect, the present invention relates to expression systems which comprise a polynucleotide or polynucleotides of the present invention, to host cells which are genetically engineered with such expression systems and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al., Basic Methods in Molecular Biology (1986) and Sambrook et al., Molecular Cloning: A Laboratory Manual, 2nd Ed., Cold Spring Harbor Laboratory Press, Cold Spring Harbor, N.Y. (1989). Preferred such methods include, for instance, calcium phosphate transfection, DEAE-dextran mediated transfection, transfection, microinjection, cationic lipid-mediated transfection, electroporation, transduction, scrape loading, ballistic introduction or infection.

A "heterologous" component refers to a component that is introduced into or produced within a different entity from that in which it is naturally located. For example, a polynucleotide derived from one organism and introduced by genetic engineering techniques into a different organism is a heterologous polynucleotide that if expressed can encode a heterologous polypeptide. Similarly, a promoter or enhancer that is removed from its native coding sequence and operably linked to a different coding sequence is a heterologous promoter or enhancer. Possible alternative terminology includes "foreign" or "exogenous". A heterologous nucleotide sequence may encode a sequence of amino acids, e.g. a peptide or a polypeptide.

A "promoter," as used herein, refers to a polynucleotide sequence that controls transcription of a gene or coding sequence to which it is operably linked. A large number of promoters, including constitutive, inducible and repressible promoters, from a variety of different sources, are well known in the art and are available as or within cloned polynucleotide sequences (from, e.g., depositories such as the ATCC as well as other commercial or subject sources).

An "enhancer," as used herein, refers to a polynucleotide sequence that enhances transcription of a gene or coding sequence to which it is operably linked. A large number of enhancers, from a variety of different sources are well known in the art and available as or within cloned polynucleotide sequences (from, e.g., depositories such as the ATCC as well as other commercial or subject sources). A number of polynucleotides comprising promoter sequences (such as the commonly-used CMV promoter) also comprise enhancer sequences.

"Operably linked" refers to a juxtaposition, wherein the components so described are in a relationship permitting them to function in their intended manner. A promoter is operably linked to a coding sequence if the promoter controls transcription of the coding sequence. Although an operably linked promoter is generally located upstream of the coding sequence, it is not necessarily contiguous with it. An enhancer is operably linked to a coding sequence if the enhancer increases transcription of the coding sequence. Operably linked enhancers can be located upstream, within or downstream of coding sequences. A polyadenylation sequence is operably linked to a coding sequence if it is located at the downstream end of the coding sequence such that transcription proceeds through the coding sequence into the polyadenylation sequence.

"Gene delivery," "gene transfer," and the like as used herein, are terms referring to the introduction of an exogenous polynucleotide (sometimes referred to as a "transgenes") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art and described herein.

As used herein, a "target cell" or "recipient cell" refers to a subject cell or cell which is desired to be, or has been, a recipient of exogenous nucleic acid molecules, polynucleotides and/or proteins. The term is also intended to include progeny of a single cell.

"In vivo" gene delivery, gene transfer, gene therapy and the like as used herein, are terms referring to the introduction of a vector comprising an exogenous polynucleotide directly into the body of an organism, such as a human or non-human mammal, whereby the exogenous polynucleotide is introduced to a cell of such organism in vivo.

A cell is "transduced" by a nucleic acid when the nucleic acid is translocated into the cell from the extracellular environment. Any method of transferring a nucleic acid into the cell may be used; the term, unless otherwise indicated, does not imply any particular method of delivering a nucleic acid into a cell. A cell is "transformed" by a nucleic acid when the nucleic acid is transduced into the cell and stably replicated. A vector includes a nucleic acid (ordinarily RNA or DNA) to be expressed by the cell. A vector optionally includes materials to aid in achieving entry of the nucleic acid into the cell, such as a viral particle, liposome, protein coating or the like. A "cell transduction vector" is a vector which encodes a nucleic acid capable of stable replication and expression in a cell once the nucleic acid is transduced into the cell.

As used herein, "homologous recombination" means a nucleotide sequence on one vector is homologous to a nucleotide sequence on another vector. Using restriction enzymes to cut the two sequences and ligating the two sequences results in the two vectors combining. Typically, several kilobases of unaltered flanking DNA (both at the 5' and 3' ends) are included in the vector (see, e.g., Thomas and Capecchi, Cell, 51:503 (1987) for a description of homologous recombination vectors).

Homologous nucleic acid sequences, when compared, exhibit significant sequence identity or similarity. The standards for sequence identity in nucleic acids are either measures for sequence identity generally used in the art by sequence comparison or based upon hybridization conditions. The hybridization conditions are described in greater detail below.

Sequence homology and sequence identity are used interchangeably herein.

"Stringency" is meant the combination of conditions to which nucleic acids are subject that cause the duplex to dissociate, such as temperature, ionic strength, and concentration of additives such as formamide. Conditions that are more likely to cause the duplex to dissociate are called "higher stringency", e.g. higher temperature, lower ionic strength and higher concentration of formamide.

For applications requiring high selectivity, one will typically desire to employ relatively stringent conditions to form the hybrids, e.g., one will select relatively low salt and/or high temperature conditions, such as provided by about 0.02 M to about 0.10 M NaCl at temperatures of about 50° C. to about 70° C.

For certain applications, it is appreciated that lower stringency conditions are required. Under these conditions, hybridization may occur even though the sequences of probe and target strand are not perfectly complementary, but are mismatched at one or more positions. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated depending on the desired results.

The phrase "hybridizing conditions" and its grammatical equivalents, when used with a maintenance time period, indicates subjecting the hybridization reaction admixture, in context of the concentration of the reactants and accompanying reagents in the admixture, to time, temperature, pH conditions sufficient to allow the polynucleotide probe to anneal with the target sequence, typically to form the nucleic acid duplex. Such time, temperature and pH conditions required to accomplish the hybridization depend, as is well known in the art on the length of the polynucleotide probe to be hybridized, the degree of complementarity between the polynucleotide probe and the target, the guanidine and cytosine content of the polynucleotide, the stringency of the hybridization desired, and the presence of salts or additional reagents in the hybridization reaction admixture as may affect the kinetics of hybridization. Methods for optimizing hybridization conditions for a given hybridization reaction admixture are well known in the art.

As used herein, "substantial sequence identity" in the nucleic acid sequence comparison context means either that the segments, or their complementary strands, when compared, are identical when optimally aligned, with appropriate nucleotide insertions or deletions, in at least about 50% of the nucleotides, generally at least 56%, more generally at least 59%, ordinarily at least 62%, more ordinarily at least 65%, often at least 68%, more often at least 71%, typically at least 74%, more typically at least 77%, usually at least 80%, more usually at least about 85%, preferably at least about 90%, more preferably at least about 95 to 98% or more, and in particular embodiments, as high at about 99% or more of the nucleotides. Alternatively, substantial sequence identity exists when the segments will hybridize under selective hybridization conditions, to a strand, or its complement, typically using a fragment derived from SEQ ID NO: 1. Typically, selective hybridization will occur when there is at least about 55% sequence identity over a stretch of at least about 14 nucleotides, preferably at least about 65%, more preferably at least about 75%, and most preferably at least about 90%. See Kanehisa (1984) Nuc. Acids Res. 12:203-213. The length of sequence identity comparison, as described, may be over longer stretches, and in certain embodiments will be over a stretch of at least about 17 nucleotides, usually at least about 20 nucleotides, more usually at least about 24 nucleotides, typically at least about 28 nucleotides, more typically at least about 40 nucleotides, preferably at least about 50 nucleotides, and more preferably at least about 75 to 100 or more nucleotides. The endpoints of the segments may be at many different pair combinations. In determining sequence identity or percent homology the below discussed protocols and programs for sequence similarity are suitably employed including the BLAST algorithm.

The term "polymorphism" refers to the coexistence of more than one form of a gene or portion (e.g., allelic variant) thereof. A portion of a gene of which there are at least two different forms, e.g., two different nucleotide sequences, is referred to as a "polymorphic region of a gene". A specific genetic sequence at a polymorphic region of a gene is an allele. A polymorphic region can be a single nucleotide, the identity of which differs in different alleles. A polymorphic region can also be several nucleotides long.

The nucleic acid and protein sequences of the present invention can further be used as a "query sequence" to perform a search against public databases to identify, for example, other family members or related sequences. Such searches can be performed using the NBLAST and XBLAST programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to NIP2b, NIP2cL, and NIP2cS nucleic acid molecules of the invention. BLAST protein searches can be performed with the XBLAST program, score=50, wordlength=3 to obtain amino acid sequences homologous to NIP2b, NIP2cL, and NIP2cS protein molecules of the invention. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and NBLAST) can be used. See ncbi.nlm.nih.gov.

Sequence similarity searches can be also performed manually or by using several available computer programs known to those skilled in the art. Preferably, Blast and Smith-Waterman algorithms, which are available and known to those skilled in the art, and the like can be used. Blast is NCBI's sequence similarity search tool designed to support analysis of nucleotide and protein sequence databases. The GCG Package provides a local version of Blast that can be used either with public domain databases or with any locally available searchable database. GCG Package v9.0 is a commercially available software package that contains over 100 interrelated software programs that enables analysis of sequences by editing, mapping, comparing and aligning them. Other programs included in the GCG Package include, for example, programs which facilitate RNA secondary structure predictions, nucleic acid fragment assembly, and evolutionary analysis. In addition, the most prominent genetic databases (GenBank, EMBL, PIR, and SWISS-PROT) are distributed along with the GCG Package and are fully accessible with the database searching and manipulation programs. GCG can be accessed through the Internet at, for example, gcg.com. Fetch is a tool available in GCG that can get annotated GenBank records based on accession numbers and is similar to Entrez. Another sequence similarity search can be performed with GeneWorld and GeneThesaurus from Pangea. GeneWorld 2.5 is an automated, flexible, high-throughput application for analysis of polynucleotide and protein sequences. GeneWorld allows for automatic analysis and annotations of sequences. Like GCG, GeneWorld incorporates several tools for sequence identity searching, gene finding, multiple sequence alignment, secondary structure prediction, and motif identification. GeneThesaurus 1.0™ is a sequence and annotation data subscription service providing information from multiple sources, providing a relational data model for public and local data.

Another alternative sequence similarity search can be performed, for example, by BlastParse. BlastParse is a PERL script running on a UNIX platform that automates the strategy described above. BlastParse takes a list of target accession numbers of interest and parses all the GenBank fields into "tab-delimited" text that can then be saved in a "relational database" format for easier search and analysis, which provides flexibility. The end result is a series of completely parsed GenBank records that can be easily sorted, filtered, and queried against, as well as an annotations-relational database.

As used herein, the term "specifically hybridizes" or "specifically detects" refers to the ability of a nucleic acid molecule to hybridize to at least approximately 6 consecutive nucleotides of a sample nucleic acid.

"Substantially purified" refers to nucleic acid molecules or proteins that are removed from their natural environment and are isolated or separated, and are at least about 60% free, preferably about 75% free, and most preferably about 90% free, from other components with which they are naturally associated.

An "antigen" is any substance that reacts specifically with antibodies or T lymphocytes (T cells). An "antigen-binding site" is the part of an immunoglobulin molecule that specifically binds an antigen. Additionally, an antigen-binding site includes any such site on any antigen-binding molecule, including, but not limited to, an MHC molecule or T cell receptor. "Antigen processing" refers to the degradation of an antigen into fragments (e.g., the degradation of a protein into peptides) and the association of one or more of these fragments (e.g., via binding) with MHC molecules for presentation by "antigen-presenting cells" to specific T cells.

"Dendritic cells" (DC) are potent antigen-presenting cells, capable of triggering a robust adaptive immune response in vivo. It has been shown that activated, mature DC provide the signals required for T cell activation and proliferation. These signals can be categorized into two types. The first type, which gives specificity to the immune response, is mediated through interaction between the T-cell receptor/CD3 ("TCR/CD3") complex and an antigenic peptide presented by a major histocompatibility complex ("MHC" defined above) class I or II protein on the surface of APCs. The second type of signal, called a co-stimulatory signal, is neither antigen-specific nor MHC-restricted, and can lead to a full proliferation response of T cells and induction of T cell effector functions in the presence of the first type of signals. This two-fold signaling can, therefore, result in a vigorous immune response. As noted supra, in most non-avian vertebrates, DC arise from bone marrow-derived precursors. Immature DC are found in the peripheral blood and cord blood and in the thymus. Additional immature populations may be present elsewhere. DC of various stages of maturity are also found in the spleen, lymph nodes, tonsils, and human intestine. Avian DC may also be found in the bursa of Fabricius, a primary immune organ unique to avians. In an embodiment, the dendritic cells of the present invention are mammalian, preferably human, mouse, or rat.

A "co-stimulatory molecule" encompasses any single molecule or combination of molecules which, when acting together with a peptide/MHC complex bound by a T cell receptor on the surface of a T cell, provides a co-stimulatory effect which achieves activation of the T cell that binds the peptide.

As used herein, "immunoreceptors" will refer to class I MHC (HLA-A, -B, -C, -G) and the like) and other immune related receptors, such as for example Gp49, PIR, PIRA, PIRB, LIR, NKR-P1, NKp46, Digr1, ILT, MIR, KIR and the like. MHC may also include other classes such as MHC class II and MHC class III, derivatives and mutants thereof. The human MHC complex is also called the human leukocyte antigen (HLA) complex. MHC antigens are divided into MHC class I antigens (in humans, this class includes HLA-A, -B, and -C antigens) and MHC class II antigens (in humans, this class includes HLA-DP, -DQ, and -DR antigens). Thus, the terms "MHC-II antigens", "MHC class II antigens", and "MHC class II transplantation antigens" are used interchangeably herein to refer to the class of proteins, which in humans, includes HLA-DP, -DQ and -DR antigens. While the terms "MHC class II genes" and "MHC-II genes" are used interchangeably herein to refer to the genes which encode the MHC class II transplantation antigens. The term "MHC-II" is used herein to refer to the gene locus which encodes the MHC class II transplantation antigens, as well as the group of proteins encoded by that locus. Transplantation antigens also include cell surface molecules other than MHC class I and II antigens. These antigens include the following: (1) the ABO antigens involved in blood cell recognition; (2) cell adhesion molecules such as ICAM, which is involved in leukocyte cell-cell recognition; and (3) β2-microglobulin, a polypeptide associated with the 44 kd heavy chain polypeptide that comprises the HLA-I antigens but is not encoded by the MHC complex. HLA haplotypes/allotypes vary from subject to subject and it is often helpful to determine the subject's HLA type. The HLA type may be determined via standard typing procedures and the peripheral blood lymphocytes (PBLs) purified by Ficoll gradients.

"Diagnostic" or "diagnosed" means identifying the presence or nature of a pathologic condition. Diagnostic methods differ in their sensitivity and specificity. The "sensitivity" of a diagnostic assay is the percentage of diseased subjects who test positive (percent of "true positives"). Diseased subjects not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

The terms "subject" or "subject" are used interchangeably herein, and is meant a mammalian subject to be treated, with human subjects being preferred. In some cases, the methods of the invention find use in experimental animals, in veterinary application, and in the development of animal models for disease, including, but not limited to, rodents including mice, rats, and hamsters; and primates.

"Label molecules" are chemical or biochemical moieties used for labeling a polynucleotide, a polypeptide, or an antibody. They include, but are not limited to, radionuclides, enzymes, substrates, cofactors, inhibitors, fluorescent agents, chromogenic agents, chemiluminescent agents, magnetic particles, and the like. Reporter molecules specifically bind, establish the presence of, and allow quantification of a particular polynucleotide, polypeptide, or antibody.

"Sample" is used herein in its broadest sense. A sample comprising polynucleotides, polypeptides, peptides, antibodies and the like may comprise a bodily fluid; a soluble fraction of a cell preparation, or media in which cells were grown; a chromosome, an organelle, or membrane isolated or extracted from a cell; genomic DNA, RNA, or cDNA, polypeptides, or peptides in solution or bound to a substrate; a cell; a tissue; a tissue print; a fingerprint, skin or hair; and the like.

As used herein, "fresh tumors" refer to tumors removed from a host by surgical or other means.

As used herein, "proliferative growth disorder, "neoplastic disease," "tumor", "cancer" are used interchangeably as used herein refers to a condition characterized by uncontrolled, abnormal growth of cells. Preferably the cancer to be treated is HERV positive cancer and the abnormal proliferation of cells can be any cell in the organ. Examples of cancer include but are not limited to, carcinoma, blastoma, and sarcoma. As used herein, the term "carcinoma" refers to a new growth that arises from epithelium, found in skin or, more commonly, the lining of body organs.

"Treatment" is an intervention performed with the intention of preventing the development or altering the pathology or symptoms of a disorder. Accordingly, "treatment" refers to both therapeutic treatment and prophylactic or preventative measures. "Treatment" may also be specified as palliative care. Those in need of treatment include those already with the disorder as well as those in which the disorder is to be prevented. In tumor (e.g., cancer) treatment, a therapeutic agent may directly decrease the pathology of tumor cells, or render the tumor cells more susceptible to treatment by other therapeutic agents, e.g., radiation and/or chemotherapy.

The term "in need of such treatment" as used herein refers to a judgment made by a care giver such as a physician, nurse, or nurse practitioner in the case of humans that a subject requires or would benefit from treatment. This judgment is made based on a variety of factors that are in the realm of a care giver's expertise, but that include the knowledge that the subject is ill, or will be ill, as the result of a condition that is treatable by the compositions of the invention.

"Cells of the immune system" or "immune cells" as used herein, is meant to include any cells of the immune system that may be assayed, including, but not limited to, B lymphocytes, also called B cells, T lymphocytes, also called T cells, natural killer (NK) cells, lymphokine-activated killer (LAK) cells, monocytes, macrophages, neutrophils, granulocytes, mast cells, platelets, Langerhans cells, stem cells, dendritic cells, peripheral blood mononuclear cells, tumor-infiltrating (TIL) cells, gene modified immune cells including hybridomas, drug modified immune cells, and derivatives, precursors or progenitors of the above cell types.

"Immune effector cells" refers to cells capable of binding an antigen and which mediate an immune response. These cells include, but are not limited to, T cells (T lymphocytes), B cells (B lymphocytes), monocytes, macrophages, natural killer (NK) cells and cytotoxic T lymphocytes (CTLs), for example CTL lines, CTL clones, and CTLs from tumor, inflammatory, or other infiltrates.

"T cells" or "T lymphocytes" are a subset of lymphocytes originating in the thymus and having heterodimeric receptors associated with proteins of the CD3 complex (e.g., a rearranged T cell receptor, the heterodimeric protein on the T cell surfaces responsible for antigen/MHC specificity of the cells). T cell responses may be detected by assays for their effects on other cells (e.g., target cell killing, macrophage, activation, B-cell activation) or for the cytokines they produce.

The term "activated T cell," as used herein, refers to a T cell that expresses antigens indicative of T-cell activation (that is, T cell activation markers). Examples of T cell activation markers include, but are not limited to, CD25, CD26, CD30, CD38, CD69, CD70, CD71, ICOS, OX-40 and 4-1BB. The expression of activation markers can be measured by techniques known to those of skill in the art, including, for example, western blot analysis, northern blot analysis, RT-PCR, immunofluorescence assays, and fluorescence activated cell sorter (FACS) analysis.

The term "resting T cell," as used herein, refers to a T cell that does not express T-cell activation markers. Resting T cells include, but are not limited to, T cells which are $CD25^-$, $CD69^-$, $ICOS^-$, $SLAM^-$, and $4\text{-}1BB^-$. The expression of these markers can be measured by techniques known to those of skill in the art, including, for example, western blot analysis, northern blot analysis, RT-PCR, immunofluorescence assays, and fluorescence activated cell sorter (FACS) analysis.

"CD4" is a cell surface protein important for recognition by the T cell receptor of antigenic peptides bound to MHC class II molecules on the surface of an APC. Upon activation, naïve CD4 T cells differentiate into one of at least two cell types, Th1 cells and Th2 cells, each type being characterized by the cytokines it produces. "Th1 cells" are primarily involved in activating macrophages with respect to cellular immunity and the inflammatory response, whereas "Th2 cells" or "helper T cells" are primarily involved in stimulating B cells to produce antibodies (humoral immunity). CD4 is the receptor for the human immunodeficiency virus (HIV). Effector molecules for Th1 cells include, but are not limited to, IFN-γ, GM-CSF, TNF-α, CD40 ligand, Fas ligand, IL-3, TNF-β, and IL-2. Effector molecules for Th2 cells include, but are not limited to, IL-4, IL-5, CD40 ligand, IL-3, GS-CSF, IL-10, TGF-β, and eotaxin. Activation of the Th1 type cytokine response can suppress the Th2 type cytokine response.

"CD8" is a cell surface protein important for recognition by the T cell receptor of antigenic peptides bound to MHC class I molecules. CD8 T cells usually become "cytotoxic T cells" or "killer T cells" and activate macrophages. Effector molecules include, but are not limited to, perforin, granzymes, Fas ligand, IFN-γ, TNF-α, and TNF-β.

The terms "specific binding" or "specifically binding", as used herein, in reference to the interaction of an antibody and a protein or peptide, mean that the interaction is dependent upon the presence of a particular structure (e.g., the antigenic determinant or epitope) on the protein; in other words, the antibody is recognizing and binding to a specific protein structure rather than to proteins in general. For example, if an antibody is specific for epitope "A", the presence of a protein comprising epitope A (or free, unlabeled A) in a reaction comprising labeled "A" and the antibody will reduce the amount of labeled A bound to the antibody. "Specific binding" in general, refers to any immune related molecule binding to its ligand, such as for example the binding of a T cell receptor expressed by a T lymphocyte, to an MHC molecule and peptide on an antigen presenting cell.

"Activity," "activation," or "augmentation" is the ability of immune cells to respond and exhibit, on a measurable level, an immune function. Measuring the degree of activation refers to a quantitative assessment of the capacity of immune cells to express enhanced activity when further stimulated as a result of prior activation. The enhanced capacity may result from biochemical changes occurring during the activation process that allow the immune cells to be stimulated to activity in response to low doses of stimulants.

Immune cell activity that may be measured include, but is not limited to, (1) cell proliferation by measuring the cell or DNA replication; (2) enhanced cytokine production, including specific measurements for cytokines, such as IFN-γ, GM-CSF, or TNF-α; (3) cell mediated target killing or lysis; (4) cell differentiation; (5) immunoglobulin production; (6) phenotypic changes; (7) production of chemotactic factors or chemotaxis, meaning the ability to respond to a chemotactin with chemotaxis; (8) immunosuppression, by inhibition of the activity of some other immune cell type; and, (9) apoptosis, which refers to fragmentation of activated immune cells under certain circumstances, as an indication of abnormal activation.

An "adjuvant" is any substance capable of enhancing the immune response to an antigen with which it is mixed. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol, as well as BCG (bacilli Calmette-Guerin) and *Corynabacterium parvum,* which are often used in humans, and ligands of CCR6 and other chemokine receptors.

A "chemokine" is a small cytokine involved in the migration and activation of cells, including phagocytes and lymphocytes, and plays a role in inflammatory responses. Three classes of chemokines have been defined by the arrangement of the conserved cysteine (C) residues of the mature proteins: the CXC or α chemokines that have one amino acid residue separating the first two conserved cysteine residues; the CC or β chemokines in which the first two conserved cysteine residues are adjacent; the C or γ chemokines which lack two (the first and third) of the four conserved cysteine residues. Within the CXC subfamily, the chemokines can be further divided into two groups. One group of the CXC chemokines have the characteristic three amino acid sequence ELR (glutamic acid-leucine-arginine) motif immediately preceding the first cysteine residue near the amino terminus. A second group of CXC chemokines lack such an ELR domain. The CXC chemokines with the ELR domain (including IL-8, GROα/β/γ, mouse KC, mouse MIP-2, ENA-78, GCP-2, PBP/CTAPIII/β-TG/NAP-2) act primarily on neutrophils as chemoattractants and activators, inducing neutrophil degranulation with release of myeloperoxidase and other enzymes. The CXC chemokines without the ELR domain (e.g., IP-10/mouse CRG, Mig, PBSF/SDF-1, PF4), the CC chemokines (e.g., MIP-1α, MIP-1β, RANTES, MCP-1/2/3/4/mouse JE/mouse MARC, eotaxin, I-309/TCA3, HCC-1, C10), and the C chemokines (e.g., lymphotactin), chemoattract and activate monocytes, dendritic cells, T-lymphocytes, natural killer cells, B-lymphocytes, basophils, and eosinophils.

A "cytokine" is a protein made by a cell that affect the behavior of other cells through a "cytokine receptor" on the surface of the cells the cytokine effects. Cytokines manufactured by lymphocytes are sometimes termed "lymphokines." Examples of cytokines include interleukins, interferons and the like.

By "immunologically effective" is meant an amount of the peptide or fragment thereof which is effective to activate an immune response to prevent or treat proliferative cell growth disorders, such as cancer. Obviously, such amounts will vary between species and subjects depending on many factors. For example, higher doses will generally be required for an effective immune response in a human compared with a mouse.

As used herein, the term "polypeptide" encompasses amino acid chains of any length, including full length proteins containing the sequences recited herein. A polypeptide comprising an epitope of a protein containing a sequence as described herein may consist entirely of the epitope, or may contain additional sequences. The additional sequences may be derived from the native protein or may be heterologous, and such sequences may (but need not) possess immunogenic or antigenic properties.

As used herein, the term "antibody" refers to a polypeptide or group of polypeptides which are comprised of at least one binding domain, where an antibody binding domain is formed from the folding of variable domains of an antibody molecule to form three-dimensional binding spaces with an internal surface shape and charge distribution complementary to the features of an antigenic determinant of an antigen, which allows an immunological reaction with the antigen. Antibodies include recombinant proteins comprising the binding domains, as wells as fragments, including Fab, Fab', $F(ab)_2$, and $F(ab')_2$ fragments. The term "antibody," as used herein, also includes antibody fragments either produced by the modification of whole antibodies or those synthesized de novo using recombinant DNA methodologies. It also includes polyclonal antibodies, monoclonal antibodies, chimeric antibodies, humanized antibodies, or single chain antibodies. "Fc" portion of an antibody refers to that portion of an immunoglobulin heavy chain that comprises one or more heavy chain constant region domains, $CH_1$, $CH_2$ and $CH_3$, but does not include the heavy chain variable region.

An "epitope", as used herein, is a portion of a polypeptide that is recognized (e.g., specifically bound) by a B-cell and/or T-cell surface antigen receptor. Epitopes may generally be identified using well known techniques, such as those summarized in Paul, Fundamental Immunology, 3rd ed., 243-247 (Raven Press, 1993) and references cited therein. Such techniques include screening polypeptides derived from the native polypeptide for the ability to react with antigen-specific antisera and/or T-cell lines or clones. An epitope of a polypeptide is a portion that reacts with such antisera and/or T-cells at a level that is similar to the reactivity of the full length polypeptide (e.g., in an ELISA and/or T-cell reactivity assay). Such screens may generally be performed using methods well known to those of ordinary skill in the art, such as those described in Harlow and Lane, Antibodies: A Laboratory Manual, Cold Spring Harbor Laboratory, 1988. B-cell and T-cell epitopes may also be predicted via computer analysis. Polypeptides comprising an epitope of a polypeptide that is preferentially expressed in a tumor tissue (with or without additional amino acid sequence) are within the scope of the present invention.

As used herein, the term "agonist polypeptide" refers to epitopes in the polypeptide which activate a stronger immune response than a native polypeptide. Examples of differences in properties between an agonist polypeptide versus a native polypeptide include, but not limited to a) binding HLA molecules at lower peptide concentrations, (b) demonstrate a higher avidity for HLA molecules in dissociation assays, (c) when used with antigen-presenting cells induce the production of more IFN-γ by T cells derived with the use of the native peptide. Increased or augmented immune response are measured as described above.

As used herein, "native polypeptide" refers to a polypeptide as found in its natural environment. For example, a native HERV tumor antigen is expressed by a tumor cell in a subject.

In an embodiment, agonist polypeptides generate stronger immune responses, as compared to the native polypeptide. For example, compared with the native P-92 peptide, agonist polypeptides (a) bind HLA A-11 at lower peptide concentrations, (b) demonstrate a higher avidity for HLA A-11 in dissociation assays, (c) when used with antigen-presenting cells induce the production of more IFN-γ by T cells derived with the use of the native peptide, and (d) were capable of more efficiently generating HERV-specific human T-cell lines from normal volunteers and pancreatic cancer subjects. Most importantly, the T-cell lines generated using the agonist epitope were more efficient than those generated with the native epitope, in the lysis of targets pulsed with the native epitope and in the lysis of HLA A-11 human tumor cells expressing HERV.

In another embodiment, subjects, suffering from or susceptible to tumors, infectious diseases and the like are treated with autologous antigen presenting cells, such as for example dendritic cells (DCs), that have been transduced with a viral vector encoding anyone of the polypeptides as identified by SEQ ID NO: 1 through 22 and 45, fragments or variants thereof. For example, autologous DCs infected with HERV are used as APC.

In another embodiment, the invention provides a method for generating an immune response to a weakly immunogenic antigen comprising administering to a subject an agonist polypeptide, as identified by any one of SEQ ID NO: 1 through 22 and 45, variants or fragments thereof, with a high avidity for HLA fused to the weak immunogen.

In an embodiment, the invention provides an isolated nucleic acid molecule which encodes an agonist polypeptide antigen derived from a tumor antigen, such as for example, HERV, wherein the agonist polypeptide stimulates a stronger immune response as compared to a native polypeptide. Other examples of tumor antigens, include, but are not limited to HER2/neu, carcinoembryonic antigen (CEA), p53.

In another embodiment, the invention provides a nucleic acid molecule comprising a nucleic acid sequence corresponding to any one of the amino acid sequences as identified by SEQ ID NO: 1 through 22 and 45, fragments or variants thereof.

In another embodiment, the invention provides for a vector comprising an isolated nucleic acid molecule expressing any one of amino acids identified by SEQ ID NO: 1 through 22 and 45, fragments or variants, thereof. The vector optionally encodes encoding immune cell co-stimulatory molecules, such as for example, B7-1, ICAM-1 and LFA-331.

In yet another embodiment, the invention provides for the transduction of dendritic cells with a vector comprising any one of the molecules as identified by SEQ ID NO: 1 through 22 and 45, fragments or variants thereof, and optionally, immune cell co-stimulatory molecules, such as for example, B7-1, ICAM-1 and LFA-3.35. These recombinant vectors provide specific anti-tumor effect for subjects who have been diagnosed with HERV tumors. However, this antigen is merely an illustrative example and is not meant to be construed as limiting in any way.

In another embodiment, antigen presenting cells, e.g., dendritic cells, monocytes, T cell, B cell or hematopoietic cells, of an subject, suffering from or susceptible to, cancer, are transduced in vivo with recombinant vectors expressing agonist polypeptide epitopes. Antigen presenting cells can be isolated from a subject, cultured ex vivo with a vector, and then re-infusing the cultured dendritic cells into the subject. For example, culturing of dendritic cells is described in detail in the examples which follow. Alternatively, the vector may be administered to a subject in need of such treatment.

In an embodiment, transduced antigen presenting cells present antigen, for example, agonist peptide fragments of the HERV antigen on their surface. Lymphocytes, specific for the presented antigens, are activated, proliferate and recognize tumor cells expressing the HERV antigen. Lymphocytes include, B cells, T helper cells and cytotoxic T cells. Recognition, of any cell expressing antigenic epitopes by the immune cells, results in the destruction of a tumor cell.

In another embodiment, the invention provides a nucleic acid vector comprising one or more nucleic acid sequences encoding polypeptides as identified by any one of SEQ ID NO: 1 through 22 and 45, fragments or variants thereof, operably linked to an inducible promoter.

In another embodiment the nucleic acid vector is a viral vector, plasmid and the like. Preferably the nucleic acid vector comprises an inducible promoter which is tissue specific, and optionally, immune cell co-stimulatory molecules.

In another embodiment, the vector comprising a nucleic acid sequence encoding any one of the polypeptides identified by SEQ ID NO: 1 through 22 and 45.

In another embodiment, the vector codes for any one of the polypeptides identified by any one of SEQ ID NO: 1 through 22 and 45 having a sequence identity to anyone one of SEQ ID NO: 1 through 22 and 45 of at least about 10%, more preferably, 25%, even more preferably about 40%, 50%, 60%, 70%, 80%, 90%, or 99.9%.

In another embodiment, the invention provides a host cell expressing the polypeptide products of the vector as identified by any one of SEQ ID NO: 1 through 22 and 45 having a sequence identity to anyone one of SEQ ID NO: 1 through 22 and 45 of at least about 10%, more preferably, 25%, even more preferably about 40%, 50%, 60%, 70%, 80%, 90%, or 99.9%. Preferably the host cell is an antigen presenting cell, such as for example, a monocyte/macrophage, dendritic cell or the like.

In accordance with the invention, the transduced dendritic cells present antigen to cells of the immune system and activate the immune system to recognize tumor antigen epitopes, such as for example a tumor cell expressing the HERV antigen.

In an embodiment, the vector is a avipox vector comprising nucleic acid molecules encoding agonist polypeptides and co-stimulatory molecules, as described in detail in the examples which follow. Other vectors may also be used. Preferred vectors include viral vectors, fusion proteins and chemical conjugates. Retroviral vectors include moloney murine leukemia viruses. DNA viral vectors are preferred. Viral vectors can be chosen to introduce the genes to cells of choice. Such vectors include pox vectors such as orthopox or avipox vectors, herpesvirus vectors such as herpes simplex I virus (HSV) vector (Geller et al., 1995, J. Neurochem., 64:487; Lim et al., 1995, in DNA Cloning: Mammalian Systems, D. Glover, ed., Oxford Univ. Press, Oxford, England; Geller et al., 1990, Proc. Natl. Acad. Sci. U.S.A. 87: 1149), other adenovirus vectors (LeGal LaSalle et al., 1993, Science 259: 988; Davidson et al., 1993, Nat. Genet. 3: 219; Yang et al., 1995, J. Virol. 69: 2004), adeno-associated virus vectors (Kaplitt et al., 1994, Nat. Genet. 8: 148; Kotin, et al. WO 98/11244 (Mar. 19, 1998) and Chiorini, et al WO 99/61601 (Dec. 2, 1999)), or lentiviral vectors (see e.g., US 2006/0057725).

Pox viral vectors introduce the gene into the cells cytoplasm. Avipox virus vectors result in only short term expression of the nucleic acid. Adenovirus vectors, adeno-associated virus vectors and herpes simplex virus vectors are preferred for introducing the nucleic acid into neural cells. The adenovirus vector results in a shorter term expression (about 2 months) than adeno-associated virus (about 4 months), which in turn is shorter than HSV vectors. The vectors can be introduced by standard techniques, e.g. infection, transfection, transduction or transformation. Examples of modes of gene transfer include for example, naked DNA calcium phosphate precipitation, DEAE dextran, electroporation, protoplast fusion, lipofection, cell microinjection and viral vectors.

The vector can be employed to target essentially any desired target cell. For example, stereotaxic injection can be used to direct the vectors (e.g. adenovirus, HSV) to a desired location. Other methods that can be used include catheters, intravenous, parenteral, intraperitoneal, and subcutaneous injection, and oral or other known routes of administration.

Another preferred method is DNA immunization. DNA immunization employs the subcutaneous injection of a plasmid DNA (pDNA) vector encoding a tumor marker. The pDNA sequence is taken up by antigen presenting cells (APC), preferably by dendritic cells. Once inside the cell, the DNA encoding protein is transcribed and translated and presented to lymphocytes.

Genetic constructs comprise a nucleotide sequence that encodes the nucleic acid sequence of choice and preferably includes an intracellular trafficking sequence operably linked to regulatory elements needed for gene expression.

When taken up by a cell, the genetic construct(s) may remain present in the cell as a functioning extrachromosomal molecule and/or integrate into the cell's chromosomal DNA. DNA may be introduced into cells where it remains as separate genetic material in the form of a plasmid or plasmids. Alternatively, linear DNA which can integrate into the chromosome may be introduced into the cell. When introducing DNA into the cell, reagents which promote DNA integration into chromosomes may be added. DNA sequences which are useful to promote integration may also be included in the DNA molecule. Alternatively, RNA may be administered to the cell. It is also contemplated to provide the genetic construct as a linear minichromosome including a centromere, telomeres and an origin of replication. Gene constructs may remain part of the genetic material in attenuated live microorganisms or recombinant microbial vectors which live in cells. Gene constructs may be part of genomes of recombinant viral vaccines where the genetic material either integrates into the chromosome of the cell or remains extrachromosomal.

Genetic constructs include regulatory elements necessary for gene expression of a nucleic acid molecule. The elements include: a promoter, an initiation codon, a stop codon, and a polyadenylation signal. In addition, enhancers may be required for gene expression of the sequence of choice, for example, the agonist polypeptides identified by SEQ ID NO: 1 through 22 and 45, variants or fragments thereof. It is necessary that these elements be operably linked to the sequence that encodes the desired proteins and that the regulatory elements are operable in the subject to whom they are administered.

Initiation codons and stop codons are generally considered to be part of a nucleotide sequence that encodes the immunogenic target protein. However, it is necessary that these elements are functional in the subject to whom the gene construct is administered. The initiation and termination codons must be in frame with the coding sequence.

Promoters and polyadenylation signals used must be functional within the cells of the subject.

Examples of promoters useful to practice the present invention, especially in the production of a genetic vaccine for humans, include but are not limited to promoters from Simian Virus 40 (SV40), Mouse Mammary Tumor Virus (MMTV) promoter, Human Immunodeficiency Virus (HIV) such as the HIV Long Terminal Repeat (LTR) promoter, Moloney virus, ALV, Cytomegalovirus (CMV) such as the CMV immediate early promoter, Epstein Barr Virus (EBV), Rous Sarcoma Virus (RSV) as well as promoters from human genes such as human Actin, human Myosin, human Hemoglobin, human muscle creatine and human metallothionein.

Examples of polyadenylation signals useful to practice the present invention, especially in the production of a genetic vaccine for humans, include but are not limited to SV40 polyadenylation signals and LTR polyadenylation signals.

In addition to the regulatory elements required for DNA expression, other elements may also be included in the DNA molecule. Such additional elements include enhancers. The enhancer may be selected from the group including but not limited to: human Actin, human Myosin, human Hemoglobin, human muscle creatine and viral enhancers such as those from CMV, RSV and EBV.

Genetic constructs can be provided with mammalian origin of replication in order to maintain the construct extrachromosomally and produce multiple copies of the construct in the cell. For example, plasmids pCEP4 and pREP4 from Invitrogen (San Diego, Calif.) contain the Epstein Barr virus origin of replication and nuclear antigen EBNA-1 coding region which produces high copy episomal replication without integration.

In order to maximize protein production, regulatory sequences may be selected which are well suited for gene expression in the cells the construct is administered into. Moreover, codons may be selected which are most efficiently transcribed in the cell. One having ordinary skill in the art can produce DNA constructs which are functional in the cells.

The method of the present invention comprises the steps of administering nucleic acid molecules to tissue of the subject. In some embodiments, the nucleic acid molecules are administered intramuscularly, intranasally, intraperitoneally, subcutaneously, intradermally, or topically or by lavage to mucosal tissue selected from the group consisting of vaginal, rectal, urethral, buccal and sublingual.

In some embodiments, the nucleic acid molecule is delivered to the cells in conjunction with administration of a facilitating agent. Facilitating agents are also referred to as polynucleotide function enhancers or genetic vaccine facilitator agents. Facilitating agents are described in e.g. International Application No. PCT/US94/00899 filed Jan. 26, 1994 and International Application No. PCT/US95/04071 filed Mar. 30, 1995, both incorporated herein by reference. Facilitating agents which are administered in conjunction with nucleic acid molecules may be administered as a mixture with the nucleic acid molecule or administered separately simultaneously, before or after administration of nucleic acid molecules.

In some embodiments, the genetic constructs of the invention are formulated with or administered in conjunction with a facilitator selected from the group consisting of, for example, benzoic acid esters, anilides, amidines, urethans and the hydrochloride salts thereof such as those of the family of local anesthetics. The facilitating agent is administered prior to, simultaneously with or subsequent to the genetic construct. The facilitating agent and the genetic construct may be formulated in the same composition.

In some embodiments of the invention, the subject is first subject to injection of the facilitator prior to administration of the genetic construct. That is, for example, up to a about a week to ten days prior to administration of the genetic construct, the subject is first injected with the facilitator. In some embodiments, the subject is injected with the facilitator about 1 to 5 days; in some embodiments 24 hours, before or after administration of the genetic construct. Alternatively, if used at all, the facilitator is administered simultaneously, minutes before or after administration of the genetic construct. Accordingly, the facilitator and the genetic construct may be combined to form a single pharmaceutical composition.

In some embodiments, the genetic constructs are administered free of facilitating agents, that is in formulations free from facilitating agents using administration protocols in which the genetic constructions are not administered in conjunction with the administration of facilitating agents.

Nucleic acid molecules which are delivered to cells according to the invention may serve as genetic templates for proteins that function as prophylactic and/or therapeutic immunizing agents. In embodiments, the nucleic acid molecules comprise the necessary regulatory sequences for transcription and translation of the coding region in the cells of the animal.

In further embodiments, the agonist polypeptides described herein may be used for the immunotherapy of HERV tumors. In these embodiments, the compounds (which may be polypeptides, antibodies or nucleic acid molecules) may be incorporated into pharmaceutical compositions or vaccines. Pharmaceutical compositions comprise one or more such compounds and a physiologically acceptable carrier. Vaccines may comprise one or more polypeptides and an immune response enhancer, such as an adjuvant or a liposome (into which the compound is incorporated). Pharmaceutical compositions and vaccines may additionally contain a delivery system, such as biodegradable microspheres which are disclosed, for example, in U.S. Pat. Nos. 4,897,268 and 5,075,109. Pharmaceutical compositions and vaccines within the scope of the present invention may also contain other compounds, including one or more separate polypeptides.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention.

Any of a variety of adjuvants may be employed in the vaccines of this invention to nonspecifically enhance the immune response. Most adjuvants contain a substance designed to protect the antigen from rapid catabolism, such as aluminum hydroxide or mineral oil, and a stimulator of immune responses, such as lipid A, *Bordetella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.), Merck Adjuvant 65 (Merck and Company, Inc., Rahway, N.J.), alum, biodegradable microspheres, monophosphoryl lipid A and quil A. Cytokines, such as GM-CSF or interleukin-2, -7, or -12, may also be used as adjuvants.

In another embodiment, the invention provides a method for treating a subject suffering from or susceptible to a HERV tumor comprising administering to a subject any one of the peptides identified by SEQ ID NO: 1 through 22 and 45, fragments or variants thereof. In a further embodiment, a method for treating a subject suffering from or susceptible to a HERV tumor is provided which comprises administering the vaccine to a healthy donor who will be used as a stem cell donor for a patients suffering from a HERV tumor undergoing an allogeneic stem cell transplant.

In accordance with the invention, an immune response to a HERV tumor antigen, is generated, by administering an agonist polypeptides in a therapeutically effective dose sufficient to generate a cellular immune response, wherein the agonist polypeptides are any one of polypeptides identified by SEQ ID NO: 1 through 22 and 45, fragments or variants thereof, and optionally immune cell co-stimulatory molecules. Preferably, the polypeptides as identified by any one of SEQ ID NO: 1 through 22 and 45 having a sequence identity to anyone one of SEQ ID NO: 1 through 22 and 45 of at least about 10%, more preferably, 25%, even more preferably about 40%, 50%, 60%, 70%, 80%, 90%, or 99.9%.

The peptides are administered to a subject suffering from or susceptible to cancers. Definite clinical diagnosis of a particular cancer warrants the administration of the peptides, including the early stages of the disease. Prophylactic applications are warranted in cases where subjects with familial history of disease and predicted to be at risk by reliable prognostic indicators could be treated prophylactically to interdict cancer prior to onset, such as HERV positive cancer; or can be administered post operatively.

Peptide vaccines can be administered in many possible formulations, in pharmacologically acceptable mediums. In the case of a short peptide, the peptide can be conjugated to a carrier, such as KLH, in order to increase its immunogenicity. The vaccine can be administered in conjunction with an adjuvant, various of which are known to those skilled in the art. After initial immunization with the vaccine, a booster can be provided. The vaccines are administered by conventional methods, in dosages which are sufficient to elicit an immunological response, which can be easily determined by those skilled in the art.

Efficacy of the peptide in the context of prevention is judged based on the following criteria: frequency of peptide reactive T cells determined by limiting dilution, proliferation response of peptide reactive T cell lines and clones, cytokine profiles of T cell lines and clones to the desired peptide established from subjects. Efficacy is established by decrease in frequency of reactive cells, a reduction in thymidine incorporation with altered peptide compared to native, and a reduction in TNF and IFN-α. Clinical measurements include the relapse rate in one and two year intervals, on a Kaplan-Meier curve, a delay in sustained cancer stage progression reduction in the number and size of tumors including a change in area and volume of T2 images on MRI, and the number and volume of lesions determined by gadolinium enhanced images.

Peptides, variants and fragments thereof, of the present invention may be administered either alone, or as a pharmaceutical composition. Briefly, pharmaceutical compositions of the present invention may comprise one or more of the peptides, in combination with one or more pharmaceutically or physiologically acceptable carriers, diluents or excipients. Such compositions may comprise buffers such as neutral buffered saline, phosphate buffered saline and the like, carbohydrates such as glucose, mannose, sucrose or dextrans, mannitol, proteins, polypeptides or amino acids such as glycine, antioxidants, chelating agents such as EDTA or glutathione, adjuvants (e.g., aluminum hydroxide) and preservatives. In addition, pharmaceutical compositions of the present invention may also contain one or more additional active ingredients, such as, for example, cytokines like β-interferon.

Compositions of the present invention may be formulated for the manner of administration indicated, including for example, for oral, nasal, venous, intracranial, intraperitoneal, subcutaneous, or intramuscular administration. Within other embodiments of the invention, the compositions described herein may be administered as part of a sustained release implant. Within yet other embodiments, compositions of the present invention may be formulized as a lyophilizate, utilizing appropriate excipients which provide stability as a lyophilizate, and subsequent to rehydration.

Pharmaceutical compositions of the present invention may be administered in a manner appropriate to the disease to be treated (or prevented). The quantity and frequency of administration will be determined by such factors as the condition of the subject, and the type and severity of the subject's disease. Within particularly embodiments of the invention, the peptides, variants, or fragments thereof, or pharmaceutical compositions described herein may be administered at a dosage ranging from about 5 to 50 mg/kg, although appropriate dosages may be determined by clinical trials. Dosages of peptide analogue will be approximately 5-50 mg/kg, but are determined more accurately following trials. Subjects may be monitored for therapeutic effectiveness by MRI, and signs of clinical exacerbation, as described above.

MRI can be used to measure active lesions using gadolinium-DTPA-enhanced imaging (McDonald et al. Ann. Neurol. 36:14, 1994) or the location and extent of lesions using T2-weighted techniques. Briefly, baseline MRIs are obtained. The same imaging plane and subject position are used for each subsequent study. Positioning and imaging sequences are chosen to maximize lesion detection and facilitate lesion tracing. The same positioning and imaging sequences are used on subsequent studies. The presence, location and extent of MS lesions are determined by radiologists. Areas of lesions are outlined and summed slice by slice for total lesion area. Three analyses may be done: evidence of new lesions, rate of appearance of active lesions, percentage change in lesion area (Paty et al., Neurology 43:665, 1993). Improvement due to therapy is established when there is a statistically significant improvement in an subject compared to baseline or in a treated group versus a placebo group.

In another aspect of the invention, any tumor antigen polypeptide can be administered to an subject diagnosed as suffering from or susceptible to cancers. The polypeptides corresponding to identified tumor antigens can be used to stimulate the cells of the immune system to recognize and lyse tumor cells expressing tumor antigens, such as for example, CEA, p53, K-ras, and the like.

While various procedures involving the use of antibodies have been applied in the treatment of tumors, few if any successful attempts using activated cytotoxic T-cells have been recorded. Theoretically, cytotoxic T-cells would be the preferable means of treating tumors. However, no procedures have been available to specifically activate cytotoxic T-cells. In contrast to antibodies, the T-cell receptors on the surface of CD8 cells cannot recognize foreign antigens directly. Antigen must first be presented to the T cell receptor, such as by a dendritic cell.

The presentation of antigen to CD8 T-cells is accomplished by major histocompatibility complex (MHC) molecules of the Class I type. The major histocompatibility complex (MHC) refers to a large genetic locus encoding an extensive family of glycoproteins which play an important role in the immune response. The MHC genes, which are also referred to as the HLA (human leukocyte antigen)

complex, are located on chromosome 6 in humans. The molecules encoded by MHC genes are present on cell surfaces and are largely responsible for recognition of tissue transplants as "non-self". Thus, membrane-bound MHC molecules are intimately involved in recognition of antigens by T-cells.

MHC products are grouped into three major classes, referred to as I, II, and III. T-cells that serve mainly as helper cells express CD4 and primarily interact with Class II molecules, whereas CD8-expressing cells, which mostly represent cytotoxic effector cells, interact with Class I molecules.

Class I molecules are membrane glycoproteins with the ability to bind peptides derived primarily from intracellular degradation of endogenous proteins. Complexes of MHC molecules with peptides derived from viral, bacterial and other foreign proteins comprise the ligand that triggers the antigen responsiveness of T-cells. In contrast, complexes of MHC molecules with peptides derived from normal cellular products play a role in "teaching" the T-cells to tolerate self-peptides, in the thymus. Class I molecules do not present entire, intact antigens; rather, they present peptide fragments thereof, "loaded" onto their "peptide binding groove".

As will be recognized by those in the art, the term "host compatible" or "autologous" cells means cells that are of the same or similar haplotype as that of the subject or "host" to which the cells are administered.

The presentation of Class I MHC molecules bound to peptide alone has generally been ineffective in activating CD8 cells. In nature, the CD8 cells are activated by antigen-presenting cells, such as, for example, dendritic cells, which present not only a peptide-bound Class I MHC molecule, but also a costimulatory molecule. Such costimulatory molecules include B7 which is now recognized to be two subgroups designated as B7.1 and B7.2, ICAM-1 and LFA-3. It has also been found that cell adhesion molecules such as integrins assist in this process.

Dendritic cells are antigen-presenting cells that are found in all tissues and organs, including the blood. Specifically, dendritic cells present antigens for T lymphocytes, e.g., they process and present antigens, and stimulate responses from naive and memory T cells. In addition to their role in antigen presentation, dendritic cells directly communicate with non-lymph tissue and survey non-lymph for an injury signal (e.g., ischemia, infection, or inflammation) or tumor growth. Once signaled, dendritic cells initiate the immune response by releasing IL-1 which triggers lymphocytes and monocytes. When the CD8 T-cell interacts with an antigen-presenting cell, such as a dendritic cell, having the peptide bound by a Class I MHC and costimulatory molecule, the CD8 T-cell is activated to proliferate and becomes an effector T-cell. See, generally, Janeway and Travers, Immunobiology, published by Current Biology Limited, London (1994), incorporated by reference.

Accordingly, what is needed and which the present invention provides, is a means to activate T-cells so that they proliferate, become cytotoxic for cells expressing the desired antigen, such as for example, an antigen derived from a HERV, and maintain memory cells specific for the administered antigen. Thus, the immune system is primed against various tumor epitopes so if spontaneous tumors arise, a pool of primed immune cells exist which become activated to recognize and kill the tumor cells.

Preferably, the epitopes presented to the immune system comprise agonist epitopes as described herein. Agonist polypeptides preferably comprise an amino acid sequence which is at least about 60% identical to the amino acid sequence of SEQ ID NO: 1 through 22 and 45, fragments or variants thereof, more preferably, the agonist polypeptide comprises an amino acid sequence which is at least about 80% identical to the amino acid sequence of SEQ ID NO: 1 through 22 and 45. More preferably, the agonist polypeptide comprises an amino acid sequence which is at least about 90%, 95%, or 99.9% identical to the amino acid sequence of SEQ ID NO: 1 through 22 and 45.

A review of the biology of memory T cells may be found in Dutton et al. (1998) Ann. Rev Immunol 16:201-23. Memory cells express a different pattern of cell surface markers, and they respond in several ways that are functionally different from those of naive cells. Human memory cells are $CD45RA^-$, $CD45RO^+$. In contrast to naïve cells, memory cells secrete a full range of T cell cytokines.

Chemokines and cytokines also play a powerful role in the development of an immune response. The role of chemokines in leukocyte trafficking is reviewed by Baggiolini (1998) Nature 392:565-8, in which it is suggested that migration responses in the complicated trafficking of lymphocytes of different types and degrees of activation will be mediated by chemokines. The use of small molecules to block chemokines is reviewed by Baggiolini and Moser (1997) J. Exp. Med. 186:1189-1191.

The role of various specific chemokines in lymphocyte homing has been previously described. For example, Campbell et al. (1998) Science, showed that SDF-1 (also called PBSF), 6-C-kine (also called Exodus-2), and MIP-3beta (also called ELC or Exodus-3) induced adhesion of most circulating lymphocytes, including most $CD4^+$ T cells; and MIP-3alpha (also called LARC or Exodus-1) triggered adhesion of memory, but not naïve, $CD4^+$ T cells. Tangemann et al. (1998) J. Immunol. 161:6330-7 disclose the role of secondary lymphoid-tissue chemokine (SLC), a high endothelial venule (HEV)-associated chemokine, with the homing of lymphocytes to secondary lymphoid organs. Campbell et al. (1998) J. Cell Biol 141(4):1053-9 describe the receptor for SLC as CCR7, and that its ligand, SLC, can trigger rapid integrin-dependent arrest of lymphocytes rolling under physiological shear.

Mature B cells can be measured in immunoassays, for example, by cell surface antigens including CD19 and CD20 with monoclonal antibodies labeled with fluorochromes or enzymes may be used to these antigens. B cells that have differentiated into plasma cells can be enumerated by staining for intracellular immunoglobulins by direct immunofluorescence in fixed smears of cultured cells.

Several different ways, to assess maturity and cell differentiation, are available. For example, one such method is by measuring cell phenotypes. The phenotypes of immune cells and any phenotypic changes can be evaluated by flow cytometry after immunofluorescent staining using monoclonal antibodies that will bind membrane proteins characteristic of various immune cell types.

A second means of assessing cell differentiation is by measuring cell function. This may be done biochemically, by measuring the expression of enzymes, mRNA's, genes, proteins, or other metabolites within the cell, or secreted from the cell. Bioassays may also be used to measure functional cell differentiation or measure specific antibody production directed at a subject's tumor, tumor cell lines or cells from fresh tumors.

Immune cells express a variety of cell surface molecules which can be detected with either monoclonal antibodies or polyclonal antisera Immune cells that have undergone differentiation or activation can also be enumerated by staining for the presence of characteristic cell surface proteins by direct immunofluorescence in fixed smears of cultured cells.

In vitro T cell cytotoxic assays are well known to those skilled in the art. A preferred method is to measure cytotoxicity in a 5 hr $^{51}$Sodium chromate ($^{51}$Cr) release assay. In particular, a 20 hr $^{51}$Cr-release assay is preferred. Tumor cells, also referred to herein as "target cells" are plated in flat-bottomed microtiter plates and incubated at 37° C. overnight. The targets are washed and labeled the next day with $^{51}$Cr at 37° C. $^{51}$Cr is taken up by the target cells, either by endocytosis or pinocytosis, and is retained in the cytoplasm. The wells containing tumor cells are washed, and then armed or unarmed ATC, referred to as "effector cells" are plated at different E:T ratios and incubated overnight at 37° C. Cytolysis is a measure of the $^{51}$Cr released from the target cells into the supernatant due to destruction of the target cells by the effector cells. The microtiter plates are centrifuged at 1000 rpm for 10 minutes and an aliquot of about 50 μl to about 100 μl is removed and the level of radioactivity is measured the next day by a gamma counter and the percent specific lysis calculated.

Percent specific lysis is measured by using the formula:

($^{51}$Cr released from the target cells)−(spontaneous $^{51}$Cr released from the target cells)/(maximum $^{51}$Cr released from the target cells)−(spontaneous $^{51}$Cr released from the target cells)×100

The spontaneous $^{51}$Cr released from the target cells is measured with tumor cells to which no effector cells have been added. Maximum $^{51}$Cr released from the target cells is obtained by adding, for example, 1M HCl and represents the total amount of $^{51}$Cr present in the cytoplasm of the target cell.

Other means of assaying for T lymphocyte activity is by the mixed lymphocyte reaction described in the examples which follow. Other cytotoxicity assays such as the labeling of target cells with tritiated thymidine ($^{3}$H-TdR) may also be used. $^{3}$H-TdR is taken up by target cells into the nucleus of the cell. Release of $^{3}$H-TdR is a measure of cell death by DNA fragmentation. The assay is conducted as above except the incubation period is at least about 48 hours and 50 μl to about 100 μl of the supernatant is measured by a beta-counter in the presence of at least about 1 ml of scintillation fluid. Calculation of percent specific lysis is performed using the above formula.

In an embodiment the polypeptide is expressed at least at a higher level in a subject with cancer as compared to expression levels in normal subjects, preferably the polypeptide is expressed at least about 5 to about 10 fold higher in a subject with cancer as compared to expression in a normal subject. Preferably the cancer is a HERV[30] cancer and the subject sample is obtained from a mammalian subject, including a primate such as a human subject.

In another embodiment, the invention provides for a method for treating a subject suffering from or susceptible to a HERV tumor comprising isolating dendritic cells from a subject suffering from cancer; and, treating the dendritic cells with one or more of the polypeptides identified by SEQ ID NO: 1 through 22 and 45; fragments and variants thereof. Preferably, the treated dendritic cells are administered to the subject.

In yet another embodiment, autologous dendritic cells can be isolated from a subject, transduced with the vectors described in detail herein, cultured, and re-infused into the subject.

An "isolated" or "purified" population of cells is substantially free of cells and materials with which it is associated in nature. By substantially free or substantially purified APCs is meant at least 50% of the population are APCs, preferably at least 70%, more preferably at least 80%, and even more preferably at least 90% free of non-APCs cells with which they are associated in nature.

Dendritic cells of different maturation stages can be isolated based on the cell surface expression markers. For example, mature dendritic cells are less able to capture new proteins for presentation but are much better at stimulating resting T cells to grow and differentiate. Thus, mature dendritic cells can be of importance. Mature dendritic cells can be identified by their change in morphology; by their nonadherence; and by the presence of various markers. Such markers include, but are not limited to, cell surface markers such as B7.2, CD40, CD11c$^{+}$, and MHC class II. Alternatively, maturation can be identified by observing or measuring the production of pro-inflammatory cytokines. Dendritic cells can be collected and analyzed using typical cytofluorography and cell sorting techniques and devices, such as a fluorescence-activated cell sorter (FACS). Antibodies specific to cell surface antigens of different stages of dendritic cell maturation are commercially available.

The amount of dendritic cells administered to the subject will also vary depending on the condition of the subject and should be determined via consideration of all appropriate factors by the practitioner. Preferably, however, about $1\times10^{6}$ to about $1\times10^{12}$, more preferably about $1\times10^{8}$ to about $1\times10^{11}$, and even more preferably, about $1\times10^{9}$ to about $1\times10^{10}$ dendritic cells are utilized for adult humans. These amounts will vary depending on the age, weight, size, condition, sex of the subject, the type of tumor to be treated, the route of administration, whether the treatment is regional or systemic, and other factors. Those skilled in the art should be readily able to derive appropriate dosages and schedules of administration to suit the specific circumstance and needs of the subject.

Methods of re-introducing cellular components are known in the art and include procedures such as those exemplified in U.S. Pat. No. 4,844,893 to Honsik, et al. and U.S. Pat. No. 4,690,915 to Rosenberg. For example, administration of activated CD8 cells via intravenous infusion is appropriate. Any toxicity, from donor cell infusion, observed in a pregnant female will result in immediate cessation of any further infusions. Toxicity is measured according to the National Cancer Institute (NCI) scale.

Toxicity Grading—The NCI Common Toxicity Scale.

If Grade I-II toxicities occur, the subject may continue with the infusion schedule.

If Grade III toxicity occurs, the "drug" will be held until the toxicity decreases to Grade I or II, then the infusion will be restarted. If Grade III or IV toxicity occurs after the restart, the "drug" infusions will be stopped.

If Grade IV toxicity occurs, the subject is scored as having Grade IV toxicity and the next infusion is reduced to the previous dose. If the previous dose causes Grade IV toxicity, then the "drug" will be stopped.

If Grade IV toxicity occurs in 1 of 3 subjects at a specific dose level, an additional 3 subjects must be entered at that cell-dose level for a total of 6 subjects at that dose level. If 2 of 6 subjects at a cell-dose level develop Grade IV toxicity, this dose is defined as the maximum tolerated dose (MTD). The next 3 subjects will be given 66% (two-thirds) of the previous cell-dose level. For the purposes of evaluation for dose-escalation, each subject at the same dose level should receive at least 4 of 6 infusions.

Large quantities of antigen-presenting dendritic cells can be generated ex vivo as described in U.S. Pat. No. 6,497, 876, which is incorporated herein, in its entirety. Following collection of an subject's $CD34^+$ hematopoietic progenitors and stem cells, cytokines such as granulocyte-macrophage colony stimulating factor (GM-CSF) and flt-3 ligand (flt3-L) can be used to expand the cells in vitro and to drive them to differentiate into cells of the dendritic cell lineage. Cytokines can also be used to increase the numbers of $CD34^+$ cells in circulation prior to collection. The resulting dendritic cells are exposed to an antigen one wishes to elicit an immune response against, and allowed to process the antigen (this procedure is sometimes referred to in the art as "antigen-pulsing"). The antigen-pulsed (or antigen-expressing) dendritic cells are then activated with a CD40 binding protein, and subsequently administered to the subject.

Dendritic cells comprise a heterogeneous cell population with distinctive morphology and a widespread tissue distribution. The dendritic cell system and its role in immunity is reviewed by Steinman, R M., Annu. Rev. Immunol., 9:271-296 (1991), incorporated herein by reference. The cell surface of dendritic cells is unusual, with characteristic veil-like projections, and is characterized by having the cell surface markers $CD1a^+$, $CD4^+$, $CD86^+$, or $HLA\text{-}DR^+$. Dendritic cells have a high capacity for sensitizing MHC-restricted T cells and are very effective at presenting antigens to T cells in situ, both self-antigens during T cell development and tolerance and foreign antigens during immunity.

Because of their effectiveness at antigen presentation, autologous dendritic cells preferably are used ex vivo as alloantigen adjuvants (see, for example, Romani, et al., J. Exp. Med., 180:83 (1994). The use of dendritic cells as immunostimulatory agents has been limited due to the low frequency of dendritic cells in peripheral blood, the limited accessibility of lymphoid organs and the dendritic cells' terminal state of differentiation. Dendritic cells originate from $CD34^+$ bone marrow or peripheral blood progenitors and peripheral blood mononuclear cells, and the proliferation and maturation of dendritic cells can be enhanced by the cytokines GM-CSF sargramostim, Leukine™ (Immunex Corporation, Seattle, Wash.), TNF-α, c-kit ligand (also known as stem cell factor (SCF), steel factor (SF), or mast cell growth factor (MGF)) and interleukin-4. Recently, flt3-L has been found to stimulate the generation of large numbers of functionally mature dendritic cells, both in vivo and in vitro.

Ex Vivo Culture of Dendritic Cells

A procedure for ex vivo expansion of hematopoietic stem and progenitor cells is described in U.S. Pat. No. 5,199,942, incorporated herein by reference. Other suitable methods are known in the art. Briefly, ex vivo culture and expansion comprises: (1) collecting $CD34^+$ hematopoietic stem and progenitor cells from a subject from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used.

Stem or progenitor cells having the CD34 marker constitute only about 1% to 3% of the mononuclear cells in the bone marrow. The amount of $CD34^+$ stem or progenitor cells in the peripheral blood is approximately 10- to 100-fold less than in bone marrow. Cytokines such as flt3-L may be used to increase or mobilize the numbers of dendritic cells in vivo. Increasing the quantity of an subject's dendritic cells may facilitate antigen presentation to T cells for antigen(s) that already exists within the subject, such as a tumor antigen, or a bacterial or viral antigen. Alternatively, cytokines may be administered prior to, concurrently with or subsequent to administration of an antigen to an subject for immunization purposes.

Peripheral blood cells are collected using apheresis procedures known in the art. See, for example, Bishop et al., Blood, vol. 83, No. 2, pp. 610-616 (1994). Briefly, peripheral blood progenitor cells (PBPC) and peripheral blood stem cells (PBSC) are collected using conventional devices, for example, a Haemonetics Model V50 apheresis device (Haemonetics, Braintree, Mass.). Four-hour collections are performed typically no more than five times weekly until approximately $6.5\times10^8$ mononuclear cells (MNC)/kg are collected. The cells are suspended in standard media and then centrifuged to remove red blood cells and neutrophils. Cells located at the interface between the two phases (the buffy coat) are withdrawn and resuspended in HBSS. The suspended cells are predominantly mononuclear and a substantial portion of the cell mixture are early stem cells.

A variety of cell selection techniques are known for identifying and separating $CD34^+$ hematopoietic stem or progenitor cells from a population of cells. For example, monoclonal antibodies (or other specific cell binding proteins) can be used to bind to a marker protein or surface antigen protein found on stem or progenitor cells. Several such markers or cell surface antigens for hematopoietic stem cells (e.g., flt-3, CD34, My-10, and Thy-1) are known in the art, as are specific binding proteins.

In one method, antibodies or binding proteins are fixed to a surface, for example, glass beads or flask, magnetic beads, or a suitable chromatography resin, and contacted with the population of cells. The stem cells are then bound to the bead matrix. Alternatively, the binding proteins can be incubated with the cell mixture and the resulting combination contacted with a surface having an affinity for the antibody-cell complex. Undesired cells and cell matter are removed providing a relatively pure population of stem cells. The specific cell binding proteins can also be labeled with a fluorescent label, e.g., chromophore or fluorophore, and the labeled cells separated by sorting. Preferably, isolation is accomplished by an immunoaffinity column.

Immunoaffinity columns can take any form, but usually comprise a packed bed reactor. The packed bed in these bioreactors is preferably made of a porous material having a substantially uniform coating of a substrate. The porous material, which provides a high surface area-to-volume ratio, allows for the cell mixture to flow over a large contact area while not impeding the flow of cells out of the bed. The substrate should, either by its own properties, or by the addition of a chemical moiety, display high-affinity for a moiety found on the cell-binding protein. Typical substrates include avidin and streptavidin, while other conventional substrates can be used.

In one useful method, monoclonal antibodies that recognize a cell surface antigen on the cells to be separated are typically further modified to present a biotin moiety. The affinity of biotin for avidin thereby removably secures the monoclonal antibody to the surface of a packed bed (see Berenson, et al., J. Immunol. Meth., 91:11, 1986). The packed bed is washed to remove unbound material, and target cells are released using conventional methods Immunoaffinity columns of the type described above that utilize biotinylated anti-CD34 monoclonal antibodies secured to an avidin-coated packed bed are described for example, in WO 93/08268.

An alternative means of selecting the quiescent stem cells is to induce cell death in the dividing, more lineage-committed, cell types using an antimetabolite such as 5-fluorouracil (5-FU) or an alkylating, agent such as 4-hydroxycyclophosphamide (4-HC). The non-quiescent cells are stimulated to proliferate and differentiate by the addition of growth factors that have little or no effect on the stem cells, causing the non-stem cells to proliferate and differentiate and making them more vulnerable to the cytotoxic effects of 5-FU or 4-HC. See Berardi et al., Science, 267:104 (1995), which is incorporated herein by reference.

Isolated stem cells can be frozen in a controlled rate freezer (e.g., Cryo-Med, Mt. Clemens, Mich.), then stored in the vapor phase of liquid nitrogen using dimethylsulfoxide as a cryoprotectant. A variety of growth and culture media can be used for the growth and culture of dendritic cells (fresh or frozen), including serum-depleted or serum-based media. Useful growth media include RPMI, TC 199, Iscoves modified Dulbecco's medium (Iscove, et al., F. J. Exp. Med., 147:923 (1978)), DMEM, Fischer's, alpha medium, NCTC, F-10, Leibovitz's L-15, MEM and McCoy's. Particular nutrients present in the media include serum albumin, transferrin, lipids, cholesterol, a reducing agent such as 2-mercaptoethanol or monothioglycerol, pyruvate, butyrate, and a glucocorticoid such as hydrocortisone 2-hemisuccinate. More particularly, the standard media includes an energy source, vitamins or other cell-supporting organic compounds, a buffer such as HEPES, or Tris, that acts to stabilize the pH of the media, and various inorganic salts. A variety of serum-free cellular growth media is described in WO 95/00632, which is incorporated herein by reference. The collected $CD34^+$ cells are cultured with suitable cytokines, for example, as described herein. $CD34^+$ cells then are allowed to differentiate and commit to cells of the dendritic lineage. These cells are then further purified by flow cytometry or similar means, using markers characteristic of dendritic cells, such as CD1a, HLA DR, CD80 and/or CD86. The cultured dendritic cells are exposed to an antigen, for example, an allogeneic class I HLA molecule, allowed to process the antigen, and then cultured with an amount of a CD40 binding protein to activate the dendritic cell. Alternatively, the dendritic cells are transfected with a gene encoding an allogeneic HLA class I molecule or immune related receptors, and then cultured with an amount of a CD40 binding protein to activate the antigen-presenting dendritic cells.

The activated, antigen-carrying dendritic cells are them administered to a subject in order to stimulate an antigen-specific immune response. The dendritic cells can be administered prior to, concurrently with, or subsequent to, antigen administration. Alternatively, T cells may be collected from the subject and exposed to the activated, antigen-carrying dendritic cells in vitro to stimulate antigen-specific T cells, which are subsequently adoptively infused into the subject with cancer.

Useful Cytokines

Various cytokines will be useful in the ex vivo culture of dendritic cells. Flt3-L refers to a genus of polypeptides that are described in EP 0627487 A2 and in WO 94/28391, both incorporated herein by reference. A human flt3-L cDNA was deposited with the American Type Culture Collection, Rockville, Md., USA (ATCC) on Aug. 6, 1993 and assigned accession number ATCC 69382. IL-3 refers to a genus of interleukin-3 polypeptides as described in U.S. Pat. No. 5,108,910, incorporated herein by reference. A DNA sequence encoding human IL-3 protein suitable for use in the invention is publicly available from the American Type Culture Collection (ATCC) under accession number ATCC 67747. c-kit ligand is also referred to as Mast Cell Growth Factor (MGF), Steel Factor or Stem Cell Factor (SCF), and is described in EP 423,980, which is incorporated herein by reference. Other useful cytokines include Interleukin-4 (IL-4; Mosley et al., Cell 59:335 (1989), Idzerda et al., J. Exp. Med. 171:861 (1990) and Galizzi et al., Intl. Immunol. 2:669 (1990), each of which is incorporated herein by reference) and granulocyte-macrophage colony stimulating factor (GM-CSF; described in U.S. Pat. Nos. 5,108,910, and 5,229,496 each of which is incorporated herein by reference). Commercially available GM-CSF (sargramostim, Leukine™) is obtainable from Immunex Corp., Seattle, Wash.). Moreover, GM-CSF/IL-3 fusion proteins (e.g., a C-terminal to N-terminal fusion of GM-CSF and IL-3) will also be useful in ex vivo culture of dendritic cells. Such fusion proteins are known and are described in U.S. Pat. Nos. 5,199,942, 5,108,910 and 5,073,627, each of which is incorporated herein by reference. A preferred fusion protein is PIXY321 as described in U.S. Pat. No. 5,199,942.

Useful cytokines act by binding a receptor present on the surface of a dendritic cell and transducing a signal. Moreover, additional binding proteins can be prepared as described herein for CD40 binding proteins, that bind appropriate cytokine receptors and transduce a signal to a dendritic cell. For example, WO 95/27062 describes agonistic antibodies to Flt-3, the receptor for Flt-3L, from which various Flt-3 binding. proteins can be prepared. Additional useful cytokines include biologically active analogs of cytokines that are useful for culturing dendritic cells. Useful cytokine analogs have an amino acid sequence that is substantially similar to the native cytokine, and are biologically active capable of binding to their specific receptor and transducing a biological signal. Such analogs can be prepared and tested by methods that are known in the art.

An alternate method for preparing dendritic cells that present antigen is to transfect the dendritic cells with a gene encoding an antigen or a specific polypeptide derived therefrom. Once the dendritic cells express the antigen in the context of MHC, the dendritic cells are activated with a CD40 binding protein, and subsequently administered to the subject to provide a stronger and improved immune response to the antigen.

The activated antigen-presenting dendritic cells can also be used as a vaccine adjuvant and can be administered prior to, concurrently with or subsequent to antigen administration. Moreover, the dendritic cells can be administered to the subject prior to, concurrently with or subsequent to administration of cytokines that modulate an immune response, for example a CD40 binding protein (e.g., soluble CD40L), or a soluble CD83 molecule. Additional useful cytokines include, but are not limited to, Interleukins (IL) 1, 2, 4, 5, 6, 7, 10, 12 and 15, colony stimulating factors (CSF) such as GM-CSF, granulocyte colony stimulating factor (G-CSF), or GM-CSF/IL-3 fusion proteins, or other cytokines such as TNF-$\alpha$ or c-kit ligand. Moreover, biologically active derivatives of these cytokines; and combinations thereof will also be useful.

CD40 is a member of the tumor necrosis factor (TNF)/nerve growth factor (NGF) receptor family, which is defined by the presence of cysteine-rich motifs in the extracellular region (Smith et al., Science 248:1019, 1990; Mallett and Barclay, Immunology Today 12:220; 1991). This family includes the lymphocyte antigen CD27, CD30 (an antigen found on Hodgkin's lymphoma and Reed-Stemberg cells), two receptors for TNF, a murine protein referred to as 4-1BB, rat OX40 antigen, NGF receptor, and Fas antigen. Human CD40 antigen (CD40) is a peptide of 277 amino acids having a molecular weight of 30,600 (Stamenkovic et al., EMBO J. 8:1403, 1989). CD40L is believed to be important in feedback regulation of an immune response. For example, a $CD40^+$ antigen presenting cell will present antigen to a T cell, which will then become activated and express CD40L. The CD40L will, in turn, further activate the antigen presenting cell, increasing its efficiency at antigen presentation, and upregulating expression of Class I and Class II MHC, CD80 and CD86 costimulatory molecules, as well as various cytokines (Caux et al., J. Exp. Med. 180: 1263, 1994).

Purified dendritic cells are then pulsed with (exposed to) antigen, to allow them to take up the antigen in a manner suitable for presentation to other cells of the immune systems. Antigens are classically processed and presented through two pathways. Peptides derived from proteins in the cytosolic compartment are presented in the context of Class I MHC molecules, whereas peptides derived from proteins that are found in the endocytic pathway are presented in the context of Class II MHC. However, those of skill in the art recognize that there are exceptions; for example, the response of $CD8^+$ tumor specific T cells, which recognize exogenous tumor antigens expressed on MHC Class I. A review of MHC-dependent antigen processing and peptide presentation is found in Germain, R. N., Cell 76:287 (1994).

Numerous methods of pulsing dendritic cells with antigen are known; those of skill in the art regard development of suitable methods for a selected antigen as routine experimentation. In general, the antigen is added to cultured dendritic cells under conditions promoting viability of the cells, and the cells are then allowed sufficient time to take up and process the antigen, and express antigen peptides on the cell surface in association with either Class I or Class II MHC, a period of about 24 hours (from about 18 to about 30 hours, preferably 24 hours). Dendritic cells may also be exposed to antigen by transfecting them with DNA encoding the antigen. The DNA is expressed, and the antigen is presumably processed via the cytosolic/Class I pathway.

The present invention provides methods of using therapeutic compositions comprising activated, antigen-pulsed dendritic cells. The use of such cells in conjunction with soluble cytokine receptors or cytokines, or other immunoregulatory molecules is also contemplated. The inventive compositions are administered to stimulate an allogeneic immune response, and can be given by bolus injection, continuous infusion, sustained release from implants, or other suitable technique. Typically, the cells on the will be administered in the form of a composition comprising the antigen-pulsed, activated dendritic cells in conjunction with physiologically acceptable carriers, excipients or diluents. Such carriers will be nontoxic to recipients at the dosages and concentrations employed. Neutral buffered saline or saline mixed with serum albumin are exemplary appropriate diluents.

For use in stimulating a certain type of immune response, administration of other cytokines along with activated, antigen-pulsed dendritic cells is also contemplated. Several useful cytokines (or peptide regulatory factors) are discussed in Schrader, J. W. (Mol Immunol 28:295; 1991). Such factors include (alone or in combination) Interleukins 1, 2, 4, 5, 6, 7, 10, 12 and 15; granulocyte-macrophage colony stimulating factor, granulocyte colony stimulating factor; a fusion protein comprising Interleukin-3 and granulocyte-macrophage colony stimulating factor; Interferon-γ, TNF, TGF-β, flt-3 ligand and biologically active derivatives thereof. A particularly preferred cytokine is CD40 ligand (CD40L). Other cytokines will also be useful, as described herein. DNA encoding such cytokines will also be useful in the inventive methods, for example, by transfecting the dendritic cells to express the cytokines. Administration of these immunomodulatory molecules includes simultaneous, separate or sequential administration with the cells of the present invention.

In another embodiment, the invention provides for a polypeptide identified by any one of SEQ ID NO: 1 through 22 and 45 having a sequence identity to anyone one of SEQ ID NO: 1 through 22 and 45 of at least about 10%, more preferably, 25%, even more preferably about 40%, 50%, 60%, 70%, 80%, 90%, or 99.9%. Dendritic cells can be pulsed with any of these polypeptides during ex-vivo culture.

In one aspect of the invention, the polypeptide comprises SEQ ID NO: 14. Preferably, the polypeptide binds to HLA molecules with a high avidity and has a higher association constant ($K_a$) for the HLA than a native polypeptide and/or a lower dissociation constant ($K_d$) for the HLA than a native polypeptide.

In another aspect of the invention, antigen presentation, by antigen presenting cells of the polypeptides induces an immune response, preferably a cellular immune response. For example, the cellular immune response is a cytotoxic T cell response, a T helper cell response, or a B cell immune response.

In yet another aspect, variants of the nucleic acid molecule encoding polypeptides as identified by SEQ ID NO: 1 through 22 and 45 can be used to transduce immune cells for the detection and lysing of, for example, HERV positive cancers. An "allele" or "variant" is an alternative form of a gene. Of particular utility in the invention are variants of the genes encoding any potential $HERV^+$ tumor cell markers identified by the methods of this invention. Variants may result from at least one mutation in the nucleic acid sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides. Each of these types of changes may occur alone, or in combination with the others, one or more times in a given sequence.

The compositions and methods of the present invention also encompass variants of the above polypeptides and nucleic acid sequences encoding such polypeptides. A polypeptide "variant," as used herein, is a polypeptide that differs from the native polypeptide in substitutions and/or modifications, such that the antigenic and/or immunogenic properties of the polypeptide are retained. Such variants may generally be identified by modifying one of the above polypeptide sequences and evaluating the reactivity of the modified polypeptide with antisera and/or T-cells as described above. Nucleic acid variants may contain one or more substitutions, deletions, insertions and/or modifications such that the antigenic and/or immunogenic properties of the encoded polypeptide are retained. One preferred variant of the polypeptides described herein is a variant that contains nucleotide substitutions, deletions, insertions and/or modifications at no more than 20% of the nucleotide positions.

Preferably, but not limited to, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) vat, ile, leu, met, ala, phe; (4) lys, arg, his; and (5) phe, tyr, trp, his. However, any type of substitution is within the scope and embodiments of the invention.

Variants may also (or alternatively) be modified by, for example, the deletion or addition of amino acids that have minimal influence on the immunogenic or antigenic properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

In general, nucleotide sequences encoding all or a portion of the polypeptides described herein may be prepared using any of several techniques. For example, cDNA molecules encoding such polypeptides may be cloned on the basis of the HERV tumor-specific expression of the corresponding mRNAs, using differential display PCR. This technique compares the amplified products from RNA template prepared from normal and HERV tumor tissue. cDNA may be prepared by reverse transcription of RNA using a random primer, such as for example, $(dT)_{12}$ AG primer. Following amplification of the cDNA using a random primer, a band corresponding to an amplified product specific to the tumor RNA may be cut out from a silver stained gel and subcloned into a suitable vector, such as the adenovirus vector described in the examples which follow. Nucleotide sequences encoding all or a portion of the HERV tumor-specific polypeptides disclosed by any one of SEQ ID NOs:1 through 6 and variants thereof may be amplified from cDNA prepared as described above using any random primers.

Alternatively, a gene encoding a polypeptide as described herein (or a portion thereof) may be amplified from human genomic DNA, or from tumor cell cDNA, via polymerase chain reaction.

In an embodiment of the invention the presence of the one or more nucleic acid molecules is correlated to a sample of a normal subject. The sample is preferably obtained from a mammal suspected of having a proliferative cell growth disorder, in particular, a $HERV^{+}$cancer.

Percent identity and similarity between two sequences (nucleic acid or polypeptide) can be determined using a mathematical algorithm (see, e.g., Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991).

In another embodiment, HERV peptide fragments and derivatives of the invention are of a sufficient length such that they activate the immune system resulting in the lysing of cancer cells, such as, for example cells expressing HERV antigens. HERV nucleic acid molecules, fragments and derivatives encoding for any one of the polypeptides identified by SEQ ID NO: 1 through 22 and 45, thus preferably comprise at least about 90% nucleotides as compared to the sequence identified by any one of SEQ ID NO: 1 through 22 and 45, usually at least about 80% nucleotides as compared to the sequence identified by any one of SEQ ID NO: 1 through 22 and 45, more usually at least about 70% nucleotides as compared to the sequence identified by anyone of SEQ ID NO: 1 through 22 and 45, even more typically at least about 40% or 50% nucleotides.

To determine the percent identity of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In an embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence. The nucleotides at corresponding nucleotide positions are then compared. When a position in the first sequence is occupied by the nucleotide as the corresponding position in the second sequence, then the molecules are identical at that position (as used herein nucleic acid "identity" is equivalent to nucleic acid "sequence identity"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In an embodiment, the percent identity between two nucleotide sequences is determined using the GAP program in the GCG software package (available at online through the Genetics Computer Group), using a NWSgapdna.CMP matrix and a gap weight of 40, 50, 60, 70, or 80 and a length weight of 1, 2, 3, 4, 5, or 6. A preferred, non-limiting example of parameters to be used in conjunction with the GAP program include a Blosum 62 scoring matrix with a gap penalty of 12, a gap extend penalty of 4, and a frameshift gap penalty of 5.

In another embodiment, the percent identity between two amino acid or nucleotide sequences is determined using the algorithm of Meyers and Miller (Comput. Appl. Biosci. 4:11-17 (1988)) which has been incorporated into the ALIGN program (version 2.0 or version 2.0U), using a PAM120 weight residue table, a gap length penalty of 12 and a gap penalty of 4.

The treatment of neoplastic disease or neoplastic cells, refers to an amount of the vectors and/or peptides, described throughout the specification and in the Examples which follow, capable of invoking one or more of the following effects: (1) inhibition, to some extent, of tumor growth, including, (i) slowing down and (ii) complete growth arrest; (2) reduction in the number of tumor cells; (3) maintaining tumor size; (4) reduction in tumor size; (5) inhibition, including (i) reduction, (ii) slowing down or (iii) complete prevention, of tumor cell infiltration into peripheral organs; (6) inhibition, including (i) reduction, (ii) slowing down or (iii) complete prevention, of metastasis; (7) enhancement of anti-tumor immune response, which may result in (i) maintaining tumor size, (ii) reducing tumor size, (iii) slowing the growth of a tumor, (iv) reducing, slowing or preventing invasion or (v) reducing, slowing or preventing metastasis; and/or (8) relief, to some extent, of one or more symptoms associated with the disorder.

Thus in one aspect of the invention any variant, fragment, mutant can be used to transduce immune cells, such as for example dendritic cells, for the treatment of an subject suffering from, or, prophylactically to an subject susceptible to cancer. As discussed above, a preferred use of nucleic acid sequences identified in the present invention, is for the generation of treatments that lyse for example, HERV cancer cells. The nucleic acid molecules can be expressed by a vector containing a DNA segment encoding the wild-type, alleles, variants, mutations or fragments of the genes. Mutations and alleles of the nucleic acid molecules are also preferably used in the construction of a vector for use in treatment. The vector comprising the desired nucleic acid sequence for conferring resistance to, for example, HERV positive cancer, preferably has at least one such nucleic acid sequence. Alternatively, the vector may be comprised of more than one such nucleic acid sequence, or combinations of allelic variants. The vector can also be comprised of cassettes of different allelic variants or wild type nucleic acid molecules.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual, Second Edition* (1989) Cold Spring Harbor Laboratory Press, Cold Spring Harbor, N.Y. (herein "Sambrook et al., 1989"); *DNA Cloning: A Practical Approach, Volumes I and II* (D. N. Glover ed. 1985); Oligonucleotide Synthesis (M. J. Gait ed. 1984); Nucleic Acid Hybridization [B. D. Hames & S. J. Higgins eds. (1985)]; Transcription And Translation [B. D. Hames & S. J. Higgins, eds. (1984)]; Animal Cell Culture [R. I. Freshney, ed. (1986)]; Immobilized Cells And Enzymes [IRL Press, (1986)]; B. Perbal, A Practical Guide To Molecular Cloning (1984); F. M. Ausubel et al. (eds.), Current Protocols in Molecular Biology, John Wiley & Sons, Inc. (1994).

Introducing the genes, fragments or alleles thereof, into a subject can include use of vectors, liposomes, naked DNA, adjuvant-assisted DNA, gene gun, catheters, etc. Vectors include chemical conjugates such as described in WO 93/04701, which has a targeting moiety (e.g. a ligand to a cellular surface receptor), and a nucleic acid binding moiety (e.g. polylysine), viral vector (e.g. a DNA or RNA viral vector), fusion proteins such as described in PCT/US95/02140 (WO 95/22618) which is a fusion protein containing a target moiety (e.g. an antibody specific for a target cell) and a nucleic acid binding moiety (e.g. a protamine), plasmids, phage etc. The vectors can be chromosomal, non-chromosomal or synthetic.

In another embodiment, cells are isolated and purified cell from a sample, subject or donor subject and are used in functional assays to determine any properties of the cells. Depending on the isolated and purified cellular population, appropriate functional assays known in the art can be conducted. For example, if the population of cells are T cells specific for a desired antigen such as a tumor antigen, cytotoxic T cell assays, T cell proliferation assays, cytokine profiles, determination of surface antigens for T cell maturity or memory T cells, etc., can be carried out.

Isolation of cells useful in the present invention are well known in the art. For example, peripheral blood mononuclear cells (PBMCs) can be obtained from a subject and isolated by density gradient centrifugation, e.g., with Ficoll/Hypaque. Specific cell populations can be depleted or enriched using standard methods. For example, monocytes/macrophages can be isolated by adherence on plastic. T cells or B cells can be enriched or depleted, for example, by positive and/or negative selection using antibodies to T cell or B cell surface markers, for example by incubating cells with a specific primary monoclonal antibody (mAb), followed by isolation of cells that bind the mAb using magnetic beads coated with a secondary antibody that binds the primary mAb. Peripheral blood or bone marrow derived hematopoietic stem cells can be isolated by similar techniques using stem cell-specific mAbs (e.g., anti-CD34 mAbs). Specific cell populations can also be isolated by fluorescence activated cell sorting according to standard methods. Monoclonal antibodies to cell-specific surface markers known in the art and many are commercially available.

The pharmaceutical compositions are generally formulated as sterile, substantially isotonic and in full compliance with all Good Manufacturing Practice (GMP) regulations of the U.S. Food and Drug Administration.

If desired, a large proportion of terminally differentiated cells may be removed by initially using a "relatively crude" separation. For example, magnetic bead separations may be used initially to remove large numbers of lineage committed cells. Desirably, at least about 80%, usually at least 70% of the total hematopoietic cells can be removed.

Procedures for separation may include but are not limited to, magnetic separation, using antibody-coated magnetic beads, affinity chromatography, cytotoxic agents joined to a monoclonal antibody or used in conjunction with a monoclonal antibody, including but not limited to, complement and cytotoxins, and "panning" with antibody attached to a solid matrix, e.g., plate, elutriation or any other convenient technique.

Procedures for screening can include, methods of screening for molecules to generate an immune response to a HERV tumor antigen. The methods may include:

altering a nucleic acid encoding a portion of the non-variable number of tandem repeats of HERV;

expressing the altered nucleic acid to produce a molecule;

contacting a dendritic cell with the molecule; and contacting a T-cell with the dendritic cell, wherein a modulation of the IFN-γ production of the T-cell indicates that the molecule may generate an immune response.

Techniques providing accurate separation include but are not limited to, flow cytometry, which can have varying degrees of sophistication, e.g., a plurality of color channels, low angle and obtuse light scattering detecting channels, impedance channels, etc.

The peptide disclosed herein may be encoded by the corresponding sequences listed herein, but may also be encoded by degenerate codons, including:

| Amino acid | Code |
|---|---|
| A | GCT, GCC, GCA, GCG |
| R | CGT, CGC, CGA, CGG, AGA, AGG |
| N | AAT, AAC |
| D | GAT, GAC |
| C | TGT, TGC |
| G | GGT, GGC, GGA, GGG |
| Q | CAA, CAG |
| E | GAA, GAG |
| H | CAT, CAC |
| I | ATC, ATT, ATA |
| L | TTA, TTG, CTT, CTC, CTA, CTG |
| K | AAA, AAG |
| M | ATG |
| F | TTT, TTC |
| P | CCT, CCC, CCA, CCG |
| S | TCT, TCC, TCA, TCG, AGT, AGC |

-continued

| Amino acid | Code |
|---|---|
| T | ACT, ACC, ACA, ACG |
| W | TGG |
| Y | TAT, TAC |
| V | GTT, GTC, GTA, GTG |

The invention has been described in detail with reference to embodiments thereof. However, it will be appreciated that those skilled in the art, upon consideration of this disclosure, may make modifications and improvements within the spirit and scope of the invention. The following non-limiting examples are illustrative of the invention.

Exemplary Embodiments

EXAMPLE 1

Immune Populations Mediating GVT Effects

Ten of the first 19 and subsequently 28 of 75 patients treated with Cy/Flu based nonmyeloablative transplantation had regression of their disease, consistent with a donor immune mediated anti-tumor effect. The first patient treated on study with metastatic RCC remains in remission now more than 8 years later. While the exact mechanisms underlying regression of metastatic RCC following allogeneic HCT are not known, clinical observations suggest an alloimmune effect mediated by donor T-cells. The majority of patients who achieve a disease response show early tumor growth in the first few months after transplantation, when the newly engrafted donor immune system was checked by immunosuppressive therapy or when mixed T-cell chimerism prevailed (leading to "tolerance" of normal host and the tumor). Tumor regression was typically delayed (4-8 months) and followed conversion to predominantly donor T cell chimerism after immunosuppression had been withdrawn or was reduced. As had previously been described in patients with hematological malignancies, acute GVHD was associated with an increased probability of tumor response. These clinical observations suggest disease regression in this setting could be the consequence of alloreactive T-cells targeting minor histocompatibility antigens (mHa) that are broadly expressed on both normal tissues and tumor cells. However, tumor shrinkage observed in the absence of or temporally distant from GVHD, implies tumor specific immune effectors might be involved in mediating RCC regression. Finally, regression of RCC following a donor lymphocyte infusion (DLI) or after treatment with low-dose subcutaneous interferon-alpha has also been observed, suggesting the mediators of the GVT effect may be analogous to those in leukemia regression.

Based on clinical data as well as knowledge of the mediators of the graft-versus-leukemia effect, donor T lymphocytes and possibly natural killer (NK) cells are the likely effector populations mediating graft-vs-RCC effects.

Difficulty in generating RCC cell lines from patients undergoing transplantation has hampered in vitro studies evaluating the role of the donor immune system in mediating tumor regression. In an effort to characterize GVT effectors and their tumor antigens, RCC cell lines were generated to use as targets in cytotoxicity assays in four patients (two non-responders and two responders) undergoing cyclophosphamide/fludarabine-based allogeneic HCT from HLA matched siblings (Table below).

| RCC Patient # | Age/Gender | Tumor Type | # Metastatic Sites | GVHD Grade/ Onset day | # DLIs | GVT Effect | Survival Day |
|---|---|---|---|---|---|---|---|
| 11 | 37/Male | Clear Cell | 2 | 0 | 4 | No | 303 |
| 27 | 40/Male | Clear Cell | 2 | +65/Grade II | 1 | Yes/PR Day +160 | 549 |
| 31 | 51/Male | Clear Cell | 3 | +115/Grade II | 3 | Yes/PR Day +183 | 1480 |
| 68 | 48/Male | Clear Cell | 1 | +22/Grade II | 1 | No | 203 |

The precursor frequency of CD8+ T cells isolated from peripheral blood lymphocytes (PBL) that were reactive against patient B-Cells and patient RCC cells was measured using an ELISPOT analysis of IFN-g secretion. Alloreactive donor T-cells that recognized patient B-cells were identified to have expanded in the blood of all 4 patients within the first few months of transplantation. No donor baseline recognition of patient RCC cells could be measured. However, following in vivo priming, RCC reactive CD8+ T-cells of donor origin were identified in 3 of 4 patients (FIG. 1). In one patient (a nonresponder), these populations expanded transiently then disappeared in contrast to the two patients who had a disease response in which RCC reactive T-cells were detected for 1.5 years and >4 years post transplant. These data provide some of the first evidence that donor CD8+ T-cells can be primed in vivo to recognize patient RCC cells following allogeneic HCT.

To better characterize the antigens expressed on tumor cells serving as a target for a GVT effect, PBMC collected from patient #31 at multiple time-points after transplantation were expanded in-vitro with irradiated autologous patient tumor cells. RCC patient #31 (Patient code SAUJ) developed liver and skin GVHD on day +121 following withdrawal of CSA on day +100. On day +160, regression of pulmonary metastasis was noted radiographically. CD8+ T cells isolated from fresh PBMC collected at multiple time points post transplant were identified that recognized patient tumor cells as measured by ELISPOT for IFN-g secretion (FIG. 1). ELISPOT analysis showed RCC reactive T-cells were detectable as early as +119 days post transplant and persisted for more than 4 years post transplant. RCC reactive T-cells could not be identified in either the patient pre-transplant or from PBMC collected from the donor consistent with in vivo priming of donor T cells to an antigen expressed on the patient's RCC cells.

PBMC collected from the patient SAUJ at multiple post transplant time points (days +119, 364, 1106, and 1213) were stimulated in vitro with irradiated patient tumor cells. At all time points tested, these CTL lines showed high degrees of cytotoxicity against patient RCC cells.

Figure 2:
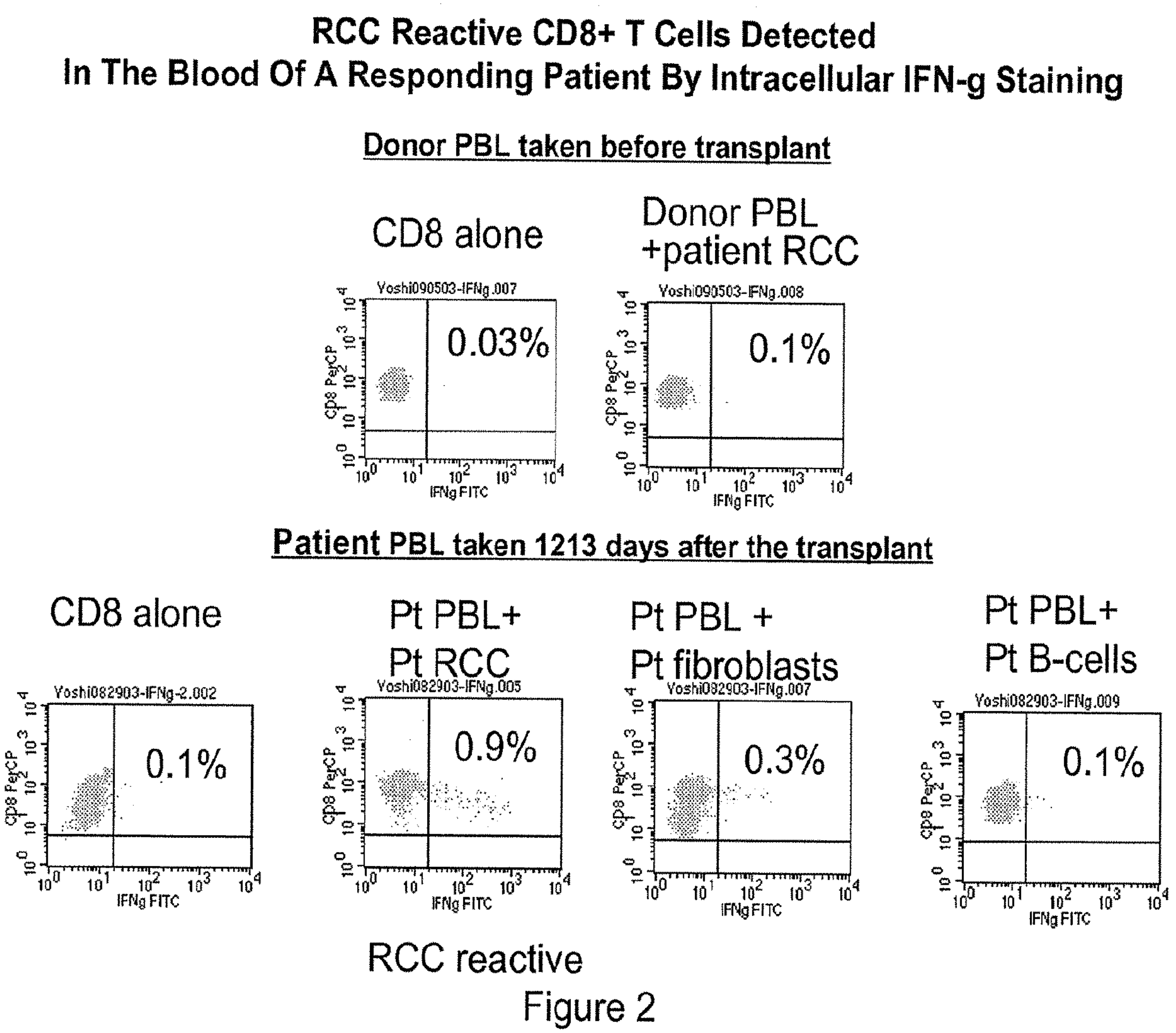
FIG. 2 depicts flow cytometry analysis of PBMC from day +1213 showing RCC Reactive CD8+ T Cells Detected In The Blood Of A Responding Patient By Intracellular IFN-g Staining
Figure 3:
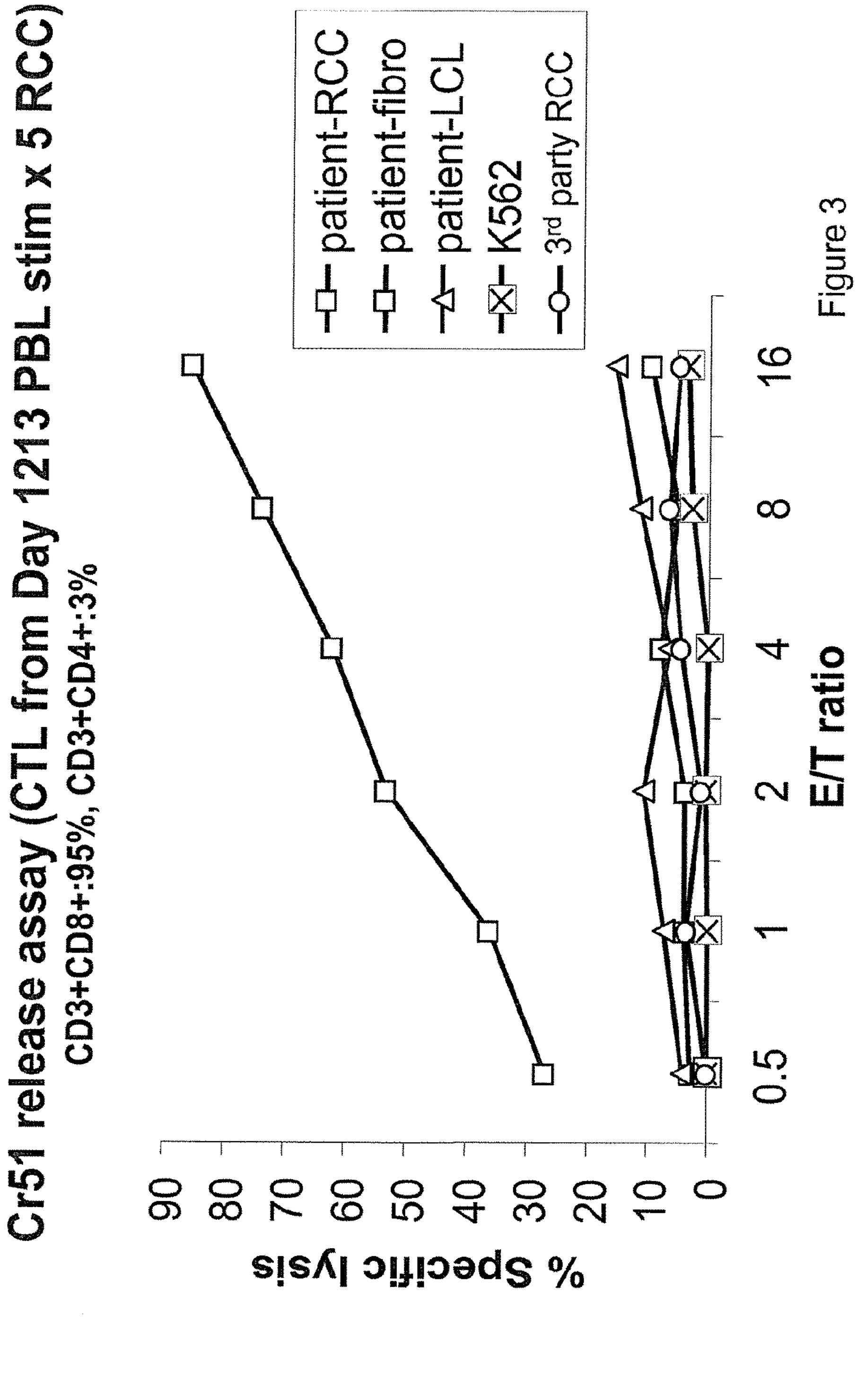
FIG. 3 depicts results of a Cr51 release assay showing a pattern consistent with tumor restricted recognition, lysing patient RCC cells but not patient EBV-LCL, patient fibroblasts, K562 cells or 3$^{rd}$ party MHC mismatched RCC cells.
Figure 4:
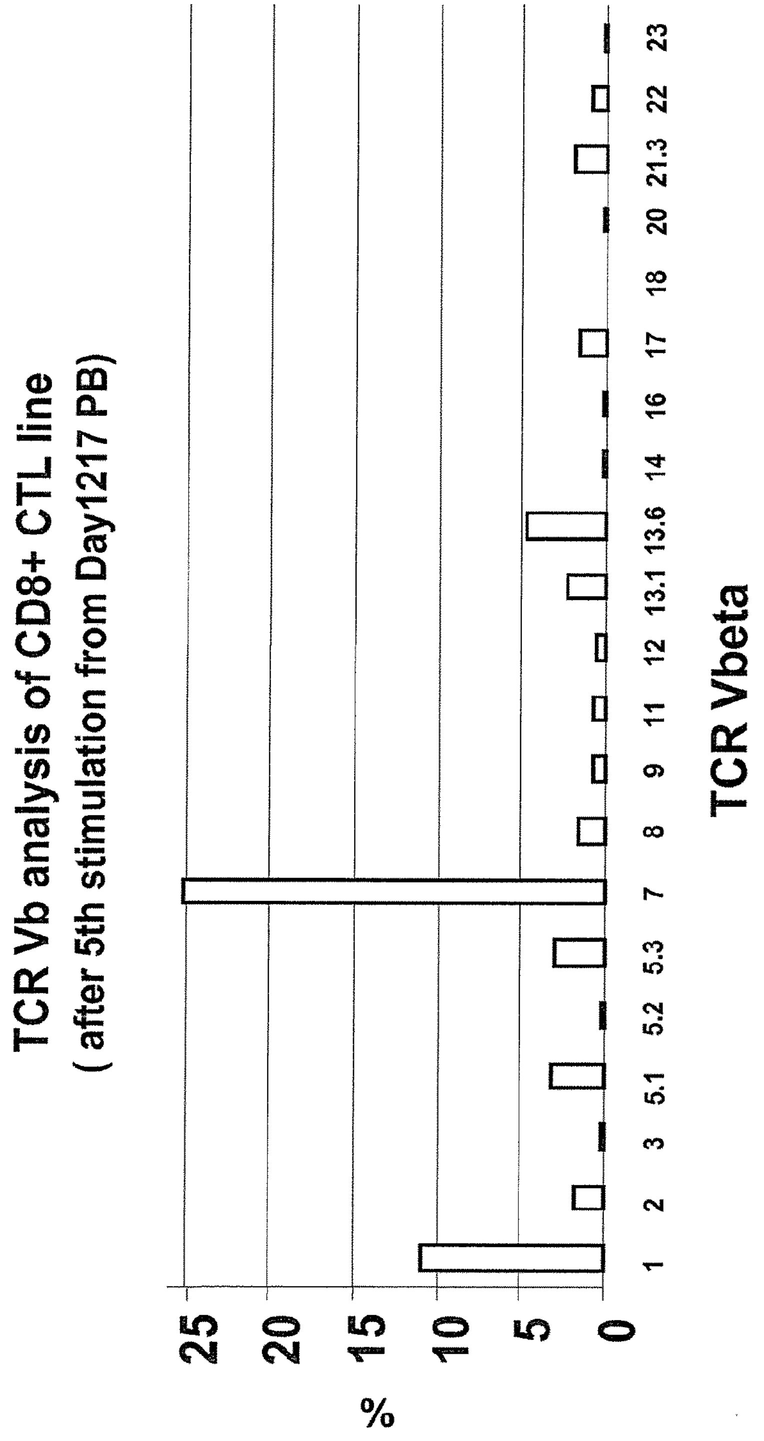
FIG. 4 graphically depicts a flow cytometric based analysis of a CTL line showing the dominant CD8+ T-cell population expressed TCR V beta 7.
Figure 5:
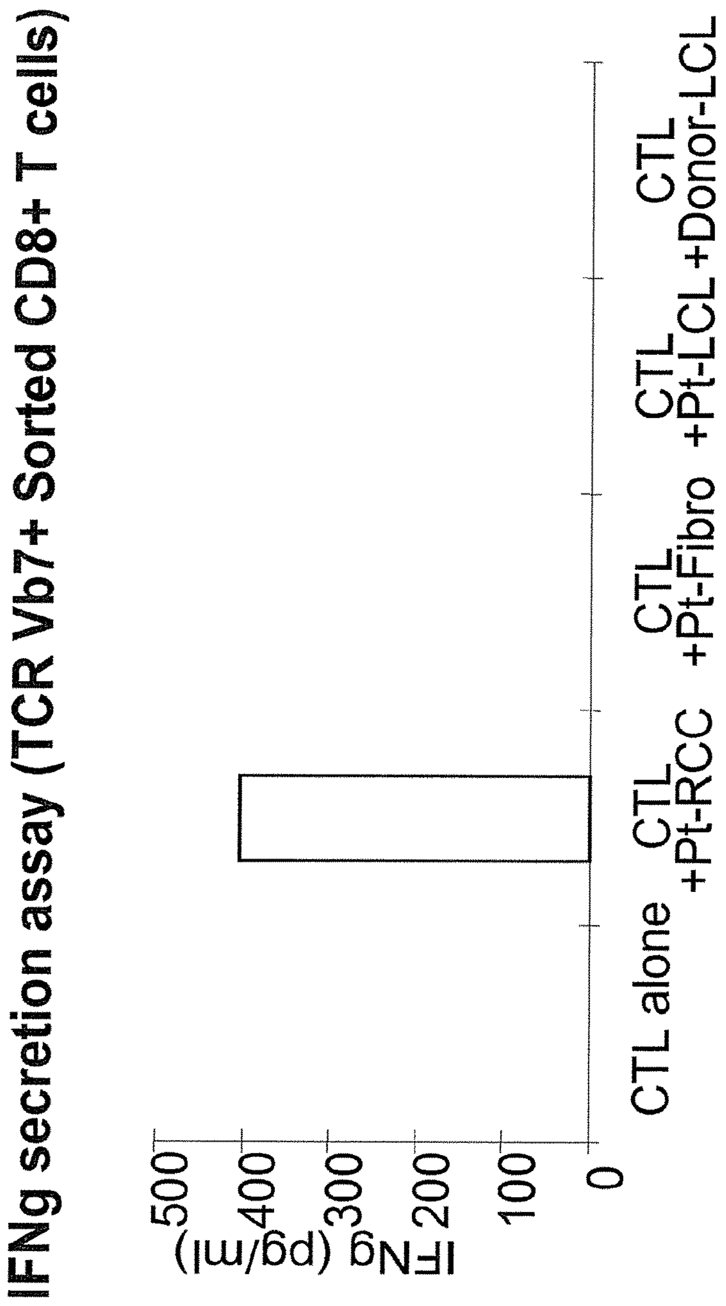
FIG. 5 graphically depicts the results of an IFNg secretion assay.
Figure 6:
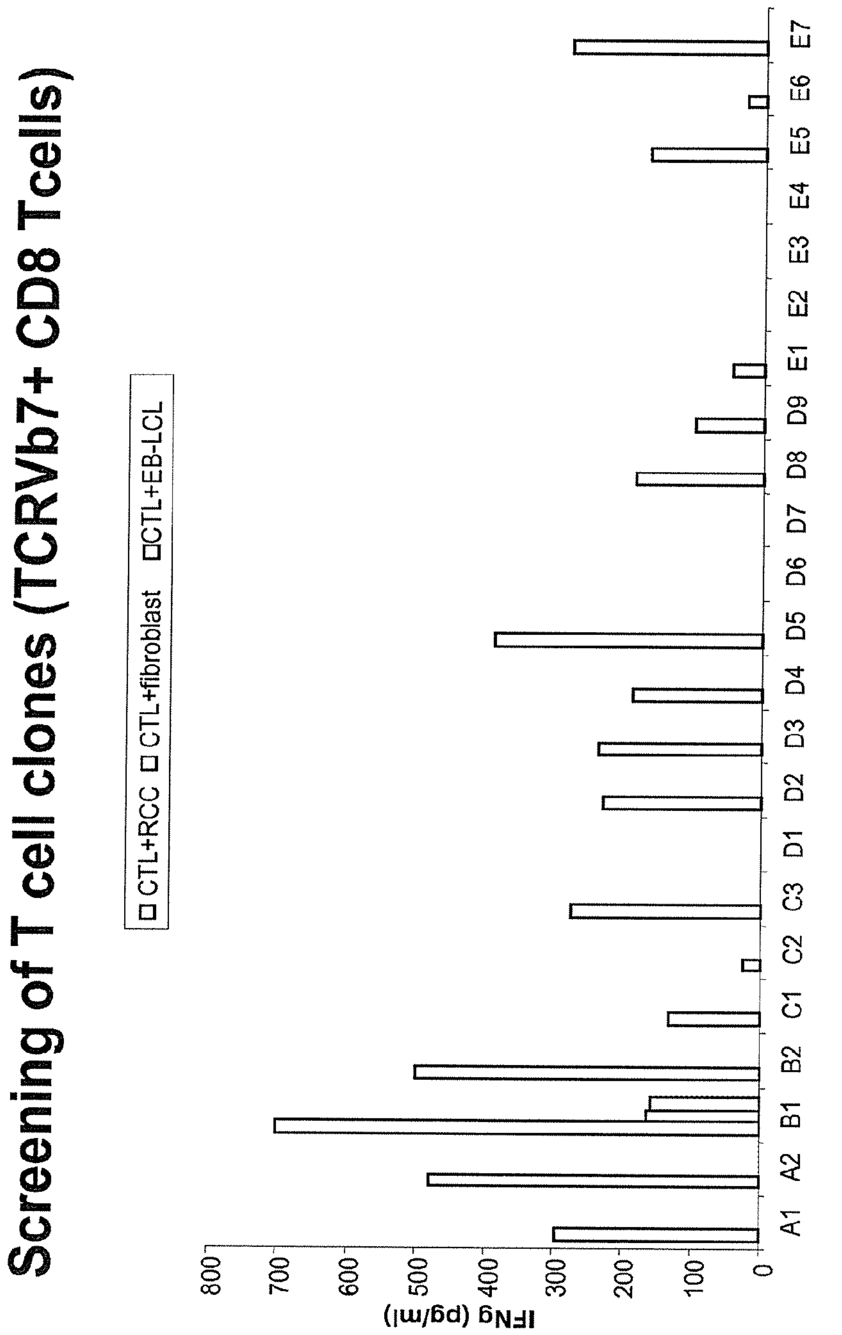
FIG. 6 depicts the results of the screening of T cell clones.
Figure 7:
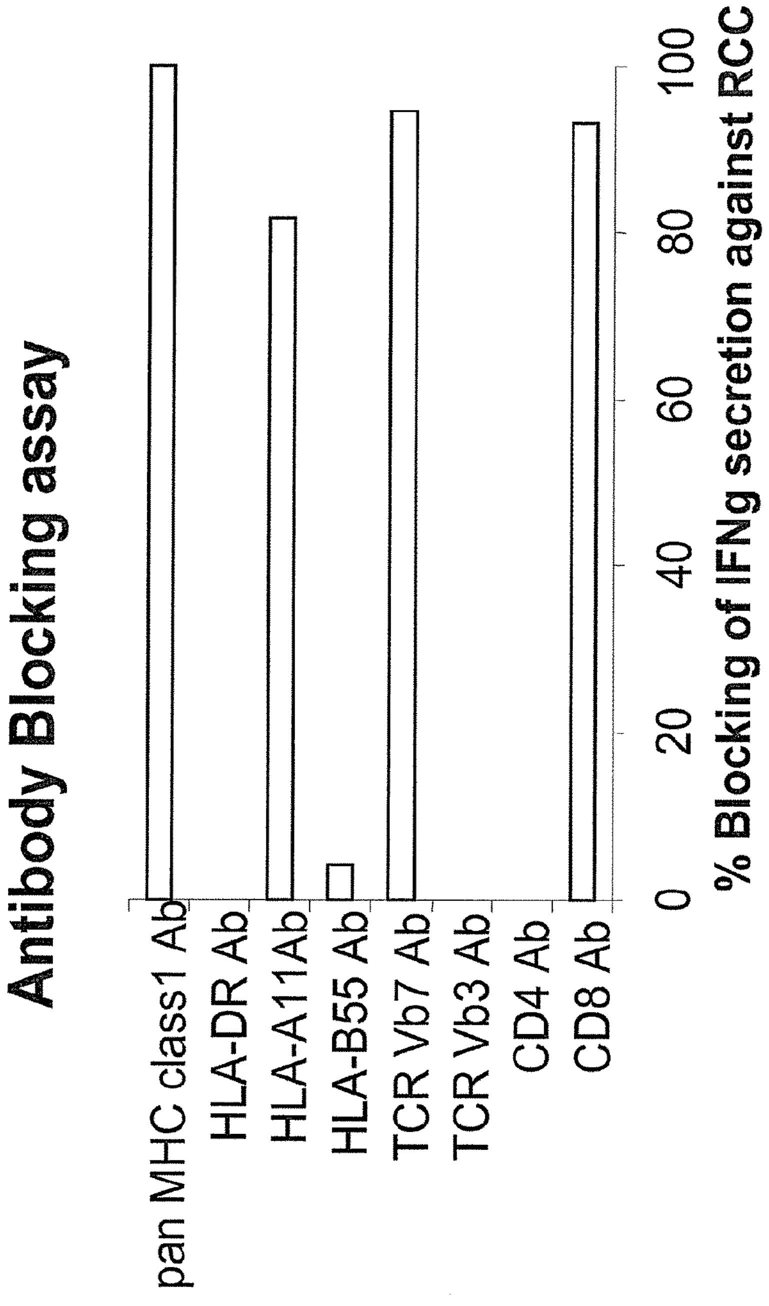
FIG. 7 depicts the results of an antibody blocking assay.

Intracellular staining for IFN-G showed fresh PBMC collected from the patient on day+1213 co-cultured with patient RCC cells contained a high frequency of CD8+ T cells (0.9%) reactive against the tumor with minimal reactivity against patient fibroblasts or patient B cells (FIG. 2). PBMC from day +1213 were stimulated with irradiated patient tumor cells every 2 weeks in media containing IL-2 and IL-15. After 5 stimulations, these CTL were analyzed by flow cytometry and consisted of 98% CD3+T cells and 95% CD3+/CD8+ T-cells. These CTL showed a pattern consistent with tumor restricted recognition, lysing patient RCC cells but not patient EBV-LCL, patient fibroblasts, K562 cells or $3^{rd}$ party MHC mismatched RCC cells (FIG. 3). Flow cytometric based analysis of this CTL line showed the dominant CD8+ T-cell population expressed TCR V beta 7 (25%; FIG. 4). A pure population (>99%) of bulk TCR V beta 7+CD8+ T-cells were subsequently isolated from this CTL line by flow sorting. An ELISA assay showed these V beta 7+CTL secreted IFN-g when co-cultured with patient RCC cells but not when co-cultured with patient or donor EBV-LCL or patient fibroblasts (FIG. 5). V beta 7+CD8+ T-cell clones were next expanded by limiting dilution (0.3, 1, or 3 cells/well of 96-well round bottom culture plates) from V beta 7+bulk T cells. A number of CD8+ V beta 7+ T-cell clones expanded with cytokine profiles consistent with tumor restricted recognition; these clones secreted IFN-g when co-cultured with patient tumor cells but not when cultured with patient EBV-LCL or patient fibroblasts (FIG. 6). An ELISA assay showed blocking of MHC class I molecules or HLA A-11 on RCC cells using monoclonal antibodies nearly completely abolished the secretion of IFN-g that occurred when bulk V beta 7+ sorted CD8+ T-cells were co-cultured with patient RCC cells (FIG. 7); in contrast, no decrease in IFN-g secretion occurred when tumor cells were incubated with blocking antibodies to HLA-DR or HLA B55 (patient HLA type is HLA A11,11, B 52, 55). These findings are consistent with V beta 7+ CD8+ CTL recognizing a peptide expressed on patient RCC cells in the context of an HLA-A 11 molecule.

Figure 8:
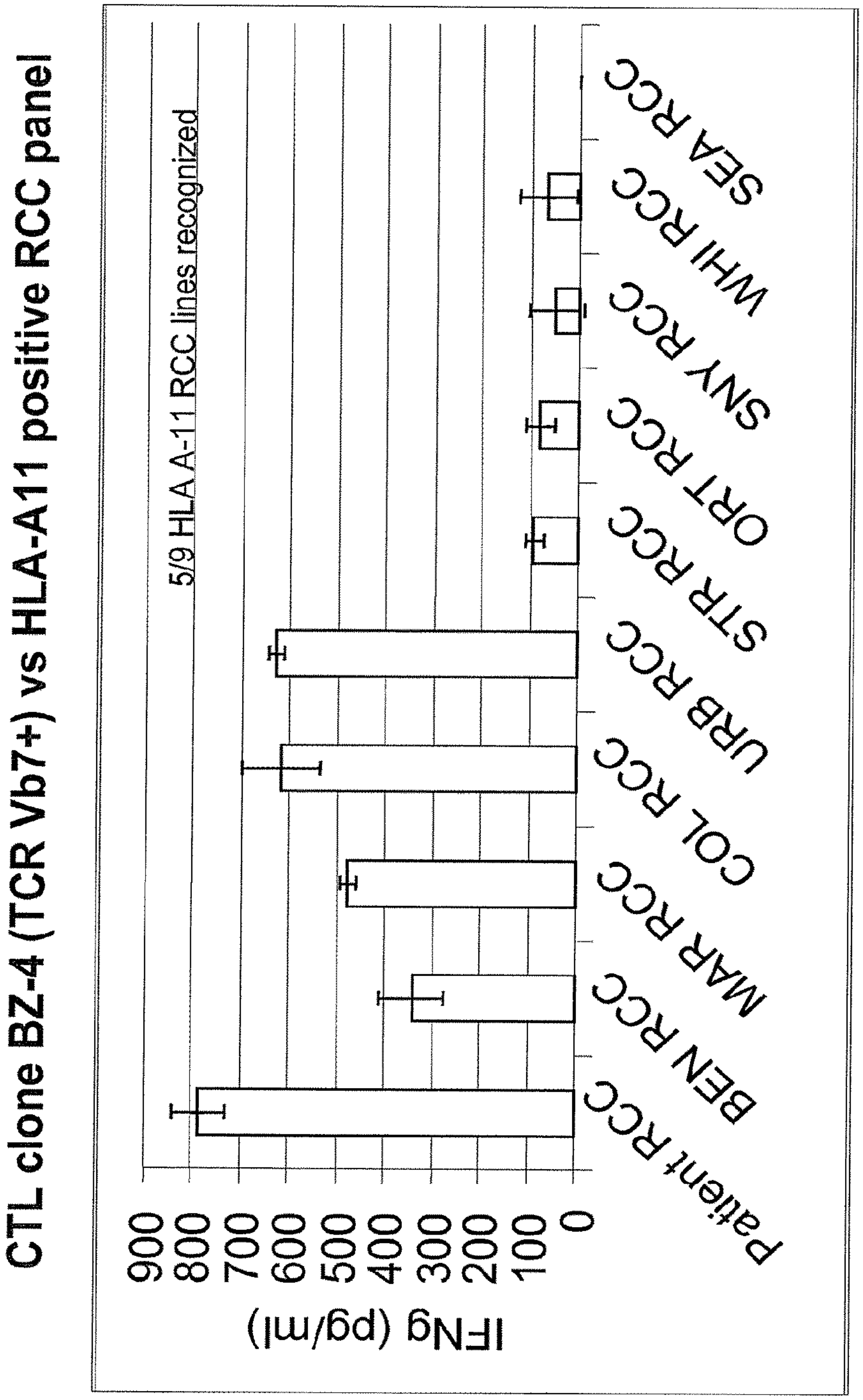
FIG. 8 depicts the results testing for clonal T-cell recognition of multiple HLA A11+RCC tumor cell lines.
Figure 9:
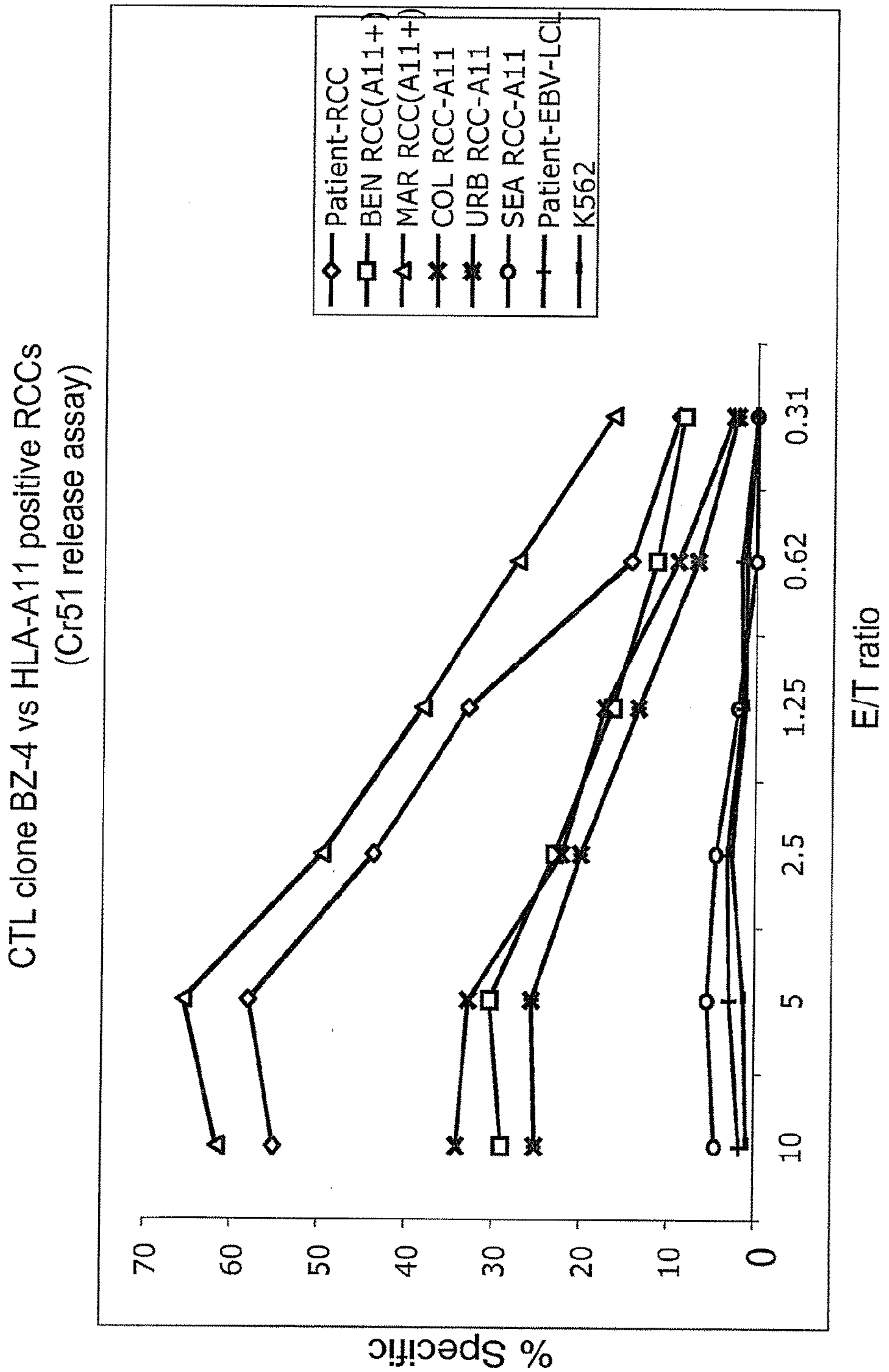
FIG. 9 depicts the results of a cytotoxicity assay, clone BZ-4 lysed all 5 RCC cell lines that induced IFN-g secretion.

CD8+ V beta 7+ clone BZ-4, isolated by limiting dilution from bulk V beta 7 sorted CTL, was then tested for recognition of multiple HLA A11+RCC tumor cell lines; this clone secreted high levels of IFN-g against 5/10 tumor lines tested (FIG. 8). In a cytotoxicity assay, clone BZ-4 lysed all 5 RCC cell lines that induced IFN-g secretion. Taken altogether, these data suggest this antigen may be commonly expressed on RCC tumor cells (FIG. 9).

cDNA Expression Cloning to Identify the Antigen Recognized by Allogeneic Vβ7+ $CD8^+$ T Cells: Construction of the cDNA Library For the construction of the cDNA library, poly (A)+ RNA was purified from the RCC cell line SAUJ-RCC (RCC patient #31) using FastTrack MAG Maxi mRNA isolation kit (Invitrogen, Carlsbad, Calif.). cDNA was prepared with the Creator SMART cDNA library construction kit (Clontech, Mountain View, Calif.) and was ligated to the eukaryotic plasmid expression vector pME-SMART (pME-SMART is derived from a eukaryotic expression vector pME18S [kind gift of Atsushi Miyajima, University of Tokyo] so that the vector accommodates cDNA flanked by SfiI sites). The ligation reaction was subjected to phenol-chloroform extraction, ethanol precipitation, two rounds of ethanol rinse, and the pellet was dissolved into 20 μl of water. Electroporation was done by adding 2 μL of the solution to 40 μl of electro competent cells DH-10B (Invitrogen) at the condition of 1.8 kV, 200 Ω, 25 μF in a cuvette with 1 mm gap. After the electroporation, *E. coli* cells were transferred to a tube containing 1 mL SOC medium, cultured at 37° C. for 1 hour and the part of the culture was plated to LB agar plate supplemented with ampicillin to titrate the library. *E. coli* cells were kept at 4° C. overnight and after the titration, inoculated into 96-well format culture blocks (10 blocks) with 1.2 ml of Super Broth (KD Medical, Columbia, Md.) at about 100 clones/well (total cDNA library complexity: ~$1\times10^5$ clones). After 24 hours culture, plasmid DNA was purified using Qiaprep 96 Turbo Mini-prep kit (Qiagen, Valencia, Calif.).

Screening of SAUJ-RCC cDNA Library

Figure 10:
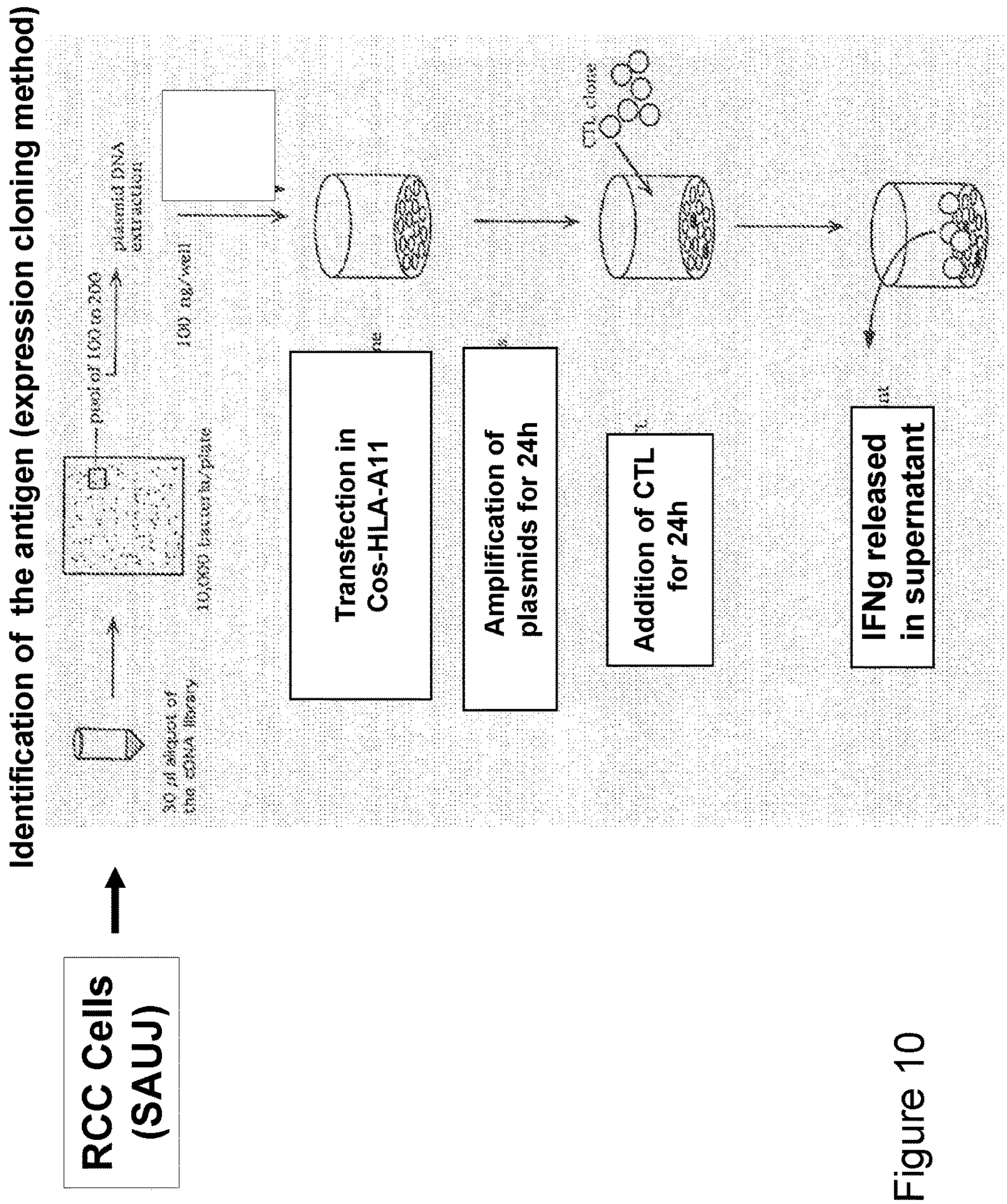
FIG. 10 depicts schematically the methodology used for the identification of a tumor antigen.

COS7 cells transfected with the human HLA-A11 molecule (COS7-A11) were used for transfecting the c-DNA library obtained from patient RCC cells. 300 ng of pooled plasmid cDNAs were transfected into $5\times10^4$ COS7-A11 cells using Lipofectamine 2000 (Invitrogen) in 96-well plates for 24 hours. These cells were cultured with serum- and antibiotic-free DMEM (Cellgro). Vb7 positive SAUJ-RCC specific CTLs were added at 10,000 cells/well and incubated an additional 24 hours; the supernatants were then harvested and GM-CSF production was measured using an ELISA assay (FIG. 10). Bacteria were transformed with cDNA pools from 4 positive wells in the first screening, and plasmids containing 15 bacterial clones were used for the second screening using CTL clones. After the second screening, two cDNAs were isolated and purified into individual cDNA clones.

Determination of the c-DNA Clones Recognized by the RCC Reactive Vb7 Positive CD8 T Cells By screening COS7-A11 cells transfected with serial dilutions of c-DNA, we identified 2 tumor derived c-DNA's when transfected into COS7-A11 cells that induced GM-CSF secretion (measured by ELISA) when co cultured with tumor reactive T-cells; DNA sequencing showed these c-DNA shared a common sequence region of 375 base pairs. A schematic representation of the structures and sequences of these two c-DNAs (named CT-RCC 8 and CT-RCC 9) are shown in FIG. 11A and FIG. 11B. The orange boxes represent the 375-bp common region of CT-RCC 8 and CT-RCC 9, and the green and blue boxes represent the unique regions of CT-RCC 8 (1780 bp) and CT-RCC 9 (203 bp) respectively. The entire cDNA length of CT-RCC 8 or CT-RCC 9 without the poly(A) sequence is shown above each double-headed horizontal arrow. The relative positions of the exons are indicated with nucleotide numbers (below boxes) corresponding to those of the Clone RP3-488C13 on Chromosome 6 (GenBank accession number, AL133408). The nucleotide sequence of the 375-bp common region of CT-RCC 8 and CT-RCC 9 is shown in FIG. 11B.

Figure 12:
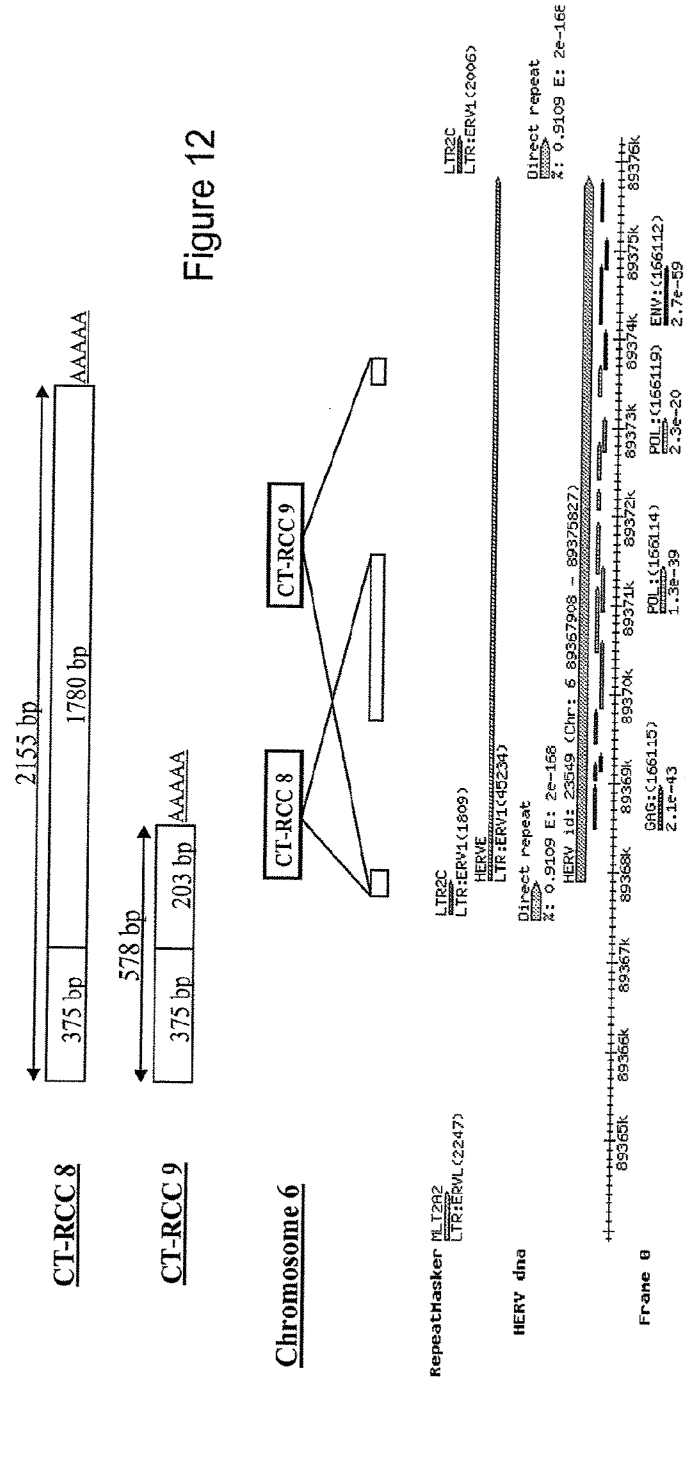
FIG. 12 depicts the localization of CT-RCC8, CT-RCC9, and HERV 23549 on chromosome 6.

FIG. 12 shows chromosome localization of CT-RCC 8 and 9. CT-RCC 8 and CT-RCC 9 were found to localize to a HERV (ID: 23549) found on chromosome 6. The upper panel on FIG. 12 illustrates the cDNA structures of CT-RCC 8 and CT-RCC 9. In a lower panel, exons (CT-RCC 8 and CT-RCC 9 cDNAs) joined by splicing are shown as boxes linked by lines. Exons are illustrated so as to show their relative positions to the HERV ID: 23549 region on chromosome 6 (nt 89367903-nt 89375827). The lower part of the panel in FIG. 12 was excerpted from retrosearch.dk.

Figure 13:
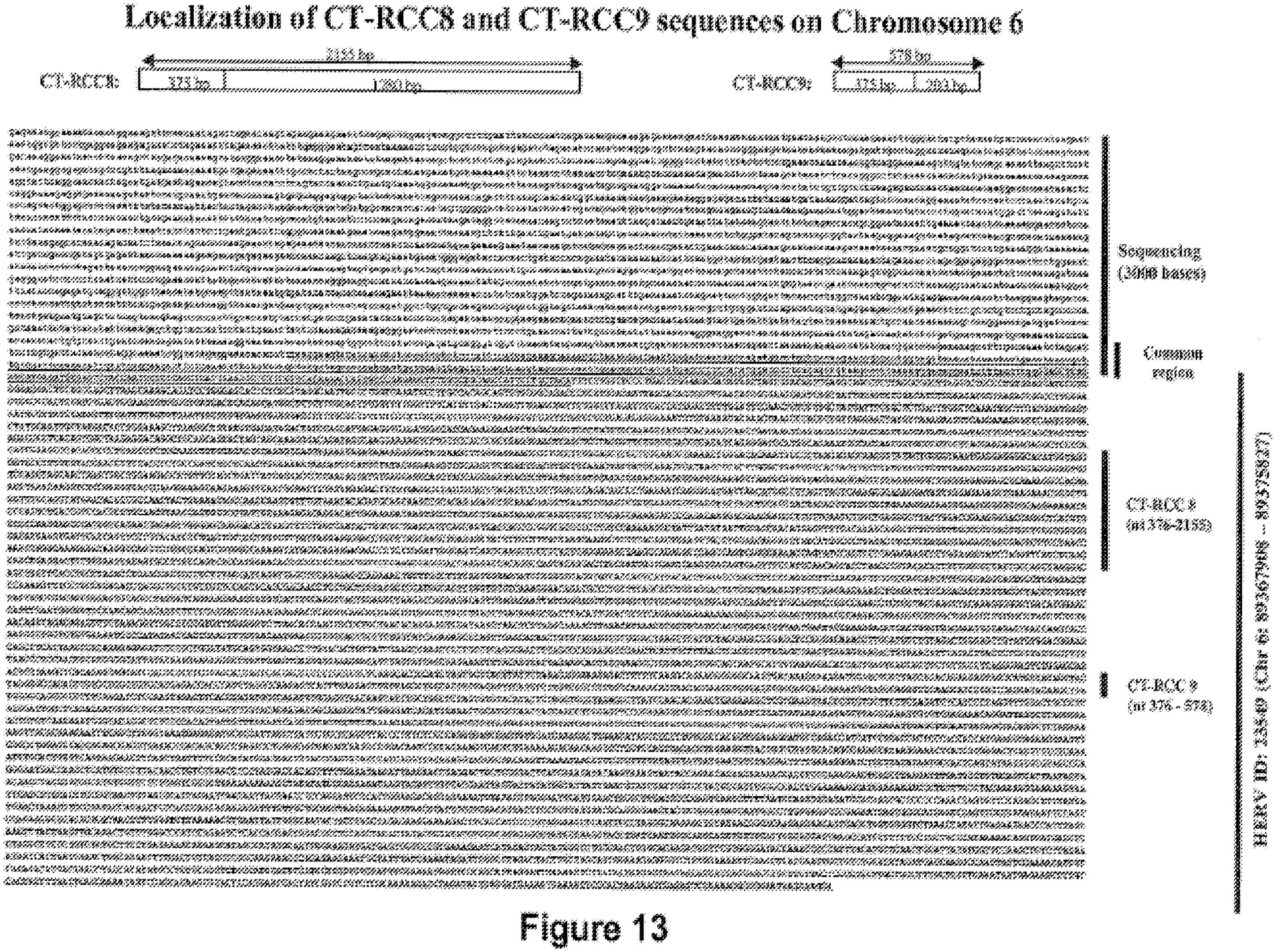
FIG. 13 depicts the localization of CT-RCC8 and CT-RCC9 sequences on HERV ID: 23549 (Chromosome 6: 89367908-89375827; SEQ ID NO: 59).

FIG. 13 shows localization of CT-RCC 8 and CT-RCC 9 sequences on chromosome 6. The cDNA sequences of CT-RCC 8 and CT-RCC 9, which localize in the HERV ID: 23549 region on chromosome 6, are highlighted in colors (FIG. 13). Bold vertical lines on the right indicate locations of the common region, and unique regions of CT-RCC 8 and CT-RCC 9 with nucleotide numbers corresponding to cDNA sequences. The HERV ID: 23549 sequence is shown in uppercase letters.

Figures 14A, 14B, 14C:
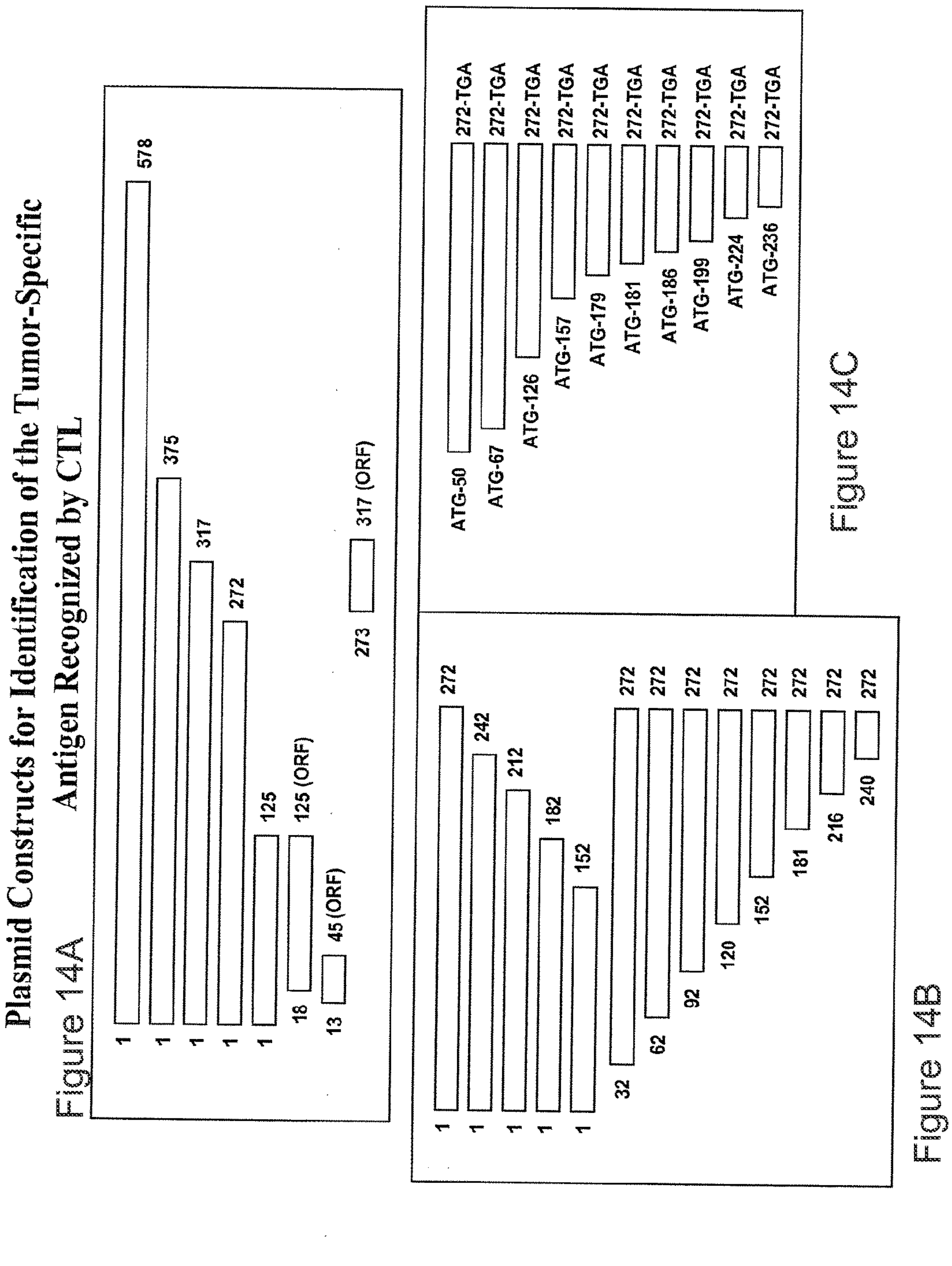
FIG. 14A, FIG. 14B and FIG. 14C depict the plasmid constructs for the identification of the tumor specific antigen recognized by CTL.

FIGS. 14A-14C show schematic representations of plasmid constructs for the identification of the tumor-specific antigen recognized by RCC reactive CTL. Plasmids carrying parts of CT-RCC 8 and CT-RCC 9 were constructed by inserting PCR-amplified DNA fragments or annealed oligonucleotides into the pcDNA3.1 Directional TOPO Expression vector in order to identify the tumor-specific antigen recognized by CTL (see "Materials and Methods"). In FIG. 14A, 18-125 (ORF), 13-45 (ORF) and 273-317 (ORF) plasmids were constructed to target ORFs of the common region. FIG. 14B depicts serially truncated forms of plasmids which were constructed on the basis of the results obtained using plasmids shown in panel A. FIG. 14C shows plasmids in which initiation (ATG) and termination (TGA) codons were created at their 5'- and 3'-sites, respectively. Numbers delineate nucleotide positions in the common region of CT-RCC 8 and CT-RCC 9.

Figures 15A, 15B, 15C:
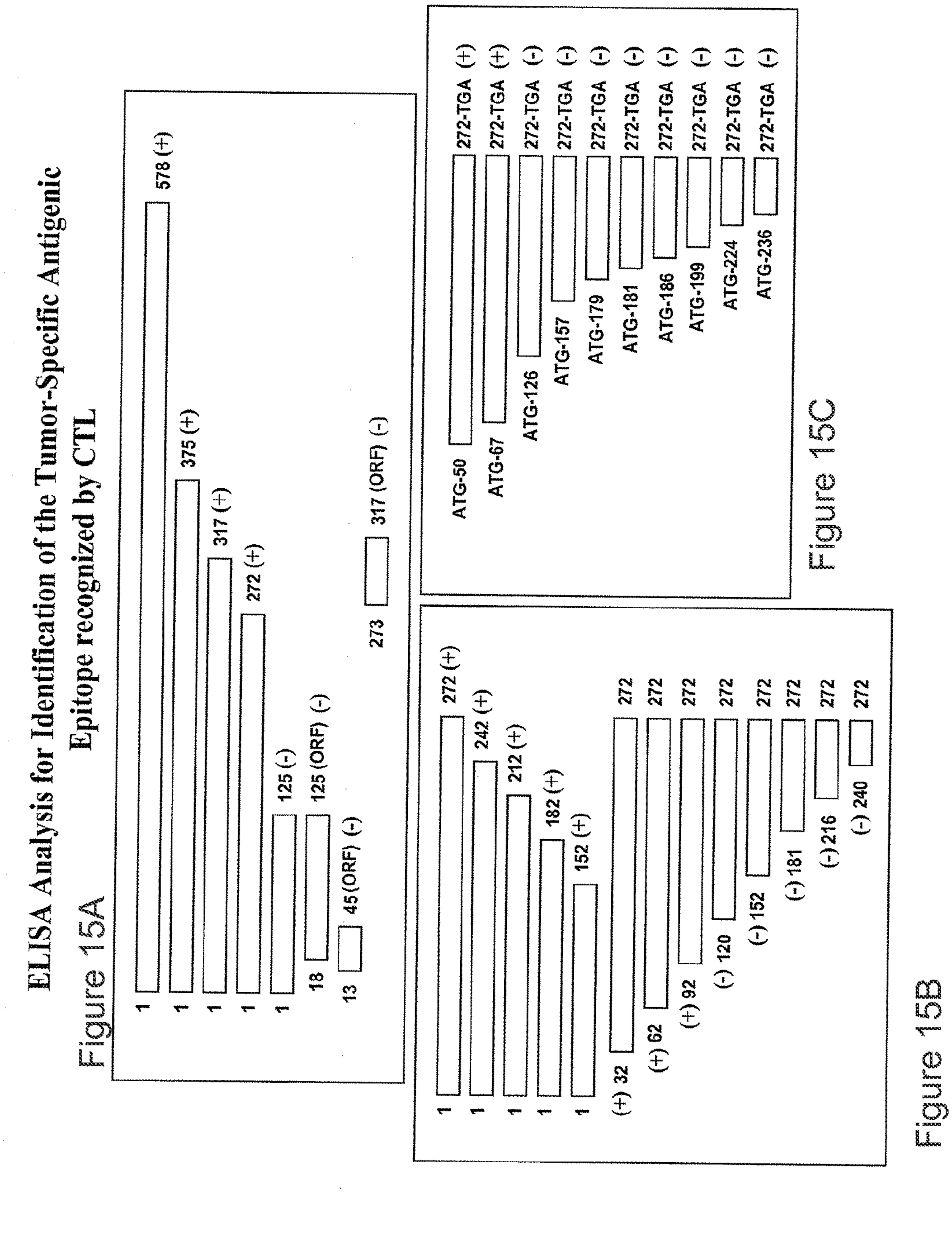
FIG. 15A, FIG. 15B and FIG. 15C depict the results of an ELISA analysis for the identification of tumor-specific antigenic epitope recognized by CTL.

FIGS. 15A-15C shows ELISA analysis for the identification of the tumor-specific antigenic epitope recognized by RCC reactive CTL. Using the above plasmid constructs, an ELISA analysis measuring GM-CSF secretion was performed to identify the tumor-specific antigenic epitope recognized by RCC reactive CTL. Cultured RCC reactive Vb7 positive T-cells were added to COS7-A11 transfected target cells in 96-well plates. After 24-hour co-culture at 37° C., supernatants were collected to measure GM-CSF release from T-cell clones in duplicate assays. Absorbance was detected at 450 nm using an ELISA Reader and data were calculated based on the standard curve generated from commercial recombinant human GM-CSF standard. Results of the ELISA assay are shown (FIGS. 15A-15C) with the positive (+) and negative (−) symbols on the right representing the presence or absence of GM-CSF production by the T-cells when co cultured with COST-A11 cells transfected with different plasmids.

FIG. 16 shows plasmid constructs encoding short peptides ("Mini-genes") used to identify the tumor-specific antigenic peptide recognized by RCC reactive T cells. On the basis of the results shown in FIG. 14, plasmid constructs encoding much shorter peptides were constructed to identify an exact antigenic peptide. Forward and reverse synthetic oligonucleotides were generated, annealed and then inserting into the pcDNA3.1 Directional TOPO Expression vector. For directional cloning, an extra CACC or GGTG sequence was attached to 5' ends of forward oligonucleotides or 3' ends of reverse oligonucleotides, respectively. (1) ATT-101P-142D plasmid carrying annealed oligonucleotides (nt 101-142) has a putative non-AUG initiation codon, ATT. The putative ATT initiation codon was replaced with ATG in ATG-101P-142D plasmid or GCT in GCT-101P-142D plasmid. In the ATTdel-101P-142D plasmid, ATT was deleted as indicated with dashes. ATG-104N-138R plasmid was created to encode a different frame of peptide, in which T (nt 100) and C (nt 95) were replaced with C and T, respectively, to disrupt the putative ATT initiation codon and one codon directly upstream of ATT. The amino acid translations of these "mini-genes" are shown under each nucleotide sequence. Stop codons are indicated with asterisks (*). (2) Plasmids encoding 8-mer to 10-mer peptides were created to identify the exact antigenic epitope. Synthetic forward and reverse oligonucleotides were designed to create annealed oligonucleotides with the ATG initiation codon at the 5' ends and TAG termination codon at the 3' ends. Cultured RCC reactive T-cells were added to COS7-A11 target cells transfected with different "mini-genes" in 96-well plates. After 24-hour co-culture at 37° C., supernatants were collected to measure GM-CSF release from T-cells in duplicate assays, as above. Results of the ELISA assay are shown (FIG. 16) with the positive (+) and negative (−) symbols on the right representing the presence or absence of GM-CSF production by the T-cells when co cultured with COS7-A11 cells transfected with different "mini-gene" plasmids.

Figure 17:
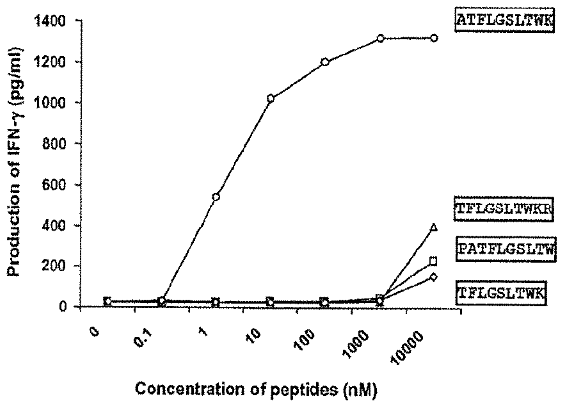
FIG. 17 depicts ELISA analysis used for the identification of tumor specific antigenic epitopes recognized by CTL. SEQ ID NOs: of the peptides are as follows: Pep-$P_{101}$-$W_{130}$, SEQ ID NO: 118; Pep-$A_{104}$-$K_{133}$, SEQ ID NO: 116; Pep-$T_{107}$-$R_{136}$, SEQ ID NO: 117; Pep-$T_{107}$-$K_{133}$, SEQ ID NO: 115.

FIG. 17 shows ELISA analysis for the identification of the tumor-specific antigenic peptide epitope recognized by CTL. The upper panel shows the four candidate peptide sequences (three 10 mers and one 9 mer) that were synthesized to identify the exact tumor-specific antigenic epitope. COS7-A11 cells were pulsed with varying concentrations of each peptide then screened for their ability to induce IFN-gamma production by RCC reactive CTL. The 10 mer Pep-A104-K133 (ATFLGSLTWK) (SEQ ID NO: 1) induced dose dependent IFN-gamma production first evident in the 1 nM concentration range consistent with this peptide being the antigenic HLA-A11 restricted antigen recognized by the RCC reactive SAUJ T-cell clone.

FIG. 18 shows location of the tumor-specific antigenic 10-mer peptide in the common region of CT-RCC 8 and CT-RCC 9. The predicted amino acid translations from 3 different ORFs of the common region of CT-RCC 8 and CT-RCC 9 are shown under the nucleotide sequence.

The amino acid residues of the tumor-specific 10-mer peptide (Pep-A104-K133) (SEQ ID NO: 1) are specified in underlined bold letters. The putative translation initiation site, ATT, is indicated in bold letters.

Figure 19:
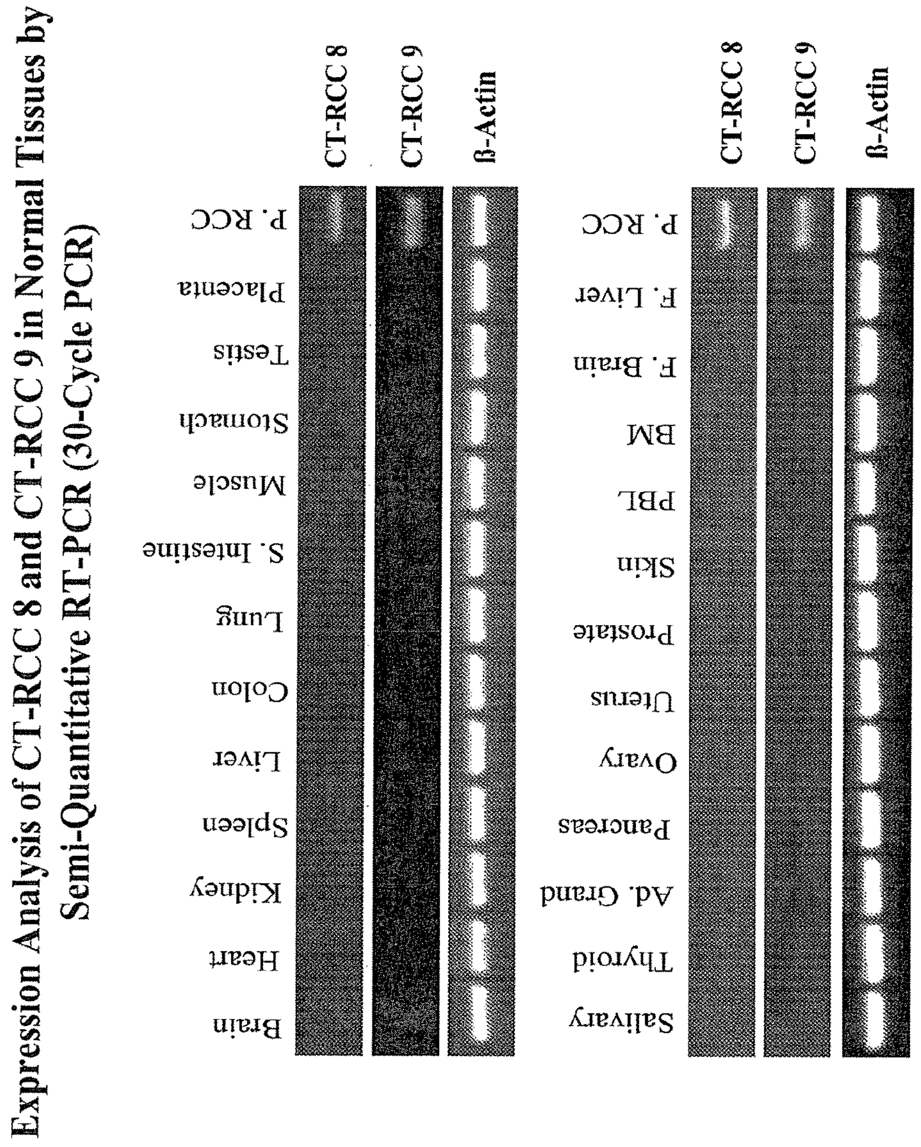
FIG. 19 depicts the analysis of expression of CT-RCC 8 and CT-RCC 9 in normal tissues by semi-quantitative RT-PCR.

FIG. 19 shows analysis of expression of CT-RCC 8 and CT-RCC 9 in normal tissues by semi-quantitative RT-PCR. The Human-24 Tissue RapidScan Gene Expression cDNA panel was obtained from Origene and used for semi-quantitative RT-PCR analysis in order to examine expression levels of the CT-RCC common region, CT-RCC 8, CT-RCC 9 and β-actin (used as an internal control). cDNA obtained from SAUJ RCC was used as a positive control. PCR amplification was carried out in a total 30 μL of reaction volume using the TaKa LA Taq Kit. PCR cycling conditions for CT-RCC 8 and β-actin were 1 cycle of 95° C. for 2 min (denaturing); 30 cycles of 95° C. for 30 sec (denaturing), 55° C. for 30 sec (annealing), 72° C. for 1 min (extension); 1 cycle of 72° C. for 5 min. CT-RCC 9 was amplified in a similar manner, except for the annealing step (52° C. for 30 sec). 5 μL aliquots of PCR-amplified products were separated on 1% agarose gels. The PCR product derived from SAUJ RCC (positive control) was loaded on the far right well of the agarose gel. Semi-quantitative RT-PCR showed no expression of CT-RCC 8 and CT-RCC 9 in normal tissues.

Figure 20:
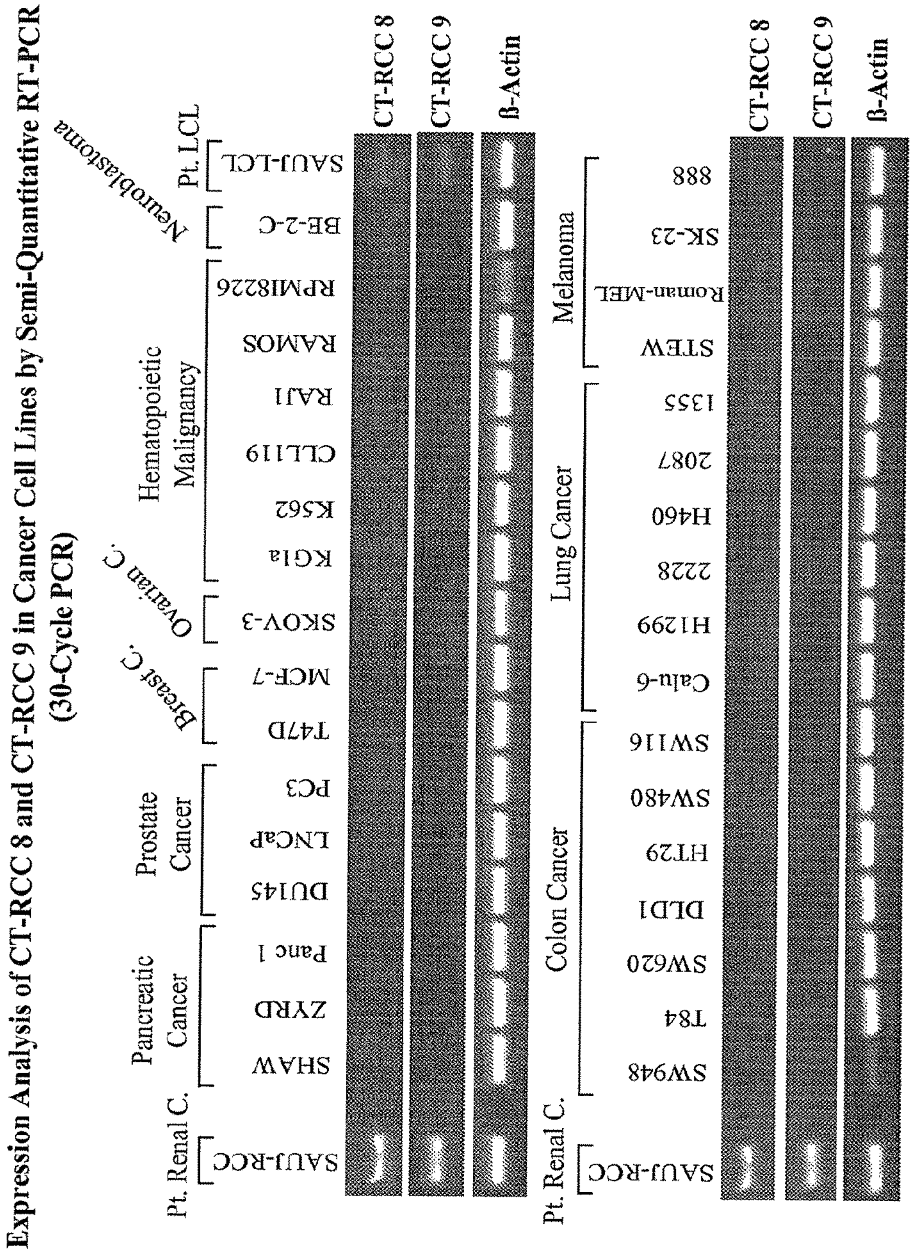
FIG. 20 depicts the analysis of expression of CT-RCC 8 and CT-RCC 9 in different non RCC cancer cell lines by semi-quantitative RT-PCR.

FIG. 20 shows analysis of expression of CT-RCC 8 and CT-RCC 9 in different non RCC cancer cell lines by semi-quantitative RT-PCR. mRNA expression levels of CT-RCC 8 and CT-RCC 9 in 33 different cancer cell lines, established from 9 different types of malignant tissues, were examined by semi-quantitative RT-PCR using cDNAs prepared as detailed in "Materials and Methods". cDNA from SAUJ-RCC and SAUJ-LCL were used as controls. PCR amplification was carried out in 30 μL of reaction volume using the TaKaRa LA Taq Kit. CT-RCC 8 and β-actin were amplified by PCR as follows: 1 cycle of 95° C. for 2min (denaturing); 30 cycles of 95° C. for 30 sec (denaturing), 55° C. for 30 sec (annealing), 72° C. for 1 min (extension); 1 cycle of 72° C. for 5 min (additional extension). CT-RCC 9 was amplified in a similar manner, except for the annealing step (52° C. for 30 sec). Semi-quantitative RT-PCR showed no expression of CT-RCC 8 and CT-RCC 9 in any of the non RCC tumor lines tested.

Figures 21A, 21B:
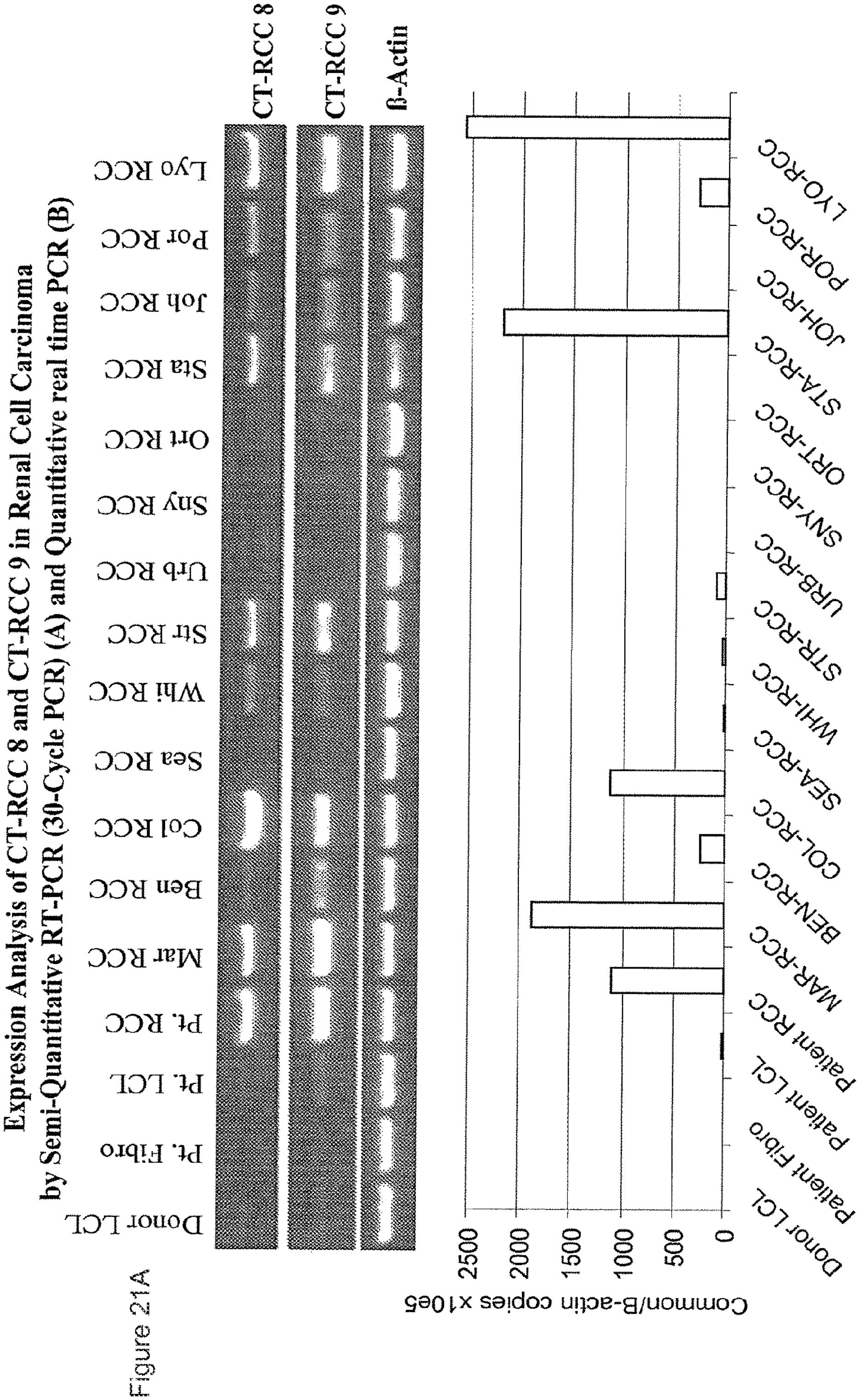
FIG. 21A and FIG. 21B depict the analysis of expression CT-RCC 8 and CT-RCC 9 in different renal cell carcinoma cell lines.
Figure 22:
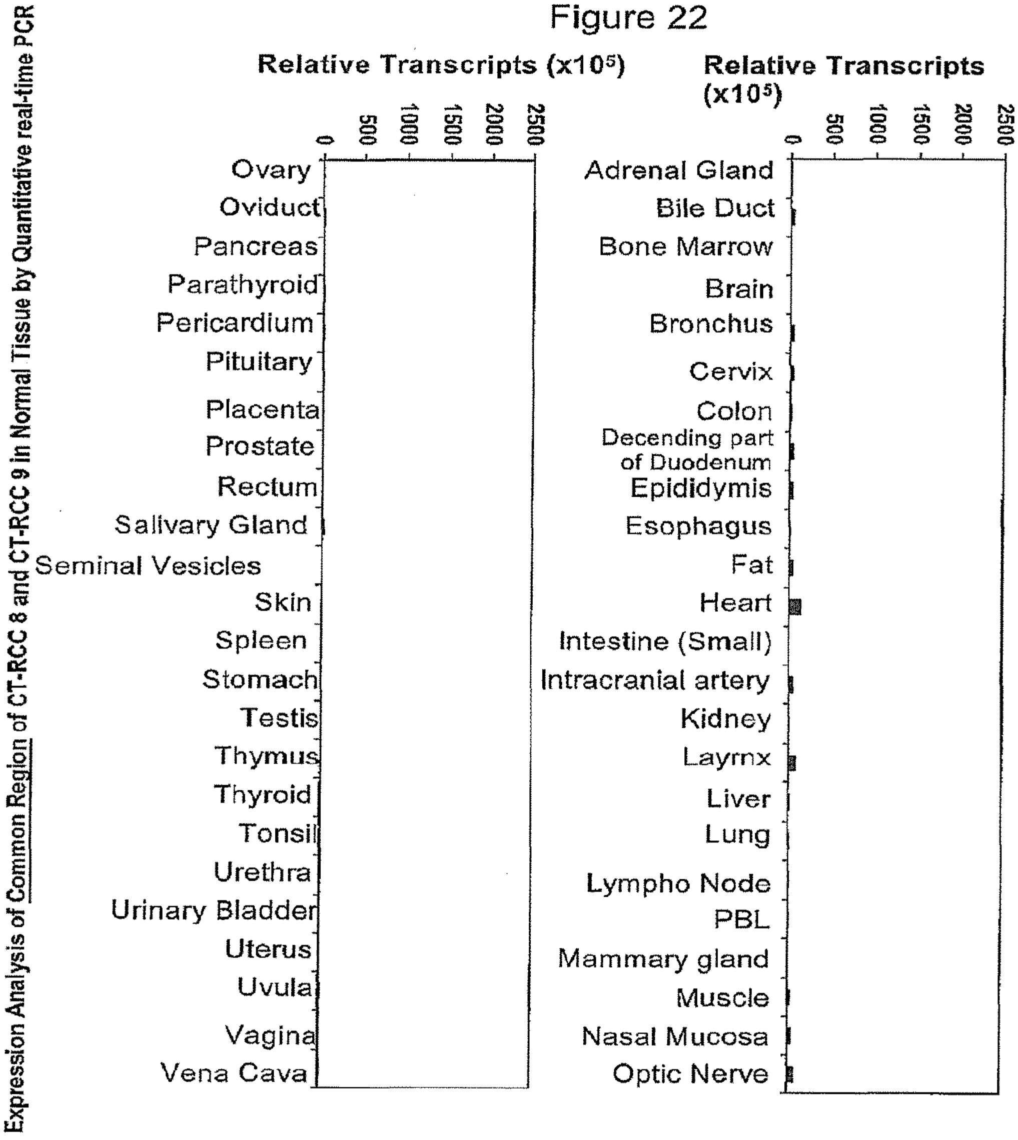
FIG. 22 depicts the analysis of expression of the common region of CT-RCC 8 and CT-RCC 9 in normal tissue by Quantitative real-time PCR.

FIGS. 21A and 21B shows analysis of expression CT-RCC 8 and CT-RCC 9 in different renal cell carcinoma cell lines. FIG. 21A: Semi-quantitative RT-PCR was performed using cDNAs prepared from RCC cell lines generated from the tumors of 14 different patients. cDNAs isolated from EBV-LCL (donor) and fibroblast cells (SAUJ-Fibro) of the patient were used as controls in a similar manner as described elsewhere. Semi-quantitative RT-PCR showed expression of CT-RCC 8 and CT-RCC 9 in 8/14 RCC tumor lines tested. FIG. 21B: quantitative real-time PCR was carried out in a total 25 μL of reaction volume containing cDNA, the TaqMan Universal PCR Master Mix (Applied Biosystems), an appropriate primer set and a TaqMan probe (see "Materials and Methods"). Quantitative real-time PCR confirmed expression of CT-RCC 8 and CT-RCC 9 in 8/14 RCC cell lines FIG. 22 shows analysis of expression of the Common Region of CT-RCC 8 and CT-RCC 9 in normal tissue by Quantitative real-time PCR. c-CDNAs from 48 normal tissues were analyzed.

Figure 23:
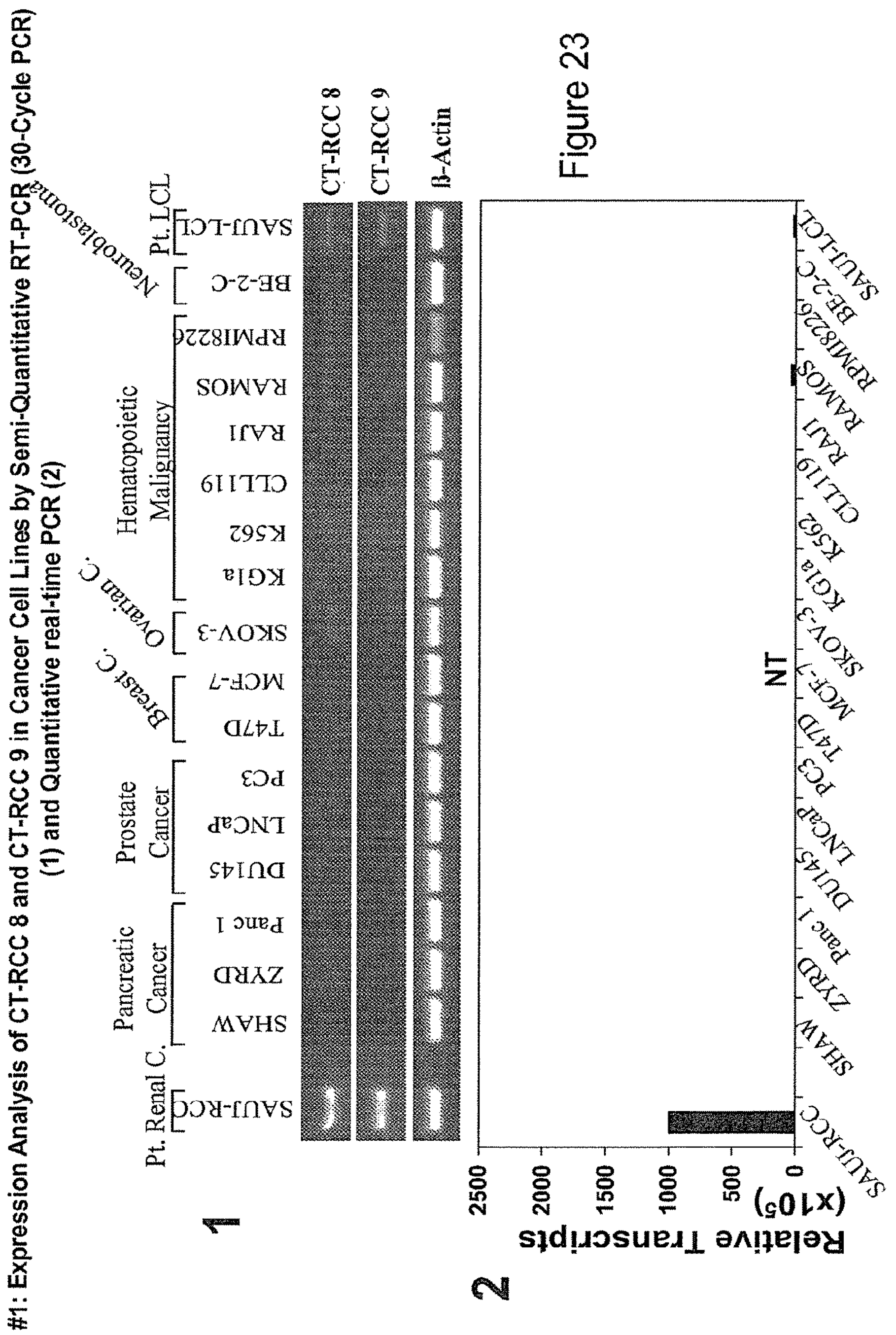
FIG. 23 shows the analysis of Expression of CT-RCC 8 and CT-RCC 9 in different cancer cell Lines by semi-quantitative RT-PCR (30-Cycle PCR) (1) and quantitative real-time PCR (2).
Figure 24:
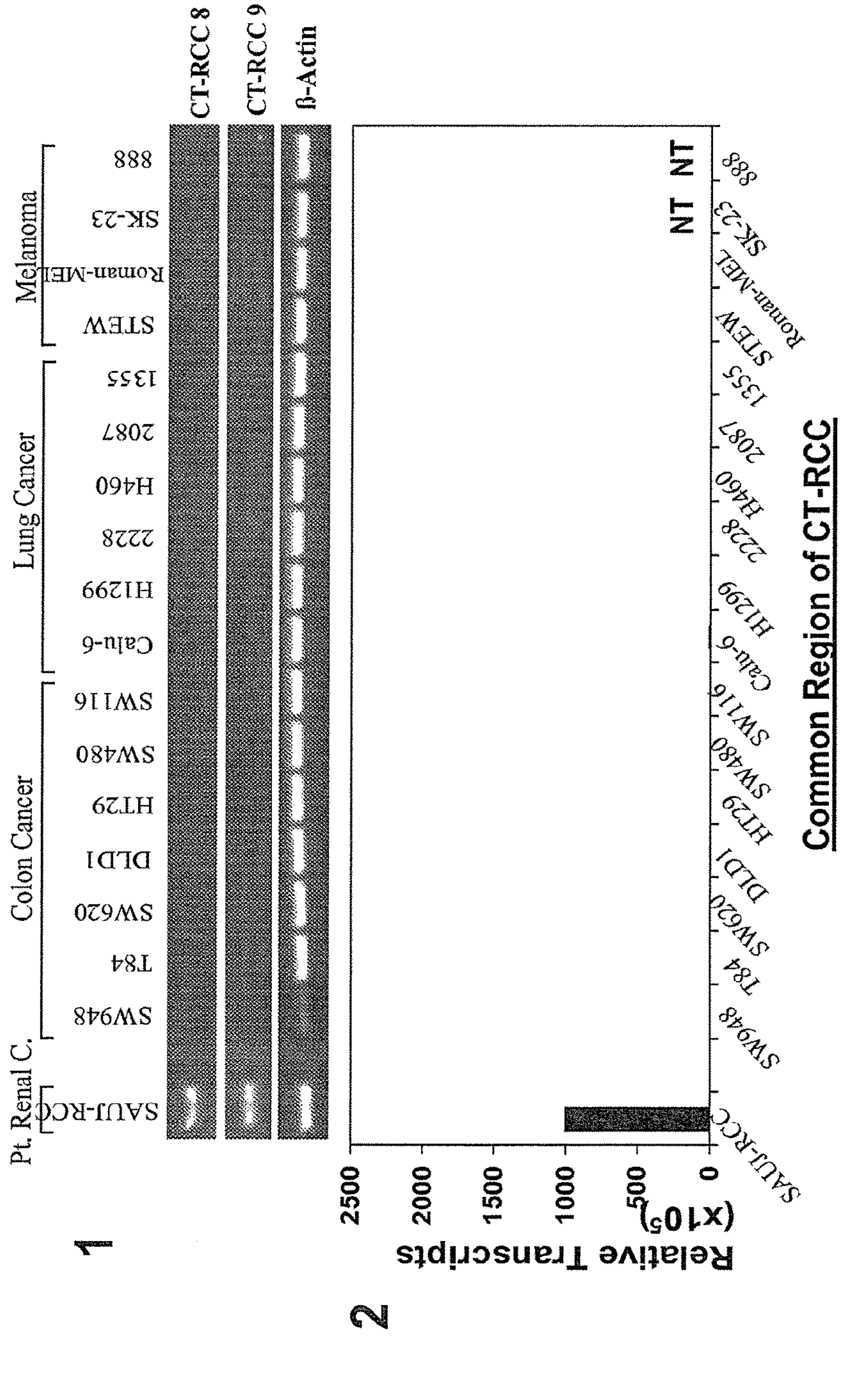
FIG. 24 shows the analysis of expression of CT-RCC 8 and CT-RCC 9 in different cancer cell lines by semi-quantitative RT-PCR (30-Cycle PCR) (1) and quantitative real-time PCR (2).
Figures 25A, 25B:
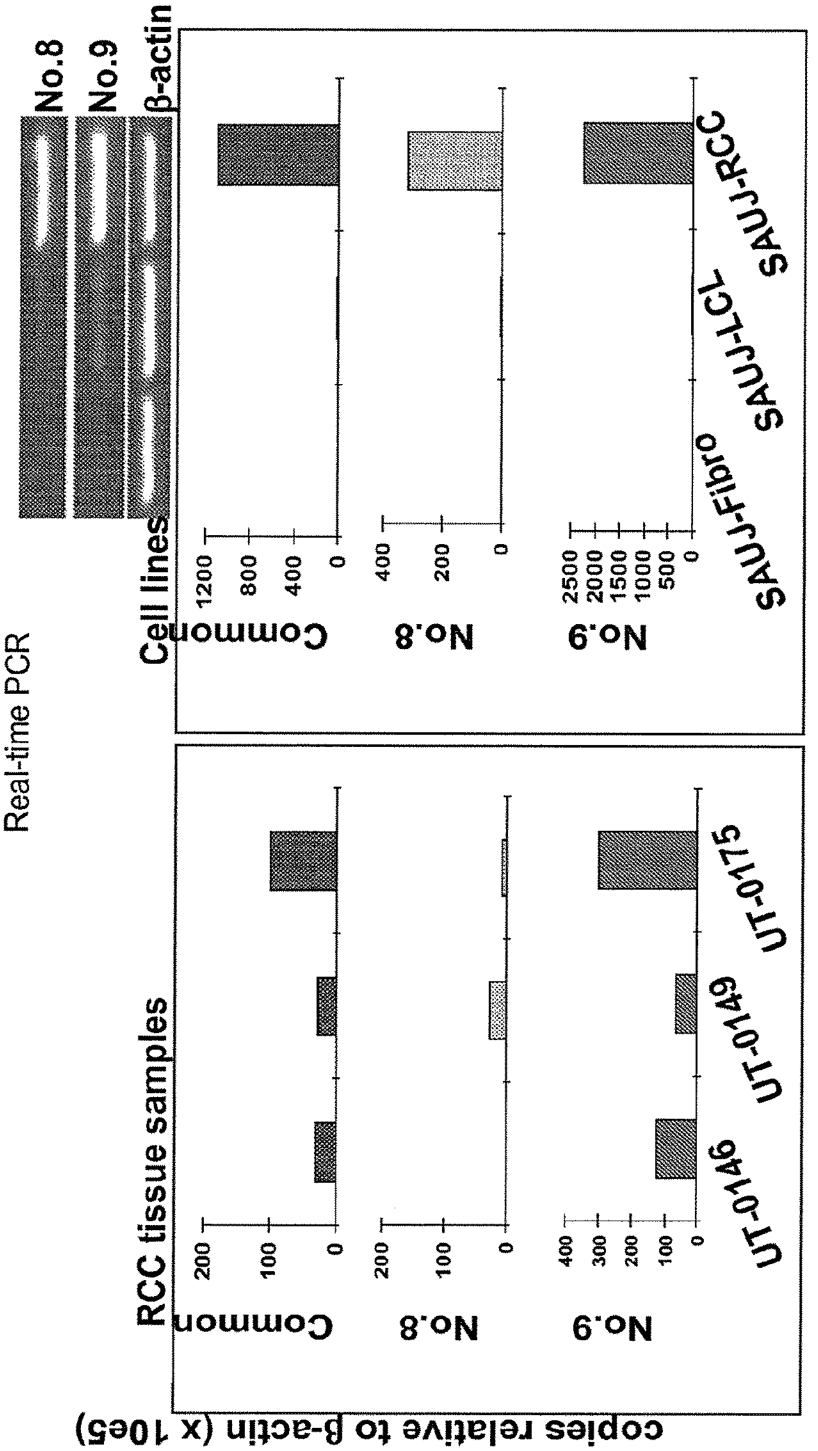
FIG. 25A and FIG. 25B show the analysis of expression of CT-RCC 8 and CT-RCC 9 in different cancer cell lines by quantitative real-time PCR.

FIG. 23 and FIG. 24 shows analysis of Expression of CT-RCC 8 and CT-RCC 9 in Different Cancer Cell Lines by Semi-Quantitative RT-PCR (30-Cycle PCR) (1) and Quantitative real-time PCR (2). This antigen meets several criteria that would make it a good target for T-cell based immunotherapy protocols (e.g., tumor restricted, recognized by T-cells, and expressed on >50% or RCC cells).

Vaccine protocols according to one aspect, to boost a cytotoxic T-cell response against this antigen in patients with metastatic RCC. Such strategies could include:

Vaccination with the immunogenic 10 amino acid peptide derived from this CT-RCC gene in RCC patients who are HLA $A11^+$;

Vaccination with other immunogenic peptides derived from this CT-RCC gene presented in the context of other HLA class I molecules in RCC patients;

The adoptive infusion of autologous patient or allogeneic donor (in the transplant setting) CT-RCC specific T-cells expanded in vitro with tumor specific cytotoxicity; and The adoptive infusion of autologous patient or allogeneic donor (in the transplant setting) dendritic cells that have been transfected with the entire common sequence region or other c-DNAs derived from the CT-RCC gene, or RNA derived from this gene.

Cell Lines

The human renal cell carcinoma (RCC) cell line, SAUJ-RCC, was established from a patient's nephrectomy sample procured at NCl/NIH and maintained in our laboratory. Using the same patient's peripheral blood mononuclear cells (PBMCs), a lymphoblastoid cell line, SAUJ-LCL, and a fibroblast cell line, SAUJ-Fibro, were established as follows: SAUJ-LCL was established by culturing with Epstein-Barr virus (EBV)-containing supernatant harvested from cell line B95-8 (American Type Culture Collection [ATCC], Manassas, Va.) in the presence of 100 μg/mL cyclosporine A (Sandoz Pharmaceuticals, Washington, D.C.); SAUJ-Fibro was established by in vitro culturing of cells obtained from a skin punch biopsy from patient SAUJ.

In a similar manner, a lymphoblastoid cell line, SKEM-LCL, was established from PBMCs collected from an HLA identical sibling of patient SAUJ who served as the patient's hematopoietic stem cell donor. Other cell lines used in this study were as follows; two HLA-A11 positive RCC cell clines (MAR-RCC, BEN-RCC); seven RCC cell lines established from patients who were not HLA-A11 positive that were subsequently stably transfected to express HLA-A11 (COL-RCC, SEA-RCC, WHI-RCC, STR-RCC, URB-RCC, SNY-RCC and ORT-RCC; a gift from Dr. Qiong Wang at NCl/NIH); four RCCs that were HLA All negative (STA-RCC, JOH-RCC, POR-RCC and LYO-RCC); seven colon cancer cell lines (SW948, SW620, SW480, SW116, T84, DLD1 and HT29); six lung cancer cell lines (Calu-6, H1299, 2228, H460, 2087 and 1355); four melanoma cell lines (STEW, Roman-MEL, SK-23 and 888); three pancreatic cancer cell lines (SHAW, ZYRD and Panc1), three prostate cancer cell lines (DU145, LNCaP and PC3); two breast cancer cell lines (T47D and MCF-7); six hematopoietic malignant cell lines (K562, KG1a, CLL119, Raji, Ramos and RPMI8226); one ovarian cancer cell line (SKOV-3); one neuroblastoma cell line (BE-2-C).

A COS7 cell line that was stably transfected with human HLA-A11 was a gift from Dr. Kenichi Hanada at NCl/NIH. COS7-A11 cells were used as target cells for transfection of the cDNA library or plasmid constructs, or peptide-pulse elements for the T-cell recognition assay. Nine HLA-A11 positive RCC cell lines were maintained in Dulbecco's Modification of Eagle's Medium (Cellgro, Herndon, Va.) supplemented with 10% fetal calf serum (FCS; Cellgro), 10% tryptose (Sigma, St. Louis, Mo.), 1% insulin-transferrin-selenium (GIBCO Invitrogen, Carlsbad, Calif.), 1 mM sodium pyruvate (GIBCO Invitrogen), 100 units of penicillin (GIBCO Invitrogen), 100 μg/mL of streptomycin (GIBCO Invitrogen), and 500 μg/mL geneticin (GIBCO Invitrogen). The fibroblast cell line SAUJ-Fibro was cultured with 10% FCS/DMEM. All other cell lines were maintained in RPMI 1640 medium containing 10% FCS, 100 units of penicillin, 100 μg/mL of streptomycin, and 500 μg/mL geneticin.

Cytotoxicity Assay

Cytotoxic activities were measured by 6-hour $^{51}$Cr-release assay at various ratios of effectors to target cells (Igarashi, Wynberg et al. 2004; Takahashi, McCoy et al. 2004). Target cells ($10^6$ cells) were incubated with 100 μCi (3.7Mbq) $Na_2{}^{51}CrO_4$ (Amersham Biosciences, Piscataway, N.J.) for 1 hour, washed, and resuspended with RPMI1640 medium at a concentration of $1\times10^5$ cells/mL. An aliquot ($1\times10^4$ cells/100 μL) of each target cell suspension were co-cultured with 100 μL of cell suspension containing various numbers of effector cells in 96-well round-bottom plate, resulting in a total volume of 200 μL/well. After 6-hour incubation at 37° C., 25 μL of supernatant was harvested, and radioactive content was measured by a gamma counter. Specific cytotoxicity was calculated as [(experimental $^{51}$Cr release−spontaneous $^{51}$Cr release)/(maximum $^{51}$Cr release−spontaneous $^{51}$Cr release)]×100%. All values shown represent the average of duplicates or triplicates ±1 SD.

Generation and Cloning of HLA-A11-Restricted Cytotoxic T-Lymphocytes (CTLs)

PBMCs collected before and after allogeneic hematopoietic stem cell transplantation from patient SAUJ (HLA-A11/A11, B51/B55, Cw0101/Cw0701) were prepared by Ficoll (Lymphosep™, Lymphocyte separation medium, MP Biomedicals, Irvine, Calif.) density gradient centrifugation. SAUJ-PBMCs were cultured in RPMI 1640 (Cellgro) culture medium supplemented with 10 ng/mL of recombinant human interleukin (IL)-15 (R&D systems, Minneapolis, Minn.), 10% of human AB serum (Gemini Bio-Products, Woodland, Calif.), 0.25M HEPES (Cellgro), 50 units of penicillin, and 50 μg of streptomycin (GIBCO Invitrogen). Cells were stimulated with irradiated (200Gy) SAUJ-RCC tumor cells at 7-14 day intervals.

Rapid Expansion of SAUJ-CTL Clone BZ-4

CD8+ V beta 7+ CTL isolated by flow sorting from bulk SAUJ-CTL were cloned by limiting dilution (0.3, 1, or 3 cells/well) into 96 well round-bottom plates containing irradiated HLA mismatched (allogeneic) PBMCs feeder cells, rhIL-2, and anti-CD3 mAb. Fourteen days later, wells exhibiting cell growth were tested for target recognition by cytotoxicity or IFN-gamma (IFN-g) secretion. The T-cell clone BZ-4, which appeared to specifically recognize SAUJ-RCC cells but not patient fibroblasts or EBV-LCL was further expanded for additional experiments.

SAUJ-CTL clone BZ-4 cells were resuspended in 25mL of AIM-V medium (GIBCO Invitrogen) containing 300 IU/mL of IL-2, 30 ng/μL of OKT3, 2.5×106 cells irradiated (50Gy) allogeneic feeder cells from a healthy volunteer. The cells were cultured in a 25-cm2 flask. On day 5, 20 ml of culture medium was removed and replaced fresh medium including IL-2. On day 8 and 11, the cells were given IL-2.

Flow Cytometric Analysis (Intracellular IFN-g Staining)

The frequency of RCC-specific T-cells from RCC patient SAUJ (1213 days after transplantation) and his HLA matched sibling donor (SKEM) was determined by intracellular IFN-g staining. PBMCs obtained from day 1213 post transplant were cultured in the presence or absence of one of 3 different stimulator populations (either SAUJ-RCC cells, SAUJ-Fibroblasts, or SAUJ-B-cells); brefeldin A (Sigma) was used block cytokine secretion. Following a 6 hour co-culture, cells were harvested, washed, permeabilized, and stained with anti-CD8-PerCP and anti-human IFN-g FITC monoclonal antibodies (BD Pharmingen, San Diego, Calif.). After a final wash, cells were resuspended in 1% formaldehyde/PBS and analyzed on a FACSCalibur flow cytometer (BD Biosciences, San Jose, Calif.).

Enzyme-Linked Immunosorbent Assay (ELISA)

Cultured T-cell lines or T cell clones were added to target cells in round-bottom 96-well plates. After 24 hours co culture at 37° C., 50 μL of supernatants was collected to measure IFN-g or GM-CSF secretion by ELISA (ENDOGEN, Woburn, Mass.) in duplicate assays. The concentration of reagents and the ELISA procedure recommended by ENDOGEN was followed without deviation. Absorbance was detected at 450 nm using an ELISA reader (VICTOR3 Multilabel counter; Perkin Elmer, Wellesley, Mass.) and data were calculated based on the standard curve generated from commercial recombinant human IFN-g or GM-CSF standards (ENDOGEN).

Antibody Blocking Assays

The impact on IFN-g secretion using monoclonal antibodies that block MHC class I, HLA-A11, HLA-B55 and HLA-DR on SAUJ-RCC cells and TCR V beta 7, TCR V beta 3, CD8, and CD4, on SAUJ V beta 7+sorted CTL was assessed by ELISA.

Enzyme-Linked Immunospot (ELISPOT) Assay

IFN-g-producing antigen-specific T cells were counted using an IFN-g-specific ELISPOT assay. A 96-well polyvinylidene difluoride plate (MAIPS4510; Millipore, Bedford, Mass.) was coated overnight at 4° C. with 100 μL of 15 ng/mL anti-IFN-g mAb, 1-D1K (Mabtech, Nacka, Sweden) in 0.1 M carbonate-bicarbonate buffer (pH 9.6; Sigma, St. Louis, Mo.). After six washes with PBS, PBMCs were added in triplicate at $5\times10^4$ cells/well in the absence or presence of the same number of stimulator cells or 10 μg/mL peptides in RPMI 1640 containing 10% fetal calf serum (FCS) and incubated overnight at 37° C. in 5% $CO_2$. The next day, cells were removed by washing with PBS/0.05% Tween 20 and biotinylated anti-IFN-g mAb, and 7-B6-1 biotin (Mabtech) was added 100 μl of 1 μg/ml and left for 2 hours at room temperature, followed by incubation with streptavidin-alkaline phosphatase (Mabtech) for an additional 1 hour. Individual cytokine-producing cells were detected as dark purple spots after 10-minute reaction with 5-bromo-4-chloro-3-indolyl phosphate/nitroblue tetrazolium alkaline phosphatase substrate (Sigma). After washing in tap water to stop color development, colored spots on the dried membranes were counted using a KS-ELISPOT microscopy system (Carl Zeiss, Jena, Germany)

TCR Usage of SAUJ-CTLs-

TCR Vbeta usage was quantitated by flow cytometric staining of bulk SAUJ CTL using monoclonal antibodies staining 22 different V beta families RNA Isolation Total cellular RNAs from RCCs and other cancer cell lines were extracted using the RNeasy Mini RNA Purification Kit (Qiagen, Valencia, Calif.), according to manufacturer's protocol. Two sets of total RNAs were prepared from individual cell lines to perform experiments in duplicate. In brief, cells ($5\times10^6$) were lysed by addition of Buffer RLT and then vortex. The cell lys ate was placed onto a QIAshredder spin column and centrifuge for 2 min at 13200 rpm using Eppendorf 5415D microcentrifuge in order to homogenize the sample. One volume of 70% ethanol was added to the homogenized lysate and mixed by pipetting. The sample was applied to an RNeasy mini column and centrifuge for 15 sec at 13200 rpm, followed by washing with Buffer RW1 and then Buffer RW2. The RNeasy column was transferred to a new 1.5 mL collection tube, added 40 μL RNase-free water and centrifuges for 1 min at 13200 rpm in order to elute RNA.

Total cellular RNAs from the OCT-embedded tissues (RCCs or kidney normal tissues) were obtained using the PicoPure RNA Isolation Kit (Arcturus, Mountain View, Calif.) as follows. Using the frozen-OCT thin sections, cells were microdissected under a microscope by a pathologist (Dr. Maria Merino, NCl/NIH) and placed into individual 0.5 mL tubes with 50 μL of Extraction Buffer (PicoPure RNA Isolation Kit), followed by gentle resuspension and then incubation at 42° C. for 30 min. After centrifugation at 3000×g (5700 rpm) for 2 min, the supernatant containing the extracted RNA was transferred into a new microcentrifuge tube, and 100 μL of 70% ethanol was added to the sample. The mixture was loaded into a pre-conditioned purification column, centrifuged for 2 min at 100×g (800 rpm) to bind RNA to the column, immediately followed by a centrifugation at 16000×g (13100 rpm) for 30 sec to remove flowthrough. The column was washed with Wash Buffer 1 and then Wash Buffer 2 by centrifugation at 8000×g (9300 rpm) for 1 or 2 min, respectively. RNA was eluted from the column with 11 μL of Elution Buffer.

RNA concentration was measured using the NanoDrop ND-1000 Spectrophotometer (NanoDrop Technologies, Inc, Wilmington, Del.).

All RNA samples were treated with DNase I (Amplification Grade; Invitrogen, Carlsbad, Calif.) to remove residual genomic DNA, according to the manufacturer's instruction. In brief, all RNA preparations (1.375 μg/each) was incubated with 20 μL of reaction mixture containing 1 μL of DNaseI (1 U/μL) and 1 μL of 10× DNaseI Buffer at room temperature for 15 min. The reaction was stopped by adding 2 μL of 25 mM EDTA, pH8.0, and then incubating at 65° C. for 10 min. The isolated RNA was used for cDNA synthesis immediately or stored at −80° C. until use.

cDNA Preparation cDNAs were synthesized using the SuperScript III First-Strand Synthesis System for RT-PCR (Invitrogen), according to the manufacturer's protocol. DNase I-treated total RNA was reverse-transcribed to cDNA. Briefly, 1 μg of DNase I-treated RNA was incubated in 10 μL of reaction mixture containing 1 μL of 50 μM oligo$(dT)_{20}$ primer, 1 μL of 10 mM dNTP Mix and DEPC-treated water at 65° C. for 5 min. The reaction mixture was further incubated for 50 min at 50° C. by adding 10 μL of a cDNA Synthesis Mix containing 2 μL of 10× RT buffer, 4 μL of 25 mM $MgCl_2$, 2 μL of 0.1 M DTT, 1 μL of RNaseOUT (40 U/μL) and 1 μL of SuperScript III RT (200 U/μL). The reaction was terminated at 85° C. for 5 min and then chilled on ice, followed by additional incubation with 1 μL of RNase H for 20 min at 37° C. The synthesized cDNA was used for PCR amplification immediately or stored at −20° C. until use.

cDNAs derived from normal human tissues were purchased from Origene Technology Inc (Rockville, Md.) and were used to test for expression of the newly discover gene CT-RCC.

Genomic DNA Isolation

Genomic DNAs were isolated from renal cell carcinomas and other cell lines using the QIAamp DNA Blood Mini Kit (Qiagen). Cell pellet ($5\times10^6$ cells) obtained by centrifugation was resuspended in 200 μL of phosphate-buffered saline, and added 20 μL of Qiagen Protease and 200 μL of Buffer AL. After mixing by vortex, the sample was incubated at 56° C. for 10 min and added 200 μL of 100% ethanol. The mixture was applied into a QIAamp spin column, centrifuged at 6000×g (8000 rpm) for 1 min, followed by washing with 500 μL of Buffer AW1 and then 500 μL of Buffer AW2. The washed column was placed in a 1.5 mL microcentrifuge tube, added 200 μL of Buffer AE, incubated at room temperature for 1 min, and then centrifuge at 6000×g (8000 rpm) for 1 min. DNA concentration was measured using the NanoDrop ND-1000 Spectrophotometer.

The DNAs were used for sequencing analysis of the genomic region encompassing cDNA clones of CT-RCC 8 and CT-RCC 9, and the upstream genomic sequence of these cDNA clones.

Plasmid Construction

Plasmids were constructed using the pcDNA3.1 Directional TOPO Expression Kit (Invitrogen) in order to identify a tumor-specific antigen recognized by the CD8+ V beta 7+ SAUJ CTLs. Mini-gene DNA fragments were prepared by PCR amplification or annealing of synthetic-forward and -reverse oligonucleotides as described below. For the PCR-based plasmid construction, PCR products were amplified with CT-RCC 8 or CT-RCC 9 cDNA clones as a template and appropriate primer sets (see "List of Primers and Probes"). Each forward primer has an extra CACC sequence at its 5' end for directional insertion into the pcDNA3.1 Directional TOPO Expression vector. The PCR products were separated by agarose gel electrophoresis and extracted from the gels using the QIAquick Gel Extraction Kit (Qiagen). For the annealing based-plasmid construction, synthetic-forward and -reverse oligonucleotides were designed to construct short DNA fragments encoding parts of the common (shared) region of CT-RCC 8 and CT-RCC 9. For directional insertion into the vector, an extra CACC or GGTG sequence was attached to 5' ends of forward oligonucleotides or 3' ends of reverse oligonucleotides, respectively. Each 20 μL of forward (10 mM) and reverse (10 mM) oligonucleotides were combined and heated at 95° C. for 5 min using the Eppendorf Thermomixer 5436 (Eppendorf, Westbury, N.Y.), followed by gradually cooling to room temperature. The gel-purified PCR products or annealed oligonucleotides were cloned into the pcDNA3.1-TOPO vector and transfected into competent *Escherichia coli* (TOP10 cells), according to the manufacturer's instruction (Invitrogen). Briefly, 2 μL of PCR product or annealed oligonucleotides were incubated with the pcDNA3.1 TOPO vector and Salt Solution at room temperature for 30 min, and 2 μL of the reaction mixture was put into a vial of One Shot TOP10 Chemically Competent *E. coli.* The mixture was incubated on ice for 30 min, heat-shocked for 30 sec at 42° C. without shaking, and immediately chilled on ice. After addition of 250 μL of S.O.C. medium, the mixture was subjected to shaking at 37° C. for 1 hr, followed by spreading on agar plates for selection of bacterial colonies. Bacteria colonies were cultured in LB medium with ampicillin overnight and subjected to the plasmid DNA extraction using the QIAprep Spin Miniprep Kit (Qiagen), following the manufacturer's protocol. Briefly, the bacteria pellet prepared by centrifugation was resuspended in 250 μL of Buffer P1, mixed well by vortex, added 250 μL of Buffer P2 and then mixed. After addition of 350 μL of Buffer N3, the sample was mixed and centrifuged for 10 min at 16100×g (13200 rpm). The supernatant was applied onto a QIAprep Spin Column and centrifuged for 1 min, followed by washing with 0.5 mL of Buffer PB and then 0.75 mL of Buffer PE by centrifuging for 1 min. To elute plasmid DNA, the Spin Column was placed in a 1.5 mL tube, added 50 μL of Buffer EB, let stand for 1 min and centrifuged for 1 min. The inserted DNA sequences were confirmed by sequencing analysis as described below.

Sequencing Analysis

Sequence analysis of PCR-amplified DNA fragments, which were generated in semi-quantitative RT-PCR, was carried out to confirm that the DNA fragments were derived from mRNAs of CT-RCC 8 or CT-RCC 9. The PCR bands electrophoresed on agarose gels were cut out, extracted using the QIAquick gel extraction Kit (Qiagen) and subjected to sequence analysis as described below. To examine genomic sequences localizing CT-RCC 8- and CT-RCC 9-exons, PCR amplification of genomic DNA was done by 1 cycle of denaturing (95° C. for 2 min); 35 cycles of denaturing (95° C. for 30 sec), annealing (52° C. or 55° C. for 50 sec) and extension (72° C. for 1 min), followed by extension (72° C. for 5 min). The obtained PCR products were purified by the QIAquick Gel Extraction Kit after cutting DNA fragments from agarose gels or QIAquick PCR Extraction Kit.

The purified PCR products derived from cDNAs or genomic DNAs were subjected to direct sequencing analysis with adequate primers (see "List of Primers and Probes") using the BigDye Terminator version 3.1 Ready Reaction Kit and ABI Prism 3100 Genetic Analyzer (Applied Biosystems), according to the manufacturer's protocol. pME-SMART- or pcDNA3.1-based plasmids described above were sequenced in a similar manner were used for pME-SMART plasmids, and T7 TOPO F and BGH TOPO R primers were used for pcDNA3.1 constructs. pME-SMART-based plasmids obtained by cDNA cloning were sequenced using the BLAST Search. Sequences of pcDNA3.1-based mini-gene plasmids were confirmed by comparing with the human DNA sequence from clone RP3-488C13 on chromosome 6 (Accession #AL133408) or oligonucleotide sequences designed using the Blast2 program.

Semi-Quantitative Reverse Transcriptase (RT)-Polymerase Chain Reaction (PCR)

Total cellular RNAs from RCC cell lines and from fresh RCC tumor biopsies and other cell lines were transcribed to cDNA using the SuperScript III First-Strand Synthesis System for RT-PCR (Invitrogen), according to the manufacturer's protocol. In brief, 1 μg of DNase I-treated total RNA was incubated in 10 μL of reaction mixture containing 1 μL of 50 μM oligo$(dT)_{20}$ primer, 1 μL of 10 mM dNTP mix and DEPC-treated water at 65° C. for 5 min. After incubation, the reaction mixture was further incubated for 50 min at 50° C. by the addition of 10 μL of a cDNA Synthesis Mix containing 2 μL of 10× RT buffer, 4 μL of 25 mM $MgCl_2$, 2 μL of 0.1M DTT, 1 μL of RNaseOUT (40 U/μL) and 1 μL of SuperScript III RT (200 U/μL). The reaction was terminated at 85° C. for 5 min and then chilled on ice. By brief centrifugation to collect the reaction, 1 μL of RNase H was added, and subjected to incubation for 20 min at 37° C. The synthesized cDNA was used for PCR immediately or stored at −20° C. until use. The TaKaRa LA Taq Kit (TaKaRa Bio, Madison, Wis.) was used for PCR. A PCR mixture for CT-RCC 8 or CT-RCC 9 was composed of 6 μL of 20-fold diluted cDNA reaction mixture, 3 μL of 10× Buffer, 6 μL of dNTP Mix (2.5 mM each), 1.5 U LA Taq and an adequate primer set in a reaction volume of 30 μL.

For semi-quantitative RT-PCR evaluating CT-RCC 8 and 9 expression in normal human tissues, we obtained the Human-24 Tissue RapidScan Gene Expression cDNA panel from Origene Technologies, Inc. (Rockville, Md.). As one panel was composed of two identical 96-well PCR plates containing cDNAs, we had two identical cDNA plates. cDNAs from normal human 24 tissues, which were diluted to a series of four concentrations based on a house keeping gene (β-actin), were arrayed into the plate. We used the highest concentration of each cDNA among the serially diluted cDNA templates for semi-quantitative RT-PCR. cDNA/well was dissolved with 25 μL of 1× TE. Each 4 μL of aliquot was used for semi-quantitative PCR to examine expression levels of CT-RCC 8, CT-RCC 9 and β-actin (an internal control). The reaction mixture condition was similar to that described above. Using the GeneAmp PCR System 9700 (Applied Biosystems), PCR amplification of CT-RCC 8 and β-actin are done by 1 cycle of 95° C. for 2min (denaturing); 30 cycles of 95° C. for 30 sec (denaturing), 55° C. for 30 sec (annealing), 72° C. for 1 min (extension); 1 cycle of 72° C. for 5 min. CT-RCC 9 was amplified in a similar manner, except for an annealing step (52° C. for 30 sec). All conditions described above for the semi-quantitative RT-PCR, especially the volume of target cDNA, annealing temperature and PCR cycles, were decided by several preliminary experiments.

Aliquots (5 μL/each well) of PCR products were separated on 1% agarose gels containing ethidium bromide. Their images were visualized under an ultraviolet lamp and saved using ChemiImager 5500 (Alpha Innotech; San Leandro, Calif.).

Quantitative RT-PCR

Real-time quantitative RT-PCR was carried out using the 2× TaqMan Universal PCR Master Mix on the 7500 Fast Real-Time PCR System in duplicate, according to the manufacturer's instruction (Applied Biosystem, Foster City, Calif.). Using the Primer Express v2.0 software (Applied Biosystem), primers for the CT-RCC-common region, CT-RCC 8- or CT-RCC 9-specific region, and β-actin (an internal control) were designed. The specificity of primers and probes was assessed after sequence alignment using the Blast data bank against the human genome. The CT-RCC-common region, CT-RCC 8 or CT-RCC 9-specific region, and β-actin probes were labeled with FAM and TAMRA at the 5' and 3' ends, respectively. β-actin was used as an internal control. These primers and probes are listed in the table below.

Primers and Probes for Real-Time PCR

| Primer & Probe (FAM-TAMRA) | Sequence (5'-3') |
|---|---|
| | CT-RCC common region |
| RCC-CommonF: | GCAGATCCTGGGAGCACTCT (SEQ ID NO: 84) |
| RCC-CommonR: | TGTTCAACCGCTGTGTTAATTCTC (SEQ ID NO: 85) |
| RCC-CommonTaq: | (FAM) TGCCCTGGTCAAATGCCTTGCC (TAMRA) (SEQ ID NO: 86) |
| | CT-RCC 8-specific region |
| RCC-8F: | GAACACCGGGAAGGAATCG (SEQ ID NO: 87) |
| RCC-8R: | TCTGCGGCTTGCTGCAT (SEQ ID NO: 88) |
| RCC8-Taq: | (FAM) CATGTTCCAGATGTCCAGACTCCAATCG (TAMRA) (SEQ ID NO: 89) |
| | CT-RCC 9-specific region |
| RCC-9F: | TGGAACATAGCCCCTTTGTG (SEQ ID NO: 90) |
| RCC-9R: | GGATCCAGGCCGGAATTC (SEQ ID NO: 91) |
| RCC9-Taq: | (FAM) TGGTCTGGCATCCTTTCCACCG (TAMRA) (SEQ ID NO: 92) |
| | β-actin |
| β-actin-420F: | GCGAGAAGATGACCCAGATC (SEQ ID NO: 93) |
| β-actin-522R: | CCAGTGGTACGGCCAGAGG (SEQ ID NO: 94) |
| β-actin-Taq: | (FAM) CCAGCCATGTACGTTGCTATCCAGGC (TAMRA) (SEQ ID NO: 95) |

The primers were synthesized by Integrated DNA Technologies, Inc (IDT; Coralville, Iowa) and TaqMan probes were synthesized by Applied Biosystem or IDT.

To examine quantitative expression levels of CT-RCC 8 and CT-RCC 9 in RCC cell lines and other cancer cell lines, cDNAs were prepared using total RNAs isolated from these cell lines. Real-time RT-PCR was performed in a total volume of 25 μL composed of 12.5 μL of the 2× TaqMan Universal PCR Master Mix, 1 μL of primer mixture (10 μM forward and 10 μM reverse primers), 0.25 μL of 10 μM TaqMan probe and 2 μL of cDNA reaction product.

For real-time PCR to measure quantitative expression levels of CT-RCC 8 and CT-RCC 9 in normal human tissues, we purchased two sets of the Human-48 tissue RapidScan real-time PCR Gene Expression Panel from Origene to obtain duplicate data. Each panel contains two identical 96-well PCR plate with cDNAs. Unlike the RapidScan gene expression panel described above, the real-time PCR panel contains only one concentration of the cDNAs normalized based to β-actin. cDNA/well was dissolved with 13 μL of 1× TE and 10 μL of each aliquot was used for real-time PCR. A real-time PCR reaction mixture (25 μL) was comprised of 12.5 μL of the 2× TaqMan Universal PCR Master Mix, 1 μL of primer mixture (10 μM forward and 10 μM reverse primers), 0.5 μL of 10 μM TaqMan probe and 10 μL of cDNA aliquot. All real-time PCR reactions were cycled during the real-time detection through the following thermal program: 50° C. for 2 min (activation of uracil N-glycosylase enzyme), 95° C. for 10 min (denaturation of uracil N-glycosylase and activation of AmpliTaq Gold enzyme), followed by 40 cycles of 95° C. for 15 sec (denaturation) and 60° C. for 1 min (anneal/extension).

All data were analyzed using the 7500 System Sequence Detection Software (version 1.3). Results of the real-time PCR data were represented as $C_T$ values, where $C_T$ was defined as the threshold cycle of PCR at which amplified product was first detected. We normalized each set of samples using the difference in threshold cycles ($\Delta C_T$) between the sample cDNA and b-actin as a control. Relative transcripts levels were calculated by the expression $2^{-\Delta\Delta CT}$ where $\Delta\Delta CT = \Delta C_{Tsample} - \Delta C_{T\beta\text{-}actin}$ (ABI 1997; Mullen, Hutchins et al. 2002; Miura, Thoburn et al. 2004). Each reaction was done in duplicate. Real-time PCR efficiencies of samples (common region, CT-RCC 8 and CT-RCC 9) and control (β-actin) were approximately equal over concentrations of 1 to100 ng total cDNA. All data files were converted to Excel files to make figures. ABI, A. B. (1997). *User Bulletin* #2.; Miura, Y., C. J. Thoburn, et al. (2004). "Association of Foxp3 regulatory gene expression with graft-versus-host disease." *Blood* 104(7): 2187-93; Mullen, A. C., A. S. Hutchins, et al. (2002). "Hlx is induced by and genetically interacts with T-bet to promote heritable T(H)1 gene induction." *Nat Immunol* 3(7): 652-8.

EXAMPLE 2

Expression of CT-RCC 8 and CT-RCC 9 in RCC and Other Tissues

Figures 26A, 26B:
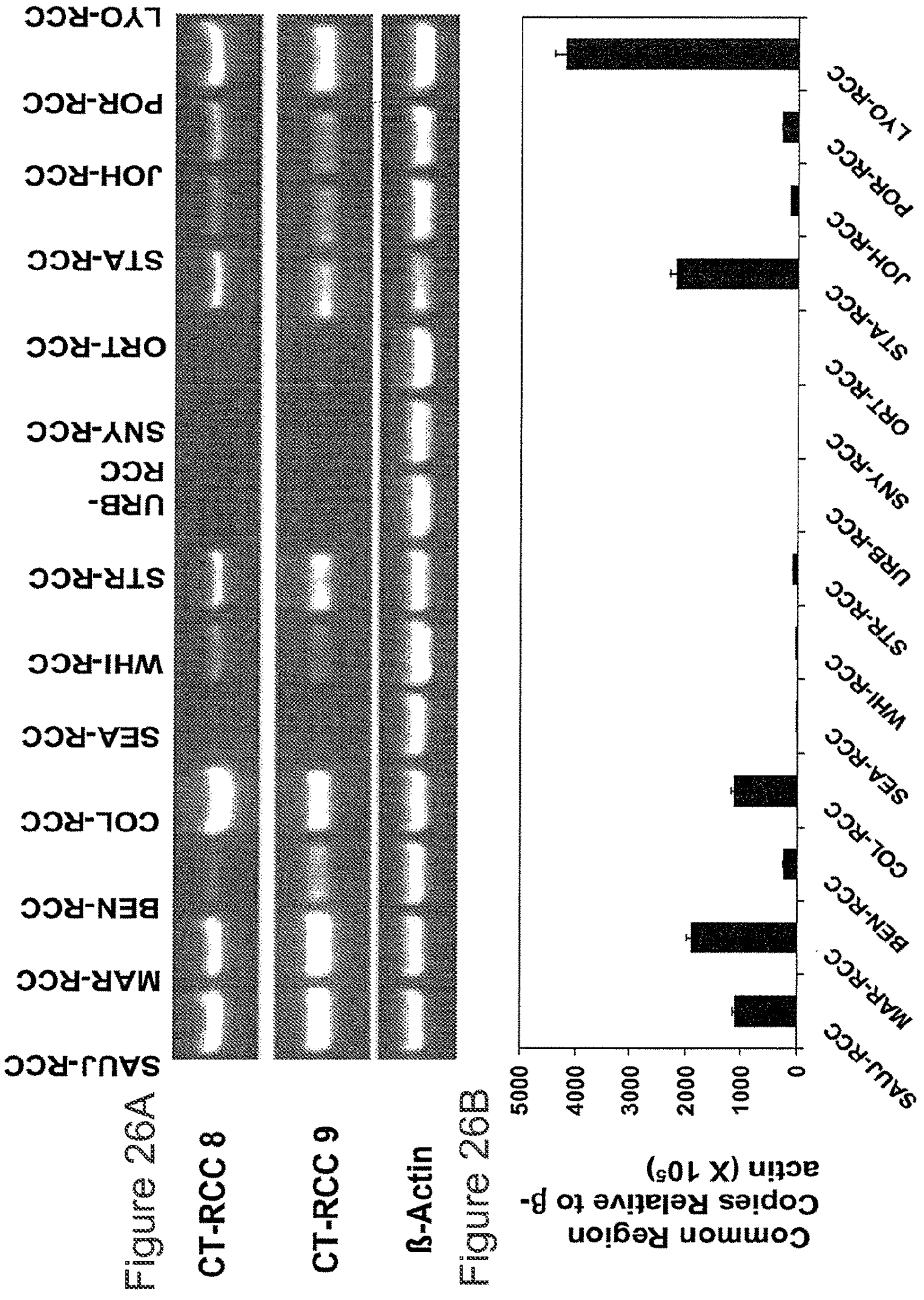
FIG. 26A, FIG. 26B, FIG. 26C, FIG. 26D, FIG. 26E and FIG. 26F show the expression pattern of CT-RCC 8 and CT-RCC 9 cDNAs in tumors and nonmalignant tissues and detection of circulating CT-RCC-1 peptide-specific T-cells after HCT in a patient with metastatic kidney cancer who had tumor regression after the transplant.
Figure 26C:
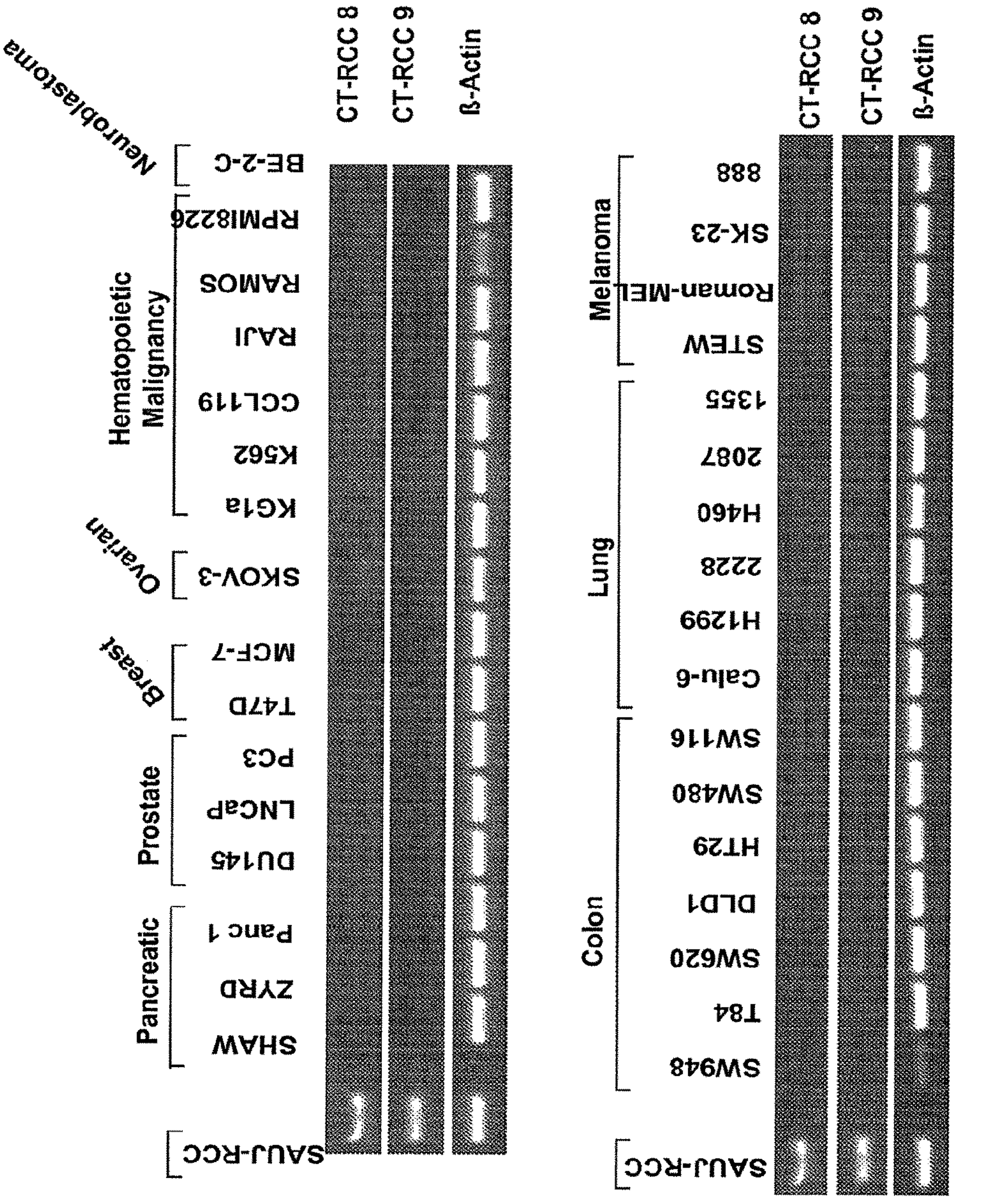
Figure 26D:
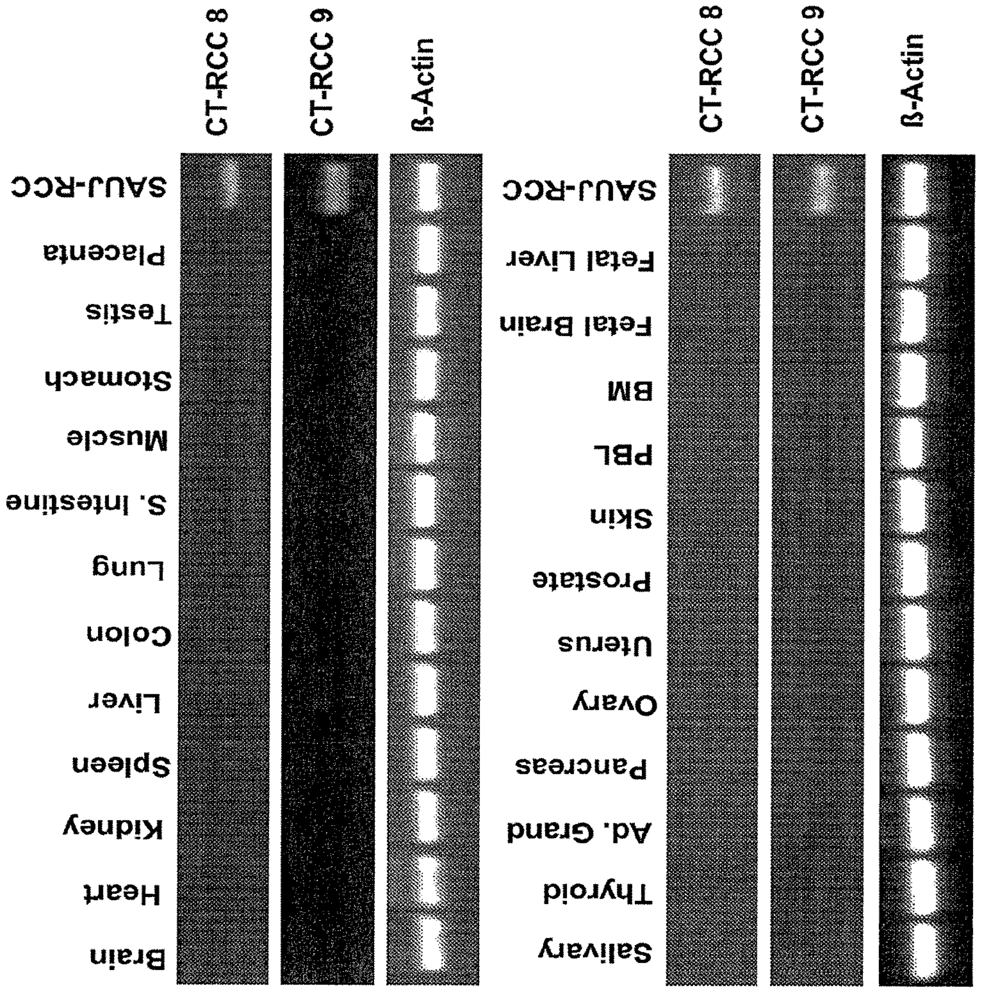

Semi-quantitative RT-PCR for expression of CT-RCC 8 and 9 was performed on cDNAs generated from different RCC cell lines and non-RCC tumors, as well as pooled cDNAs from 24 normal human tissues. CT-RCC 8 and 9 were detected in 8 of 14 RCC cell lines (FIG. 26*a*). Quantitative real-time PCR using CT-RCC common region specific primers showed CT-RCC common region transcripts were detectable in these same 8 RCC cell lines at varying levels (FIG. 26*b*). Both CT-RCC 8 and 9 were not detected by RT-PCR in a variety of different non-RCC tumor cell lines (FIG. 26*c*). Neither transcript was detected by RT-PCR in pooled cDNAs obtained from 24 normal tissues including the kidney and testis (FIG. 26*d*). The CT-RCC common region was also be detected by real-time PCR in freshly resected RCC tumors of clear cell histology (Table 1); in contrast, minimal to no expression of the CT-RCC common region was detected in a fresh oncocytoma specimen (obtained by nephrectomy), SAUJ-fibroblasts, patient (SAUJ) and donor (SKEM) LCL cells and pooled cDNAs obtained from normal kidneys, PBL and 48 different normal human tissue panels.

Table 1 shows results of the real-time PCR data were represented as threshold cycle ($C_T$) values (see Methods) and normalized each set of samples using the difference in $C_T$ between the sample cDNA and β-actin as a control. Relative transcripts levels were shown as the mean±SD of all pooled cDNA samples from the human-48 tissue RapidScan real-time PCR Gene Expression Panel (Origene).

TABLE 1

| | Sample # | Relative Transcripts to β-actin (x$10^5$) CT-RCC Common Region |
|---|---|---|
| Primary Clear Cell | C1 | 601.9 ± 61.8 |
| RCC tumors | C2 | 99.7 ± 10.7 |
| | C3 | 26.9 ± 5.5 |
| | C4 | 30.7 ± 4.2 |
| | C5 | 93.6 ± 24.1 |
| RCC Oncocytoma | O1 | 9.1 ± 0.2 |
| Normal Kidney | (Pooled cDNA) | 13.7 |
| PBL | (Pooled cDNA) | 9.4 |
| RCC Cell line | SAUJ | 1033.1 ± 196.3 |
| LCL | SAUJ | 9.0 ± 1.2 |
| LCL | SKEM | 4.4 ± 0.7 |
| Fibroblasts | SAUJ | 0.5 ± 0.1 |

*Results of the real-time PCR data were represented as $C_T$ values (see Methods) and normalized to each set of samples using the difference in threshold cycles between the sample cDNA and β-actin as a control.

TABLE 2

| Primer and Probe | Localization | Sequence | SEQ ID NO: |
|---|---|---|---|
| | | for RT-PCR | |
| RT-F1 | CT-RCC Common region | 5'-GAGCTCAGATCATGAGATGCGAGTC | 96 |
| RT-8R1 | CT-RCC 8 (nt 376-2155) | 5'-GTCAGGTCAGGTAGACCCAGGGCTG | 97 |
| RT-9R1 | CT-RCC 9 (nt 376-578) | 5'-GTCTCACCTCCCAGGTGTCAGGTG | 98 |
| | | for Real-time PCR | |
| Common F | CT-RCC Common region | 5'-GCAGATCCTGGGAGCACTCT | 99 |
| Common R | CT-RCC Common region | 5'TGTTCAACCGCTGTGTTAATTCTC | 100 |
| Common Taq | CT-RCC Common region | (FAM)TGCCCTGGTCAAATGCCTTGCC(TAMRA) | 101 |
| 8F | CT-RCC 8 (nt 376-2155) | 5'-GAACACCGGGAAGGAATCG | 102 |
| 8R | CT-RCC 8 (nt 376-2155) | 5'-TCTGCGGCTTGCTGCAT | 103 |

TABLE 2-continued

| Primer and Probe | Localization | Sequence | SEQ ID NO: |
|---|---|---|---|
| 8 Taq | CT-RCC 8 (nt 376-2155) | (FAM)CATGTTCCAGATGTCCAGACTCCAATCG(TAMRA) | 104 |
| 9F | CT-RCC 9 (nt 376-578) | 5'-TGGAACATAGCCCCTTTGTG | 105 |
| 9R | CT-RCC 9 (nt 376-578) | 5'-GGATCCAGGCCGGAATTC | 106 |
| 9 Taq | CT-RCC 9 (nt 376-578) | (FAM)TGGTCTGGCATCCTTTCCACCG(TAMRA) | 107 |
| β-actin 420F | β-actin | 5'-GCGAGAAGATGACCCAGATC | 108 |
| β-actin 522R | β-actin | 5'-CCAGTGGTACGGCCAGAGG | 109 |
| β-actin Taq | β-actin | (FAM)CCAGCCATGTACGTTGCTATCCAGGC(TAMRA) | 110 |

EXAMPLE 3

Detection of CT-RCC-1 Specific CTL In Vitro and In Vivo

A PE-conjugated HLA-A11/CT-RCC-1 tetramer was synthesized to evaluate for CT-RCC-1-reactive T-cells in vivo; 56.6% of the TCR-Vβ7$^+$ CD8+SAUJ-CTL line established from SAUJ-PBMC (day +1213) bound to the CT-RCC-1 tetramer confirming the specificity of the tetramer for CT-RCC-1-reactive T-cells. Tetramer analysis showed CT-RCC-1-specific T-cells were absent in patient SAUJ before HCT but became detectable in the post-transplant setting (FIGS. 26A-26E), comprising comprised 1.12% and 0.48% of the CD3$^+$CD8$^+$ T-cell repertoire of PBMCs collected on post-transplant days +913 and +1213 respectively.

Figures 26E, 26F:
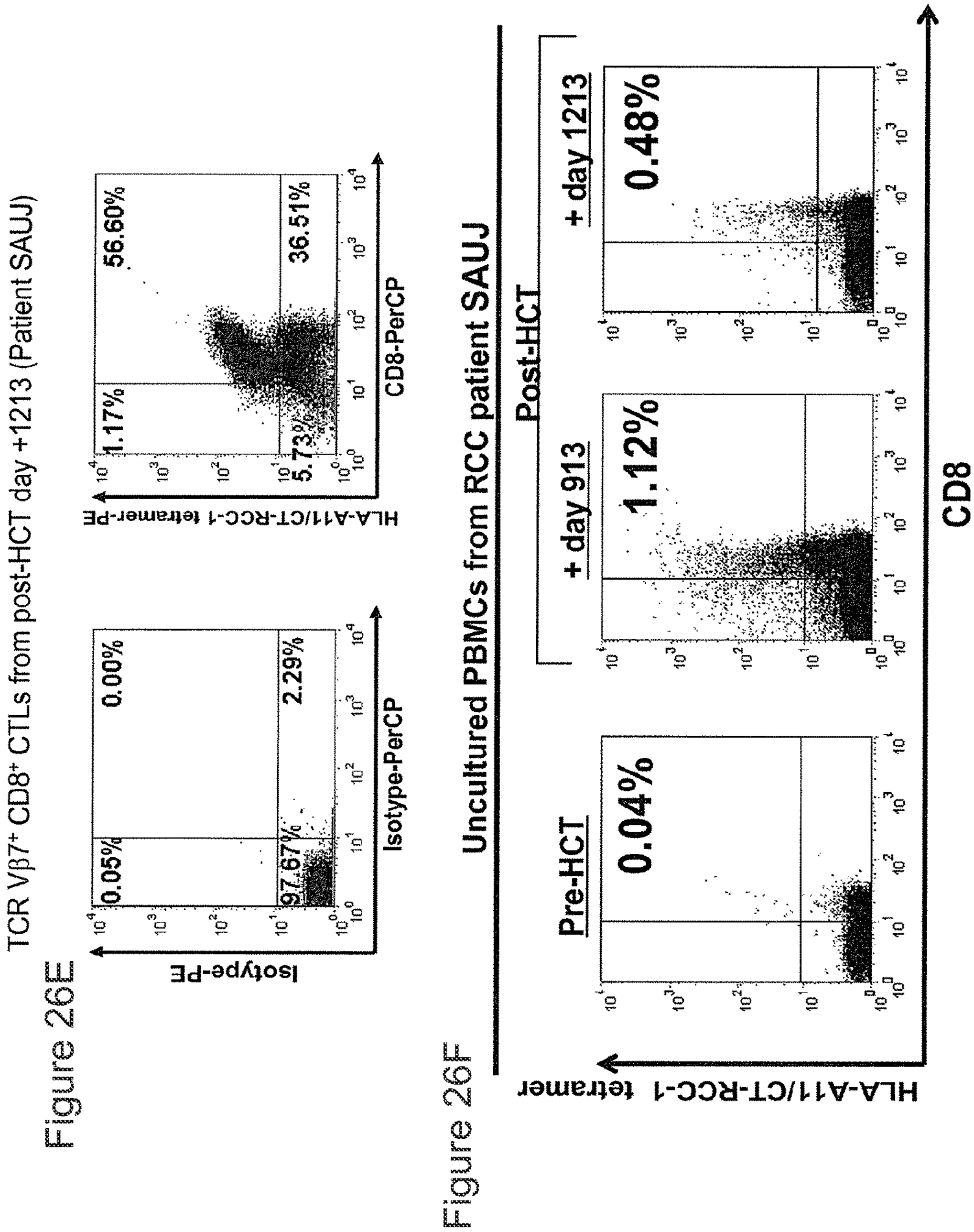

FIG. 26A and FIG. 26B shows expression of CT-RCC 8 and 9 cDNAs in tumors and nonmalignant tissues and detection of circulating CT-RCC-1 peptide-specific T-cells after HCT. FIG. 26A Semi-quantitative RT-PCR for CT-RCC 8 and 9 was performed using cDNAs prepared from 14 different human RCC tumor lines or from cDNAs isolated from LCL obtained from the patient (SAUJ-LCL) or transplant donor (SKEM-LCL) or from fibroblasts of the patient (SAUJ-Fibro). Both CT-RCC 8 and 9 were detected in 8 of 14 RCC cell lines. FIG. 26B CT-RCC common region transcripts were detectable in these same 8 RCC cell lines at variable levels by quantitative real-time RT-PCR analysis using CT-RCC common region specific primers. FIG. 26C With the exception of LCLs, no significant expression of CT-RCC 8 and 9 transcripts was detected by RT-PCR in a variety of different non-RCC malignant cell lines. FIG. 26D Neither transcript was detected by RT-PCR in pooled cDNAs obtained from 24 normal human tissues including the kidney and testis. β-actin used as an internal control and cDNA from SAUJ-RCC was used as a positive control. FIG. 26E RCC-reactive SAUJ-CTL was generated by stimulating post-transplant SAUJ-PBMC (day +1213) with irradiated SAUJ-RCC cells followed by flow sorting for TCR-Vβ7$^+$ CD8$^+$ T-cells. CTLs and non-cultured PBMCs from patient SAUJ after HCT (FIG. 26F) were stained with a PE-conjugated HLA-A*1101/CT-RCC-1 (ATFLGSLTWK) tetramer with APC-labeled anti-CD3 mAb and PerCP-labeled anti-CD8 mAb. Tetramer analysis showed 56.6% of the CD3$^+$ CD8$^+$ cells in this CTL line had antigen specificity for the CT-RCC-1 peptide. FIG. 26F CT-RCC-1 specific T-cells were absent in the patient before HCT but expanded in the post-transplant setting; PBMCs collected from SAUJ before HCT did not bind to the CT-RCC-1 tetramer. CT-RCC-1 specific T-cells were detected after HCT following tumor regression, comprising 1.12% and 0.48% of the CD3$^+$ CD8$^+$ T-cell repertoire by tetramer analysis. Quantification of CD8 positive and tetramer binding cells was carried out on a CD3$^+$ gated population. A total of 200,000 events were analyzed in each case).

EXAMPLE 4

Broadly Expressed Minor Histocompatibility Antigens and Antigens Restricted to the Tumor are Targets for Donor T-Cells in Treatment of Renal Cell Carcinoma Although clinical observations suggest T-cells mediate graft-versus-RCC effects, difficulty in generating tumor lines from patients undergoing transplantation has hampered in vitro studies aimed at characterizing antigens targeted by donor T-cells. In this study, we found evidence suggesting broadly expressed minor histocompatibility antigens and antigens restricted to the tumor are targets for donor T-cells isolated from patients with evidence for a graft-versus-RCC effect.

ELISPOT analysis of the 4 patients with metastatic RCC and their HLA-matched donors showed tumor-reactive T-cells were absent at baseline. Following transplantation, CD8$^+$ donor T-cells that recognized patient hematopoietic cells and RCC were detected in all 4 patients analyzed. In the 2 non-responders, T-cells recognizing patient tumor cells were detected only transiently. In contrast, in the 2 patients who had tumor regression, RCC-reactive T-cells persisted in the blood over a prolonged interval. Using PBMC collected tumor regression was noted, CTLs that were cytotoxic to the patient's RCC cells were expanded in vitro in both responding patients. In one of these responders (LYO), CTL and a CD8$^+$ T-cell clone was isolated with a cytotoxicity pattern consistent with recognition of an antigen that was not restricted to the tumor, lysing both patient LCL cells and RCC cells but not donor LCLs. These findings are consistent with donor T-cell recognition of a mHas expressed broadly on both tumor cells and hematopoietic cells of the recipient. Tykodi et al (Tykodi et al., *Clin Cancer Res* 10:7799-811, 2004) previously demonstrated that mHa-specific T-cell clones cytotoxic to RCC cells in vitro could be isolated from patients with metastatic kidney cancer following an allogeneic HCT. mHas are known to be expressed on a variety of hematological malignancies and are thought to be dominant targets of donor T-cells mediating graft-vs.-leukemia effects. Our data confirms that mHas absent in the donor but present in the patient are expressed on patient RCC cells. The identification of an RCC-reactive (LYO-RCC) mHa specific T-cell clone in a responding patient suggests donor T-cells were primed in vivo after HCT to this antigen and provides indirect evidence that mHas may be a target for a graft-versus-RCC effect. This finding is also consistent with the clinical observation that GVT effects are frequently associated with GVHD. Bregni et al., *Bone Marrow Transplant* 38:527-37, 2006; Childs et al., *N Engl J Med* 343:750-8, 2000.

$CD8^+$ CTL lines and T-cell clones with in vitro tumor-specific cytotoxicity were expanded from PBMC collected after HCT from patient SAUJ who had regression of metastatic RCC associated with prolonged survival. Using cDNA expression cloning, we identified two cDNAs (CT-RCC 8 and CT-RCC 9) that shared a common sequence region of 375 bps encoding an antigen recognized by HLA-A11-restricted RCC-reactive CTL clones. By transfecting truncated mini genes derived from the common region of these cDNAs, we identified a 10-mer peptide (CT-RCC-1) recognized by HLA-A11-restricted RCC-reactive donor T-cells. Remarkably, CT-RCC-1-specific CTL recognized approximately 50% of RCC cell lines that expressed HLA-A11 but not patient fibroblasts or patient LCL, suggesting this antigen is commonly expressed in RCC tumors at levels that induce CTL killing but not in normal tissues. Semi-quantitative RT-PCR for expression of CT-RCC 8 and 9 and real-time PCR for their shared common sequence region showed these transcripts were expressed at variable levels in primary kidney tumor tissues and in >50% of cultured RCC cell lines but not in pooled cDNA from normal tissues including the kidneys and testis nor in a number of other non-RCC tumor lines.

The DNA encoding CT-RCC 8 and 9 localize to a previously uncharacterized gene of unknown function on chromosome 6q. Genomic DNA sequences show this gene to be consistent with a HERV type E previously unknown to be expressed in human cells. The 132 bp common sequence region shared by the CT-RCC 8 and 9 transcripts encoding the CT-RCC-1 peptide have 100% sequence homology with the 5' long terminal repeat (LTR) of this HERV. The function of the genetic sequences encoding CT-RCC 8 and 9 in RCC and their full protein products are currently unknown. Likewise, it is unknown if other immunogenic peptides derived from these HERV genes in RCC are presented in the context of other HLA-class I molecules.

HERVs exist as proviruses, the integrated form of retroviral DNA, within the germ line DNA of their host species. Lower et al., *Proc Natl Acad Sci USA* 93:5177-84, 1996. HERVs and other LTR-like elements are widely dispersed compromising >8% of the entire human genome. Bock, M. and Stoye, J. P., *Curr Opin Genet Dev* 10:651-5, 2000; Li et al., *Nature* 409:847-9, 2001; Smit, A. F., *Curr Opin Genet Dev* 9:657-63, 1999. HERVs are thought to have inserted into the germ cells of primates and have remained an integral part of primate genomes during evolution. HERVs have multiple stop codons, insertions, deletions, and frame shifts and retain some of the hallmarks of exogenous retroviruses with a genomic structure that includes group-associated antigen (gag), pol and env genes sandwiched between LTR regions [7,10]. Lower et al., *Proc Natl Acad Sci USA* 93:5177-84, 1996; Griffiths, D. J., *Genome Biol* 2:REVIEWS1017, 2001. Despite mutational decay, some components of HERVs retain biological activity. Griffiths, D. J., *Genome Biol* 2:REVIEWS1017, 2001.

This is the first report to identify a HERV-derived tumor antigen expressed in RCC. The HERV sequences identified in this study encoding the CT-RCC transcripts expressed in RCC are a part of the HERV-E family clone 4-14 (HERV ID: 23549). The CT-RCC 8 and 9 cDNAs have a typical HERV-E LTR and contain a putative TATA-box (CCTTAAAAG) and a polyadenylation signal (AATAAA). In contrast to HERV-E clone 4-1 shown by Seifathet et al. (Seifarth et al., *J Virol* 79:341-52, 2005) to have active transcription in many normal tissues (including the kidney), the transcriptional products identified to be expressed in RCC derived from the HERV-E clone 4-14 were not detected in normal tissues.

HERV-K expression of gag, rec, and env proteins has been identified in some malignancies. Buscher et al., *Cancer Res* 65:4172-80, 2005; Depil et al., *Leukemia* 16:254-9, 2002; Muster et al., *Cancer Res* 63:8735-41, 2003; Schiavetti et al., *Cancer Res* 62:5510-6, 2002. An antigenic peptide named HERV-K-MEL derived from the env gene of a HERV-K provirus was found to be expressed in a majority of primary and metastatic melanomas as well as in the testis and skin cells. Schiavetti et al., *Cancer Res* 62:5510-6, 2002. HERV-K expression of gag, rec, and env proteins was also found to be highly specific for malignant melanoma tumor cells, being present in melanoma cells but not in normal melanocytes or lymph nodes. Muster et al., *Cancer Res* 63:8735-41, 2003. In addition, expression of spliced HERV-K env and rec proteins was detected in a teratocarcinoma cell line and in melanoma cells. Buscher et al., *Cancer Res* 65:4172-80, 2005. In hematological malignancies, transcriptional activity of a HERV-K10-like gag gene was detected at higher levels in leukemia cells than was found in normal PBMCs or umbilical cord blood cells. Depil et al., *Leukemia* 16:254-9, 2002. Although more than 50 HERV-E's are estimated to exist in the human genome, this is the first report to identify a HERV-E transcription product expressed in tumor cells. Furthermore, in contrast to HERV-K expression in tumors, the sequences derived from HERV-E clone 4-14 genes comprising the CT-RCC antigens appear to be selectively expressed in RCC cells and have no or virtually undetectable levels of expression in normal tissues, potentially making them ideal targets for tumor immunotherapy.

Recently, CTL specific for HERV-derived peptides that kill tumor cells in vitro have been identified in a few cancer patients. Schiavetti et al., *Cancer Res* 62:5510-6, 2002; Rakoff-Nahoum et al., *AIDS Res Hum Retroviruses* 22:52-6, 2006. In our study, we expanded CTL clones from PBMC obtained from a responding patient after HCT that killed patient RCC cells and $HLA-A11^+$ RCC cells in vitro. The HLA-A11-restricted 10-mer peptide named CT-RCC-1 was identified to be the target antigen of these RCC reactive CTL. Tetramer analysis showed CT-RCC-1-specific T-cells were absent at baseline but were detected after HCT following regression of metastatic disease, suggesting this antigen had immunogenicity in vivo. To the best of our knowledge, this is the first report to identify a T-cell population recognizing a HERV-derived antigen with expression restricted to tumor cells.

Because the phenotypic frequency of HLA-A11 expression is only 33% in Chinese, 20% in Japanese, and 10% in Caucasians (Sette, A. and Sidney, J., *Immunogenetics* 50:201-12, 1999; Sidney et al., *Immunol Today* 17:261-6, 1996), immunotherapy approaches targeting the CT-RCC-1 antigen would be limited to a minority of patients with metastatic kidney cancer. However, it is possible that other immunogenic peptides derived from this HERV could be expressed on more common HLA class I molecules, a finding that potentially could broaden the application of immunotherapy approaches targeting antigens derived from this HERV to a greater percentage of patients with metastatic RCC.

The factors regulating expression of the CT-RCC antigens in RCC are currently unknown. However, the observation that CT-RCC 8 and CT-RCC 9 were not detected in a variety of hematological malignancies and other solid tumors suggest genetic mutations specific to RCC such as the von Hippel-Lindau gene may in part regulate expression of transcripts derived from this HERV.

In conclusion, this is the first report providing evidence that allogeneic HCT can be associated with tumor-specific immune responses to antigens expressed on RCC. It is also the first report to identify a tumor-restricted antigen expressed on a solid tumor using allogeneic T-cells. The in vivo expansion of CT-RCC antigen-specific T cells in a patient who had a GVT effect associated with prolonged regression of metastatic RCC suggests that gene products derived from this HERV may be a novel target for RCC immunotherapy.

EXAMPLE 5

Treatment of Patients with Metastatic Renal Cell Carcinoma

For treatment of patients with renal cell carcinoma, patients will have their tumors analyzed for expression of genes derived from HERV Type E. Two treatment scenarios are envisioned.

Adjuvant Therapy: For patients with a primary kidney tumor that express gene products from this HERV type E who are without metastatic disease. We envision vaccinating such patients with either a single peptide, a polypeptide, or a whole protein derived from genes expressed by the HERV Type E to induce a long-lasting protective T-cell anti-tumor antigen immune response that would decrease the chances of disease relapse. Such proteins or peptides could be derived from either the CT-RCC-8 and/or CT-RCC-9 transcripts or could be derived from the HERV Envelope gene or other gene products of HERV type E. As an example, patients who are HLA-A11 positive could be vaccinated with the CT-RCC-1 10 mer peptide or the entire protein from which the peptide is derived.

Treatment of Metastatic RCC: For patients with metastatic RCC whose tumor is found to express gene products from this HERV type E who are without metastatic disease; We envision vaccinating such patients with either a single peptide vs. a polypeptide vs. whole protein derived from genes expressed by this HERV to induce a long-lasting T-cell anti-tumor antigen immune response that would result in regression and possible cure of metastatic disease. Such proteins or peptides could be derived from either the CT-RCC-8 and/or CT-RCC-9 transcripts or could be derived from the HERV Envelope gene or other gene products of this HERV type E. As an example, patients who are HLA-A11 positive could be vaccinated with the CT-RCC-1 10 mer peptide or the entire protein from which the peptide is derived.

Peptides that are useful for treatment of renal cell carcinoma in patients include, but are not limited to a peptide derived from the CT-RCC-8 (2155 bps-SEQ ID NO: 45), CT-RCC-9 (578 bp; SEQ ID NO: 11) or the Env/HERV-E (SEQ ID NO: 47). These peptides can encode a transcript for an antigen that could be a target for an anti-tumor immune response. Based on the current data, the CT-RCC-1 peptide (SEQ ID NO: 1) and any peptide derived from SEQ ID NO: 12 or from the SEQ ID NO: 48 protein is a good candidate to elicit an anti-tumor immune response.

Future studies include ability to expand $CD8^+$ CT-RCC-1 peptide specific T-cells in vitro using dendritic cells pulsed with CT-RCC-1 peptide (Pep-A104-K133; ATWLGSK-TWK; SEQ ID NO: 1) will be tested in vitro In vitro, the above expanded T-cells will be tested for their ability to recognize monocytes pulsed with the CT-RCC-1 peptide and for their ability to kill RCC cells that are HLA-A11 positive.

Assuming CT-RCC-1 specific CD8+ T-cells can be generated in vitro that kill RCC cells, we envision a clinical trial to evaluate whether CT-RCC-1 peptide vaccination can induce an anti-tumor immune response resulting in tumor regression in patients with metastatic RCC.

EXAMPLE 6

Materials and Methods

Transplant Approach. From February 1998 through May 2006, 74 consecutive patients with biopsy confirmed metastatic RCC underwent a nonmyeloablative allogeneic hematopoietic cell transplant from an HLA-matched or single antigen mismatched sibling donor at the NHLBI on IRB approved protocol 97-H-0196 investigating for donor immune mediated graft-versus-RCC effects. Eligible patients were required to have biopsy proven metastatic disease that was confirmed radiographically to be progressive. The nonmyeloablative transplant approach has previously been described. Griffiths, D. J., *Genome Biol* 2:REVIEWS1017, 2001. Briefly, transplant conditioning consisted of cyclophosphamide (120 mg/$m^2$) and fludarabine (125 mg/$m^2$) followed by infusion of an un-manipulated, granulocyte colony-stimulating factor (G-CSF) mobilized hematopoietic stem cell allograft from an HLA compatible family donor. Cyclosporine A (CSA) alone or in combination with mycophenolate mofetil (1 gram orally twice a day) or intravenous methotrexate (5 mg/$m^2$ on days 1, 3, 6) was used as GVHD prophylaxis. To optimize the induction of a GVT effect, tapering of immunosuppression was initiated in patients with mixed T-cell chimerism or disease progression as early as day 30 post-transplant. Patients with progressive disease following CSA tapering were eligible to receive escalating doses of donor lymphocyte infusions (DLI) and/or cytokines (IFN-$\alpha$ or interleukin-2.)

Cell lines. The human RCC cell lines, SAUJ-RCC, JOH-RCC, LYO-RCC, and POR-RCC were established from surgically resected tumors procured at the NHLBI and the NCI (IRB approved protocols 97-H-0196 and 97-C-0147) and maintained in our laboratory. The fibroblast cell line SAUJ-Fibro was established by culturing of cells obtained from a skin punch biopsy from patient SAUJ. LCLs were established from transplant patients and their donors by culturing PBMCs with EBV-containing supernatant harvested from cell line B95-8 (American Type Culture Collection) in the presence of 100 μg/ml CSA (Sandoz Pharmaceuticals).

Two HLA-A11 positive RCC cell clines (MAR-RCC, BEN-RCC) and seven RCC cell lines established from patients who were not HLA-A11 positive that were subsequently stably transfected to express HLA-A11 (COL-RCC, SEA-RCC, WHI-RCC, STR-RCC, URB-RCC, SNY-RCC and ORT-RCC; a gift from Dr. Qiong Wang at NCl/NIH) were used as tumor targets. Ten RCCs that were HLA-A11 negative (STA-RCC, JOH-RCC, POR-RCC, LYO-RCC, Mayo1-RCC, MANFC-RCC, WENJ-RCC, UCRCC3, UCRCC4 and COLH-RCC) were established in our laboratory. Patient B-cells were expanded from PBMCs taken before HCT using CD40 ligand-transfected NIH3T3 cells (t-CD40L) as previously described. Takahashi et al., *Blood* 103:1383-90, 2004. CD19 expression on expanded B-cells was confirmed by flow cytometry; expanded B-cells were harvested between days 14 to 28 and were used to assess for T-cell allo-reactivity in an ELISPOT analysis.

ELISPOT assay. IFN-γ-producing antigen-specific T-cells were counted using an ELISPOT assay. PBMCs were incubated in triplicate at $5\times10^4$ cells/well overnight at 37° C. in 5% $CO_2$ in RPMI 1640 containing 10% fetal calf serum in the absence or presence of the same number of stimulator cells (stimulator cells included the patient's RCC cells, CD40L expanded B-cells and the donor's CD40L expanded B-cells as negative control). The next day, cells were removed by washing buffer with PBS/0.05% Tween 20 and biotinylated anti-IFN-γmAb, and 7-B6-1 biotin (Mabtech) added (100 μl of 1 μg/ml) and left for 2 hours at room temperature, followed by incubation with streptavidin-alkaline phosphatase (Mabtech) for an additional 1 hour. Individual cytokine-producing cells were detected as dark purple spots after 10-minute reaction with 5-bromo-4-chloro-3-indolyl phosphate/nitroblue tetrazolium alkaline phosphatase substrate (Sigma). After washing in tap water to stop color development, colored spots on the dried membranes were counted using a KS-ELISPOT microscopy system (Carl Zeiss).

Generation of CTLs. PBMCs collected from patient LYO (HLA type-A2301/A68, B35/B5801, Cw0301/-) and SAUJ (HLA type-A11/A11, B51/B55, Cw1/Cw7) before and after HCT were prepared by Ficoll density gradient centrifugation. PBMCs were collected after tumor regression from patients LYO on post-transplant day +211 and patient SAUJ on post-transplant day +1213 were cultured in RPMI 1640 (Cellgro) medium supplemented with 10 ng/ml of recombinant human interleukin (IL)-15 (R&D systems), 10% of human AB serum (Gemini Bio-Products), 0.25M HEPES, 50 units of penicillin, and 50 μg of streptomycin. CTL lines LYO-CTL and SAUJ-CTL were established by repeatedly stimulating post-HCT day +211 LYO-PBMCs with irradiated (200Gy) LYO-RCC tumor cells and post-HCT day +1213 SAUJ-PBMCs with irradiated (200Gy) SAUJ-RCC tumor cells at 7 to 10-day intervals.

Bulk LYO-CTL or SAUJ-CTL were cloned by limiting dilution (0.3, 1, or 3 cells/well) into 96-well round bottom plates containing irradiated allogeneic HLA mismatched allogeneic PBMCs as feeder cells, recombinant human IL-2, and anti-CD3 mAb. Fourteen days later, wells exhibiting cell growth were screened for recognition of the patient's RCC cells, the patient's LCL and the donor's LCL by a cytotoxicity assay or an ELISA for IFN-γ secretion. The $CD8^+$ T-cell clone LYO-clone 1 which had cytotoxicity against LYO-RCC was further expanded for additional experiments. The T-cell clone BZ-4 (isolated from SAUJ-CTL) that recognized SAUJ-RCC cells but not patient fibroblasts or SAUJ-LCL was further expanded for additional experiments.

Generation and cloning of SAUJ HLA-A11-restricted CTLs. To expand the RCC-reactive T-cell clone, BZ-4 cells (isolated from SAUJ-CTL) were resuspended in 25 ml of AIM-V medium (GIBCO Invitrogen) containing 300 IU/ml of IL-2, 30 ng/μl of OKT3, $2.5\times10^6$ cells irradiated (50Gy) allogeneic feeder cells from a healthy volunteer. On day 5, 20 ml of culture medium was removed and replaced fresh medium including IL-2. On day 8 and 11, the cells were given IL-2. Expanded CTL clones were used on days 14 or 15 for further experiments.

Cytotoxicity and cytokine secretion assays. Following a 24-hour co-culture of T-cell lines with target cells, IFN-γ or granulocyte macrophage-colony stimulating factor (GM-CSF) secretion was measured by ELISA (ENDOGEN) in triplicate assays; absorbance was detected at 450 nm using an ELISA reader. The inhibition of IFN-γ secretion using monoclonal antibodies (mAbs) bound to MHC-class I (on SAUJ-RCC and LYO-RCC) and HLA-A11, HLA-B55 and HLA-DR on SAUJ-RCC cells and TCR-Vβ7, TCR-Vβ3, CD8, and CD4 on SAUJ TCR-$V\beta7^+$ sorted CTL was assessed by ELISA.

Cytotoxic activity were measured by a standard 6-hour $^{51}Cr$-release assay at various effector to target ratios. Takahashi et al., *Blood* 103:1383-90, 2004; Igarashi et al., *Blood* 104:170-7, 2004. After a 6-hour incubation at 37° C., supernatant was harvested and radioactive content was measured by a gamma counter. Specific cytotoxicity was calculated as [(experimental $^{51}Cr$ release−spontaneous $^{51}Cr$ release)/(maximum $^{51}Cr$ release−spontaneous $^{51}Cr$ release)]×100%. All values shown represent the average of duplicates or triplicates±SD.

Construction and screening of SAUJ-RCC cDNA library. The cDNA library from SAUJ-RCC was constructed with poly (A)±RNA using an mRNA isolation system (FastTrack 2.0 kit; Invitrogen). cDNA was prepared with the SuperScript Plasmid system (Invitrogen) and ligated into the eukaryotic plasmid expression vector pME-SMART. Hanada et al., *Nature* 427:252-6, 2004. Plasmid DNA was isolated from each pool using Qiaprep 96 Turbo Miniprep kit (QIAGEN). 300 ng of pooled plasmid cDNAs were transfected into $5\times10^4$ COS7-A11 cells using Lipofectamine 2000 (Invitrogen) in 96-well plates for 24 hours. These cells were cultured with serum and antibiotic-free DMEM. SAUJ-CTL clone BZ-4 were added and incubated for 24 hours, the supernatants were harvested, and GM-CSF production was measured using ELISA.

Cloning of gene CT-RCC 8 and 9 cDNAs. Sequence analysis of PCR-amplified DNA fragments, which were generated in semi-quantitative RT-PCR, was carried out to confirm that the DNA fragments were derived from mRNAs of CT-RCC 8 or CT-RCC 9. PCR bands electrophoresed on agarose gels were cut out then extracted using the QIAquick gel extraction Kit (QIAGEN) and subjected to sequence analysis as described below. To examine the genomic sequences localizing CT-RCC 8 and CT-RCC 9-exons, PCR amplification of genomic DNA was performed as follows: 1 cycle of denaturing (95° C. for 2 min); 35 cycles of denaturing (95° C. for 30 sec), annealing (52° C. or 55° C. for 50 sec) and extension (72° C. for 1 min), followed by extension (72° C. for 5 min). The products obtained by PCR were purified by the QIAquick Gel Extraction Kit after cutting DNA fragments from agarose gels or QIAquick PCR Extraction Kit. The purified PCR products derived from cDNAs or genomic DNAs were subjected to direct sequencing analysis with adequate primers using the BigDye Terminator version 3.1 Ready Reaction Kit and ABI Prism 3100 Genetic Analyzer (Applied Biosystems,), according to the manufacturer's protocol. pME-SMART- or pcDNA3.1-based plasmids described above were sequenced in a similar manner. pME-SMART-based plasmids obtained by cDNA cloning were sequenced using the BLAST Search. Sequences of pcDNA3.1-based mini-gene plasmids were confirmed by comparing with the human DNA sequence from clone RP3-488C13 on chromosome 6 (Accession #AL133408) or oligonucleotide sequences designed using the Blast2 program.

Construction of Mini-genes. Mini-genes encoding CT-RCC within the human DNA sequence from clone RP3-

488C13 were constructed by PCR amplification or annealing of synthetic-forward and -reverse oligonucleotides.

For the PCR-based plasmid construction, PCR products were amplified with CT-RCC 8 or CT-RCC 9 cDNA clones serving as a template using the appropriate primer sets. Each forward primer has an extra CACC sequence at its 5' end for directional insertion into the pcDNA3.1 Directional TOPO Expression vector (Invitrogen). The PCR products were separated by agarose gel electrophoresis then were extracted from the gels. For the annealing based-plasmid construction, synthetic-forward and -reverse oligonucleotides were designed to construct short DNA fragments encoding parts of the common region of CT-RCC 8 and 9.

Genomic DNA isolation and DNA sequence analysis. Genomic DNAs were isolated from renal cell carcinomas and other cell lines using the QIAamp DNA Blood Mini Kit (QIAGEN). These DNAs were used for sequencing analysis of the genomic regions encompassing cDNA clones CT-RCC 8 and CT-RCC 9, including genomic sequences upstream of these cDNA clones. DNA sequencing reactions were performed with appropriate primers using the BigDye Terminator version 3.1 Ready Reaction Kit and ABI Prism 3100 Genetic Analyzer (Applied Biosystems).

Identification of the antigenic peptide derived from CT-RCC cDNAs. A total of 8 peptides (three 9-mers and five 10-mers) from the common sequence of CT-RCC 8 and CT-RCC 9 were synthesized and purchased from Genemed Synthesis, Inc. The identity and purity of each of the peptides were confirmed by mass spectrometer and high-performance liquid chromatography analysis. The amino acid sequences are as follows: Pep-R21-K50, RVYQCSQ-LIK (SEQ ID NO: 111); Pep-V24-K50, VYQCSQLIK (SEQ ID NO: 112); Pep-Q39-K68, QLIKASSFIK (SEQ ID NO: 113); Pep-L42-K68, LIKASSFIK (SEQ ID NO: 114); Pep-T107-K133, TFLGSLTWK (SEQ ID NO: 115); Pep-A104-K133, ATFLGSLTWK (SEQ ID NO: 116); Pep-T107-R136, TFLGSLTWKR (SEQ ID NO: 117); and Pep-P101-K133, PATFLGSLTWK (SEQ IDNO: 118). The peptides were dissolved in DMSO and stored at −20° C. until use. COS7-A11 cells were loaded with each peptide at varying concentrations (0.1 to 10000 nM) and IFN-γ secretion by the SAUJ-CTL clone BZ-4 following co-culture with peptide pulsed COS7-A11 cells was measured by ELISA.

RNA isolation, synthesis of cDNAs and Reverse Transcriptase (RT)-Polymerase Chain Reaction (PCR) analysis for the antigen encoding genes. Total cellular RNAs from RCCs and other cancer cell lines were extracted using the RNeasy Mini RNA Purification Kit (QIAGEN). Two sets of total RNAs were prepared from each individual cell line to perform experiments in duplicate.

Kidney tumors obtained from nephrectomy samples frozen in OCT (obtained on protocol 97-C-0147) were used to assess expression of CT-RCC 8 and CT-RCC 9 in fresh RCC tumors. Slides were made from frozen sections of fresh tumor; using a small scalpel, tumor cells were micro-dissected under light microscopy by a pathologist (Dr. Maria Merino, NCl/NIH) and total cellular RNAs were obtained using the PicoPure RNA Isolation Kit (Arcturus, Mountain View, Calif.). RNA samples were treated with DNase I to remove residual genomic DNA. cDNAs were synthesized using the SuperScript III First-Strand Synthesis System for RT-PCR (Invitrogen). For detection of cDNA expression of CT-RCC 8 and CT-RCC 9 in human normal tissues, Human 24 Tissue RapidScan gene expression cDNA panels (Oligene) were used in duplicate.

CT-RCC 8, CT-RCC 9, and 13-actin gene expression was assessed using semi-quantitative RT-PCR and quantitative real-time PCR. PCR amplification was done in 30μl of PCR mixture containing 0.41 cDNA template, TaKaRa LA Taq (TaKaRa Bio), and 200 nM of primers described in supplementary Table 1. The PCR mixtures for CT-RCC 8 and β-actin were initially incubated at 95° C. for 2min, followed by 30 cycles of denaturation at 95° C. for 30 sec, annealing for 55° C. for 30 sec, extension at 72° C. for 1 min, and one cycle of 72° C. for 5 min. CT-RCC 9 was amplified in a similar manner, except a reduced temperature was used for the annealing step (52° C. for 30 sec).

Quantitative real-time RT-PCR was carried out in 7500 Fast Real-Time PCR System in duplicate (Applied Biosystem). Using the Primer Express v2.0 software (Applied Biosystem), primers for the CT-RCC-common region (shared between CT-RCC 8 and CT-RCC 9), CT-RCC 8 and CT-RCC 9-specific regions, and β-actin (internal control) were designed (supplementary Table 1). Twelve primers were synthesized by Integrated DNA Technologies (IDT) and TaqMan probes were synthesized by Applied Biosystem or IDT. cDNAs obtained from the Human-48 tissue Rapid-Scan real-time PCR Gene Expression Panel (Origene) were used to measure by real-time PCR (in duplicate) the quantitative expression levels of the common sequence region of CT-RCC 8 and 9 in normal human tissues. Unlike the RapidScan gene expression panel described above, the real-time PCR panel contained only one concentration of the cDNAs normalized to β-actin. All data were analyzed using the 7500 System Sequence Detection Software (version 1.3). Results of the real-time PCR data were represented as $C_T$ values, where $C_T$ was defined as the threshold cycle of PCR at which the amplified product was first detected. We normalized each set of samples using the difference in threshold cycles ($\Delta C_T$) between the sample cDNA and β-actin as a control. Relative transcripts levels were calculated by the expression $2^{-\Delta\Delta CT}$ where $\Delta\Delta CT=\Delta C_{Tsample}-\Delta C_{T\beta\text{-}actin}$. Applied Biosystems, *User Bulletin* #2, *ABI PRISM* 7700 *Sequence Detection System,* 1997; Miura et al., *Blood* 104: 2187-93, 2004; Mullen et al., *Nat Immunol* 3:652-8, 2002. Each reaction was done in duplicate. Real-time PCR efficiencies of samples (CT-RCC common region, CT-RCC 8 and CT-RCC 9) and control (β-actin) were approximately equal over concentrations of 1 to100 ng of total cDNA.

Flow Cytometry and tetramer analysis for CT-RCC-1 ($A_{104}$-$K_{133}$) peptide specific T-cells. T-cell TCR-Vβ usage in the bulk SAUJ-CTL line was quantitated by flow cytometry staining using mAbs staining 22 different TCR-Vβ families (Beckman-Coulter). Phycoerythrin (PE)-conjugated HLA-A*1101/CT-RCC-1 ($A_{104}$-$K_{133}$; ATFLGSLTWK) tetramer was synthesized by the National Institute of Allergy and Infectious Diseases Tetramer Facility, Emory University Vaccine Center at Yerkes. Cultured CTL lines and uncultured PBMCs obtained before and after transplantation from the patient SAUJ were stained with the CT-RCC-1 ($A_{104}$-$K_{133}$) PE-conjugated tetramer (1:800 diluted) for 30 min at room temperature, then allophycocyanin (APC)-conjugated anti-CD3 mAb and peridinin-chlorophyll-protein complex (PerCP)-conjugated anti-CD8 mAb were added and incubated for an additional 15 min at 4° C. After washing with PBS, LIVE/DEAD fixable dead cell stain kit (Molecular Probes) was used for uncultured and frozen PBMCs to analyze only live cells by FACScalibur (Becton Dickinson) or CYAN MLE (Dako-Cytomation). Data analysis was performed using FCS Express V3 (De Novo software).

EXAMPLE 7

Detection of HERV-E Specific T Cells in Patients with RCC

FIG. 27 shows detection of CT-RCC-1 (ATFLGSLTWK) specific T cells in SAUJ CTL Thine. RCC reactive CTLs from patient SAUJ after HCT were stained with a PE-conjugated HLA-A*1101/CT-RCC-1 (ATFLGSLTWK) tetramer with APC-labeled anti-CD3 mAb and PerCP-labeled anti-CD8 mAb. Tetramer analysis showed 56.6% of the $CD3^+$ $CD8^+$ cells in this CTL line had antigen specificity for the CT-RCC-1 peptide.

Figure 28:
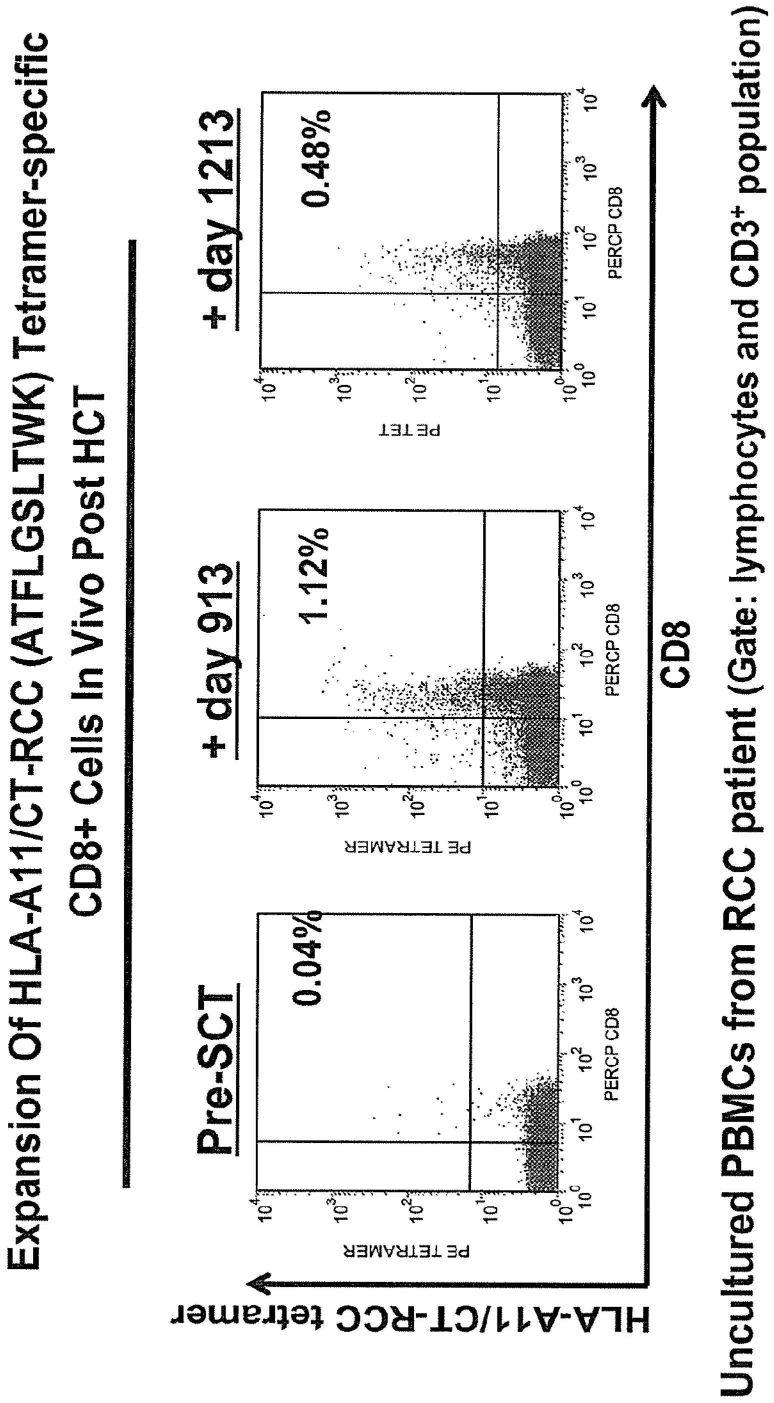
FIG. 28 shows expansion Of HLA-A11/CT-RCC (ATFLGSLTWK) Tetramer-specific CD8+ Cells In vivo Post HCT

FIG. 28 shows expansion of HLA-A11/CT-RCC (ATFLGSLTWK) tetramer-specific $CD8^+$ Cells In vivo Post HCT. Non-cultured PBMCs from patient SAUJ before and after HCT were stained with a PE-conjugated HLA-A*1101/CT-RCC-1 (ATFLGSLTWK) tetramer with APC-labeled anti-CD3 mAb and PerCP-labeled anti-CD8 mAb. CT-RCC-1 specific T-cells were absent in the patient before HCT but expanded in the post-transplant setting; PBMCs collected from SAUJ before HCT did not bind to the CT-RCC-1 tetramer. CT-RCC-1 specific T-cells were detected after HCT following tumor regression, comprising 1.12% and 0.48% of the CD3+ CD8+ T-cell repertoire by tetramer analysis. Quantification of CD8 positive and tetramer binding cells was carried out on a CD3+ gated population. A total of 200,000 events were analyzed in each case).

Figure 29:
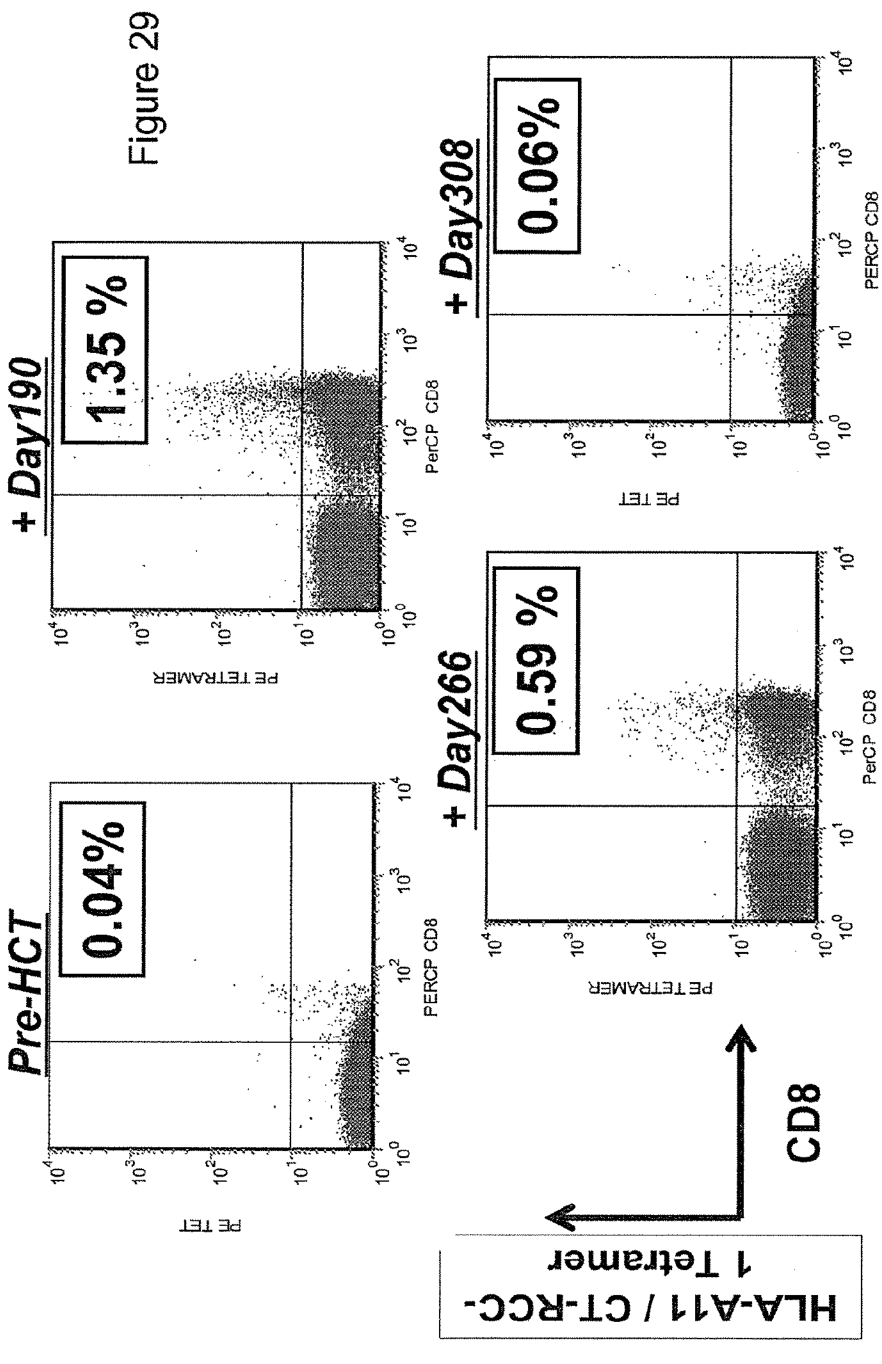
FIG. 29 shows: HLA-A11+ RCC Patients with HCT: #2 (JACSC); Kinetics of HLA-A11/CT-RCC-1-specific CD8+ cells in unstimulated-PBMCs in a RCC patient before and after HCT.

FIG. 29 shows HLA-A11+RCC Patients with HCT: #2 (JACSC). Kinetics of HLA-A11/CT-RCC-1-specific CD8+ cells in unstimulated-PBMCs in a RCC patient before and after HCT. Expansion of HLA-A11/CT-RCC (ATFLGSLTWK) Tetramer-specific CD8+ Cells In vivo Post HCT in patient JACSC who had evidence for tumor regression consistent with a GVT effect on day +130. Non-cultured PBMCs from patient JACSC before and after HCT were stained with a PE-conjugated HLA-A*1101/CT-RCC-1 (ATFLGSLTWK) tetramer with APC-labeled anti-CD3 mAb and PerCP-labeled anti-CD8 mAb. CT-RCC-1 specific T-cells were absent in the patient before HCT but expanded in the post-transplant setting; PBMCs collected from JACSC before HCT did not bind to the CT-RCC-1 tetramer. CT-RCC-1 specific T-cells were detected after HCT following tumor regression, comprising 1.35% on post transplant day +190. Quantification of CD8 positive and tetramer binding cells was carried out on a CD3+ gated population. A total of 200,000 events were analyzed in each case).

Figure 30:
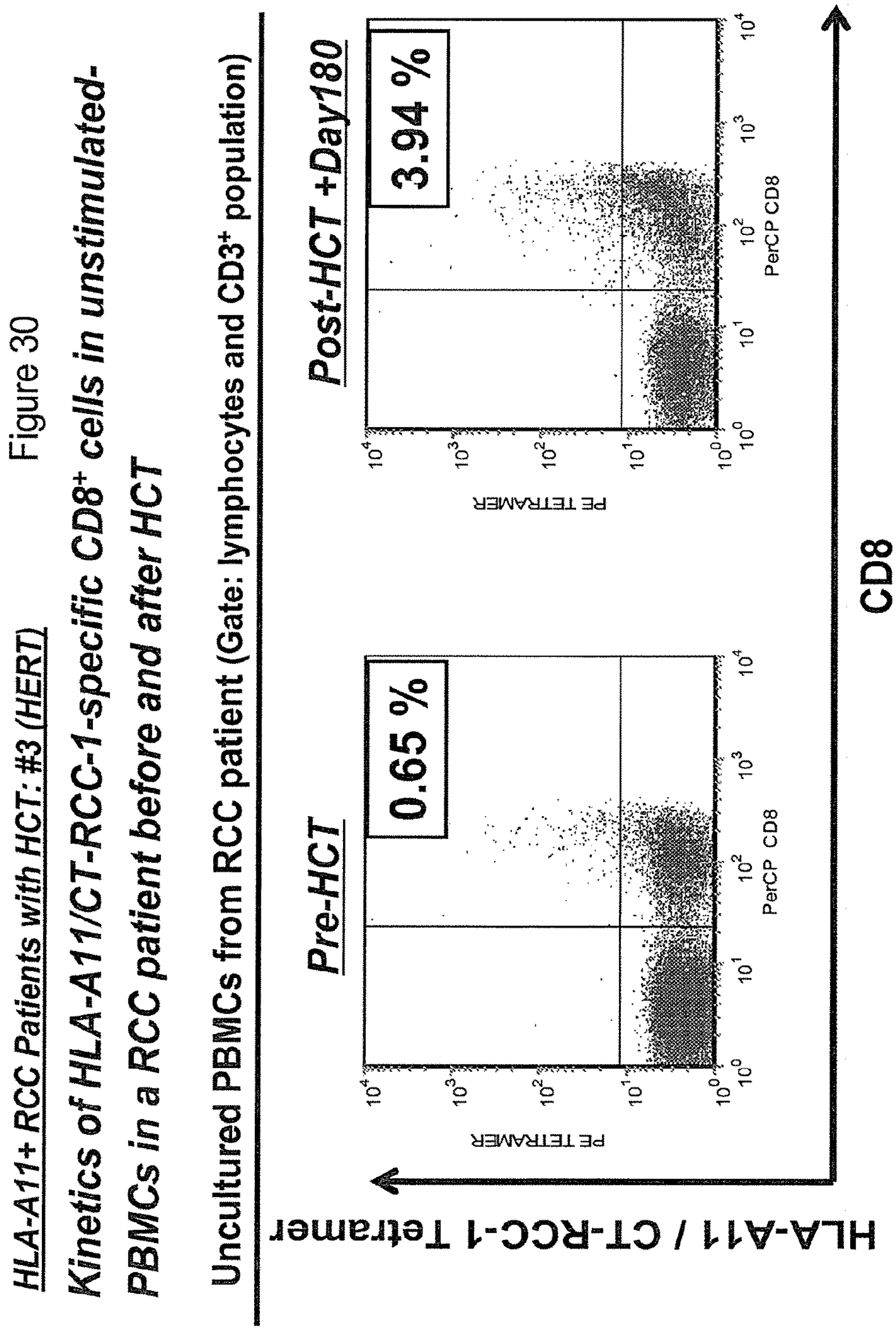
FIG. 30 shows: HLA-A11+ RCC Patients with HCT: #3 (HERT); Kinetics of HLA-A11/CT-RCC-1-specific CD8+ cells in unstimulated-PBMCs in a RCC patient before and after HCT.

FIG. 30 shows: HLA-A11+ RCC Patients with HCT: #3 (HERT); Kinetics of HLA-A11/CT-RCC-1-specific CD8+ cells in unstimulated-PBMCs in a RCC patient before and after HCT. Expansion of HLA-A11/CT-RCC (ATFLGSLTWK) Tetramer-specific CD8+ Cells In vivo Post HCT in patient HERT who had evidence for tumor regression consistent with a GVT effect on day +130. Non-cultured PBMCs from patient HERT before and after HCT were stained with a PE-conjugated HLA-A*1101/CT-RCC-1 (ATFLGSLTWK) tetramer with APC-labeled anti-CD3 mAb and PerCP-labeled anti-CD8 mAb. CT-RCC-1 specific T-cells were present at baseline comprising 3.94% of CD8+ T-cells on post transplant day 178. Quantification of CD8 positive and tetramer binding cells was carried out on a CD3+ gated population. A total of 200,000 events were analyzed in each case).

An embodiment of the invention provides a human endogenous retrovirus with selective expression in renal carcinoma cells (RCC) in a mammalian subject. A peptide derived from the CT-RCC genes called CT-RCC-1 is immunogenic in vitro. Tumor regression has been observed concomitant with expansion of CT-RCC-1 reactive $CD8^+$ CTL in 3 of 3 HLA $A11^+$ RCC patients who underwent an allogeneic HCT.

Figure 33:
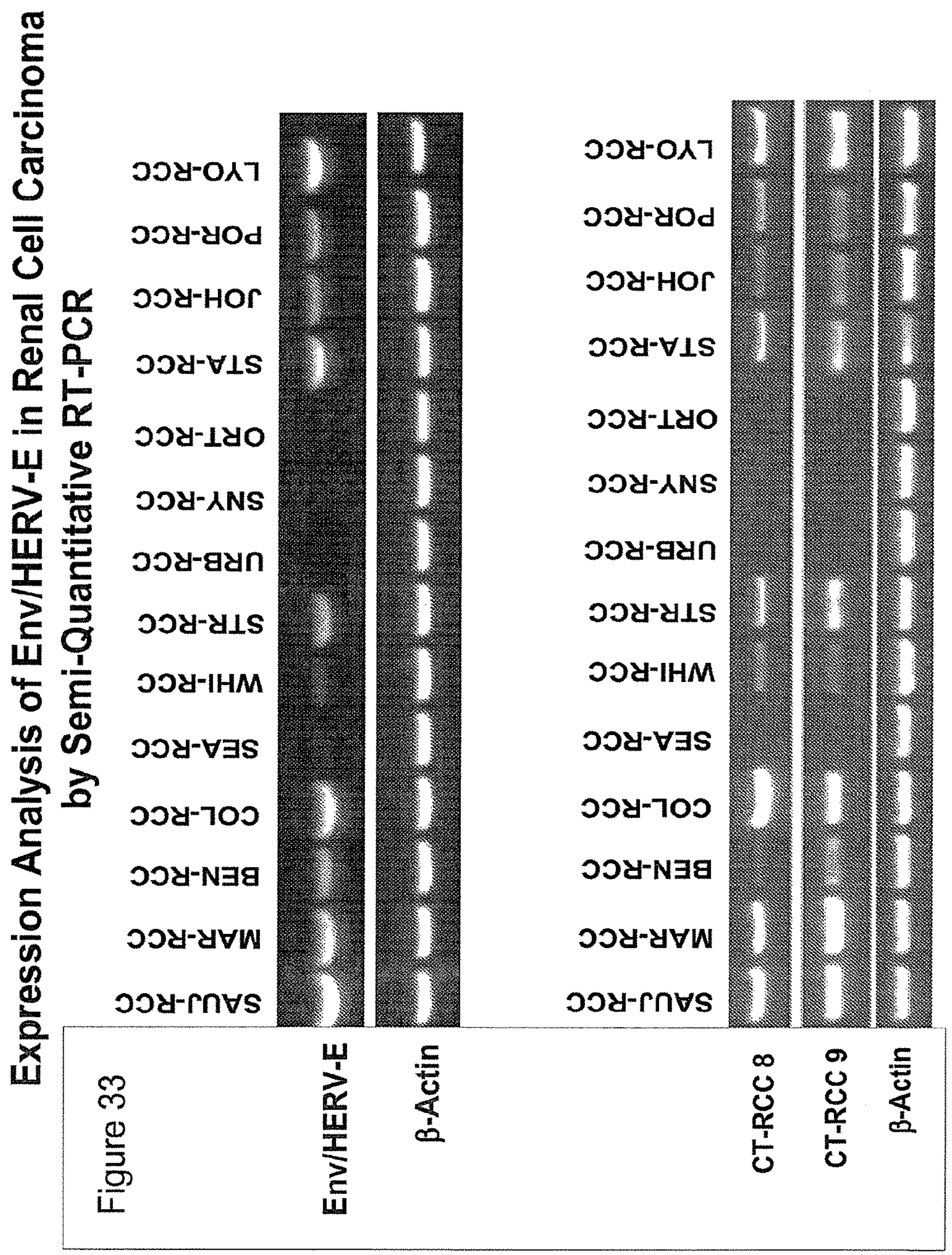
FIG. 33 shows expression analysis of Env/HERV-E in renal cell carcinoma by semi-quantitative RT-PCR.

FIG. 31 shows the localization of CT-RCC 8, CT-RCC 9 and HERV on Chromosome 6. We evaluated whether the envelope gene of this HERV type E was expressed in RCC. Using web site "retrosearch.dk", the HERV (ID 23549) env gene (Env:166112) was identified which is predicted to encode a 2331 bp mRNA (nt 89435013-89437343) derived from a single exon. The protein derived from this gene is predicted to be 211 aa in size and to localize to the cytoplasm and does not belong to any recognized protein family FIG. 32 shows characteristic Features of Env/HERV-E, the DNA coding sequence of Env/HERV-E (SEQ ID NO: 47) and the predicted protein sequence (SEQ ID NO: 48). Using web site "retrosearch.dk", the HERV (ID 23549) env gene (Env:166112) was identified which is predicted to encode a 2331 bp mRNA (nt 89435013-89437343) from a single exon. The protein derived from this gene is predicted to be 211 aa in size and to localize to the cytoplasm and does not belong to any recognized protein family FIG. 33 shows expression analysis of Env/HERV-E in renal cell carcinoma by semi-quantitative RT-PCR. Env/HERV-E was expressed on 10/14 RCC cell lines tested by semi-quantitative RT-PCR. Semi-quantitative RT-PCR to detect cDNA of this env gene in RCC and non-RCC cancer cell lines was performed. Expression Analysis of Env/HERV-E in Renal Cell Carcinoma by Semi-Quantitative RT-PCR revealed the Env/HERV-E was expressed in 10/14 RCC cell lines by semi-quantitative RT-PCR. Importantly, expression of the Env/HERV-E correlated 100% with expression of both CT-RCC 8+9 (i.e., only RCC cell lines that expressed CT RCC 8+9 expressed the Env/HERV-E.

Figure 34:
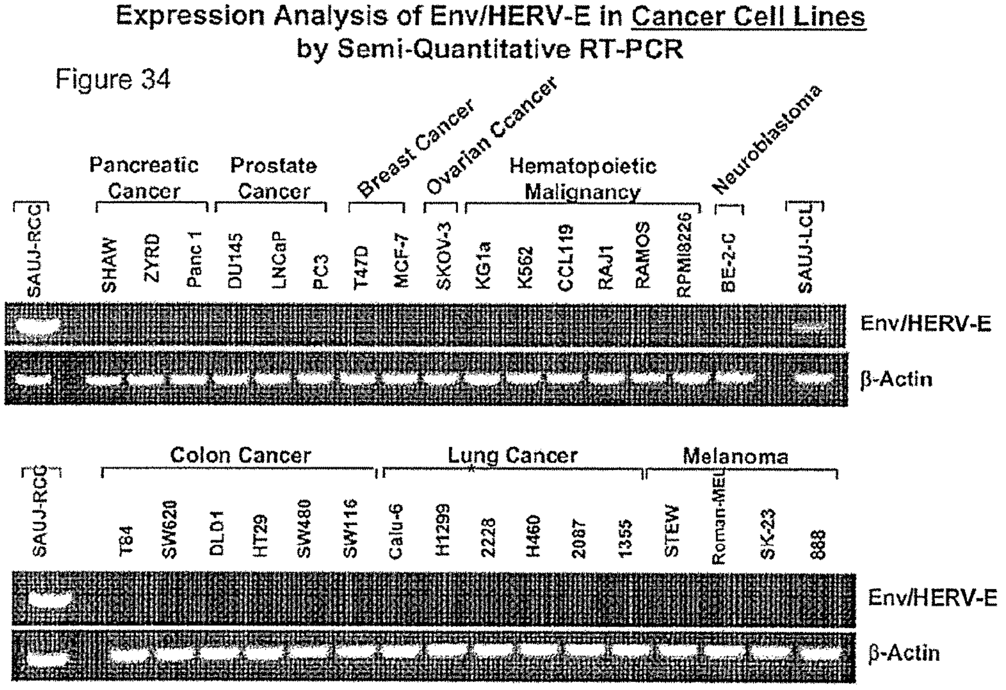
FIG. 34 shows expression analysis of Env/HERV-E in cancer cell lines by semi-quantitative RT-PCR.

FIG. 34 shows expression analysis of Env/HERV-E in cancer cell lines by semi-quantitative RT-PCR. Env/HERV-E was not detected in other cancer cell lines except RCC and MV-4-11 from biphenotypic B myelomonocytic leukemia. Semi-quantitative RT-PCR to detect cDNA of the env gene in non-RCC cancer cell lines was performed. Similar to Ct RCC 8+9, expression analysis of Env/HERV-E in by Semi-Quantitative RT-PCR revealed the Env/HERV-E was not expressed in any non RCC cell lines tested.

When ranges are used herein for physical properties, such as molecular weight, or chemical properties, such as chemical formulae, all combinations and subcombinations of ranges and specific embodiments therein are intended to be included.

The disclosures of each patent, patent application and publication cited or described in this document are hereby incorporated herein by reference in their entirety.

Those skilled in the art will appreciate that numerous changes and modifications can be made to the embodiments of the invention and that such changes and modifications can be made without departing from the spirit of the invention. It is, therefore, intended that the appended claims cover all such equivalent variations as fall within the true spirit and scope of the invention.

---

What is claimed:

1. A composition comprising a dendritic cell population transduced or transfected with a vector comprising a nucleic acid encoding a human endogenous retrovirus type E (HERV-E) amino acid sequence at least 90% identical to any one of SEQ ID NOs: 1-10 or a HERV-E nucleic acid having a sequence at least 90% identical to any one of SEQ ID NOs: 11, 12, 35-45, or 47.

2. The composition of claim 1, wherein the dendritic cell population is transduced or transfected with a vector comprising a nucleic acid encoding a HERV-E amino acid sequence at least 95% identical to any one of SEQ ID NOs: 1-10 or a HERV-E nucleic acid having a sequence at least 95% identical to any one of SEQ ID NOs: 11, 12, 35-45, or 47.

3. The composition of claim 2, wherein the dendritic cell population is transduced or transfected with a vector comprising a nucleic acid encoding the HERV-E amino acid sequence of any one of SEQ ID NOs: 1-10 or a HERV-E nucleic acid comprising any one of SEQ ID NOs: 11, 12, 35-45, or 47.

4. The composition of claim 1, wherein the vector further comprises a nucleic acid encoding one or more immune co-stimulatory molecules.

5. The composition of claim 4, wherein the immune co-stimulatory molecules comprise one or more of B7-1, ICAM-1, and LFA-3.35.

6. The composition of claim 1, wherein the vector further comprises an inducible promoter.

7. The composition of claim 1, wherein the vector is a viral vector.

8. A method of treating a patient having renal cell carcinoma comprising administering to the patient an effective amount of the composition of claim 1.

9. The method of claim 8, wherein the composition comprises an allogeneic dendritic cell population or an autologous dendritic cell population.

10. The composition of claim 1, wherein the nucleic acid encoding a HERV-E amino acid sequence at least 90% identical to any one of SEQ ID NOs: 1-10 comprises the nucleic acid sequence of any one of SEQ ID NOs: 23-32.

11. The composition of claim 10, wherein the nucleic acid encoding a HERV-E amino acid sequence at least 90% identical to any one of SEQ ID NOs: 1-10 consists of the nucleic acid sequence of any one of SEQ ID NOs: 23-32.

* * * * *